(12) United States Patent
Sadelain et al.

(10) Patent No.: US 11,932,690 B2
(45) Date of Patent: Mar. 19, 2024

(54) ENHANCED CHIMERIC ANTIGEN RECEPTORS AND USES THEREOF

(71) Applicant: MEMORIAL SLOAN-KETTERING CANCER CENTER, New York, NY (US)

(72) Inventors: Michel Sadelain, New York, NY (US); Judith Feucht, Upfingen (DE); Mohamad Hamieh, New York, NY (US); Jie Sun, New York, NY (US); Jorge A. Mansilla-Soto, Forest Hills, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 760 days.

(21) Appl. No.: 16/911,148

(22) Filed: Jun. 24, 2020

(65) Prior Publication Data
US 2020/0317777 A1    Oct. 8, 2020

Related U.S. Application Data

(63) Continuation of application No. PCT/US2018/068134, filed on Dec. 31, 2018.

(60) Provisional application No. 62/612,031, filed on Dec. 29, 2017.

(51) Int. Cl.
| | |
|---|---|
| *C07K 16/28* | (2006.01) |
| *A61K 35/17* | (2015.01) |
| *A61P 35/00* | (2006.01) |
| *C07K 14/705* | (2006.01) |
| *C07K 14/725* | (2006.01) |
| *C12N 5/0783* | (2010.01) |

(52) U.S. Cl.
CPC .......... *C07K 16/2803* (2013.01); *A61K 35/17* (2013.01); *A61P 35/00* (2018.01); *C07K 14/7051* (2013.01); *C07K 14/70521* (2013.01); *C12N 5/0636* (2013.01); *C07K 2317/24* (2013.01); *C07K 2317/53* (2013.01); *C07K 2319/02* (2013.01); *C07K 2319/03* (2013.01); *C07K 2319/33* (2013.01)

(58) Field of Classification Search
CPC ............ C07K 16/2803; C07K 14/7051; C07K 14/70521; C07K 2317/24; C07K 2317/53; C07K 2319/02; C07K 2319/03; C07K 2319/33; C07K 2317/622; A61K 35/17; A61K 2039/5156; A61K 2039/5158; A61K 39/001112; A61P 35/00; C12N 5/0636
See application file for complete search history.

(56) References Cited

U.S. PATENT DOCUMENTS

| | | |
|---|---|---|
| 4,956,778 A | 9/1990 | Naito |
| 5,091,513 A | 2/1992 | Huston et al. |
| 5,132,405 A | 7/1992 | Huston et al. |
| 2005/0196754 A1 | 9/2005 | Drmanac et al. |
| 2015/0031624 A1 | 1/2015 | Feldman et al. |
| 2015/0376296 A1 | 12/2015 | Fedorov et al. |

FOREIGN PATENT DOCUMENTS

| | | | | |
|---|---|---|---|---|
| WO | WO 2013/166051 A1 | 11/2013 | | |
| WO | WO 2014/134165 A1 | 9/2014 | | |
| WO | WO 2016/075612 A1 | 5/2016 | | |
| WO | WO 2017/027392 | * | 2/2017 | ............. C07K 16/28 |
| WO | WO 2017/091753 A1 | 6/2017 | | |
| WO | WO 2018/132506 | † | 7/2018 | |
| WO | WO 2018/132506 A1 | 7/2018 | | |

OTHER PUBLICATIONS

Zhao et al. (J. Immunol., 183(9): 5563-5574, 2009).*
Eyquem et al. (Nature, 543(7643): 113-117, Mar. 2017).*
Partial Supplementary European search report dated Aug. 23, 2021 in Application No. EP18896769.
Acuto et al., "CD28-mediated co-stimulation: a quantitative support for TCR signaling," Nat. Rev. Immunol. 3, 939-951 (2003).
Ardouin et al., "Crippling of CD3-zeta ITAMs Does Not Impair T Cell Receptor Signaling," Immunity 10 409-420 (1999).
Bai et al., "Kruppel-Like Factor 2 Controls T Cell Trafficking by Activating L-Selectin (CD62L) and Sphingosine-1-Phosphate Receptor 1 Transcription[1]," J. Immunol. 178, 7632-7639 (2007).
Benton et al., "Screening lambdagt recombinant clones by hybridization to single plaques in situ," Science 196:180-182 (1977).
Berger and Kimmel,"Guide to Molecular Cloning Techniques," Academic Press, New York, pp. 3-812 (1987).

(Continued)

*Primary Examiner* — Nelson B Moseley, II
(74) *Attorney, Agent, or Firm* — Baker Botts L.L.P.

(57) ABSTRACT

The presently disclosed subject matter provides methods and compositions for enhancing the immune response toward cancers and pathogens. It relates to novel designs of chimeric antigen receptors (CARs) and engineered immunoresponsive cells comprising the same. The engineered immunoresponsive cells comprising the novel CARs are antigen-directed and have extended persistence without compromising function.

40 Claims, 73 Drawing Sheets

Specification includes a Sequence Listing.

(56) References Cited

OTHER PUBLICATIONS

Brentjens et al., "CD19-targeted T cells rapidly induce molecular remissions in adults with chemotherapy-refractory acute lymphoblastic leukemia," Sci Transl Med. 5, 177ra38 (2013).
Brentjens et al., "Genetically targeted T cells eradicate systemic acute lymphoblastic leukemia xenografts," Clin Cancer Res 13, 5426-5435 (2007).
Brentjens et al., "Eradication of systemic B-cell tumors by genetically targeted human T lymphocytes co-stimulated by CD80 and interleukin-15," Nature Medicine 9, 279-286 (2003).
Bridgeman et al., "CD3 zeta-Based Chimeric Antigen Receptors Mediate T Cell Activation via Cis- and Trans-Signalling Mechanisms: Implications for Optimization of Receptor Structure for Adoptive Cell Therapy," Clinical and Experimental Immunology 175 258-267 (2014).
Brocks et al., " A TNF receptor antagonistic scFv, which is not secreted in mammalian cells, is expressed as a s soluble mono- and bivalent scFv derivative in insect cells," Immunotechnology 3:173-184 (1997).
Carlson et al., "Kruppel-like factor 2 regulates thymocyte and T-cell migration," Nature 442, 299-302 (2006).
Chae et al., "Qualitatively differential regulation of T cell activation and apoptosis by T cell receptor zeta chain ITAMs and their tyrosine residues," Int. Immunol. 16, 1225-1236 (2004).
Chang et al., "Molecular regulation of effector and memory T cell differentiation," Nat. Immunol. 15, 1104-1115 (2014).
Daniels et al., "TCR signaling in T cell memory," Front. Immunol. 6:617 (2015).
DeFord-Watts et al., "The CD3 Zeta Subunit Contains a Phosphoinositide-Binding Motif that is Required for the Stable Accumulation of TCR-CD3 Complex at the Immunological Synapse." Journal of Immunology, 186 6839-6847 (2011).
Dobin et al., "Star: ultrafast universal RNA-seq aligner," Bioinformatics 29, 15-21 (2013).
Eyquem et al., "Targeting a CAR to the TRAC locus with CRISPR/Cas9 enhances tumour rejection," Nature 543 113-117 (2017).
Fife et al., "Inhibition of T cell activation and autoimmune diabetes using a B cell surface-lined CTLA-4 agonist," J Clin Invst 116(8):2252-2261 (2006).
Fraietta et al., "Determinants of response and resistance to CD19 chimeric antigen receptor (CAR) T cell therapy of chronic lymphocytic leukemia," Nat Med 24, 563-571 (2018).
Gade et al., "Targeted Elimination of Prostate Cancer by Genetically Directed Human T Lymphocytes," Cancer Res 65, 9080-9088 (2005).
Gattinoni et al, "A human memory T cell subset with stem cell-like properties," Nat Med 17, 1290-1297 (2011).
Ghosh et al., "Adoptively transferred Trail+ T cells suppress GVHD and augment antitumor activity," *J Clin Invest* 123, 2654-2662 (2013).
Giomarelli et al., "Inhibition of thrombin-induced platelet aggregation using human single-chain Fv antibodies specific for TREM-like transcript-1," Thromb Haemost 97:955-963 (2007).
Gong et al., "Cancer patient T cells genetically targeted to prostate-specific membrane antigen specifically lyse prostate cancer cells and release cytokines in response to prostate-specific membrane antigen," Neoplasia 1, 123-127 (1999).
Grunstein et al., "Colony hybridization: A method for the isolation of cloned DNAs that contain a specific gene," Proc. Nat. Acad. Sci., USA 72:3961-3965 (1975).
Ho et al., "Inhibition of Cocaine Binding to the Human Dopamine Transporter by a Single Chain Anti-Idiotypic Antibody: Its Cloning, Expression and Functional Properties," BioChim Biophys Acta 1638(3):257-266 (2003).
Huston et al., "Protein engineering of antibody binding sites: recovery of specific activity in an anti-digoxin single-chain Fv analogue produced in *Escherichia coli*," Proc. Natl. Acad. Sci. USA 85, 5879-5883 (1988).

Ichii et al., "Role for Bcl-6 in the generation and maintenance of memory $CD8^+T$ cells," Nat. Immunol. 3, 558-563 (2002).
International Search Report dated Jun. 19, 2019 in International Application No. PCT/US2018/068134.
Isakov et al., "ZAP-70 binding specificity to T cell receptor tyrosine-based activation motifs: the tandem SH2 domains of ZAP-70 bind distinct tyrosine-based activation motifs with varying affinity," J. Exp. Med. 181, 375-380 (1995).
James, "Tuning ITAM multiplicity on T cell receptors can control potency and selectivity to ligand density," Sci. Signal. 11, eaan1088 (2018).
Kaech et al., "Transcriptional control of effector and memory CD8+ T cell differentiation," Nat. Rev. Immunol. 12, 749-761 (2012).
Kabat et al., "Sequences of Proteins of Immunological Interest," vol. 1 Fifth Edition, U.S. Department of Health and Human Services, NIH Publication No. 91-3242 (1991).
Kersh et al., "Fidelity of T cell activation through multistep T cell receptor zeta Phosphorylation," Science 281, 572-575 (1998).
Kimmel, "Identification and Characterization of Specific Clones: Strategy for Confirming the Validity of Presumptive Clones," Methods Enzymology 152:507-511 (1987).
Kochenderfer et al., "Adoptive transfer of syngeneic T cells transduced with a chimeric antigen receptor that recognizes murine CD19 can eradicate lymphoma and normal B cells," Blood 116, 3875-3886 (2010).
Ledbetter et al., "Agonistic Activity of a CD40-Specific Single-Chain Fv Constructed from the Variable Regions of mAb G28-5," Crit Rev Immunol 17:427-455 (1997).
Lee et al., "T cells expressing CD19 chimeric antigen receptors for acute lymphoblastic leukaemia in children and young adults: a phase 1 dose-escalation trial," Lancet 385, 517-528 (2015).
Love et al., "ITAM-mediated Signaling by the T-Cell Antigen Receptor," Cold Spring Harb. Perspect. Biol. 2, a002485 (2010).
Maher et al., "Human T-lymphocyte cytotoxicity and proliferation directed by a single chimeric TCRzeta/CD28 receptor," Nat. Biotechnol. 20, 70-75 (2002).
Moosmayer et al., "A single-chain TNF receptor antagonistic is an effective inhibitor of TNF mediated cytotoxicity," Ther Immunol 2:31-40 (1995).
Mukhopadhyay et al., "Systems Model of T Cell Receptor Proximal Signaling Reveals Emergent Ultrasensitivit," PLoS Comput. Biol. 9, e1003004 (2013).
Neelapu et al., "Axicabtagene Ciloleucel CAR T-cell therapy in refractory large B-cell lymphoma," N Engl J Med 377: 2531-2544 (2017).
Park et al., "Long-term follow-up of CD19 Car therapy in acute lymphoblastic leukemia," N Engl J Med 378:449-459 (2018).
Peter et al., "Protective effects of an anti-melanocortin-4 receptor scFv derivative in lipopolysaccharide-induced cachexia in rats," J. Cachexia Sarcopenia Muscle 4:79-88 (2013).
Peter et al., "scFv Single Chain Antibody Variable Fragment as Inverse Agonist of the $B_2$-Adrenergic Receptor," J Biol Chem 278(38):36740-36747 (2003).
Rivière et al., "Effects of retroviral vector design on expression of human adenosine deaminase in murine bone marrow transplant recipients engrafted with genetically modified cells," Proc. Natl. Acad. Sci. USA 92, 6733-6737 (1995).
Sadelain et al., "Therapeutic T cell engineering," Nature 545, 423-431 (2017).
Sadelain, "CD19 Car T Cells," Cell 171, 1471 (2017).
Sambrook et al., "Molecular Cloning: A Laboratory Manual," Cold Spring Harbor Laboratory Press, New York (1989).
Shieh et al., "Transgenic Expression of Single-Chain Anti-CTLA-4 Fv on β Cells Protects Nonobese Diabetic Mice from Autoimmune Diabetes," J Imunol 183(4):2277-2285 (2009).
Smith-Garvin et al., "T cell activation," Annu Rev Immunol 27, 591-619 (2009).
Sommermeyer et al., "Chimeric antigen receptor-modified T cells derived from defined CD8+ and CD4+ subsets confer superior antitumor reactivity in vivo," Leukemia 30, 492-500 (2016).
Van Oers et al., "The 21- and 23-kD forms of TCR zeta are generated by specific ITAM phosphorylations," Nat. Immunol. 1, 322-328 (2000).

(56) References Cited

OTHER PUBLICATIONS

Wahl et al., "Molecular Hybridization of Immobilized Nucleic Acids: Theoretical Concepts and Practical Considerations," Methods Enzymol. 152:399-407 (1987).
Wahl et al., Improved Radioimaging and Tumor Localization with Monoclonal F(ab')$_2$, J. Nucl. Med. 24:316-325 (1983).
Wherry et al., "Molecular and cellular insights into T cell exhaustion," Nat. Rev. Immunol. 15, 486-499 (2015).
Xie et al., "Direct demonstration of MuSK involvement in acetylcholine receptor clustering through identification of agonist ScFv," Nat Biotech 15(8):768-771 (1997).
Youngblood et al., "Making memories that last a lifetime: heritable functions of self-renewing memory," CD8 T cells, Int. Immunol. 22, 797-803 (2010).
Yu et al., "Epigenetic landscapes reveal transcription factors that regulate CD8+ T cell differentiation," Nat Immunol 18, 573-582 (2017).
Zhao et al., "Structural Design of Engineered Costimulation Determines Tumor Rejection Kinetics and Persistence of CAR T Cells," Cancer Cell 28, 415-428 (2015).
Zhao et al., "A Herceptin-Based Chimeric Antigen Receptor with Modified Signaling Domains Leads to Enhanced Survival of Transduced T Lymphocytes and Antitumor Activity," J Immunol 183, 5563-5574 (2009).
Zhao et al., "MAb ZB Against TSAb," Hyrbidoma (Larchmt) 2008 27(6):501, Doi:10.1089/hyb.2008.0063.mab.
Zhou et al., "Cutting edge: generation of memory precursors and functional memory CD8+ T cells depends on T cell factor-1 and lymphoid enhancer-binding factor-1," J Immunol 189, 2722-2726 (2012).
Search Report dated Mar. 22, 2022 corresponding to Singapore Patent Application No. 11202006050X.
Zhao, Y. et al., A Herceptin-Based Chimeric Antigen Receptor with Modified Signaling Domains Leads to Enhanced Survival of Transduced T Lymphocytes and Antitumor Activity. J. Immunol. 2009; 183(9): 5563-5574. ("Zhao").†

\* cited by examiner
† cited by third party

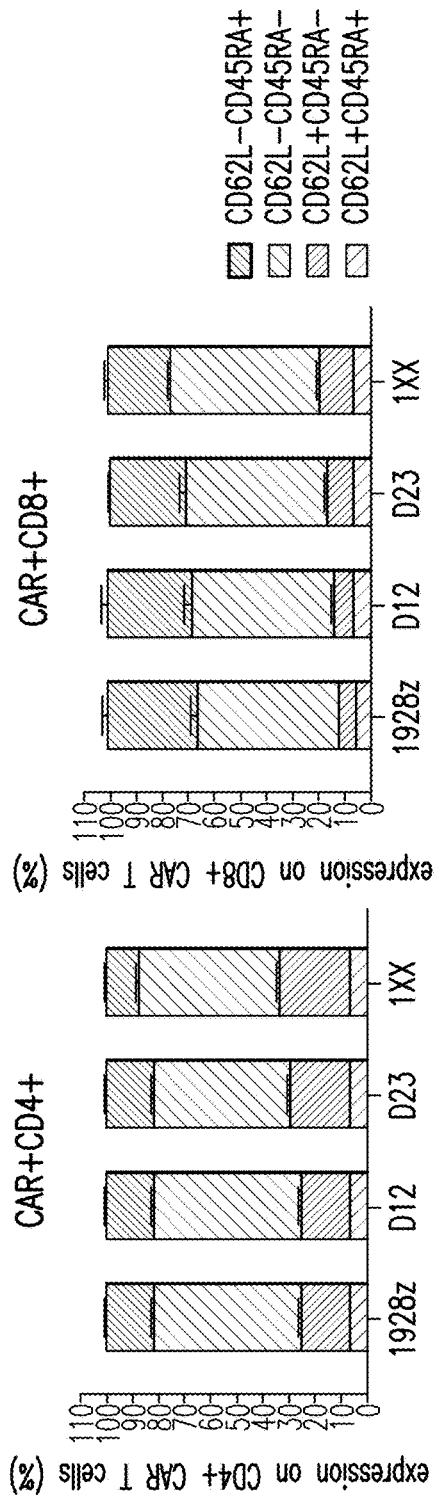
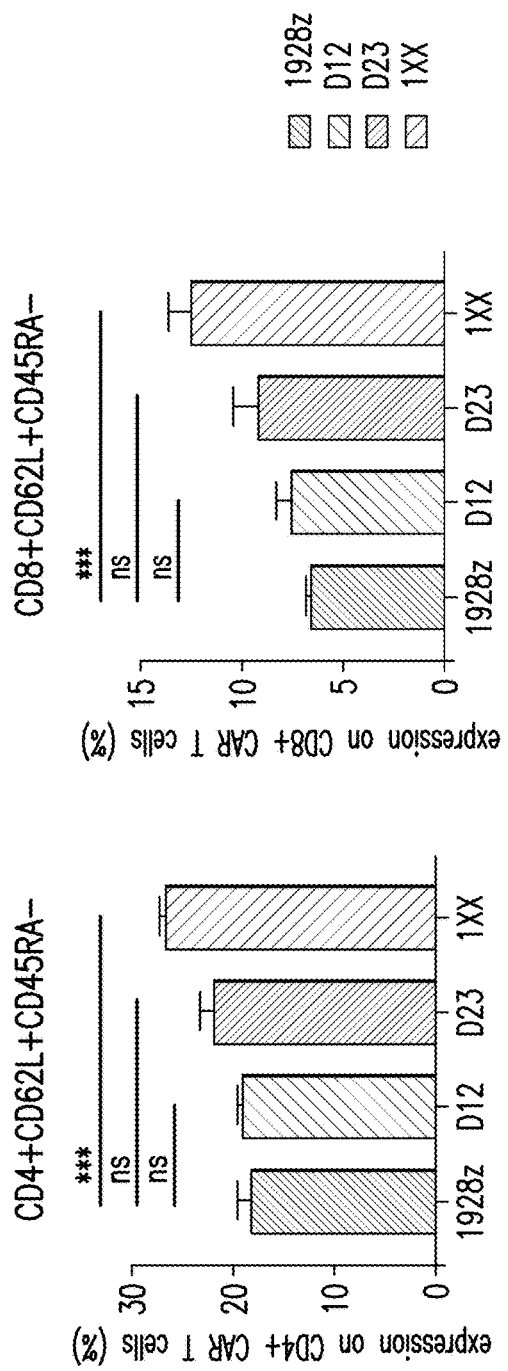
FIG. 5A
FIG. 5B

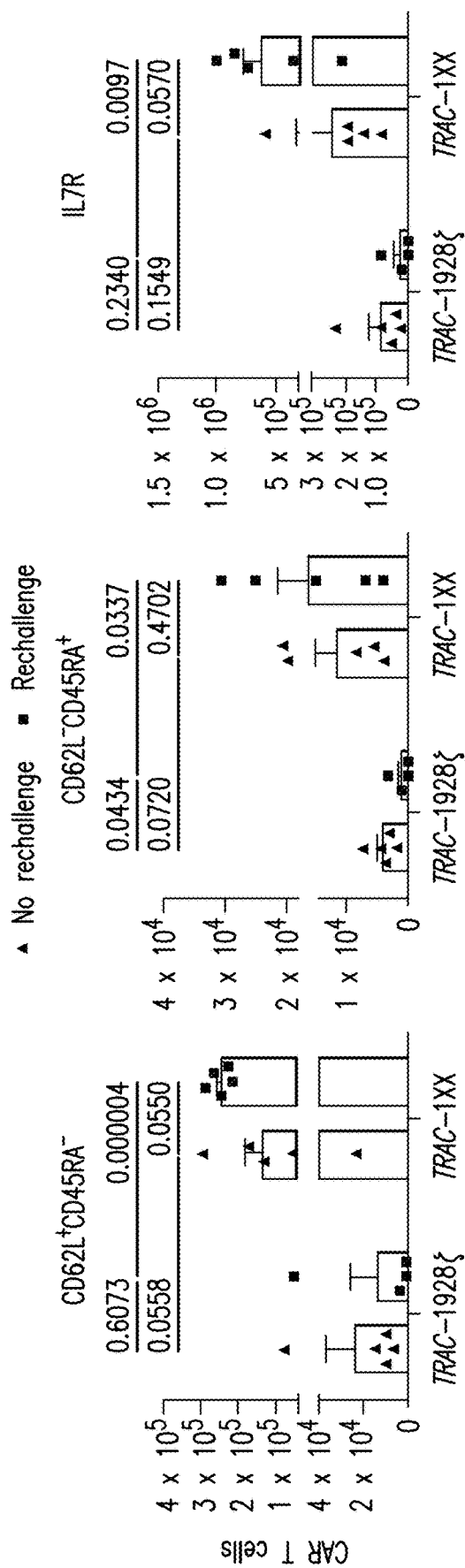
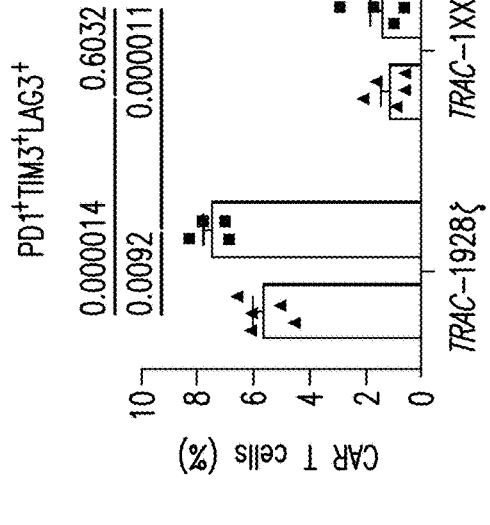
FIG. 18G
FIG. 18H

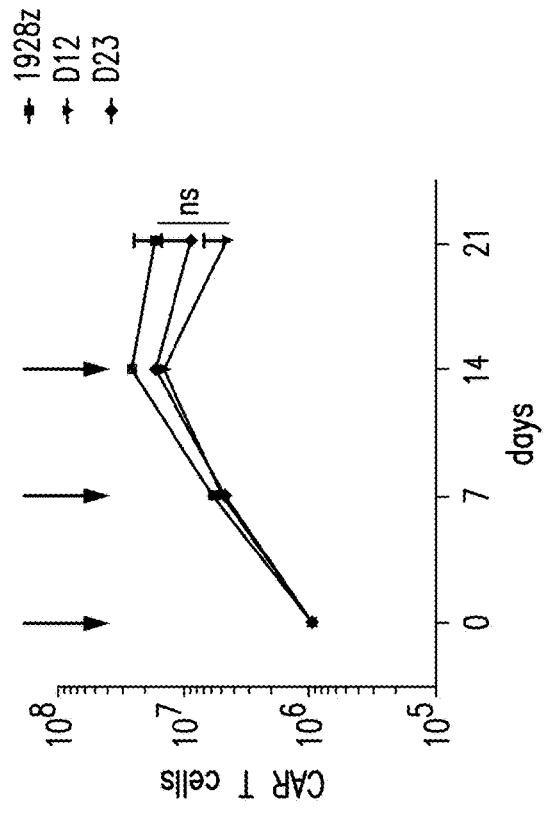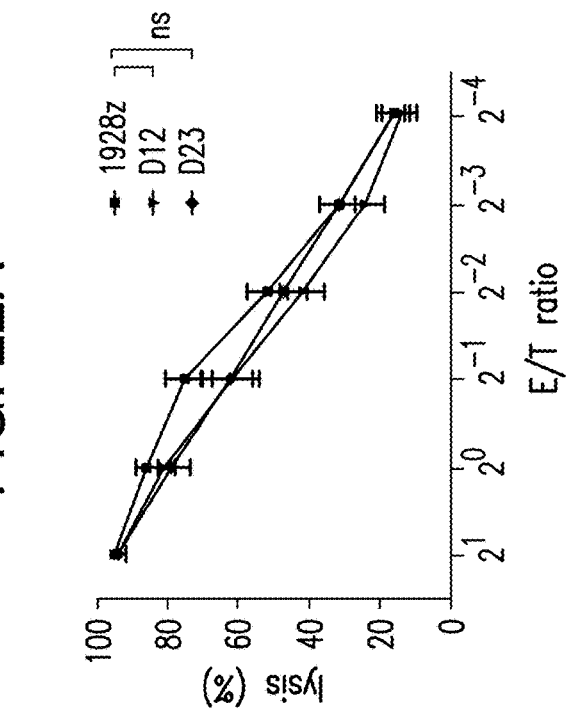
FIG. 22A, FIG. 22B, FIG. 22C, FIG. 22D

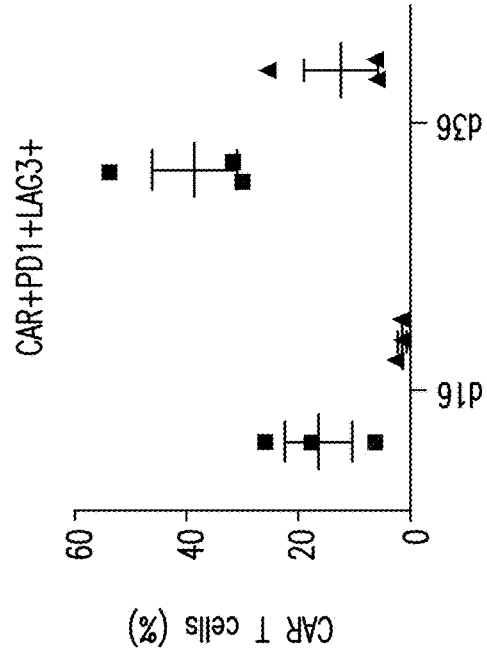
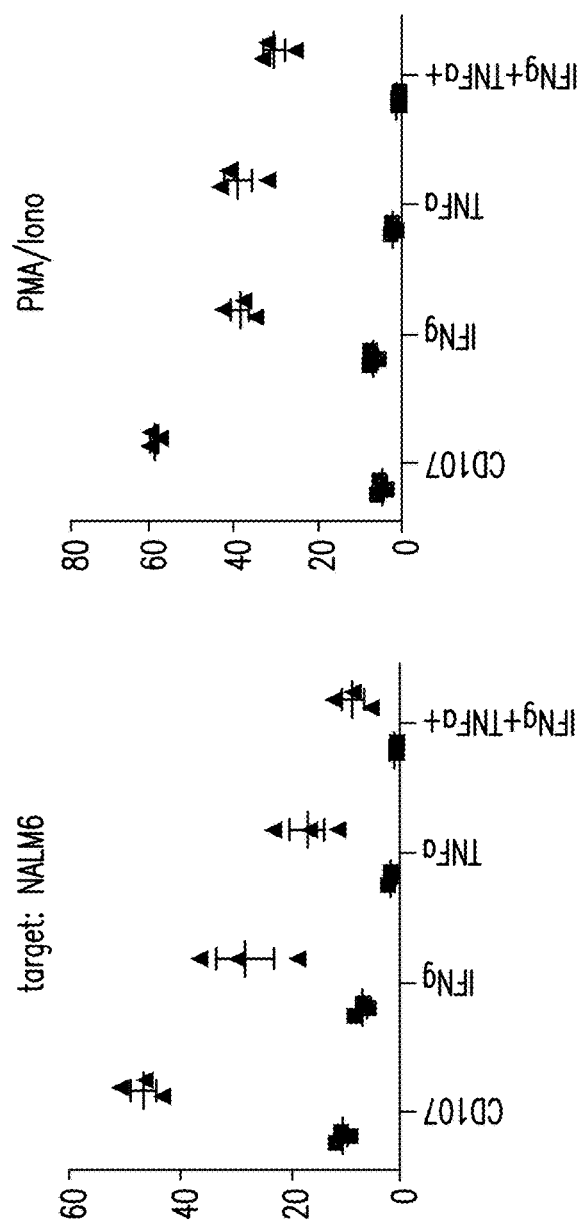

SEQUENCE LISTING

<160> NUMBER OF SEQ ID NOS: 119

<210> SEQ ID NO 1
<211> LENGTH: 345
<212> TYPE: PRT
<213> ORGANISM: Homo sapiens

<400> SEQUENCE: 1

```
Met Ala Gln His His Leu Trp Ile Leu Leu Leu Cys Leu Gln Thr Trp
1               5                   10                  15

Pro Glu Ala Ala Gly Lys Asp Ser Glu Ile Phe Thr Val Asn Gly Ile
            20                  25                  30

Leu Gly Glu Ser Val Thr Phe Pro Val Asn Ile Gln Glu Pro Arg Gln
        35                  40                  45

Val Lys Ile Ile Ala Trp Thr Ser Lys Thr Ser Val Ala Tyr Val Thr
    50                  55                  60

Pro Gly Asp Ser Glu Thr Ala Pro Val Val Thr Val Thr His Arg Asn
65                  70                  75                  80

Tyr Tyr Glu Arg Ile His Ala Leu Gly Pro Asn Tyr Asn Leu Val Ile
                85                  90                  95

Ser Asp Leu Arg Met Glu Asp Ala Gly Asp Tyr Lys Ala Asp Ile Asn
            100                 105                 110

Thr Gln Ala Asp Pro Tyr Thr Thr Thr Lys Arg Tyr Asn Leu Gln Ile
        115                 120                 125

Tyr Arg Arg Leu Gly Lys Pro Lys Ile Thr Gln Ser Leu Met Ala Ser
    130                 135                 140

Val Asn Ser Thr Cys Asn Val Thr Leu Thr Cys Ser Val Glu Lys Glu
145                 150                 155                 160

Glu Lys Asn Val Thr Tyr Asn Trp Ser Pro Leu Gly Glu Glu Gly Asn
                165                 170                 175

Val Leu Gln Ile Phe Gln Thr Pro Glu Asp Gln Glu Leu Thr Tyr Thr
            180                 185                 190

Cys Thr Ala Gln Asn Pro Val Ser Asn Asn Ser Asp Ser Ile Ser Ala
        195                 200                 205

Arg Gln Leu Cys Ala Asp Ile Ala Met Gly Phe Arg Thr His His Thr
    210                 215                 220
```

```
Gly Leu Leu Ser Val Leu Ala Met Phe Phe Leu Val Leu Ile Leu
225                 230                 235                 240

Ser Ser Val Phe Leu Phe Arg Leu Phe Lys Arg Arg Gln Gly Arg Ile
            245                 250                 255

Phe Pro Glu Gly Ser Cys Leu Asn Thr Phe Thr Lys Asn Pro Tyr Ala
        260                 265                 270

Ala Ser Lys Lys Thr Ile Tyr Thr Tyr Ile Met Ala Ser Arg Asn Thr
        275                 280                 285

Gln Pro Ala Glu Ser Arg Ile Tyr Asp Glu Ile Leu Gln Ser Lys Val
        290                 295                 300

Leu Pro Ser Lys Glu Glu Pro Val Asn Thr Val Tyr Ser Glu Val Gln
305                 310                 315                 320

Phe Ala Asp Lys Met Gly Lys Ala Ser Thr Gln Asp Ser Lys Pro Pro
                325                 330                 335

Gly Thr Ser Ser Tyr Glu Ile Val Ile
                340                 345

<210> SEQ ID NO 2
<211> LENGTH: 75
<212> TYPE: DNA
<213> ORGANISM: Homo sapiens

<400> SEQUENCE: 2
ttgctgagcg tgctggctat gttctttctg cttgttctca ttctgtcttc agtgttttg    60 ttccgtttgt tcaag                                                    75

<210> SEQ ID NO 3
<211> LENGTH: 583
<212> TYPE: PRT
<213> ORGANISM: Homo sapiens

<400> SEQUENCE: 3

Met Glu Ser Lys Gly Ala Ser Ser Cys Arg Leu Leu Phe Cys Leu Leu
1               5                   10                  15

Ile Ser Ala Thr Val Phe Arg Pro Gly Leu Gly Trp Tyr Thr Val Asn
            20                  25                  30

Ser Ala Tyr Gly Asp Thr Ile Ile Pro Cys Arg Leu Asp Val Pro
            35                  40                  45

Gln Asn Leu Met Phe Gly Lys Trp Lys Tyr Glu Lys Pro Asp Gly Ser
        50                  55                  60

Pro Val Phe Ile Ala Phe Arg Ser Ser Thr Lys Lys Ser Val Gln Tyr
65                  70                  75                  80

Asp Asp Val Pro Glu Tyr Lys Asp Arg Leu Asn Leu Ser Glu Asn Tyr
                85                  90                  95

Thr Leu Ser Ile Ser Asn Ala Arg Ile Ser Asp Glu Lys Arg Phe Val
            100                 105                 110

Cys Met Leu Val Thr Glu Asp Asn Val Phe Glu Ala Pro Thr Ile Val
            115                 120                 125

Lys Val Phe Lys Gln Pro Ser Lys Pro Glu Ile Val Ser Lys Ala Leu
        130                 135                 140

Phe Leu Glu Thr Glu Gln Leu Lys Lys Leu Gly Asp Cys Ile Ser Glu
145                 150                 155                 160

Asp Ser Tyr Pro Asp Gly Asn Ile Thr Trp Tyr Arg Asn Gly Lys Val
                165                 170                 175

Leu His Pro Leu Glu Gly Ala Val Val Ile Ile Phe Lys Lys Glu Met
```

```
            180                 185                 190
Asp Pro Val Thr Gln Leu Tyr Thr Met Thr Ser Thr Leu Glu Tyr Lys
            195                 200                 205
Thr Thr Lys Ala Asp Ile Gln Met Pro Phe Thr Cys Ser Val Thr Tyr
            210                 215                 220
Tyr Gly Pro Ser Gly Gln Lys Thr Ile His Ser Glu Gln Ala Val Phe
225                 230                 235                 240
Asp Ile Tyr Tyr Pro Thr Glu Gln Val Thr Ile Gln Val Leu Pro Pro
                245                 250                 255
Lys Asn Ala Ile Lys Glu Gly Asp Asn Ile Thr Leu Lys Cys Leu Gly
            260                 265                 270
Asn Gly Asn Pro Pro Glu Glu Phe Leu Phe Tyr Leu Pro Gly Gln
            275                 280                 285
Pro Glu Gly Ile Arg Ser Asn Thr Tyr Thr Leu Thr Asp Val Arg
            290                 295                 300
Arg Asn Ala Thr Gly Asp Tyr Lys Cys Ser Leu Ile Asp Lys Lys Ser
305                 310                 315                 320
Met Ile Ala Ser Thr Ala Ile Thr Val His Tyr Leu Asp Leu Ser Leu
                325                 330                 335
Asn Pro Ser Gly Glu Val Thr Arg Gln Ile Gly Asp Ala Leu Pro Val
            340                 345                 350
Ser Cys Thr Ile Ser Ala Ser Arg Asn Ala Thr Val Val Trp Met Lys
            355                 360                 365
Asp Asn Ile Arg Leu Arg Ser Ser Pro Ser Phe Ser Ser Leu His Tyr
            370                 375                 380
Gln Asp Ala Gly Asn Tyr Val Cys Glu Thr Ala Leu Gln Glu Val Glu
385                 390                 395                 400
Gly Leu Lys Lys Arg Glu Ser Leu Thr Leu Ile Val Glu Gly Lys Pro
                405                 410                 415
Gln Ile Lys Met Thr Lys Lys Thr Asp Pro Ser Gly Leu Ser Lys Thr
                420                 425                 430
Ile Ile Cys His Val Glu Gly Phe Pro Lys Pro Ala Ile Gln Trp Thr
                435                 440                 445
Ile Thr Gly Ser Gly Ser Val Ile Asn Gln Thr Glu Glu Ser Pro Tyr
            450                 455                 460
Ile Asn Gly Arg Tyr Tyr Ser Lys Ile Ile Ser Pro Glu Glu Asn
465                 470                 475                 480
Val Thr Leu Thr Cys Thr Ala Glu Asn Gln Leu Glu Arg Thr Val Asn
                485                 490                 495
Ser Leu Asn Val Ser Ala Ile Ser Ile Pro Glu His Asp Glu Ala Asp
            500                 505                 510
Glu Ile Ser Asp Glu Asn Arg Glu Lys Val Asn Asp Gln Ala Lys Leu
            515                 520                 525
Ile Val Gly Ile Val Val Gly Leu Leu Leu Ala Ala Leu Val Ala Gly
            530                 535                 540
Val Val Tyr Trp Leu Tyr Met Lys Lys Ser Lys Thr Ala Ser Lys His
545                 550                 555                 560
Val Asn Lys Asp Leu Gly Asn Met Glu Glu Asn Lys Lys Leu Glu Glu
                565                 570                 575
Asn Asn His Lys Thr Glu Ala
            580

<210> SEQ ID NO 4
```

<211> LENGTH: 78
<212> TYPE: DNA
<213> ORGANISM: Homo sapiens

<400> SEQUENCE: 4
ctaattgtgg gaatcgttgt tggtctcctc cttgctgccc ttgttgctgg tgtcgtctac    60
tggctgtaca tgaagaag                                                  78

<210> SEQ ID NO 5
<211> LENGTH: 235
<212> TYPE: PRT
<213> ORGANISM: Homo sapiens

<400> SEQUENCE: 5

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 6
<211> LENGTH: 75
<212> TYPE: DNA
<213> ORGANISM: Homo sapiens

<400> SEQUENCE: 6
atctacatct gggcgcccct tggccgggac tgtggggtcc ttctcctgtc actggttatc    60
accctttact gcaac                                                     75

<210> SEQ ID NO 7
<211> LENGTH: 221
<212> TYPE: PRT

<213> ORGANISM: Homo sapiens

<400> SEQUENCE: 7

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Leu
        195                 200                 205

Arg Leu His Pro Leu Glu Lys Cys Ser Arg Met Asp Tyr
    210                 215                 220

<210> SEQ ID NO 8
<211> LENGTH: 75
<212> TYPE: DNA
<213> ORGANISM: Homo sapiens

<400> SEQUENCE: 8
atcacccttg gcctgctggt ggctggcgtc ctggttctgc tggtttccct gggagtggcc    60
atccacctgt gctgc    75

<210> SEQ ID NO 9
<211> LENGTH: 199
<212> TYPE: PRT
<213> ORGANISM: Homo sapiens

<400> SEQUENCE: 9

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu

```
              65                  70                  75                  80
Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
               100                 105                 110

Ile Phe Asp Pro Pro Phe Lys Val Thr Leu Thr Gly Gly Tyr Leu
               115                 120                 125

His Ile Tyr Glu Ser Gln Leu Cys Cys Gln Leu Lys Phe Trp Leu Pro
       130                 135                 140

Ile Gly Cys Ala Ala Phe Val Val Cys Ile Leu Gly Cys Ile Leu
145                 150                 155                 160

Ile Cys Trp Leu Thr Lys Lys Tyr Ser Ser Val His Asp Pro
                165                 170                 175

Asn Gly Glu Tyr Met Phe Met Arg Ala Val Asn Thr Ala Lys Lys Ser
                180                 185                 190

Arg Leu Thr Asp Val Thr Leu
        195

<210> SEQ ID NO 10
<211> LENGTH: 75
<212> TYPE: DNA
<213> ORGANISM: Homo sapiens

<400> SEQUENCE: 10
ttctggttac ccataggatg tgcagccttt gttgtagtct gcattttggg atgcatactt    60
atttgttggc ttaca                                                     75

<210> SEQ ID NO 11
<211> LENGTH: 223
<212> TYPE: PRT
<213> ORGANISM: Homo sapiens

<400> SEQUENCE: 11

Met Ala Cys Leu Gly Phe Gln Arg His Lys Ala Gln Leu Asn Leu Ala
1               5                  10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175
```

```
Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
    210                 215                 220

<210> SEQ ID NO 12
<211> LENGTH: 75
<212> TYPE: DNA
<213> ORGANISM: Homo sapiens

<400> SEQUENCE: 12
ttcctcctct ggatccttgc agcagttagt tcggggttgt tttttatag ctttctcctc      60 acagctgttt ctttg                                                     75

<210> SEQ ID NO 13
<211> LENGTH: 532
<212> TYPE: PRT
<213> ORGANISM: Homo sapiens

<400> SEQUENCE: 13

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
                20                  25                  30

Pro Ser Lys Val Ile Leu Pro Arg Gly Gly Ser Val Leu Val Thr Cys
            35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270
```

-continued

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
    450                 455                 460

Glu Val Thr Arg Lys Val Thr Val Asn Val Leu Ser Pro Arg Tyr Glu
465                 470                 475                 480

Ile Val Ile Ile Thr Val Ala Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
        515                 520                 525

Ala Thr Pro Pro
        530

<210> SEQ ID NO 14
<211> LENGTH: 81
<212> TYPE: DNA
<213> ORGANISM: Homo sapiens

<400> SEQUENCE: 14
attgtcatca tcactgtggt agcagccgca gtcataatgg gcactgcagg cctcagcacg      60
tacctctata accgccagcg g                                               81

<210> SEQ ID NO 15
<211> LENGTH: 39
<212> TYPE: PRT
<213> ORGANISM: Homo sapiens

<400> SEQUENCE: 15

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro

<210> SEQ ID NO 16
<211> LENGTH: 117
<212> TYPE: DNA
<213> ORGANISM: Homo sapiens

<400> SEQUENCE: 16
caagagctga cttacacgtg tacagcccag aaccctgtca gcaacaattc tgactccatc    60
tctgcccggc agctctgtgc agacatcgca atgggcttcc gtactcacca caccggg      117

<210> SEQ ID NO 17
<211> LENGTH: 116
<212> TYPE: DNA
<213> ORGANISM: Homo sapiens

<400> SEQUENCE: 17
accaactgga gagaacagta aactccttga atgtctctgc tataagtatt ccagaacacg    60
atgaggcaga cgagataagt gatgaaaaca gagaaaaggt gaatgaccag gcaaaa       116

<210> SEQ ID NO 18
<211> LENGTH: 138
<212> TYPE: DNA
<213> ORGANISM: Homo sapiens

<400> SEQUENCE: 18
cccaccacga cgccagcgcc gcgaccacca acaccggcgc ccaccatcgc gtcgcagccc    60
ctgtccctgc gcccagaggc gtgccggcca gcggcggggg gcgcagtgca cacgaggggg   120
ctggacttcg cctgtgat                                                 138

<210> SEQ ID NO 19
<211> LENGTH: 117
<212> TYPE: DNA
<213> ORGANISM: Homo sapiens

<400> SEQUENCE: 19
ctgagtgtgg ttgatttcct tcccaccact gcccagccca ccaagaagtc caccctcaag    60
aagagagtgt gccggttacc caggccagag acccagaagg gcccactttg tagcccc      117

<210> SEQ ID NO 20
<211> LENGTH: 117
<212> TYPE: DNA
<213> ORGANISM: Homo sapiens

<400> SEQUENCE: 20
tctcatgcca actattactt ctgcaaccta tcaattttg atcctcctcc ttttaaagta     60
actcttacag gaggatattt gcatatttat gaatcacaac tttgttgcca gctgaag      117

<210> SEQ ID NO 21
<211> LENGTH: 117
<212> TYPE: DNA
<213> ORGANISM: Homo sapiens

<400> SEQUENCE: 21
gacacgggac tctacatctg caaggtggag ctcatgtacc caccgccata ctacctgggc    60
ataggcaacg gaacccagat ttatgtaatt gatccagaac cgtgcccaga ttctgac      117

<210> SEQ ID NO 22
<211> LENGTH: 117

```
<212> TYPE: DNA
<213> ORGANISM: Homo sapiens

<400> SEQUENCE: 22
ggggaatcag tgactgtcac tcgagatctt gagggcacct acctctgtcg ggccaggagc      60
actcaagggg aggtcacccg caaggtgacc gtgaatgtgc tctcccccg gtatgag         117

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Asn Gln Leu Tyr Asn Glu Leu Asn Leu Gly Arg Arg Glu Glu Tyr
1               5                   10                  15

Asp Val Leu Asp Lys Arg
            20

<210> SEQ ID NO 24
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cagaaccagc tctataacga gctcaatcta ggacgaagag aggagtacga tgttttggac      60
aagaga                                                                66

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Asn Gln Leu Phe Asn Glu Leu Asn Leu Gly Arg Arg Glu Glu Phe
1               5                   10                  15

Asp Val Leu Asp Lys Arg
            20

<210> SEQ ID NO 26
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cagaaccagc tctttaacga gctcaatcta ggacgaagag aggagttcga tgttttggac      60
aagaga                                                                66

<210> SEQ ID NO 27
<211> LENGTH: 23
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 27

Gln Glu Gly Leu Tyr Asn Glu Leu Gln Lys Asp Lys Met Ala Glu Ala
1               5                   10                  15

Tyr Ser Glu Ile Gly Met Lys
            20

<210> SEQ ID NO 28
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
caggaaggcc tgtacaatga actgcagaaa gataagatgg cggaggccta cagtgagatt      60
gggatgaaa                                                              69

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Glu Gly Leu Phe Asn Glu Leu Gln Lys Asp Lys Met Ala Glu Ala
1               5                   10                  15

Phe Ser Glu Ile Gly Met Lys
            20

<210> SEQ ID NO 30
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
caggaaggcc tgttcaatga actgcagaaa gataagatgg cggaggcctt cagtgagatt      60
gggatgaaa                                                              69

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His Asp Gly Leu Tyr Gln Gly Leu Ser Thr Ala Thr Lys Asp Thr Tyr
1               5                   10                  15

Asp Ala Leu His Met Gln
            20

<210> SEQ ID NO 32
<211> LENGTH: 66
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 32
cacgatggcc tttaccaggg tctcagtaca gccaccaagg acacctacga cgcccttcac    60
atgcag                                                               66

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His Asp Gly Leu Phe Gln Gly Leu Ser Thr Ala Thr Lys Asp Thr Phe
1               5                   10                  15

Asp Ala Leu His Met Gln
            20

<210> SEQ ID NO 34
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cacgatggcc ttttccaggg gctcagtaca gccaccaagg acaccttcga cgcccttcac    60
atgcag                                                               66

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Arg Arg Gly Arg
1               5

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aagagacgtg gccgg                                                     15

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 37

Lys Pro Arg Arg Lys
1               5

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aagccgagaa ggaag                                                      15

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Gly Glu Arg Arg Arg Gly Lys
1               5

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aaaggcgagc gccggagggg caag                                            24

<210> SEQ ID NO 41
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly
            130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Ile Glu Val Met Tyr Pro
            260                 265                 270

Pro Pro Tyr Leu Asp Asn Glu Lys Ser Asn Gly Thr Ile Ile His Val
        275                 280                 285

Lys Gly Lys His Leu Cys Pro Ser Pro Leu Phe Pro Gly Pro Ser Lys
    290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 42
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
atggctctcc cagtgactgc cctactgctt cccctagcgc ttctcctgca tgcagaggtg      60
aagctgcagc agtctggggc tgagctggtg aggcctgggt cctcagtgaa gatttcctgc     120
aaggcttctg gctatgcatt cagtagctac tggatgaact gggtgaagca gaggcctgga     180
cagggtcttg agtggattgg acagatttat cctggagatg gtgatactaa ctacaatgga     240
aagttcaagg gtcaagccac actgactgca gacaaatcct ccagcacagc ctacatgcag     300
ctcagcggcc taacatctga ggactctgcg gtctatttct gtgcaagaaa gaccattagt     360
tcggtagtag atttctactt tgactactgg ggccaaggga ccacggtcac cgtctcctca     420
ggtggaggtg gatcaggtgg aggtggatct ggtggaggtg gatctgacat tgagctcacc     480
cagtctccaa aattcatgtc cacatcagta ggagacaggg tcagcgtcac ctgcaaggcc     540
agtcagaatg tgggtactaa tgtagcctgg tatcaacaga aaccaggaca atctcctaaa     600
ccactgattt actcggcaac ctaccggaac agtggagtcc ctgatcgctt cacaggcagt     660
ggatctggga cagatttcac tctcaccatc actaacgtgc agtctaaaga cttggcagac     720
tatttctgtc aacaatataa caggtatccg tacacgtccg agggggggac caagctggag     780
atcaaacggg cggccgcaat tgaagttatg tatcctcctc cttacctaga caatgagaag     840
agcaatggaa ccattatcca tgtgaaaggg aaacaccttt gtccaagtcc cctatttccc     900
ggaccttcta agccctttg ggtgctggtg gtggttggtg gagtcctggc ttgctatagc     960
ttgctagtaa cagtggcctt tattattttc tgggtgagga gtaagaggag caggctcctg    1020
cacagtgact acatgaacat gactccccgc cgccccgggc ccacccgcaa gcattaccag    1080
ccctatgccc caccacgcga cttcgcagcc tatcgctcca gagtgaagtt cagcaggagc    1140
gcagacgccc ccgcgtacca gcagggccag aaccagctct ataacgagct caatctagga    1200
cgaagagagg agtacgatgt tttggacaag agacgtggcc gggaccctga gatggggga    1260
aagccgagaa ggaagaaccc tcaggaaggc ctgtacaatg aactgcagaa agataagatg    1320
gcggaggcct acagtgagat tgggatgaaa ggcgagcgcc ggaggggcaa ggggcacgat    1380
ggcctttacc agggtctcag tacagccacc aaggacacct acgacgccct tcacatgcag    1440
gccctgcccc ctcgctaa                                                  1458
```

<210> SEQ ID NO 43
<211> LENGTH: 485
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
```

```
                        85                  90                  95
Ala Tyr Met Gln Leu Ser Gly Leu Thr Ser Glu Asp Ser Ala Val Tyr
                100                 105                 110

Phe Cys Ala Arg Lys Thr Ile Ser Ser Val Val Asp Phe Tyr Phe Asp
                115                 120                 125

Tyr Trp Gly Gln Gly Thr Thr Val Thr Val Ser Ser Gly Gly Gly Gly
            130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
                180                 185                 190

Gln Lys Pro Gly Gln Ser Pro Lys Pro Leu Ile Tyr Ser Ala Thr Tyr
            195                 200                 205

Arg Asn Ser Gly Val Pro Asp Arg Phe Thr Gly Ser Gly Ser Gly Thr
210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Ile Glu Val Met Tyr Pro
                260                 265                 270

Pro Pro Tyr Leu Asp Asn Glu Lys Ser Asn Gly Thr Ile Ile His Val
            275                 280                 285

Lys Gly Lys His Leu Cys Pro Ser Pro Leu Phe Pro Gly Pro Ser Lys
290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
            355                 360                 365

Ala Ala Tyr Arg Ser Arg Val Lys Phe Ser Arg Ser Ala Asp Ala Pro
            370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Phe
            420                 425                 430

Asn Glu Leu Gln Lys Asp Lys Met Ala Glu Ala Phe Ser Glu Ile Gly
            435                 440                 445

Met Lys Gly Glu Arg Arg Arg Gly Lys Gly His Asp Gly Leu Phe Gln
450                 455                 460

Gly Leu Ser Thr Ala Thr Lys Asp Thr Phe Asp Ala Leu His Met Gln
465                 470                 475                 480

Ala Leu Pro Pro Arg
            485

<210> SEQ ID NO 44
```

<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
atggctctcc cagtgactgc cctactgctt cccctagcgc ttctcctgca tgcagaggtg      60
aagctgcagc agtctggggc tgagctggtg aggcctgggt cctcagtgaa gatttcctgc     120
aaggcttctg gctatgcatt cagtagctac tggatgaact gggtgaagca gaggcctgga     180
cagggtcttg agtggattgg acagatttat cctggagatg gtgatactaa ctacaatgga     240
aagttcaagg gtcaagccac actgactgca gacaaatcct ccagcacagc ctacatgcag     300
ctcagcggcc taacatctga ggactctgcg gtctatttct gtgcaagaaa gaccattagt     360
tcggtagtag atttctactt tgactactgg ggccaaggga ccacggtcac cgtctcctca     420
ggtggaggtg gatcaggtgg aggtggatct ggtggaggtg gatctgacat tgagctcacc     480
cagtctccaa aattcatgtc cacatcagta ggagacaggg tcagcgtcac ctgcaaggcc     540
agtcagaatg tgggtactaa tgtagcctgg tatcaacaga aaccaggaca atctcctaaa     600
ccactgattt actcggcaac ctaccggaac agtggagtcc ctgatcgctt cacaggcagt     660
ggatctggga cagatttcac tctcaccatc actaacgtgc agtctaaaga cttggcagac     720
tatttctgtc aacaatataa caggtatccg tacacgtccg agggggggac caagctggag     780
atcaaacggg cggccgcaat tgaagttatg tatcctcctc cttacctaga caatgagaag     840
agcaatggaa ccattatcca tgtgaaaggg aaacaccttt gtccaagtcc cctatttccc     900
ggaccttcta agccctttg ggtgctggtg gtggttggtg gagtcctggc ttgctatagc     960
ttgctagtaa cagtggcctt tattattttc tgggtgagga gtaagaggag caggctcctg    1020
cacagtgact acatgaacat gactccccgc cgccccgggc ccacccgcaa gcattaccag    1080
ccctatgccc caccacgcga cttcgcagcc tatcgctcca gagtgaagtt cagcaggagc    1140
gcagacgccc ccgcgtacca gcagggccag aaccagctct ataacgagct caatctagga    1200
cgaagagagg agtacgatgt tttggacaag agacgtggcc gggaccctga tgggggga    1260
aagccgagaa ggaagaaccc tcaggaaggc ctgttcaatg aactgcagaa agataagatg    1320
gcggaggcct tcagtgagat tgggatgaaa ggcgagcgcc ggaggggcaa ggggcacgat    1380
ggcctttttcc aggggctcag tacagccacc aaggacacct cgacgccct tcacatgcag    1440
gccctgcccc ctcgctaa                                                   1458
```

<210> SEQ ID NO 45
<211> LENGTH: 416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
                20                  25                  30

Gly Ser Ser Val Lys Ile Ser Cys Lys Ala Ser Gly Tyr Ala Phe Ser
            35                  40                  45

```
Ser Tyr Trp Met Asn Trp Val Lys Gln Arg Pro Gln Gly Leu Glu
 50                  55                  60
Trp Ile Gly Gln Ile Tyr Pro Gly Asp Gly Asp Thr Asn Tyr Asn Gly
 65                  70                  75                  80
Lys Phe Lys Gly Gln Ala Thr Leu Thr Ala Asp Lys Ser Ser Ser Thr
                 85                  90                  95
Ala Tyr Met Gln Leu Ser Gly Leu Thr Ser Glu Asp Ser Ala Val Tyr
            100                 105                 110
Phe Cys Ala Arg Lys Thr Ile Ser Val Val Asp Phe Tyr Phe Asp
            115                 120                 125
Tyr Trp Gly Gln Gly Thr Thr Val Thr Val Ser Ser Gly Gly Gly
130                 135                 140
Ser Gly Gly Gly Gly Ser Gly Gly Gly Ser Asp Ile Glu Leu Thr
145                 150                 155                 160
Gln Ser Pro Lys Phe Met Ser Thr Ser Val Gly Asp Arg Val Ser Val
                165                 170                 175
Thr Cys Lys Ala Ser Gln Asn Val Gly Thr Asn Val Ala Trp Tyr Gln
            180                 185                 190
Gln Lys Pro Gly Gln Ser Pro Lys Pro Leu Ile Tyr Ser Ala Thr Tyr
            195                 200                 205
Arg Asn Ser Gly Val Pro Asp Arg Phe Thr Gly Ser Gly Ser Gly Thr
210                 215                 220
Asp Phe Thr Leu Thr Ile Thr Asn Val Gln Ser Lys Asp Leu Ala Asp
225                 230                 235                 240
Tyr Phe Cys Gln Gln Tyr Asn Arg Tyr Pro Tyr Thr Ser Gly Gly Gly
            245                 250                 255
Thr Lys Leu Glu Ile Lys Arg Ala Ala Ala Ile Glu Val Met Tyr Pro
            260                 265                 270
Pro Pro Tyr Leu Asp Asn Glu Lys Ser Asn Gly Thr Ile Ile His Val
            275                 280                 285
Lys Gly Lys His Leu Cys Pro Ser Pro Leu Phe Pro Gly Pro Ser Lys
290                 295                 300
Pro Phe Trp Val Leu Val Val Val Gly Gly Val Leu Ala Cys Tyr Ser
305                 310                 315                 320
Leu Leu Val Thr Val Ala Phe Ile Ile Phe Trp Val Arg Ser Lys Arg
            325                 330                 335
Ser Arg Leu Leu His Ser Asp Tyr Met Asn Met Thr Pro Arg Arg Pro
            340                 345                 350
Gly Pro Thr Arg Lys His Tyr Gln Pro Tyr Ala Pro Pro Arg Asp Phe
            355                 360                 365
Ala Ala Tyr Arg Ser Arg Val Lys Phe Ser Arg Ser Ala Asp Ala Pro
370                 375                 380
Ala Tyr Gln Gln Gly His Asp Gly Leu Tyr Gln Gly Leu Ser Thr Ala
385                 390                 395                 400
Thr Lys Asp Thr Tyr Asp Ala Leu His Met Gln Ala Leu Pro Pro Arg
                405                 410                 415

<210> SEQ ID NO 46
<211> LENGTH: 1251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
```

```
atggctctcc cagtgactgc cctactgctt cccctagcgc ttctcctgca tgcagaggtg    60
aagctgcagc agtctggggc tgagctggtg aggcctgggt cctcagtgaa gatttcctgc   120
aaggcttctg gctatgcatt cagtagctac tggatgaact gggtgaagca gaggcctgga   180
cagggtcttg agtggattgg acagatttat cctggagatg gtgatactaa ctacaatgga   240
aagttcaagg gtcaagccac actgactgca gacaaatcct ccagcacagc ctacatgcag   300
ctcagcggcc taacatctga ggactctgcg gtctatttct gtgcaagaaa gaccattagt   360
tcggtagtag atttctactt tgactactgg ggccaaggga ccacggtcac cgtctcctca   420
ggtgaggtg atcaggtgg aggtggatct ggtggaggtg atctgacat tgagctcacc   480
cagtctccaa aattcatgtc cacatcagta ggagacaggg tcagcgtcac ctgcaaggcc   540
agtcagaatg tgggtactaa tgtagcctgg tatcaacaga accaggaca atctcctaaa   600
ccactgattt actcggcaac ctaccggaac agtggagtcc ctgatcgctt cacaggcagt   660
ggatctggga cagatttcac tctcaccatc actaacgtgc agtctaaaga cttggcagac   720
tatttctgtc aacaatataa caggtatccg tacacgtccg agggggggac caagctggag   780
atcaaacggg cggccgcaat tgaagttatg tatcctcctc cttacctaga caatgagaag   840
agcaatggaa ccattatcca tgtgaaaggg aaacaccttt gtccaagtcc cctatttccc   900
ggaccttcta agcccttttg gtgctggtg gtggttggtg gagtcctggc ttgctatagc   960
ttgctagtaa cagtggcctt tattattttc tgggtgagga gtaagaggag caggctcctg  1020
cacagtgact acatgaacat gactcccgc gcccccgggc ccacccgcaa gcattaccag  1080
ccctatgccc caccacgcga cttcgcagcc tatcgctcca gagtgaagtt cagcaggagc  1140
gcagacgccc ccgcgtacca gcagggccac gatggccttt accaggggct cagtacagcc  1200
accaaggaca cctacgacgc ccttcacatg caggccctgc cccctcgcta a          1251
```

<210> SEQ ID NO 47
<211> LENGTH: 416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly

| | | | | | | | | | | | |
|---|---|---|---|---|---|---|---|---|---|---|---|
| | | 130 | | | | 135 | | | | 140 | |

Ser Gly Gly Gly Ser Gly Gly Gly Ser Asp Ile Glu Leu Thr
145                       150                   155                   160

Gln Ser Pro Lys Phe Met Ser Thr Ser Val Gly Asp Arg Val Ser Val
              165                   170                 175

Thr Cys Lys Ala Ser Gln Asn Val Gly Thr Asn Val Ala Trp Tyr Gln
         180                   185                 190

Gln Lys Pro Gly Gln Ser Pro Lys Pro Leu Ile Tyr Ser Ala Thr Tyr
        195                   200                 205

Arg Asn Ser Gly Val Pro Asp Arg Phe Thr Gly Ser Gly Ser Gly Thr
     210                   215                 220

Asp Phe Thr Leu Thr Ile Thr Asn Val Gln Ser Lys Asp Leu Ala Asp
225                     230                   235                   240

Tyr Phe Cys Gln Gln Tyr Asn Arg Tyr Pro Tyr Thr Ser Gly Gly Gly
         245                   250                 255

Thr Lys Leu Glu Ile Lys Arg Ala Ala Ala Ile Glu Val Met Tyr Pro
        260                   265                 270

Pro Pro Tyr Leu Asp Asn Glu Lys Ser Asn Gly Thr Ile Ile His Val
     275                   280                 285

Lys Gly Lys His Leu Cys Pro Ser Pro Leu Phe Pro Gly Pro Ser Lys
     290                   295                 300

Pro Phe Trp Val Leu Val Val Val Gly Gly Val Leu Ala Cys Tyr Ser
305                     310                   315                   320

Leu Leu Val Thr Val Ala Phe Ile Ile Phe Trp Val Arg Ser Lys Arg
         325                   330                 335

Ser Arg Leu Leu His Ser Asp Tyr Met Asn Met Thr Pro Arg Arg Pro
        340                   345                 350

Gly Pro Thr Arg Lys His Tyr Gln Pro Tyr Ala Pro Pro Arg Asp Phe
     355                   360                 365

Ala Ala Tyr Arg Ser Arg Val Lys Phe Ser Arg Ser Ala Asp Ala Pro
     370                   375                 380

Ala Tyr Gln Gln Gly Gln Asn Gln Leu Tyr Asn Glu Leu Asn Leu Gly
385                     390                   395                   400

Arg Arg Glu Glu Tyr Asp Val Leu Asp Lys Arg Arg Gly Arg Asp Pro
         405                   410                 415

<210> SEQ ID NO 48
<211> LENGTH: 1251
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 48

| | |
|---|---|
| atggctctcc cagtgactgc cctactgctt ccctagcgc ttctcctgca tgcagaggtg | 60 |
| aagctgcagc agtctggggc tgagctggtg aggcctgggt cctcagtgaa gatttcctgc | 120 |
| aaggcttctg gctatgcatt cagtagctac tggatgaact gggtgaagca gaggcctgga | 180 |
| cagggtcttg agtggattgg acagatttat cctggagatg gtgatactaa ctacaatgga | 240 |
| aagttcaagg gtcaagccac actgactgca gacaaatcct ccagcacagc ctacatgcag | 300 |
| ctcagcggcc taacatctga ggactctgcg gtctatttct gtgcaagaaa gaccattagt | 360 |
| tcggtagtag atttctactt tgactactgg ggccaaggga ccacggtcac cgtctcctca | 420 |
| ggtggaggtg gatcaggtgg aggtggatct ggtggaggtg gatctgacat tgagctcacc | 480 |

-continued

```
cagtctccaa aattcatgtc cacatcagta ggagacaggg tcagcgtcac ctgcaaggcc      540
agtcagaatg tgggtactaa tgtagcctgg tatcaacaga aaccaggaca atctcctaaa      600
ccactgattt actcggcaac ctaccggaac agtggagtcc ctgatcgctt cacaggcagt      660
ggatctggga cagatttcac tctccaccat actaacgtgc agtctaaaga cttggcagac      720
tatttctgtc aacaatataa caggtatccg tacacgtccg agggggggac caagctggag      780
atcaaacggg cggccgcaat tgaagttatg tatcctcctc cttacctaga caatgagaag      840
agcaatggaa ccattatcca tgtgaaaggg aaacaccttt gtccaagtcc cctatttccc      900
ggaccttcta agccctttg ggtgctggtg gtggttggtg gagtcctggc ttgctatagc       960
ttgctagtaa cagtggcctt tattattttc tgggtgagga gtaagaggag caggctcctg     1020
cacagtgact acatgaacat gactccccgc cgccccgggc ccacccgcaa gcattaccag     1080
ccctatgccc caccacgcga cttcgcagcc tatcgctcca gagtgaagtt cagcaggagc     1140
gcagacgccc ccgcgtacca gcagggccag aaccagctct ataacgagct caatctagga     1200
cgaagagagg agtacgatgt tttggacaag agacgtggcc gggaccctta a              1251
```

<210> SEQ ID NO 49
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220
```

-continued

```
Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
            245                 250                 255

Thr Lys Leu Glu Ile Lys Arg Ala Ala Ala Ile Glu Val Met Tyr Pro
        260                 265                 270

Pro Pro Tyr Leu Asp Asn Glu Lys Ser Asn Gly Thr Ile Ile His Val
    275                 280                 285

Lys Gly Lys His Leu Cys Pro Ser Pro Leu Phe Pro Gly Pro Ser Lys
290                 295                 300

Pro Phe Trp Val Leu Val Val Val Gly Val Leu Ala Cys Tyr Ser
305                 310                 315                 320

Leu Leu Val Thr Val Ala Phe Ile Ile Phe Trp Val Arg Ser Lys Arg
            325                 330                 335

Ser Arg Leu Leu His Ser Asp Tyr Met Asn Met Thr Pro Arg Arg Pro
        340                 345                 350

Gly Pro Thr Arg Lys His Tyr Gln Pro Tyr Ala Pro Pro Arg Asp Phe
    355                 360                 365

Ala Ala Tyr Arg Ser Arg Val Lys Phe Ser Arg Ser Ala Asp Ala Pro
370                 375                 380

Ala Tyr Gln Gln Gly Gln Asn Gln Leu Phe Asn Glu Leu Asn Leu Gly
385                 390                 395                 400

Arg Arg Glu Glu Phe Asp Val Leu Asp Lys Arg Arg Gly Arg Asp Pro
            405                 410                 415

Glu Met Gly Gly Lys Pro Arg Arg Lys Asn Pro Gln Glu Gly Leu Phe
        420                 425                 430

Asn Glu Leu Gln Lys Asp Lys Met Ala Glu Ala Phe Ser Glu Ile Gly
    435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485
```

<210> SEQ ID NO 50
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
atggctctcc cagtgactgc cctactgctt cccctagcgc ttctcctgca tgcagaggtg     60
aagctgcagc agtctggggc tgagctggtg aggcctgggt cctcagtgaa gatttcctgc    120
aaggcttctg gctatgcatt cagtagctac tggatgaact gggtgaagca gaggcctgga    180
cagggtcttg agtggattgg acagatttat cctggagatg gtgatactaa ctacaatgga    240
aagttcaagg gtcaagccac actgactgca gacaaatcct ccagcacagc ctacatgcag    300
ctcagcggcc taacatctga ggactctgcg gtctatttct gtgcaagaaa gaccattagt    360
tcggtagtag atttctactt tgactactgg ggccaaggga ccacggtcac cgtctcctca    420
ggtggaggtg gatcaggtgg aggtggatct ggtggaggtg gatctgacat tgagctcacc    480
```

```
cagtctccaa aattcatgtc cacatcagta ggagacaggg tcagcgtcac ctgcaaggcc    540
agtcagaatg tgggtactaa tgtagcctgg tatcaacaga aaccaggaca atctcctaaa    600
ccactgattt actcggcaac ctaccggaac agtggagtcc ctgatcgctt cacaggcagt    660
ggatctggga cagatttcac tctcaccatc actaacgtgc agtctaaaga cttggcagac    720
tatttctgtc aacaatataa caggtatccg tacacgtccg agggggggac caagctggag    780
atcaaacggg cggccgcaat tgaagttatg tatcctcctc cttacctaga caatgagaag    840
agcaatggaa ccattatcca tgtgaaaggg aaacaccttt gtccaagtcc cctatttccc    900
ggaccttcta agccctttg gtgctggtg gtggttggtg gagtcctggc ttgctatagc    960
ttgctagtaa cagtggcctt tattattttc tgggtgagga gtaagaggag caggctcctg   1020
cacagtgact acatgaacat gactccccgc cgccccgggc ccacccgcaa gcattaccag   1080
ccctatgccc caccacgcga cttcgcagcc tatcgctcca gagtgaagtt cagcaggagc   1140
gcagacgccc ccgcgtacca gcagggccag aaccagctct ttaacgagct caatctagga   1200
cgaagagagg agttcgatgt tttggacaag agacgtggcc gggaccctga tgggggga   1260 aagccgagaa ggaagaaccc tcaggaaggc ctgttcaatg aactgcagaa agataagatg   1320
gcggaggcct tcagtgagat tgggatgaaa ggcgagcgcc ggaggggcaa ggggcacgat   1380
ggcctttacc agggtctcag tacagccacc aaggacacct acgacgccct tcacatgcag   1440
gccctgcccc ctcgctaa                                                 1458
```

<210> SEQ ID NO 51
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
                20                  25                  30

Gly Ser Ser Val Lys Ile Ser Cys Lys Ala Ser Gly Tyr Ala Phe Ser
            35                  40                  45

Ser Tyr Trp Met Asn Trp Val Lys Gln Arg Pro Gly Gln Gly Leu Glu
        50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
                100                 105                 110

Phe Cys Ala Arg Lys Thr Ile Ser Ser Val Val Asp Phe Tyr Phe Asp
            115                 120                 125

Tyr Trp Gly Gln Gly Thr Thr Val Thr Val Ser Ser Gly Gly Gly Gly
        130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
```

|     |     |     |     |     |     |     | 180 |     |     |     |     | 185 |     |     |     |     | 190 |     |     |
| --- | --- | --- | --- | --- | --- | --- | --- | --- | --- | --- | --- | --- | --- | --- | --- | --- | --- | --- | --- |

Gln Lys Pro Gly Gln Ser Pro Lys Pro Leu Ile Tyr Ser Ala Thr Tyr
                195                      200                      205

Arg Asn Ser Gly Val Pro Asp Arg Phe Thr Gly Ser Gly Ser Gly Thr
210                      215                      220

Asp Phe Thr Leu Thr Ile Thr Asn Val Gln Ser Lys Asp Leu Ala Asp
225                      230                      235                      240

Tyr Phe Cys Gln Gln Tyr Asn Arg Tyr Pro Tyr Thr Ser Gly Gly Gly
                245                      250                      255

Thr Lys Leu Glu Ile Lys Arg Ala Ala Ala Ile Glu Val Met Tyr Pro
                260                      265                      270

Pro Pro Tyr Leu Asp Asn Glu Lys Ser Asn Gly Thr Ile Ile His Val
                275                      280                      285

Lys Gly Lys His Leu Cys Pro Ser Pro Leu Phe Pro Gly Pro Ser Lys
                290                      295                      300

Pro Phe Trp Val Leu Val Val Val Gly Gly Val Leu Ala Cys Tyr Ser
305                      310                      315                      320

Leu Leu Val Thr Val Ala Phe Ile Ile Phe Trp Val Arg Ser Lys Arg
                325                      330                      335

Ser Arg Leu Leu His Ser Asp Tyr Met Asn Met Thr Pro Arg Arg Pro
                340                      345                      350

Gly Pro Thr Arg Lys His Tyr Gln Pro Tyr Ala Pro Pro Arg Asp Phe
                355                      360                      365

Ala Ala Tyr Arg Ser Arg Val Lys Phe Ser Arg Ser Ala Asp Ala Pro
370                      375                      380

Ala Tyr Gln Gln Gly Gln Asn Gln Leu Phe Asn Glu Leu Asn Leu Gly
385                      390                      395                      400

Arg Arg Glu Glu Phe Asp Val Leu Asp Lys Arg Arg Gly Arg Asp Pro
                405                      410                      415

Glu Met Gly Gly Lys Pro Arg Arg Lys Asn Pro Gln Glu Gly Leu Tyr
                420                      425                      430

Asn Glu Leu Gln Lys Asp Lys Met Ala Glu Ala Tyr Ser Glu Ile Gly
                435                      440                      445

Met Lys Gly Glu Arg Arg Arg Gly Lys Gly His Asp Gly Leu Tyr Gln
                450                      455                      460

Gly Leu Ser Thr Ala Thr Lys Asp Thr Tyr Asp Ala Leu His Met Gln
465                      470                      475                      480

Ala Leu Pro Pro Arg
                485

<210> SEQ ID NO 52
<211> LENGTH: 1458
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 52

```
atggctctcc cagtgactgc cctactgctt ccctagcgc ttctcctgca tgcagaggtg      60
aagctgcagc agtctggggc tgagctggtg aggcctgggt cctcagtgaa gatttcctgc     120
aaggcttctg gctatgcatt cagtagctac tggatgaact gggtgaagca gaggcctgga     180
cagggtcttg agtggattgg acagatttat cctggagatg gtgatactaa ctacaatgga     240
aagttcaagg gtcaagccac actgactgca gacaaatcct ccagcacagc ctacatgcag     300
```

```
ctcagcggcc taacatctga ggactctgcg gtctatttct gtgcaagaaa gaccattagt    360
tcggtagtag atttctactt tgactactgg ggccaaggga ccacggtcac cgtctcctca    420
ggtggaggtg gatcaggtgg aggtggatct ggtggaggtg gatctgacat tgagctcacc    480
cagtctccaa aattcatgtc cacatcagta ggagacaggg tcagcgtcac ctgcaaggcc    540
agtcagaatg tgggtactaa tgtagcctgg tatcaacaga aaccaggaca atctcctaaa    600
ccactgattt actcggcaac ctaccggaac agtggagtcc ctgatcgctt cacaggcagt    660
ggatctggga cagatttcac tctcaccatc actaacgtgc agtctaaaga cttggcagac    720
tatttctgtc aacaatataa caggtatccg tacacgtccg gagggggac  caagctggag    780 atcaaacggg cggccgcaat tgaagttatg tatcctcctc cttacctaga caatgagaag    840
agcaatggaa ccattatcca tgtgaaaggg aaacaccttt gtccaagtcc cctatttccc    900
ggaccttcta agccctttg  ggtgctggtg gtggttggtg gagtcctggc ttgctatagc    960
ttgctagtaa cagtggcctt tattattttc tgggtgagga gtaagaggag caggctcctg   1020
cacagtgact acatgaacat gactccccgc cgccccgggc ccacccgcaa gcattaccag   1080
ccctatgccc caccacgcga cttcgcagcc tatcgctcca gagtgaagtt cagcaggagc   1140
gcagacgccc ccgcgtacca gcagggccag aaccagctct ttaacgagct caatctagga   1200
cgaagagagg agttcgatgt tttggacaag agacgtggcc gggaccctga tggggggga   1260 aagccgagaa ggaagaaccc tcaggaaggc ctgtacaatg aactgcagaa agataagatg   1320
gcggaggcct acagtgagat tgggatgaaa ggcgagcgcc ggaggggcaa ggggcacgat   1380
ggcctttacc agggtctcag tacagccacc aaggacacct acgacgccct tcacatgcag   1440
gccctgcccc ctcgctaa                                                 1458
```

<210> SEQ ID NO 53
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
    130                 135                 140
```

Ser Gly Gly Gly Gly Ser Gly Gly Gly Ser Asp Ile Glu Leu Thr
145                 150                 155                 160

Gln Ser Pro Lys Phe Met Ser Thr Ser Val Gly Asp Arg Val Ser Val
            165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
            195                 200                 205

Arg Asn Ser Gly Val Pro Asp Arg Phe Thr Gly Ser Gly Ser Gly Thr
            210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
            245                 250                 255

Thr Lys Leu Glu Ile Lys Arg Ala Ala Ala Ile Glu Val Met Tyr Pro
            260                 265                 270

Pro Pro Tyr Leu Asp Asn Glu Lys Ser Asn Gly Thr Ile Ile His Val
            275                 280                 285

Lys Gly Lys His Leu Cys Pro Ser Pro Leu Phe Pro Gly Pro Ser Lys
290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
            325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
            355                 360                 365

Ala Ala Tyr Arg Ser Arg Val Lys Phe Ser Arg Ser Ala Asp Ala Pro
            370                 375                 380

Ala Tyr Gln Gln Gly Gln Asn Gln Leu Phe Asn Glu Leu Asn Leu Gly
385                 390                 395                 400

Arg Arg Glu Glu Phe Asp Val Leu Asp Lys Arg Arg Gly Arg Asp Pro
            405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Phe Gln
            450                 455                 460

Gly Leu Ser Thr Ala Thr Lys Asp Thr Phe Asp Ala Leu His Met Gln
465                 470                 475                 480

Ala Leu Pro Pro Arg
            485

<210> SEQ ID NO 54
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atggctctcc cagtgactgc cctactgctt cccctagcgc ttctcctgca tgcagaggtg    60

```
aagctgcagc agtctggggc tgagctggtg aggcctgggt cctcagtgaa gatttcctgc    120
aaggcttctg gctatgcatt cagtagctac tggatgaact gggtgaagca gaggcctgga    180
cagggtcttg agtggattgg acagatttat cctggagatg gtgatactaa ctacaatgga    240
aagttcaagg gtcaagccac actgactgca gacaaatcct ccagcacagc ctacatgcag    300
ctcagcggcc taacatctga ggactctgcg gtctatttct gtgcaagaaa gaccattagt    360
tcggtagtag atttctactt tgactactgg ggccaaggga ccacggtcac cgtctcctca    420
ggtggaggtg gatcaggtgg aggtggatct ggtggaggtg gatctgacat tgagctcacc    480
cagtctccaa aattcatgtc cacatcagta ggagacaggg tcagcgtcac ctgcaaggcc    540
agtcagaatg tgggtactaa tgtagcctgg tatcaacaga aaccaggaca atctcctaaa    600
ccactgattt actcggcaac ctaccggaac agtggagtcc ctgatcgctt cacaggcagt    660
ggatctggga cagatttcac tctcaccatc actaacgtgc agtctaaaga cttggcagac    720
tatttctgtc aacaatataa caggtatccg tacacgtccg gaggggggac caagctggag    780
atcaaacggg cggccgcaat tgaagttatg tatcctcctc cttacctaga caatgagaag    840
agcaatggaa ccattatcca tgtgaaaggg aaacaccttt gtccaagtcc cctatttccc    900
ggaccttcta agccctttg ggtgctggtg gtggttggtg gagtcctggc ttgctatagc    960
ttgctagtaa cagtggcctt tattattttc tgggtgagga gtaagaggag caggctcctg   1020
cacagtgact acatgaacat gactccccgc cgccccgggc ccacccgcaa gcattaccag   1080
ccctatgccc caccacgcga cttcgcagcc tatcgctcca gagtgaagtt cagcaggagc   1140
gcagacgccc ccgcgtacca gcagggccag aaccagctct ttaacgagct caatctagga   1200
cgaagagagg agttcgatgt tttggacaag agacgtggcc gggaccctga tggggggga   1260 aagccgagaa ggaagaaccc tcaggaaggc ctgtacaatg aactgcagaa agataagatg   1320
gcggaggcct acagtgagat tgggatgaaa ggcgagcgcc ggaggggcaa ggggcacgat   1380
ggccttttcc aggggctcag tacagccacc aaggacacct cgacgccct tcacatgcag   1440 gccctgcccc ctcgctaa                                                 1458
```

<210> SEQ ID NO 55
<211> LENGTH: 485
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 55

```
Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110
```

Phe Cys Ala Arg Lys Thr Ile Ser Ser Val Val Asp Phe Tyr Phe Asp
            115                 120                 125

Tyr Trp Gly Gln Gly Thr Thr Val Thr Val Ser Ser Gly Gly Gly Gly
        130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Ile Glu Val Met Tyr Pro
            260                 265                 270

Pro Pro Tyr Leu Asp Asn Glu Lys Ser Asn Gly Thr Ile Ile His Val
        275                 280                 285

Lys Gly Lys His Leu Cys Pro Ser Pro Leu Phe Pro Gly Pro Ser Lys
    290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Phe Gln
    450                 455                 460

Gly Leu Ser Thr Ala Thr Lys Asp Thr Phe Asp Ala Leu His Met Gln
465                 470                 475                 480

Ala Leu Pro Pro Arg
                485

<210> SEQ ID NO 56
<211> LENGTH: 1458
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 56

```
atggctctcc cagtgactgc cctactgctt cccctagcgc ttctcctgca tgcagaggtg      60
aagctgcagc agtctggggc tgagctggtg aggcctgggt cctcagtgaa gatttcctgc     120
aaggcttctg gctatgcatt cagtagctac tggatgaact gggtgaagca gaggcctgga     180
cagggtcttg agtggattgg acagatttat cctggagatg gtgatactaa ctacaatgga     240
aagttcaagg gtcaagccac actgactgca gacaaatcct ccagcacagc ctacatgcag     300
ctcagcggcc taacatctga ggactctgcg gtctatttct gtgcaagaaa gaccattagt     360
tcggtagtag atttctactt tgactactgg ggccaaggga ccacggtcac cgtctcctca     420
ggtgaaggtg atcaggtgg aggtggatct ggtggaggtg gatctgacat tgagctcacc     480
cagtctccaa aattcatgtc cacatcagta ggagacaggg tcagcgtcac ctgcaaggcc     540
agtcagaatg tgggtactaa tgtagcctgg tatcaacaga accaggacaa atctcctaaa     600
ccactgattt actcggcaac ctaccggaac agtggagtcc ctgatcgctt cacaggcagt     660
ggatctggga cagatttcac tctcaccatc actaacgtgc agtctaaaga cttggcagac     720
tatttctgtc aacaatataa caggtatccg tacacgtccg gagggggac caagctggag     780
atcaaacggg cggccgcaat tgaagttatg tatcctcctc cttacctaga caatgagaag     840
agcaatggaa ccattatcca tgtgaaaggg aaacaccttt gtccaagtcc cctatttccc     900
ggaccttcta agccctttg ggtgctggtg gtggttggtg gagtcctggc ttgctatagc     960
ttgctagtaa cagtggcctt tattattttc tgggtgagga gtaagaggag caggctcctg    1020
cacagtgact acatgaacat gactccccgc cgccccgggc ccacccgcaa gcattaccag    1080
ccctatgccc caccacgcga cttcgcagcc tatcgctcca gagtgaagtt cagcaggagc    1140
gcagacgccc ccgcgtacca gcagggccag aaccagctct ataacgagct caatctagga    1200
cgaagagagg agtacgatgt tttggacaag agacgtggcc gggaccctga tggggga      1260
aagccgagaa ggaagaaccc tcaggaaggc ctgtacaatg aactgcagaa agataagatg    1320
gcggaggcct acagtgagat tgggatgaaa ggcgagcgcc ggagggcaa ggggcacgat    1380
ggcctttcc aggggctcag tacagccacc aaggacacct tcgacgccct tcacatgcag    1440
gccctgcccc ctcgctaa                                                   1458
```

<210> SEQ ID NO 57
<211> LENGTH: 455
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 57

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly

```
                65                  70                  75                  80
Lys Phe Lys Gly Gln Ala Thr Leu Thr Ala Asp Lys Ser Ser Thr
                    85                  90                  95

Ala Tyr Met Gln Leu Ser Gly Leu Thr Ser Glu Asp Ser Ala Val Tyr
                100                 105                 110

Phe Cys Ala Arg Lys Thr Ile Ser Ser Val Val Asp Phe Tyr Phe Asp
            115                 120                 125

Tyr Trp Gly Gln Gly Thr Thr Val Thr Val Ser Ser Gly Gly Gly Gly
130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Ile Glu Val Met Tyr Pro
            260                 265                 270

Pro Pro Tyr Leu Asp Asn Glu Lys Ser Asn Gly Thr Ile Ile His Val
        275                 280                 285

Lys Gly Lys His Leu Cys Pro Ser Pro Leu Phe Pro Gly Pro Ser Lys
    290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg
    450                 455

<210> SEQ ID NO 58
<211> LENGTH: 1368
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 58

```
atggctctcc cagtgactgc cctactgctt ccctagcgc ttctcctgca tgcagaggtg      60
aagctgcagc agtctggggc tgagctggtg aggcctgggt cctcagtgaa gatttcctgc    120
aaggcttctg gctatgcatt cagtagctac tggatgaact gggtgaagca gaggcctgga    180
cagggtcttg agtggattgg acagatttat cctggagatg gtgatactaa ctacaatgga    240
aagttcaagg gtcaagccac actgactgca gacaaatcct ccagcacagc ctacatgcag    300
ctcagcggcc taacatctga ggactctgcg gtctatttct gtgcaagaaa gaccattagt    360
tcggtagtag atttctactt tgactactgg ggccaaggga ccacggtcac cgtctcctca    420
ggtggaggtg gatcaggtgg aggtggatct ggtggaggtg gatctgacat tgagctcacc    480
cagtctccaa aattcatgtc cacatcagta ggagacaggg tcagcgtcac ctgcaaggcc    540
agtcagaatg tgggtactaa tgtagcctgg tatcaacaga aaccaggaca atctcctaaa    600
ccactgattt actcggcaac ctaccggaac agtggagtcc ctgatcgctt cacaggcagt    660
ggatctggga cagatttcac tctcaccatc actaacgtgc agtctaaaga cttggcagac    720
tatttctgtc aacaatataa caggtatccg tacacgtccg agggggggac caagctggag    780
atcaaacggg cggccgcaat tgaagttatg tatcctcctc cttacctaga caatgagaag    840
agcaatggaa ccattatcca tgtgaaaggg aaacaccttt gtccaagtcc cctatttccc    900
ggaccttcta agccctttg ggtgctggtg gtggttggtg gagtcctggc ttgctatagc    960
ttgctagtaa cagtggcctt tattattttc tgggtgagga gtaagaggag caggctcctg   1020
cacagtgact acatgaacat gactccccgc cgccccgggc ccacccgcaa gcattaccag   1080
ccctatgccc caccacgcga cttcgcagcc tatcgctcca gagtgaagtt cagcaggagc   1140
gcagacgccc ccgcgtacca gcagggccag aaccagctct ataacgagct caatctagga   1200
cgaagagagg agtacgatgt tttggacaag agacgtggcc gggaccctga tggggga     1260
aagccgagaa ggaagaaccc tcaggaaggc ctgtacaatg aactgcagaa agataagatg   1320
gcggaggcct acagtgagat tgggatgaaa ggcgagcgcc ggaggtaa               1368
```

<210> SEQ ID NO 59
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr

```
            85                  90                  95
Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
            115                 120                 125

Tyr Trp Gly Gln Gly Thr Thr Val Thr Val Ser Ser Gly Gly Gly Gly
            130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                    165                 170                 175

Thr Cys Lys Ala Ser Gln Asn Val Gly Thr Asn Val Ala Trp Tyr Gln
                    180                 185                 190

Gln Lys Pro Gly Gln Ser Pro Lys Pro Leu Ile Tyr Ser Ala Thr Tyr
                    195                 200                 205

Arg Asn Ser Gly Val Pro Asp Arg Phe Thr Gly Ser Gly Ser Gly Thr
            210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                    245                 250                 255

Thr Lys Leu Glu Ile Lys Arg Asn Gln Leu Glu Arg Thr Val Asn Ser
            260                 265                 270

Leu Asn Val Ser Ala Ile Ser Ile Pro Glu His Asp Glu Ala Asp Glu
            275                 280                 285

Ile Ser Asp Glu Asn Arg Glu Lys Val Asn Asp Gln Ala Lys Leu Ile
            290                 295                 300

Val Gly Ile Val Val Gly Leu Leu Leu Ala Ala Leu Val Ala Gly Val
305                 310                 315                 320

Val Tyr Trp Leu Tyr Met Lys Lys Arg Ser Lys Arg Ser Arg Leu Leu
                    325                 330                 335

His Ser Asp Tyr Met Asn Met Thr Pro Arg Arg Pro Gly Pro Thr Arg
            340                 345                 350

Lys His Tyr Gln Pro Tyr Ala Pro Pro Arg Asp Phe Ala Ala Tyr Arg
            355                 360                 365

Lys Arg Val Lys Phe Ser Arg Ser Ala Asp Ala Pro Ala Tyr Gln Gln
            370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
            405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
            450                 455                 460

Ala Thr Lys Asp Thr Tyr Asp Ala Leu His Met Gln Ala Leu Pro Pro
465                 470                 475                 480

Arg

<210> SEQ ID NO 60
<211> LENGTH: 1446
```

<210> SEQ ID NO 60
<211> LENGTH: 1446
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

```
atggctctcc cagtgactgc cctactgctt ccctagcgc ttctcctgca tgcagaggtg      60
aagctgcagc agtctggggc tgagctggtg aggcctgggt cctcagtgaa gatttcctgc    120
aaggcttctg gctatgcatt cagtagctac tggatgaact gggtgaagca gaggcctgga    180
cagggtcttg agtggattgg acagatttat cctggagatg gtgatactaa ctacaatgga    240
aagttcaagg gtcaagccac actgactgca gacaaatcct ccagcacagc ctacatgcag    300
ctcagcggcc taacatctga ggactctgcg gtctatttct gtgcaagaaa gaccattagt    360
tcggtagtag atttctactt tgactactgg ggccaaggga ccacggtcac cgtctcctca    420
ggtggaggtg gatcaggtgg aggtggatct ggtggaggtg gatctgacat tgagctcacc    480
cagtctccaa aattcatgtc cacatcagta ggagacaggg tcagcgtcac ctgcaaggcc    540
agtcagaatg tgggtactaa tgtagcctgg tatcaacaga accaggaca atctcctaaa    600
ccactgattt actcggcaac ctaccggaac agtggagtcc ctgatcgctt cacaggcagt    660
ggatctggga cagatttcac tctcaccatc actaacgtgc agtctaaaga cttggcagac    720
tatttctgtc aacaatataa caggtatccg tacacgtccg gaggggggac caagctggag    780
atcaaacgga ccaactggga gaacagtaaa actccttga atgtctctgc tataagtatt    840
ccagaacacg atgaggcaga cgagataagt gatgaaaaca gagaaaaggt gaatgaccag    900
gcaaaactaa ttgtgggaat cgttgttggt ctcctccttg ctgcccttgt tgctggtgtc    960
gtctactggc tgtacatgaa gagaggagt aagaggagca ggctcctgca cagtgactac   1020
atgaacatga ctccccgccg ccccgggccc accgcaagc attaccagcc ctatgcccca   1080
ccacgcgact cgcagcccta tcgcaaaaga gtgaagttca gcaggagcgc agacgccccc   1140
gcgtaccagc agggccagaa ccagctctat aacgagctca atctaggacg aagagaggag   1200
tacgatgttt tggacaagag acgtggccgg gaccctgaga tggggggaaa gccgagaagg   1260
aagaaccctc aggaaggcct gtacaatgaa ctgcagaaag ataagatggc ggaggcctac   1320
agtgagattg gcatgaaagg cgagcgccgg aggggcaagg ggcacgatgg cctttaccag   1380
ggtctcagta cagccaccaa ggacacctac gacgcccttc acatgcaggc cctgccccct   1440
cgctaa                                                              1446
```

<210> SEQ ID NO 61
<211> LENGTH: 481
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
```

```
            50                  55                  60
Trp Ile Gly Gln Ile Tyr Pro Gly Asp Gly Asp Thr Asn Tyr Asn Gly
 65                  70                  75                  80

Lys Phe Lys Gly Gln Ala Thr Leu Thr Ala Asp Lys Ser Ser Ser Thr
                 85                  90                  95

Ala Tyr Met Gln Leu Ser Gly Leu Thr Ser Glu Asp Ser Ala Val Tyr
                100                 105                 110

Phe Cys Ala Arg Lys Thr Ile Ser Ser Val Val Asp Phe Tyr Phe Asp
                115                 120                 125

Tyr Trp Gly Gln Gly Thr Thr Val Thr Val Ser Ser Gly Gly Gly Gly
            130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
                180                 185                 190

Gln Lys Pro Gly Gln Ser Pro Lys Pro Leu Ile Tyr Ser Ala Thr Tyr
            195                 200                 205

Arg Asn Ser Gly Val Pro Asp Arg Phe Thr Gly Ser Gly Ser Gly Thr
            210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Asn Gln Leu Glu Arg Thr Val Asn Ser
            260                 265                 270

Leu Asn Val Ser Ala Ile Ser Ile Pro Glu His Asp Glu Ala Asp Glu
            275                 280                 285

Ile Ser Asp Glu Asn Arg Glu Lys Val Asn Asp Gln Ala Lys Leu Ile
            290                 295                 300

Val Gly Ile Val Val Gly Leu Leu Ala Ala Leu Val Ala Gly Val
305                 310                 315                 320

Val Tyr Trp Leu Tyr Met Lys Lys Arg Ser Lys Arg Ser Arg Leu Leu
                325                 330                 335

His Ser Asp Tyr Met Asn Met Thr Pro Arg Arg Pro Gly Pro Thr Arg
            340                 345                 350

Lys His Tyr Gln Pro Tyr Ala Pro Pro Arg Asp Phe Ala Ala Tyr Arg
            355                 360                 365

Lys Arg Val Lys Phe Ser Arg Ser Ala Asp Ala Pro Ala Tyr Gln Gln
            370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
                405                 410                 415

Lys Pro Arg Arg Lys Asn Pro Gln Glu Gly Leu Phe Asn Glu Leu Gln
            420                 425                 430

Lys Asp Lys Met Ala Glu Ala Phe Ser Glu Ile Gly Met Lys Gly Glu
            435                 440                 445

Arg Arg Arg Gly Lys Gly His Asp Gly Leu Phe Gln Gly Leu Ser Thr
            450                 455                 460

Ala Thr Lys Asp Thr Phe Asp Ala Leu His Met Gln Ala Leu Pro Pro
465                 470                 475                 480
```

Arg

<210> SEQ ID NO 62
<211> LENGTH: 1446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

| atggctctcc | cagtgactgc | cctactgctt | ccctagcgc | ttctcctgca | tgcagaggtg | 60 |
| aagctgcagc | agtctggggc | tgagctggtg | aggcctgggt | cctcagtgaa | gatttcctgc | 120 |
| aaggcttctg | gctatgcatt | cagtagctac | tggatgaact | gggtgaagca | gaggcctgga | 180 |
| cagggtcttg | agtggattgg | acagatttat | cctggagatg | gtgatactaa | ctacaatgga | 240 |
| aagttcaagg | gtcaagccac | actgactgca | gacaaatcct | ccagcacagc | ctacatgcag | 300 |
| ctcagcggcc | taacatctga | ggactctgcg | gtctatttct | gtgcaagaaa | gaccattagt | 360 |
| tcggtagtag | atttctactt | tgactactgg | ggccaaggga | ccacggtcac | cgtctcctca | 420 |
| ggtggaggtg | gatcaggtgg | aggtggatct | ggtggaggtg | gatctgacat | tgagctcacc | 480 |
| cagtctccaa | aattcatgtc | cacatcagta | ggagacaggg | tcagcgtcac | ctgcaaggcc | 540 |
| agtcagaatg | tgggtactaa | tgtagcctgg | tatcaacaga | aaccaggaca | atctcctaaa | 600 |
| ccactgattt | actcggcaac | ctaccggaac | agtggagtcc | ctgatcgctt | cacaggcagt | 660 |
| ggatctggga | cagatttcac | tctcaccatc | actaacgtgc | agtctaaaga | cttggcagac | 720 |
| tatttctgtc | aacaatataa | caggtatccg | tacacgtccg | agggggggac | caagctggag | 780 |
| atcaaacgga | accaactgga | gagaacagta | aactccttga | atgtctctgc | tataagtatt | 840 |
| ccagaacacg | atgaggcaga | cgagataagt | gatgaaaaca | gagaaaaggt | gaatgaccag | 900 |
| gcaaaactaa | ttgtgggaat | cgttgttggt | ctcctccttg | ctgcccttgt | tgctggtgtc | 960 |
| gtctactggc | tgtacatgaa | gaagaggagt | aagaggagca | ggctcctgca | cagtgactac | 1020 |
| atgaacatga | ctccccgccg | ccccgggccc | acccgcaagc | attaccagcc | ctatgcccca | 1080 |
| ccacgcgact | tcgcagccta | tcgcaaaaga | gtgaagttca | gcaggagcgc | agacgccccc | 1140 |
| gcgtaccagc | agggccagaa | ccagctctat | aacgagctca | atctaggacg | aagagaggag | 1200 |
| tacgatgttt | tggacaagag | acgtggccgg | gaccctgaga | tggggggaaa | gccgagaagg | 1260 |
| aagaaccctc | aggaaggcct | gttcaatgaa | ctgcagaaag | ataagatggc | ggaggccttc | 1320 |
| agtgagattg | ggatgaaagg | cgagcgccgg | aggggcaagg | ggcacgatgg | cctttttccag | 1380 |
| ggtctcagta | cagccaccaa | ggacaccttc | gacgcccttc | acatgcaggc | cctgccccct | 1440 |
| cgctaa | | | | | | 1446 |

<210> SEQ ID NO 63
<211> LENGTH: 412
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro

```
              20                  25                  30
Gly Ser Ser Val Lys Ile Ser Cys Lys Ala Ser Gly Tyr Ala Phe Ser
             35                  40                  45

Ser Tyr Trp Met Asn Trp Val Lys Gln Arg Pro Gly Gln Gly Leu Glu
 50                  55                  60

Trp Ile Gly Gln Ile Tyr Pro Gly Asp Gly Thr Asn Tyr Asn Gly
 65                  70                  75                  80

Lys Phe Lys Gly Gln Ala Thr Leu Thr Ala Asp Lys Ser Ser Ser Thr
                 85                  90                  95

Ala Tyr Met Gln Leu Ser Gly Leu Thr Ser Glu Asp Ser Ala Val Tyr
                100                 105                 110

Phe Cys Ala Arg Lys Thr Ile Ser Ser Val Val Asp Phe Tyr Phe Asp
                115                 120                 125

Tyr Trp Gly Gln Gly Thr Val Thr Val Ser Ser Gly Gly Gly Gly
                130                 135                 140

Ser Gly Gly Gly Ser Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
                180                 185                 190

Gln Lys Pro Gly Gln Ser Pro Lys Pro Leu Ile Tyr Ser Ala Thr Tyr
                195                 200                 205

Arg Asn Ser Gly Val Pro Asp Arg Phe Thr Gly Ser Gly Ser Gly Thr
                210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Gly Gly Gly
                245                 250                 255

Thr Lys Leu Glu Ile Lys Arg Asn Gln Leu Glu Arg Thr Val Asn Ser
                260                 265                 270

Leu Asn Val Ser Ala Ile Ser Ile Pro Glu His Asp Glu Ala Asp Glu
                275                 280                 285

Ile Ser Asp Glu Asn Arg Glu Lys Val Asn Asp Gln Ala Lys Leu Ile
                290                 295                 300

Val Gly Ile Val Val Gly Leu Leu Leu Ala Ala Leu Val Ala Gly Val
305                 310                 315                 320

Val Tyr Trp Leu Tyr Met Lys Lys Arg Ser Lys Arg Ser Arg Leu Leu
                325                 330                 335

His Ser Asp Tyr Met Asn Met Thr Pro Arg Arg Pro Gly Pro Thr Arg
                340                 345                 350

Lys His Tyr Gln Pro Tyr Ala Pro Pro Arg Asp Phe Ala Ala Tyr Arg
                355                 360                 365

Lys Arg Val Lys Phe Ser Arg Ser Ala Asp Ala Pro Ala Tyr Gln Gln
                370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro
                405                 410

<210> SEQ ID NO 64
<211> LENGTH: 1239
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 64

```
atggctctcc cagtgactgc cctactgctt cccctagcgc ttctcctgca tgcagaggtg      60
aagctgcagc agtctggggc tgagctggtg aggcctgggt cctcagtgaa gatttcctgc     120
aaggcttctg gctatgcatt cagtagctac tggatgaact gggtgaagca gaggcctgga     180
cagggtcttg agtggattgg acagatttat cctggagatg gtgatactaa ctacaatgga     240
aagttcaagg gtcaagccac actgactgca gacaaatcct ccagcacagc ctacatgcag     300
ctcagcggcc taacatctga ggactctgcg gtctatttct gtgcaagaaa gaccattagt     360
tcggtagtag atttctactt tgactactgg ggccaaggga ccacggtcac cgtctcctca     420
ggtggaggtg gatcaggtgg aggtggatct ggtggaggtg gatctgacat tgagctcacc     480
cagtctccaa aattcatgtc cacatcagta ggagacaggg tcagcgtcac ctgcaaggcc     540
agtcagaatg tgggtactaa tgtagcctgg tatcaacaga accaggacaa atctcctaaa     600
ccactgattt actcggcaac ctaccggaac agtggagtcc ctgatcgctt cacaggcagt     660
ggatctggga cagatttcac tctcaccatc actaacgtgc agtctaaaga cttggcagac     720
tatttctgtc aacaatataa caggtatccg tacacgtccg agggggggac caagctggag     780
atcaaacgga accaactgga gagaacagta aactccttga atgtctctgc tataagtatt     840
ccagaacacg atgaggcaga cgagataagt gatgaaaaca gagaaaaggt gaatgaccag     900
gcaaaactaa ttgtgggaat cgttgttggt ctcctccttg ctgcccttgt tgctggtgtc     960
gtctactggc tgtacatgaa gagaggagt aagaggagca ggctcctgca cagtgactac    1020
atgaacatga ctccccgccg ccccgggccc acccgcaagc attaccagcc ctatgcccca    1080
ccacgcgact cgcagcccta tcgcaaaaga gtgaagttca gcaggagcgc agacgccccc    1140
gcgtaccagc agggccagaa ccagctctat aacgagctca atctaggacg aagagaggag    1200
tacgatgttt tggacaagag acgtggccgg gacccttaa                          1239
```

<210> SEQ ID NO 65
<211> LENGTH: 199
<212> TYPE: PRT
<213> ORGANISM: Homo sapiens

<400> SEQUENCE: 65

```
Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Phe Lys Val Thr Leu Thr Gly Gly Tyr Leu
        115                 120                 125
```

```
His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Gly Gly Gly Ser Gly Gly Gly Gly Ser Gly Gly Gly Gly Ser
1               5                   10                  15

<210> SEQ ID NO 67
<211> LENGTH: 20
<212> TYPE: PRT
<213> ORGANISM: Homo sapiens

<400> SEQUENCE: 67

Met Tyr Arg Met Gln Leu Leu Ser Cys Ile Ala Leu Ser Leu Ala Leu
1               5                   10                  15

Val Thr Asn Ser
            20

<210> SEQ ID NO 68
<211> LENGTH: 20
<212> TYPE: PRT
<213> ORGANISM: Mus musculus

<400> SEQUENCE: 68

Met Tyr Ser Met Gln Leu Ala Ser Cys Val Thr Leu Thr Leu Val Leu
1               5                   10                  15

Leu Val Asn Ser
            20

<210> SEQ ID NO 69
<211> LENGTH: 20
<212> TYPE: PRT
<213> ORGANISM: Homo sapiens

<400> SEQUENCE: 69

Met Glu Thr Pro Ala Gln Leu Leu Phe Leu Leu Leu Leu Trp Leu Pro
1               5                   10                  15

Asp Thr Thr Gly
            20

<210> SEQ ID NO 70
<211> LENGTH: 20
<212> TYPE: PRT
<213> ORGANISM: Mus musculus

<400> SEQUENCE: 70
```

```
Met Glu Thr Asp Thr Leu Leu Leu Trp Val Leu Leu Leu Trp Val Pro
1               5                   10                  15

Gly Ser Thr Gly
            20
```

<210> SEQ ID NO 71
<211> LENGTH: 21
<212> TYPE: PRT
<213> ORGANISM: Homo sapiens

<400> SEQUENCE: 71

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 72
<211> LENGTH: 18
<212> TYPE: PRT
<213> ORGANISM: Homo sapiens

<400> SEQUENCE: 72

```
Met Ala Leu Pro Val Thr Ala Leu Leu Leu Pro Leu Ala Leu Leu Leu
1               5                   10                  15

His Ala
```

<210> SEQ ID NO 73
<211> LENGTH: 16
<212> TYPE: PRT
<213> ORGANISM: Homo sapiens

<400> SEQUENCE: 73

```
Met Lys Trp Val Thr Phe Ile Ser Leu Leu Phe Ser Ser Ala Tyr Ser
1               5                   10                  15
```

<210> SEQ ID NO 74
<211> LENGTH: 30
<212> TYPE: PRT
<213> ORGANISM: Homo sapiens

<400> SEQUENCE: 74

```
Met Asp Ser Lys Gly Ser Ser Gln Lys Gly Ser Arg Leu Leu Leu Leu
1               5                   10                  15

Leu Val Val Ser Asn Leu Leu Cys Gln Gly Val Val Ser
            20                  25                  30
```

<210> SEQ ID NO 75
<211> LENGTH: 272
<212> TYPE: PRT
<213> ORGANISM: Homo sapiens

<400> SEQUENCE: 75

```
Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60
```

```
Ile Phe Asn Val Ser Gln Gln Met Gly Gly Phe Tyr Leu Cys Gln Pro
 65                  70                  75                  80

Gly Pro Pro Ser Glu Lys Ala Trp Gln Pro Gly Trp Thr Val Asn Val
                 85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
            260                 265                 270

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Tyr Ala Phe Ser Ser
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Pro Gly Asp Gly Asp
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Thr Ile Ser Ser Val Val Asp Phe
```

```
1               5
```

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Lys Ala Ser Gln Asn Val Gly Thr Asn Val Ala
1               5                   10
```

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Ser Ala Thr Tyr Arg Asn
1               5
```

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Gln Gln Tyr Asn Arg Tyr Pro Tyr Thr
1               5
```

<210> SEQ ID NO 82
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser
        115                 120
```

```
<210> SEQ ID NO 83
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105

<210> SEQ ID NO 84
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190
```

Gln Lys Pro Gly Gln Ser Pro Lys Pro Leu Ile Tyr Ser Ala Thr Tyr
            195                 200                 205

Arg Asn Ser Gly Val Pro Asp Arg Phe Thr Gly Ser Gly Ser Gly Thr
        210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
            245                 250                 255

Thr Lys Leu Glu Ile Lys Arg
            260

<210> SEQ ID NO 85
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
atggctctcc cagtgactgc cctactgctt cccctagcgc ttctcctgca tgcagaggtg      60
aagctgcagc agtctggggc tgagctggtg aggcctgggt cctcagtgaa gatttcctgc     120
aaggcttctg gctatgcatt cagtagctac tggatgaact gggtgaagca gaggcctgga     180
cagggtcttg agtggattgg acagatttat cctggagatg gtgatactaa ctacaatgga     240
aagttcaagg gtcaagccac actgactgca gacaaatcct ccagcacagc ctacatgcag     300
ctcagcggcc taacatctga ggactctgcg gtctatttct gtgcaagaaa gaccattagt     360
tcggtagtag atttctactt tgactactgg ggccaaggga ccacggtcac cgtctcctca     420
ggtggaggtg gatcaggtgg aggtggatct ggtggaggtg gatctgacat tgagctcacc     480
cagtctccaa aattcatgtc cacatcagta ggagacaggg tcagcgtcac ctgcaaggcc     540
agtcagaatg tgggtactaa tgtagcctgg tatcaacaga accaggaca atctcctaaa     600 ccactgattt actcggcaac ctaccggaac agtggagtcc ctgatcgctt cacaggcagt     660
ggatctggga cagatttcac tctcaccatc actaacgtgc agtctaaaga cttggcagac     720
tatttctgtc aacaatataa caggtatccg tacacgtccg gaggggggac caagctggag     780
atcaaacgg                                                             789

<210> SEQ ID NO 86
<211> LENGTH: 235
<212> TYPE: PRT
<213> ORGANISM: Homo sapiens

<400> SEQUENCE: 86

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
            85                  90                  95

```
Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
            195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 87
<211> LENGTH: 247
<212> TYPE: PRT
<213> ORGANISM: Mus musculus

<400> SEQUENCE: 87

Met Ala Ser Pro Leu Thr Arg Phe Leu Ser Leu Asn Leu Leu Leu Met
1               5                   10                  15

Gly Glu Ser Ile Ile Leu Gly Ser Gly Glu Ala Lys Pro Gln Ala Pro
            20                  25                  30

Glu Leu Arg Ile Phe Pro Lys Lys Met Asp Ala Glu Leu Gly Gln Lys
        35                  40                  45

Val Asp Leu Val Cys Glu Val Leu Gly Ser Val Ser Gln Gly Cys Ser
50                  55                  60

Trp Leu Phe Gln Asn Ser Ser Ser Lys Leu Pro Gln Pro Thr Phe Val
65                  70                  75                  80

Val Tyr Met Ala Ser Ser His Asn Lys Ile Thr Trp Asp Glu Lys Leu
                85                  90                  95

Asn Ser Ser Lys Leu Phe Ser Ala Val Arg Asp Thr Asn Asn Lys Tyr
            100                 105                 110

Val Leu Thr Leu Asn Lys Phe Ser Lys Glu Asn Glu Gly Tyr Tyr Phe
        115                 120                 125

Cys Ser Val Ile Ser Asn Ser Val Met Tyr Phe Ser Ser Val Val Pro
130                 135                 140

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
                165                 170                 175

Asp Cys Arg Pro Arg Gly Ser Val Lys Gly Thr Gly Leu Asp Phe Ala
            180                 185                 190

Cys Asp Ile Tyr Ile Trp Ala Pro Leu Ala Gly Ile Cys Val Ala Pro
        195                 200                 205

Leu Leu Ser Leu Ile Ile Thr Leu Ile Cys Tyr His Arg Ser Arg Lys
210                 215                 220

Arg Val Cys Lys Cys Pro Arg Pro Leu Val Arg Gln Glu Gly Lys Pro
```

Arg Pro Ser Glu Lys Ile Val
            245

<210> SEQ ID NO 88
<211> LENGTH: 69
<212> TYPE: PRT
<213> ORGANISM: Mus musculus

<400> SEQUENCE: 88

Ser Thr Thr Thr Lys Pro Val Leu Arg Thr Pro Ser Pro Val His Pro
1               5                   10                  15

Thr Gly Thr Ser Gln Pro Gln Arg Pro Glu Asp Cys Arg Pro Arg Gly
            20                  25                  30

Ser Val Lys Gly Thr Gly Leu Asp Phe Ala Cys Asp Ile Tyr Ile Trp
        35                  40                  45

Ala Pro Leu Ala Gly Ile Cys Val Ala Leu Leu Ser Leu Ile Ile
    50                  55                  60

Thr Leu Ile Cys Tyr
65

<210> SEQ ID NO 89
<211> LENGTH: 207
<212> TYPE: DNA
<213> ORGANISM: Mus musculus

<400> SEQUENCE: 89
tctactacta ccaagccagt gctgcgaact ccctcacctg tgcaccctac cgggacatct      60
cagccccaga gaccagaaga ttgtcggccc cgtggctcag tgaaggggac cggattggac     120
ttcgcctgtg atatttacat ctgggcaccc ttggccggaa tctgcgtggc ccttctgctg     180
tccttgatca tcactctcat ctgctac                                         207

<210> SEQ ID NO 90
<211> LENGTH: 220
<212> TYPE: PRT
<213> ORGANISM: Homo sapiens

<400> SEQUENCE: 90

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

```
Leu Phe Pro Gly Pro Ser Lys Pro Phe Trp Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
    210                 215                 220

<210> SEQ ID NO 91
<211> LENGTH: 81
<212> TYPE: DNA
<213> ORGANISM: Homo sapiens

<400> SEQUENCE: 91
ttttgggtgc tggtggtggt tggtggagtc ctggcttgct atagcttgct agtaacagtg    60
gcctttatta ttttctgggt g                                              81

<210> SEQ ID NO 92
<211> LENGTH: 27
<212> TYPE: PRT
<213> ORGANISM: Homo sapiens

<400> SEQUENCE: 92

Phe Trp Val Leu Val Val Gly Gly Val Leu Ala Cys Tyr Ser Leu
1               5                   10                  15

Leu Val Thr Val Ala Phe Ile Ile Phe Trp Val
                20                  25

<210> SEQ ID NO 93
<211> LENGTH: 81
<212> TYPE: DNA
<213> ORGANISM: Homo sapiens

<400> SEQUENCE: 93
ttttgggtgc tggtggtggt tggtggagtc ctggcttgct atagcttgct agtaacagtg    60
gcctttatta ttttctgggt g                                              81

<210> SEQ ID NO 94
<211> LENGTH: 164
<212> TYPE: PRT
<213> ORGANISM: Homo sapiens

<400> SEQUENCE: 94

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
                35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95
```

```
Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 95
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 96
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat    180
gaactgcaga agataagat ggcggaggcc tacagtgaga ttgggatgaa aggcgagcgc      240
cggaggggca agggcacga tggcctttac cagggtctca gtacagccac caaggacacc     300
tacgacgccc ttcacatgca ggccctgccc cctcgc                              336

<210> SEQ ID NO 97
<211> LENGTH: 218
<212> TYPE: PRT
<213> ORGANISM: Mus musculus

<400> SEQUENCE: 97

Met Thr Leu Arg Leu Leu Phe Leu Ala Leu Asn Phe Phe Ser Val Gln
1               5                   10                  15
```

Val Thr Glu Asn Lys Ile Leu Val Lys Gln Ser Pro Leu Val Val
         20                  25                  30

Asp Ser Asn Glu Val Ser Leu Ser Cys Arg Tyr Ser Tyr Asn Leu Leu
         35                  40                  45

Ala Lys Glu Phe Arg Ala Ser Leu Tyr Lys Gly Val Asn Ser Asp Val
 50                  55                  60

Glu Val Cys Val Gly Asn Gly Asn Phe Thr Tyr Gln Pro Gln Phe Arg
 65                  70                  75                  80

Ser Asn Ala Glu Phe Asn Cys Asp Gly Asp Phe Asn Glu Thr Val
             85                  90                  95

Thr Phe Arg Leu Trp Asn Leu His Val Asn His Thr Asp Ile Tyr Phe
                100                 105                 110

Cys Lys Ile Glu Phe Met Tyr Pro Pro Tyr Leu Asp Asn Glu Arg
                115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
            180                 185                 190

Thr Pro Arg Arg Pro Gly Leu Thr Arg Lys Pro Tyr Gln Pro Tyr Ala
                195                 200                 205

Pro Ala Arg Asp Phe Ala Ala Tyr Arg Pro
    210                 215

<210> SEQ ID NO 98
<211> LENGTH: 123
<212> TYPE: DNA
<213> ORGANISM: Mus musculus

<400> SEQUENCE: 98
aatagtagaa ggaacagact ccttcaaagt gactacatga acatgactcc ccggaggcct    60
gggctcactc gaaagcctta ccagccctac gcccctgcca gagactttgc agcgtaccgc   120
ccc                                                                 123

<210> SEQ ID NO 99
<211> LENGTH: 41
<212> TYPE: PRT
<213> ORGANISM: Mus musculus

<400> SEQUENCE: 99

Asn Ser Arg Arg Asn Arg Leu Leu Gln Ser Asp Tyr Met Asn Met Thr
  1               5                  10                  15

Pro Arg Arg Pro Gly Leu Thr Arg Lys Pro Tyr Gln Pro Tyr Ala Pro
                 20                  25                  30

Ala Arg Asp Phe Ala Ala Tyr Arg Pro
             35                  40

<210> SEQ ID NO 100
<211> LENGTH: 123
<212> TYPE: DNA
<213> ORGANISM: Mus musculus

<400> SEQUENCE: 100

```
aatagtagaa ggaacagact ccttcaaagt gactacatga acatgactcc ccggaggcct    60
gggctcactc gaaagcctta ccagccctac gcccctgcca gagactttgc agcgtaccgc   120
ccc                                                                  123
```

<210> SEQ ID NO 101
<211> LENGTH: 41
<212> TYPE: PRT
<213> ORGANISM: Homo sapiens

<400> SEQUENCE: 101

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 102
<211> LENGTH: 123
<212> TYPE: DNA
<213> ORGANISM: Mus musculus

<400> SEQUENCE: 102

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                  123
```

<210> SEQ ID NO 103
<211> LENGTH: 255
<212> TYPE: PRT
<213> ORGANISM: Homo sapiens

<400> SEQUENCE: 103

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
```

```
                180             185             190
Ala Leu Thr Ser Thr Ala Leu Leu Phe Leu Leu Phe Phe Leu Thr Leu
            195                 200                 205

Arg Phe Ser Val Val Lys Arg Gly Arg Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 104
<211> LENGTH: 42
<212> TYPE: PRT
<213> ORGANISM: Homo sapiens

<400> SEQUENCE: 104

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Gly Gly Cys Glu Leu
        35                  40

<210> SEQ ID NO 105
<211> LENGTH: 126
<212> TYPE: DNA
<213> ORGANISM: Homo sapiens

<400> SEQUENCE: 105
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 106
<211> LENGTH: 277
<212> TYPE: PRT
<213> ORGANISM: Homo sapiens

<400> SEQUENCE: 106

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140
```

```
Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
        210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
            275
```

```
<210> SEQ ID NO 107
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Ser Gly Ala Thr Asn Phe Ser Leu Leu Lys Gln Ala Gly Asp Val
1               5                   10                  15

Glu Glu Asn Pro Gly Pro
            20
```

```
<210> SEQ ID NO 108
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Lys
            35                  40
```

```
<210> SEQ ID NO 109
<211> LENGTH: 39
<212> TYPE: PRT
<213> ORGANISM: Homo sapiens

<400> SEQUENCE: 109

Asn Gln Leu Glu Arg Thr Val Asn Ser Leu Asn Val Pro Ala Ile Ser
1               5                   10                  15

Ile Pro Glu His Asp Glu Ala Asp Glu Ile Ser Asp Glu Asn Arg Glu
            20                  25                  30
```

Lys Val Asn Asp Gln Ala Lys
        35

<210> SEQ ID NO 110
<211> LENGTH: 42
<212> TYPE: PRT
<213> ORGANISM: Homo sapiens

<400> SEQUENCE: 110

Ala Ala Ala Asn Gln Leu Glu Arg Thr Val Asn Ser Leu Asn Val Ser
1               5                   10                  15

Ala Ile Ser Ile Pro Glu His Asp Glu Ala Asp Glu Ile Ser Asp Glu
            20                  25                  30

Asn Arg Glu Lys Val Asn Asp Gln Ala Lys
        35                  40

<210> SEQ ID NO 111
<211> LENGTH: 48
<212> TYPE: PRT
<213> ORGANISM: Homo sapiens

<400> SEQUENCE: 111

Pro Glu His Asp Glu Ala Asp Glu Ile Ser Glu Asn Arg Glu Lys
1               5                   10                  15

Val Asn Asp Gln Ala Lys Leu Ile Val Gly Ile Val Val Gly Leu Leu
            20                  25                  30

Leu Ala Ala Leu Val Ala Gly Val Val Tyr Trp Leu Tyr Met Lys Lys
        35                  40                  45

<210> SEQ ID NO 112
<211> LENGTH: 37
<212> TYPE: PRT
<213> ORGANISM: Homo sapiens

<400> SEQUENCE: 112

Glu Asn Arg Glu Lys Val Asn Asp Gln Ala Lys Leu Ile Val Gly Ile
1               5                   10                  15

Val Val Gly Leu Leu Leu Ala Ala Leu Val Ala Gly Val Val Tyr Trp
            20                  25                  30

Leu Tyr Met Lys Lys
        35

<210> SEQ ID NO 113
<211> LENGTH: 65
<212> TYPE: PRT
<213> ORGANISM: Homo sapiens

<400> SEQUENCE: 113

Asn Gln Leu Glu Arg Thr Val Asn Ser Leu Asn Val Pro Ala Ile Ser
1               5                   10                  15

Ile Pro Glu His Asp Glu Ala Asp Glu Ile Ser Asp Glu Asn Arg Glu
            20                  25                  30

Lys Val Asn Asp Gln Ala Lys Leu Ile Val Gly Ile Val Val Gly Leu
        35                  40                  45

Leu Leu Ala Ala Leu Val Ala Gly Val Val Tyr Trp Leu Tyr Met Lys
    50                  55                  60

Lys
65

<210> SEQ ID NO 114

```
<211> LENGTH: 66
<212> TYPE: PRT
<213> ORGANISM: Homo sapiens

<400> SEQUENCE: 114

Thr Cys Thr Ala Glu Asn Gln Leu Glu Arg Thr Val Asn Ser Leu Asn
1               5                   10                  15

Val Ser Ala Ile Ser Ile Pro Glu His Asp Glu Ala Asp Glu Ile Ser
            20                  25                  30

Asp Glu Asn Arg Glu Lys Val Asn Asp Gln Ala Lys Leu Ile Val Gly
        35                  40                  45

Ile Val Val Gly Leu Leu Leu Ala Ala Leu Val Ala Gly Val Val Tyr
    50                  55                  60

Trp Leu
65

<210> SEQ ID NO 115
<211> LENGTH: 44
<212> TYPE: PRT
<213> ORGANISM: Homo sapiens

<400> SEQUENCE: 115

Pro Glu His Asp Glu Ala Asp Glu Ile Ser Asp Glu Asn Arg Glu Lys
1               5                   10                  15

Val Asn Asp Gln Ala Lys Leu Ile Val Gly Ile Val Val Gly Leu Leu
            20                  25                  30

Leu Ala Ala Leu Val Ala Gly Val Val Tyr Trp Leu
        35                  40

<210> SEQ ID NO 116
<211> LENGTH: 61
<212> TYPE: PRT
<213> ORGANISM: Homo sapiens

<400> SEQUENCE: 116

Asn Gln Leu Glu Arg Thr Val Asn Ser Leu Asn Val Ser Ala Ile Ser
1               5                   10                  15

Ile Pro Glu His Asp Glu Ala Asp Glu Ile Ser Asp Glu Asn Arg Glu
            20                  25                  30

Lys Val Asn Asp Gln Ala Lys Leu Ile Val Gly Ile Val Val Gly Leu
        35                  40                  45

Leu Leu Ala Ala Leu Val Ala Gly Val Val Tyr Trp Leu
    50                  55                  60

<210> SEQ ID NO 117
<211> LENGTH: 68
<212> TYPE: PRT
<213> ORGANISM: Homo sapiens

<400> SEQUENCE: 117

Ala Ala Ala Asn Gln Leu Glu Arg Thr Val Asn Ser Leu Asn Val Ser
1               5                   10                  15

Ala Ile Ser Ile Pro Glu His Asp Glu Ala Asp Glu Ile Ser Asp Glu
            20                  25                  30

Asn Arg Glu Lys Val Asn Asp Gln Ala Lys Leu Ile Val Gly Ile Val
        35                  40                  45

Val Gly Leu Leu Leu Ala Ala Leu Val Ala Gly Val Val Tyr Trp Leu
    50                  55                  60

Tyr Met Lys Lys
```

```
<210> SEQ ID NO 118
<211> LENGTH: 4
<212> TYPE: PRT
<213> ORGANISM: Unknown
<220> FEATURE:
<223> OTHER INFORMATION: Description of Unknown:
      CD28 motif sequence

<400> SEQUENCE: 118

Tyr Met Asn Met
1

<210> SEQ ID NO 119
<211> LENGTH: 4
<212> TYPE: PRT
<213> ORGANISM: Unknown
<220> FEATURE:
<223> OTHER INFORMATION: Description of Unknown:
      CD28 motif sequence

<400> SEQUENCE: 119

Pro Tyr Ala Pro
1
```

ENHANCED CHIMERIC ANTIGEN RECEPTORS AND USES THEREOF

CROSS-REFERENCE TO RELATED APPLICATION

This application is a Continuation of International Application No. PCT/US18/68134 filed Dec. 31, 2018, which claims priority to U.S. Provisional Application No. 62/612,031 filed on Dec. 29, 2017, the content of each of which is incorporated by reference in its entirety, and to each of which priority is claimed.

SEQUENCE LISTING

The specification further incorporates by reference the Sequence Listing submitted herewith via EFS on Jun. 24, 2020. Pursuant to 37 C.F.R. § 1.52(e)(5), the Sequence Listing text file, identified as 0727341044SL.txt, is 142,428 bytes and was created on Jun. 24, 2020. The Sequence Listing electronically filed herewith, does not extend beyond the scope of the specification and thus does not contain new matter.

INTRODUCTION

The presently disclosed subject matter provides methods and compositions for enhancing the immune response toward cancers and pathogens. It relates to novel designs of chimeric antigen receptors (CARs) and engineered immunoresponsive cells comprising the same. The engineered immunoresponsive cells comprising the novel CARs are antigen-directed and have extended persistence without compromising function.

BACKGROUND OF THE INVENTION

Chimeric antigen receptor (CAR) therapy has achieved great clinical success against hematological malignancies (PMID:23515080). It is based on synthetic receptors with both antigen recognition and signal transduction functions (PMID: 20467460). The single-chain variable fragment (scFv) in a CAR retains its antigen recognition specificity from the variable regions of the heavy and light chains of the original monoclonal antibody. Meanwhile, signal transduction of the CAR construct largely depends on the signaling domains of the original immune receptors. Currently all versions of second generation CARs in clinical trials have two signaling capacities/modalities as they contain domains from two immune receptors, one being CD3ζ and the other being a co-stimulatory receptor, such as CD28 or 41BB (PMID: 26129802). In essence, it combines the two signals transduced by separate receptors into one synthetic receptor. Presumably, signal transduction in CARs could be similar to that in CD3ζ and CD28/41BB.

CD3ζ is part of a multimeric T cell antigen receptor (TCR) complex that binds to antigen and transduces the binding across the plasma membrane to intracellular signals. While TCRαδ (or TCRγδ) subunits recognize antigens through their specific extracellular regions, CD3ζ mainly carries out signal transduction functions in the complex through its well-conserved three immune-receptor-tyrosine-based-activation-motifs (ITAMs) (PMID: 20516133). First identified based on their sequence homology, ITAMs consist of two consecutive YxxL/I motifs separated by a defined number of amino acids (YxxL/I-$X_{6-8}$-YxxL/I) (PMID: 2927501). ITAMs are usually found in receptors expressed in hematopoetic cells and especially well studied in the context of TCR signaling. TCR binding to peptide-MHC leads to the activation of a Src family kinase Lck, which phosphorylates two tyrosine residues in each of the three ITAMs in CD3ζ (PMID: 25861978). Each biphosphrylated ITAM then gains the ability to bind to the two tandem SH2 domains of a Syk family kinase, ZAP-70. This interaction brings ZAP-70 in close proximity to Lck, resulting in the phosphorylation and activation of ZAP-70 by Lck. Activated ZAP-70 further phosphorylates its downstream targets, such as adaptor protein LAT and SLP-76. Phosphorylated LAT and SLP-76 provide scaffolds for many other proteins, such as PLC-γ, Grb2/Sos, Gads and Itk, Vav and Nck, eventually leading to calcium mobilization, Ras/Erk activation and actin cytoskeletal rearrangement and ultimately activation of gene expression (PMID: 20516133). Therefore, the three ITAMs in CD3ζ are the major if not only signaling moieties in TCR signaling.

CD28, on the other hand, doesn't contain any ITAM. Instead, its cytoplasmic domain contains an YMNM motif that once phosphorylated upon CD28 binding to its ligand CD80/CD86, can bind to the p85 subunit of PI3K and Grb2/Gads (PMID: 20534709). Additionally, proline-rich regions of CD28 can interact with Itk, Tec, Lck, Grb2/Vav and filamin A (PMID: 20534709). Therefore, antigen-binding initiated TCR signaling through CD3ζ and CD80/86-binding initiated CD28 signaling share many common players, such as Grb2, Vav, Gads, Lck, Itk, which makes crosstalk between these two pathways possible. In addition, the activation of both pathways occurs in the signaling complexes assembled near the plasma membrane at the immunological synapse, physically bringing signaling molecules from the two pathways together in space. Last but not least, CD28 induced calcium signaling occurs seconds after TCR-initiated intracellular calcium increase if not sooner, reflecting the temporal proximity/closeness of two pathways (PMID: 18848472).

SUMMARY OF THE INVENTION

The present disclosure provides chimeric antigen receptors (CARs) that bind to an antigen of interest. The CAR can bind to a tumor antigen or a pathogen antigen. In certain non-limiting embodiments, the CAR comprises an extracellular antigen-binding domain, a transmembrane domain, and an intracellular signaling domain comprising a modified CD3ζ polypeptide.

In certain embodiments, the modified CD3ζ polypeptide lacks all or part of immunoreceptor tyrosine-based activation motifs (ITAMs), wherein the ITAMs are ITAM1, ITAM2, and ITAM3. In certain embodiments, the modified CD3ζ polypeptide lacks ITAM2 or a portion thereof. In certain embodiments, the modified CD3ζ polypeptide further lacks ITAM3 or a portion thereof. In certain embodiments, the modified CD3ζ polypeptide further lacks ITAM1 or a portion thereof. In certain embodiments, the modified CD3ζ polypeptide lacks ITAM1 or a portion thereof. In certain embodiments, the modified CD3ζ polypeptide further lacks ITAM3 or a portion thereof. In certain embodiments, the modified CD3ζ polypeptide lacks ITAM3 or a portion thereof. In certain embodiments, the modified CD3ζ polypeptide comprises a deletion of ITAM2 or a portion thereof. In certain embodiments, the modified CD3ζ polypeptide further comprises a deletion of ITAM3 or a portion thereof. In certain embodiments, the modified CD3ζ polypeptide further comprises a deletion of ITAM1 or a portion thereof. In certain embodiments, the modified CD3ζ polypeptide comprises a deletion of ITAM1 or a portion thereof. In certain embodiments, the modified CD3ζ polypeptide further comprises a deletion of ITAM3 or a portion thereof. In certain embodiments, the modified CD3ζ polypeptide comprises a deletion of ITAM3 or a portion thereof.

In certain embodiments, the modified CD3ζ polypeptide further lacks all or part of basic-rich stretch (BRS) regions, wherein the BRS regions are BRS1, BRS2, and BRS3. In certain embodiments, the modified CD3ζ polypeptide lacks BRS2 or a portion thereof. In certain embodiments, the modified CD3ζ polypeptide further lacks BRS3 or a portion thereof. In certain embodiments, the modified CD3ζ polypeptide further lacks BRS1 or a portion thereof. In certain embodiments, the modified CD3ζ polypeptide lacks BRS1 or a portion thereof. In certain embodiments, the modified CD3ζ polypeptide further lacks BRS3 or a portion thereof. In certain embodiments, the modified CD3ζ polypeptide lacks BRS3 or a portion thereof. In certain embodiments, the modified CD3ζ polypeptide lacks BRS1 or portion thereof, BRS2 or portion thereof, and BRS3 or a portion thereof. In certain embodiments, the modified CD3ζ polypeptide comprises a deletion of BRS2 or a portion thereof. In certain embodiments, the modified CD3ζ polypeptide further comprises a deletion of BRS3 or a portion thereof. In certain embodiments, the modified CD3ζ polypeptide further comprises a deletion of BRS1 or a portion thereof. In certain embodiments, the modified CD3ζ polypeptide comprises a deletion of BRS1 or a portion thereof. In certain embodiments, the modified CD3ζ polypeptide further comprises a deletion of BRS3 or a portion thereof. In certain embodiments, the modified CD3ζ polypeptide comprises a deletion of BRS3 or a portion thereof. In certain embodiments, the modified CD3ζ polypeptide comprises a deletion of BRS1 or portion thereof, BRS2 or portion thereof, and BRS3 or a portion thereof. In certain embodiments, the modified CD3ζ polypeptide comprises a deletion of ITAM2, ITAM3, BRS2, and BRS3. In certain embodiments, the modified CD3ζ polypeptide lacks ITAM2, ITAM3, BRS2, and BRS3. In certain embodiments, the CAR comprises the amino acid sequence set forth in SEQ ID NO: 45 or SEQ ID NO: 47.

In certain embodiments, the modified CD3ζ polypeptide lacks all or part of basic-rich stretch (BRS) regions, wherein the BRS regions are BRS1, BRS2, and BRS3. In certain embodiments, the modified CD3ζ polypeptide lacks BRS2 or a portion thereof. In certain embodiments, the modified CD3ζ polypeptide further lacks BRS3 or a portion thereof. In certain embodiments, the modified CD3ζ polypeptide further lacks BRS1 or a portion thereof. In certain embodiments, the modified CD3ζ polypeptide lacks BRS1 or a portion thereof. In certain embodiments, the modified CD3ζ polypeptide further lacks BRS3 or a portion thereof. In certain embodiments, the modified CD3ζ polypeptide lacks BRS3 or a portion thereof. In certain embodiments, the modified CD3ζ polypeptide lacks BRS1 or portion thereof, BRS2 or portion thereof, and BRS3 or a portion thereof.

In certain embodiments, the modified CD3ζ polypeptide comprises a BRS variant selected from a BRS1 variant, a BRS2 variant, and a BRS3 variant, wherein the BRS variant comprises one or more loss-of-function mutations.

In certain embodiments, any of the various CARs disclosed above further comprises a hinge/spacer region, wherein the hinge/spacer region comprises a CD8 polypeptide, a CD28 polypeptide, a CD3ζ polypeptide, a CD40 polypeptide, a 4-1BB polypeptide, an OX40 polypeptide, a CD84 polypeptide, a CD166 polypeptide, a CD8a polypeptide, a CD8b polypeptide, an ICOS polypeptide, an ICAM-1 polypeptide, a CTLA-4 polypeptide, a CD27 polypeptide, a CD40/My88 peptide, a NKGD2 peptide or a combination thereof. In certain embodiments, the hinge/spacer region comprises CD166 polypeptide. In certain embodiments, the hinge/spacer region comprises a CD166 polypeptide that has amino acids 489 to 527 of SEQ ID NO: 3.

In certain embodiments, the transmembrane domain any of the various CARs disclosed above comprises a CD8 polypeptide, a CD28 polypeptide, a CD3ζ polypeptide, a CD40 polypeptide, a 4-1BB polypeptide, an OX40 polypeptide, a CD84 polypeptide, a CD166 polypeptide, a CD8a polypeptide, a CD8b polypeptide, an ICOS polypeptide, an ICAM-1 polypeptide, a CTLA-4 polypeptide, a CD27 polypeptide, a CD40/My88 peptide, a NKGD2 peptide or a combination thereof. In certain embodiments, the transmembrane domain comprises CD166 polypeptide. In certain embodiments, the transmembrane domain comprises CD166 polypeptide that has amino acids 528 to 527 of SEQ ID NO: 3.

In certain embodiments, the transmembrane domain and the hinge/spacer region are derived from the same molecule. In certain embodiments, the hinge/spacer region comprises a CD28 polypeptide and the transmembrane domain comprises a CD28 polypeptide. In certain embodiments, the hinge/spacer region comprises a CD84 polypeptide and the transmembrane domain comprises a CD84 polypeptide. In certain embodiments, the hinge/spacer region comprises a CD166 polypeptide and the transmembrane domain comprises a CD166 polypeptide. In certain embodiments, the CAR comprises amino acids 489 to 553 of SEQ ID NO: 3.

In certain embodiments, the hinge/spacer region comprises a CD8a polypeptide and the transmembrane domain comprises a CD8a polypeptide. In certain embodiments, the hinge/spacer region comprises a CD8b polypeptide and the transmembrane domain comprises a CD8b polypeptide.

In certain embodiments, the transmembrane domain and the hinge/spacer region are derived from different molecules. In certain embodiments, the hinge/spacer region comprises a CD28 polypeptide and the transmembrane domain comprises an ICOS polypeptide.

In certain embodiments, the intracellular signaling domain any of the various CARs disclosed above further comprises a co-stimulatory signaling domain. In certain embodiments, the co-stimulatory signaling domain comprises a CD28 polypeptide.

The presently disclosed subject matter also provides chimeric antigen receptors (CARs) comprising an extracellular antigen-binding domain, a hinge/spacer region, a transmembrane domain, and an intracellular signaling domain comprising a modified CD3ζ polypeptide, wherein the modified CD3ζ polypeptide comprises an ITAM variant comprising one or more loss-of-function mutations, wherein the ITAM variant is selected from the group consisting of an ITAM1 variant, an ITAM2 variant, and an ITAM3 variant. In certain embodiments, the hinge/spacer region comprises a CD8 polypeptide, a CD28 polypeptide, a CD3ζ polypeptide, a CD40 polypeptide, a 4-1BB polypeptide, an OX40 polypeptide, a CD84 polypeptide, a CD166 polypeptide, a CD8a polypeptide, a CD8b polypeptide, an ICOS polypeptide, an ICAM-1 polypeptide, a CTLA-4 polypeptide, a CD27 polypeptide, a CD40/My88 peptide, a NKGD2 peptide or a combination thereof. In certain embodiments, the ITAM2 variant has the amino acid sequence set forth in SEQ ID NO: 29. In certain embodiments, the ITAM3 variant has the amino acid sequence set forth in SEQ ID NO: 33. In certain embodiments, the CAR comprises a hinge/spacer region of a CD166 polypeptide and a transmembrane domain of a CD166 polypeptide. In certain embodiments, the CAR comprises the amino acids 489 to 553 of SEQ ID NO: 3. In certain embodiments, the modified CD3ζ polypeptide has amino acids 374 to 485 of SEQ ID NO: 43. In certain embodiments, the CAR comprises the amino acid sequence set forth in SEQ ID NO: 43.

The presently disclosed subject matter also provides an immunoresponsive cell comprising a CAR disclosed herein. In certain embodiments, the CAR is recombinantly expressed. In certain embodiments, the CAR is expressed from a vector. In certain embodiments, the CAR is placed at an endogenous gene locus of the immunoresponsive cell. In certain embodiments, the endogenous gene locus is a TRAC locus, a TRBC locus or a TRGC locus. In certain embodiments, the endogenous gene locus is a TRAC locus. In certain embodiments, the placement of the CAR disrupts or abolishes the endogenous expression of a TCR.

The presently disclosed subject matter also provides immunoresponsive cells comprising two or more CARs. In certain embodiments, the immunoresponsive cell comprises a) a first CAR comprising a first extracellular antigen-binding domain that binds to a first antigen, a first transmembrane domain, and a first intracellular signaling domain; and b) a second CAR comprising a second extracellular antigen-binding domain that binds to a second antigen, a second transmembrane domain, and a second intracellular signaling domain, wherein the first CAR is a CAR disclosed above or the first intracellular signaling domain comprises a modified CD3ζ polypeptide that comprises one or more ITAM variant comprising one or more loss-of-function mutations, wherein each of the one or more ITAM variant is independently selected from the group consisting of an ITAM1 variant, an ITAM2 variant, and an ITAM3 variant. In certain embodiments, the first CAR further comprises a first hinge/spacer region. In certain embodiments, the second CAR further comprises a second hinge/spacer region. In certain embodiments, each of the first and second hinge/spacer regions can be independently selected from any of the hinge/spacer regions disclosed herein.

In certain embodiments, the second CAR is a CAR disclosed above. In certain embodiments, the second intracellular signaling domain of the second CAR comprises a modified CD3ζ polypeptide that comprises one or more ITAM variant comprising one or more loss-of-function mutations, wherein the ITAM variant is selected from the group consisting of an ITAM1 variant, an ITAM2 variant, and an ITAM3 variant. In certain embodiments, the second intracellular signaling domain of the second CAR comprises a modified CD3ζ polypeptide that is the same as the modified CD3ζ polypeptide comprised in the first intracellular signaling domain of the first CAR. In certain embodiments, the second intracellular signaling domain of the second CAR comprises a modified CD3ζ polypeptide that is different from the modified CD3ζ polypeptide comprised in the first intracellular signaling domain of the first CAR. In certain embodiments, the second intracellular signaling domain of the second CAR comprises a native CD3ζ polypeptide.

In certain embodiments, the first intracellular signaling domain of the first CAR is the same as the second intracellular signaling domain of the second CAR. In certain embodiments, the first intracellular signaling domain of the first CAR is different from the second intracellular signaling domain of the second CAR.

In certain embodiments, the first antigen is different from the second antigen.

In certain embodiments, the first intracellular signaling domain comprises or has an ITAM2 variant and an ITAM3 variant, and the second intracellular signaling domain comprises or has a deletion of ITAM2 or a portion thereof and a deletion of ITAM3 or a portion thereof.

In certain embodiments, the first intracellular signaling domain comprises or has an ITAM2 variant and an ITAM3 variant, and the second intracellular signaling domain comprises or has an ITAM1 variant and an ITAM2 variant.

In certain embodiments, the cell further comprises a third CAR comprising a third extracellular antigen-binding domain that binds to a third antigen, a third transmembrane domain, and a third intracellular signaling domain.

In certain embodiments, the first intracellular signaling domain comprises or has an ITAM2 variant and an ITAM3 variant, the second intracellular signaling domain comprises or has a deletion of ITAM2 or a portion thereof and a deletion of ITAM3 or a portion thereof, and the third intracellular signaling domain comprises or has an ITAM1 variant and an ITAM2 variant.

In certain embodiments, the first intracellular signaling domain comprises or has a deletion of ITAM2 or a portion thereof and a deletion of ITAM3 or a portion thereof, the second intracellular signaling domain comprises or has a deletion of ITAM2 or a portion thereof and a deletion of ITAM3 or a portion thereof, and the third intracellular signaling domain comprises or has an ITAM1 variant and an ITAM2 variant.

In certain embodiments, the first intracellular signaling domain comprises or has a deletion of ITAM2 or a portion thereof and a deletion of ITAM3 or a portion thereof, the second intracellular signaling domain comprises or has an ITAM1 variant and an ITAM2 variant, and the third intracellular signaling domain comprises or has an ITAM1 variant and an ITAM2 variant.

In certain embodiments, the first intracellular signaling domain comprises or has an ITAM1 variant and an ITAM2 variant, the second intracellular signaling domain comprises or has an ITAM1 variant and an ITAM2 variant, and the third intracellular signaling domain comprises or has an ITAM1 variant and an ITAM2 variant.

In certain embodiments, the cell is selected from the group consisting of a T cell, a Natural Killer (NK) cell, a human embryonic stem cell, and a pluripotent stem cell from which lymphoid cells may be differentiated. In certain embodiments, the cell is a T cell. In certain embodiments, the T cell is selected from the group consisting of a cytotoxic T lymphocyte (CTL), a regulatory T cell, and a Natural Killer T (NKT) cell. In certain embodiments, the immunoresponsive cell is a myeloid cell such as macrophage. In certain embodiments, said immunoresponsive cell is autologous. In certain embodiments, said antigen is a tumor antigen. In certain embodiments, the tumor antigen is selected from the group consisting of CD19, MUC16, MUC1, CAIX, CEA, CD8, CD7, CD10, CD20, CD22, CD30, CLL1, CD33, CD34, CD38, CD41, CD44, CD49f, CD56, CD74, CD133, CD138, EGP-2, EGP-40, EpCAM, erb-B2,3,4, FBP, Fetal acetylcholine receptor, folate receptor-a, GD2, GD3, HER-2, hTERT, IL-13R-a2, K-light chain, KDR, LeY, L1 cell adhesion molecule, MAGE-A1, Mesothelin, ERBB2, MAGEA3, p53, MART1, GP100, Proteinase3 (PR1), Tyrosinase, Survivin, hTERT, EphA2, NKG2D ligands, NY-ESO-1, oncofetal antigen (h5T4), PSCA, PSMA, ROR1, TAG-72, VEGF-R2, WT-1, BCMA, CD123, CD44V6, NKCS1, EGF1R, EGFR-VIII, and CD99, CD70, ADGRE2, CCR1, LILRB2, PRAME, CCR4, CD5, CD3, TRBC1, TRBC2, TIM-3, Integrin B7, ICAM-1, CD70, Tim3, CLEC12A and ERBB. In certain embodiments, said antigen is CD19.

The presently disclosed subject matter further provides a pharmaceutical composition comprising an effective amount of an immunoresponsive cell disclosed herein and a pharmaceutically acceptable excipient. In certain embodiments, the pharmaceutical composition is for treating a neoplasm.

The presently disclosed subject matter further provides a method of reducing tumor burden in a subject, the method comprising administering to the subject an effective amount of the immunoresponsive cells or the pharmaceutical composition disclosed herein. The presently disclosed subject matter also provides a method, the method comprising administering to the subject an effective amount of immunoresponsive cells or a pharmaceutical composition comprising thereof, wherein the immunoresponsive cells comprises a chimeric antigen receptor (CAR) comprising an extracellular antigen-binding domain, a hinge/spacer region, a transmembrane domain, and an intracellular signaling domain comprising a modified CD3ζ polypeptide, wherein the modified CD3ζ polypeptide comprises one or more ITAM variant comprising one or more loss-of-function mutations, wherein each of the one or more ITAM variant is independently selected from the group consisting of an ITAM1 variant, an ITAM2 variant, and an ITAM3 variant. In certain embodiments, the modified CD3ζ polypeptide comprises an ITAM2 variant and an ITAM3 variant. In certain embodiments, one or both of the ITAM2 variant and the ITAM3 variant comprise two loss-of-function mutations. In certain embodiments, the ITAM2 variant has the amino acid sequence set forth in SEQ ID NO: 29. In certain embodiments, the ITAM3 variant has the amino acid sequence set forth in SEQ ID NO: 33. In certain embodiments, the one or more loss-of-function mutation is at a tyrosine amino acid residue. In certain embodiments, the intracellular signaling domain further comprises a co-stimulatory signaling domain. In certain embodiments, the co-stimulatory signaling domain comprises a CD28 polypeptide.

In certain embodiments, the method reduces the number of tumor cells. In certain embodiments, the method reduces tumor size. In certain embodiments, the method eradicates the tumor in the subject.

The presently disclosed subject matter further provides methods of treating or preventing a neoplasm. In certain embodiments, the method comprises administering to the subject an effective amount of the immunoresponsive cells or the pharmaceutical composition disclosed herein. In certain embodiments, the method comprises administering to the subject an effective amount of immunoresponsive cells or a pharmaceutical composition comprising thereof, wherein the immunoresponsive cell comprises a chimeric antigen receptor (CAR) comprising an extracellular antigen-binding domain, a hinge/spacer region, a transmembrane domain, and an intracellular signaling domain comprising a modified CD3ζ polypeptide, wherein the modified CD3ζ polypeptide comprises one or more ITAM variant comprising one or more loss-of-function mutations, wherein each of the one or more ITAM variant is independently selected from the group consisting of an ITAM1 variant, an ITAM2 variant, and an ITAM3 variant.

The presently disclosed subject matter further provides a method of treating a subject having a relapse of a neoplasm, wherein the subject received an immunoresponsive cell comprising an antigen recognizing receptor, wherein the antigen recognizing receptor comprises a 4-1BB costimulatory signal. In certain embodiments, the method comprises administering to the subject an effective amount of the immunoresponsive cells or the pharmaceutical composition disclosed herein. In certain embodiments, the method comprises administering to the subject an effective amount of immunoresponsive cells or a pharmaceutical composition comprising thereof, wherein the immunoresponsive cells comprises a chimeric antigen receptor (CAR) comprising an extracellular antigen-binding domain, a hinge/spacer region, a transmembrane domain, and an intracellular signaling domain comprising a modified CD3ζ polypeptide, wherein the modified CD3ζ polypeptide comprises one or more ITAM variant comprising one or more loss-of-function mutations, wherein each of the one or more ITAM variant is independently selected from the group consisting of an ITAM1 variant, an ITAM2 variant, and an ITAM3 variant. In certain embodiments, the intracellular signaling domain further comprises a co-stimulatory signaling domain. In certain embodiments, the co-stimulatory signaling domain comprises a CD28 polypeptide.

In certain embodiments, the neoplasm or tumor is selected from the group consisting of blood cancer, B cell leukemia, multiple myeloma, acute lymphoblastic leukemia (ALL), chronic lymphocytic leukemia, non-Hodgkin's lymphoma, and ovarian cancer. In certain embodiments, the neoplasm is B cell leukemia, multiple myeloma, acute lymphoblastic leukemia (ALL), chronic lymphocytic leukemia, or non-Hodgkin's lymphoma, and the CAR binds to CD19. In certain embodiments, the neoplasm is CD19+ ALL. In certain embodiments, the neoplasm comprises a tumor cell having a low expression level of a tumor specific antigen.

The presently disclosed subject matter further provides a method for producing an antigen-specific immunoresponsive cell, the method comprising introducing into an immunoresponsive cell a nucleic acid sequence encoding a CAR disclosed herein. In certain embodiments, the nucleic acid sequence is comprised in a vector. In certain embodiments, the vector is a retroviral vector.

The presently disclosed subject matter further provides an isolated nucleotide acid encoding the CAR disclosed herein. In certain embodiments, the isolated nucleotide acid further comprises the nucleotide sequence set forth in SEQ ID NO: 45 and SEQ ID NO: 47.

The presently disclosed subject matter further provides a nucleic acid composition comprising a CAR disclosed herein. In certain embodiments, the nucleic acid sequences are comprised in a vector. In certain embodiments, the vector is a retroviral vector.

The presently disclosed subject matter further provides a vector comprising the nucleic acid composition disclosed herein.

The presently disclosed subject matter further provides a kit comprising a CAR, an immunoresponsive cell, a pharmaceutical composition, a nucleic acid composition or a vector disclosed herein. In certain embodiments, the kit further comprises written instructions for treating and/or preventing a neoplasm, a pathogen infection, an autoimmune disorder, or an allogeneic transplant.

BRIEF DESCRIPTION OF THE FIGURES

The following Detailed Description, given by way of example, but not intended to limit the presently disclosed subject matter to specific embodiments described, may be understood in conjunction with the accompanying drawings.

FIG. 1A shows cytoplasmic regions of different 1928ζ(1928z) CARs. The (chain of the original 1928ζ CAR is mutated to construct 1928ζ CAR T cells with distinctive (signaling domains. The three ITAM motifs in the ζ domain are named ITAM1, ITAM2 and ITAM3 from membrane proximal to distal direction. In 1XX, X2X, XX3 and X23 CARs, the two tyrosine residues (Y) in the respective ITAM are point mutated to two phenylalanine residues (F) for the indicated ITAMs. In D12 and D23, deletion mutations are made to remove ITAM1 and ITAM2 (D12) or ITAM2 and ITAM3 (D23). FIG. 1B shows cytoplasmic regions of 1928z CARs with improved antitumor efficacy compared to the original 1928z structure. In 1XX, the ζ chain of the original 1928ζ CAR is point-mutated (conversion from tyrosine (T) to phenylalanine (F)) in ITAM2 and ITAM3 whereas the basic rich stretch (BRS-1, -2, -3) of amino acids remains. In D12 and D23, ITAM1 and ITAM2 (D12) or ITAM2 and ITAM3 (D23) are deleted; D23 comprises one BRS region (BRS-1) whereas there is no BRS in D12. FIG. 1C shows representative flow cytometric analysis showing expression levels of CAR and LNGFR for 1928ζ and indicated 1928ζ mutants. UT: untransduced T cells were used as control.

FIG. 1A shows in vivo response of 1928ζ mutants with unmodified CD3ζ, ITAM3 (XX3), ITAM2 (X2X) or the combination of ITAM2 and ITAM3 (X23) in their original CAR position and mutation of the remaining ITAM motifs. FIG. 2B shows tumor burden of NALM-6 mice treated with 1928ζ mutants consisting of one single unmutated CD3ζ sequence in first position (ITAM3 for D12 and ITAM1 for D23) and deletion of the remaining ζ-chain domain.

FIGS. 3A and 3B show Kaplan-Meier analysis of survival of mice comparing the in vivo efficacy of a single dose of 1928z WT and 1928z mutants XX3, X23 and X2X (FIG. 3A) or 1928z mutants D12, D23 and 1XX (FIG. 3B). Pooled data from 2 independent experiments, representing n=10 mice. Control refers to untreated mice (n=3). *p<0.05 (log-rank Mantel-Cox test)

FIGS. 5A-5C depict analysis of T cell differentiation. Phenotype of CD4+ and CD8+ CAR T cells in the bone marrow of mice 10 days after CAR infusion (data are means±SEM, each bar represents n=5 mice). FIG. 5A shows percentage of CD62L/CD45RA expression on CAR T cells for the indicated 1928ζ mutants compared to 1928ζ WT. FIG. 5B shows percentage of central memory (CD62L+ CD45RA−) and FIG. 5C shows effector cells (CD62L− CD45RA+) in CD4+ and CD8+ CAR T cells. Data are compared to 1928ζ WT. P<0.01, *P<0.001 (unpaired student's t test).

FIG. 8A shows cytotoxic activity as determined by 4 hr $^{51}$Cr release assay, using EL4-CD19 as targets (n=2 independent experiments performed in triplicates, data are means±SEM). FIGS. 8B and 8C show cytotoxic activity using an 18 hr bioluminescence assay with firefly luciferase (FFL)-expressing NALM-6 as targets. Data are means±SEM (n=5 independent experiments performed in triplicates. Experiments were performed one week after expansion of effector cells on irradiated 3T3-CD19.

FIG. 16A shows cytoplasmic regions of wild-type and mutated 1928ζ CARs. The ζ chain of the 1928ζ CAR was mutated in one or two of its three signaling domains, named ITAM1, ITAM2, and ITAM3, from a membrane-proximal to a membrane-distal direction. In 1XX, X2X, XX3, and X23 CARs, the two tyrosines (Y) in the respective ITAM are point-mutated to two phenylalanines (F) for the indicated ITAMs. FIG. 16B shows flow cytometric analysis showing expression levels of CAR and LNGFR for the constructs depicted in A). Data are representative of at least five independent experiments with similar results. Untransduced T (UT) cells were used as the control. FIGS. 16C to 16E show that Nalm6-bearing mice were treated with $5\times10^4$ CAR+ T cells. FIG. 16C shows tumor burden (average radiance) of mice, comparing the in vivo efficacy of wild-type 1928ζ, 1XX, X2X, XX3, and X23 (n=10 mice per group, results were pooled from two independent experiments). Control refers to untreated mice (n=6). FIG. 16D shows number of CAR T cells in the bone marrow of mice 17d post-infusion (results were pooled from two independent experiments, n=10 mice per group). FIG. 16E shows phenotype of CAR T cells in the bone marrow of mice 10 d after CAR infusion, as demonstrated by the percentage of $T_{CM}$ and $T_{EFF}$ cells. Representative results of two independent experiments are shown (n=5 mice per group). All data are mean±s.e.m. In FIGS. 16D and E, P values were determined by two-tailed Mann-Whitney U-tests.

FIG. 17A shows cytoplasmic domains of 1928ζ CARs with deletions in the CD3ζ chain. In D12, deletion mutations remove ITAM1 and ITAM2, while ITAM2 and ITAM3 are removed in D23. FIG. 17B shows flow cytometric analysis showing the expression levels of CAR and LNGFR for the indicated constructs. Data are representative of at least five independent experiments with similar results. UT, untransduced T cells were used as the control. FIGS. 17C-17E show that Nalm6-bearing mice were treated with $5\times10^4$ CAR+ T cells. FIG. 17CA shows tumor burden (average radiance) of mice treated with wild-type 1928ζ, D12, or D23 (wild-type 1928ζ and D23: n=10; D12: n=9; pooled data from two independent experiments). FIG. 17D shows number of CAR T cells in the bone marrow of mice 17d post-infusion (results were pooled from two independent experiments, n=10 mice per group). FIG. 17E shows phenotype of CAR T cells in the bone marrow of mice 10 d after CAR infusion, as demonstrated by the percentage of $T_{CM}$ and $T_{EFF}$ cells (pooled data from two independent experiments, n=10 mice per group). All data are mean±s.e.m. In FIGS. 17D and 17E, P values were determined by two-tailed Mann-Whitney U-tests.

FIGS. 18A-18H depict that TRAC-1XX augments T cell potency by decreasing T cell exhaustion and developing into long-lived memory T cells with effective recall responses. A)-D), Nalm6-bearing mice were treated with $1\times10^5$ or $5\times10^5$ TRAC-CAR T cells. FIG. 18A shows Kaplan-Meier analysis of survival of mice treated with $1\times10^5$ TRAC-1XX or TRAC-XX3 compared with TRAC-1928ζ (TRAC-1928ζ and TRAC-XX3: n=5 mice per group; TRAC-1XX: n=7). Control refers to untreated mice (n=3). P values were determined by a one-sided log-rank Mantel-Cox test. FIG. 18B shows Kaplan-Meier analysis of survival of mice treated with $5\times10^5$ (n=5 mice per group) or $1\times10^5$ (TRAC-1928ζ: n=10 mice, TRAC-1XX: n=5 mice) TRAC-CAR T cells. P values were determined by a one-sided log-rank Mantel-Cox test. FIGS. 18C and 18D show the number of cells (FIG. 18C) and expression of the exhaustion markers PD1+TIM3+LAG3+ on bone marrow CAR T cells (FIG. 18D) were determined for TRAC-1XX and TRAC-XX3 and compared with TRAC-1928ζ. Data are shown as mean±s.e.m., and each symbol denotes an individual mouse (n=5 mice per group). P values were determined by two-tailed Mann-Whitney U-tests. FIGS. 18E-18H show Nalm6-bearing mice were treated with $5\times10^5$ TRAC-edited naive T cells and were rechallenged with Nalm6 cells (n=5 mice per group), as indicated by the arrows. No further rechallenge with tumor was performed for the controls (TRAC-1928ζ: n=6 mice; TRAC-1XX: n=7 mice). FIG. 18E shows tumor burden (average radiance) of mice, comparing the in vivo efficacy of TRAC-1928ζ and TRAC-1XX following tumor rechallenge versus no further rechallenge. All data are mean±s.e.m. A two-tailed unpaired Student's t-test was used for the statistical analysis of tumor burden at day 59 post-CAR administration (TRAC-1928ζ: n=4; TRAC-1XX: n=5). FIGS. 18F and 18G show the number of total CAR T cells (F), $T_{CM}$, $T_{EFF}$, and IL7R+ CAR T cells (G) in the bone marrow of treated mice 63d post-CAR administration (rechallenge: TRAC-1928ζ: n=4 mice, TRAC-1XX: n=5 mice; no rechallenge: n=5 mice per group). All data are mean±s.e.m.; a two-tailed unpaired Student's t-test was used for the statistical analysis. FIG. 18H shows expression of the exhaustion markers PD1+TIM3+LAG3+ on bone marrow CAR T cells. All data are mean±s.e.m. P values were determined by a two-tailed unpaired Student's t-test.

FIG. 19A shows normalized enrichment score of significantly up- or downregulated gene sets in 1928 ζ versus 1XX and 1928 ζ versus XX3 (n=3 replicates per group) as determined by GSEA using the MSigDB C7 gene ontology sets. For all pathways, the false discovery rate (FDR) q≤0.02. GSE datasets are indicated in parentheses. stim, stimulated. FIG. 19B shows differentially expressed genes (FDR q<0.05) between sorted effector and naive/memory T cells (left) (n=6 replicates per group) and heat map demonstrating the expression profiles of the same genes for CAR T cells (n=3 replicates per group). TF, transcription factor. FIG. 19C shows normalized enrichment score of significantly enriched gene sets (FDR q≤0.03) related to phenotypic and functional T cell features comparing TRAC-1928 ζ versus TRAC-XX3, TRAC-1928 ζ versus TRAC-1XX, and TRAC-1XX versus TRAC-XX3 as identified with GSEA analysis (n=3 replicates per group). JAK-STAT, Janus kinase-signal transducer and activator of transcription. FIG. 19D shows impact of defined CD3z ITAM mutations in 1928 ζ CAR T cells on effector- and memory-associated T cell attributes. 1XX CAR T cells display balanced effector and memory traits.

FIG. 20A shows cytotoxic activity as determined by 4-h $^{51}Cr$ release assay 1 week after expansion of effector cells on irradiated 3T3-CD19 (data are shown as means of n=2 independent experiments performed in triplicates). FIG. 20B shows cumulative cell counts of indicated CAR T cells upon weekly stimulation with CD19+ target cells (n=3 independent experiments). All data are means±s.e.m. P values were calculated with two-tailed paired Student's t-test. FIG. 20C shows NALM6-bearing mice were treated with 5×10⁴ CAR+ T cells. Kaplan-Meier analysis of survival comparing the in vivo efficacy of wild-type 1928ζ or indicated 1928ζ mutants (n=10 mice, pooled data from two independent experiments). Control (Ctl) refers to untreated mice (n=6). P value was determined by a one-sided log-rank Mantel-Cox test. FIG. 20D shows phenotype of CAR T cells as demonstrated by percentage of central memory (CD62L+CD45RA−) and effector memory (CD62L-CD45RA−) CD4+ CAR T cells 48 h upon second stimulation with CD19+ target cells. Two-tailed paired Student's t-test was performed, data represent means±s.e.m. of n=4 independent experiments. FIG. 20E shows NALM6-bearing mice were treated with 5×10⁴ CAR T cells and euthanized at day 10 after infusion; bone marrow CAR T cells were analyzed by FACS. Representative flow cytometric analysis of phenotype for indicated CAR T cells as determined by CD62L/CD45RA expression, gated on CAR+ CD4+ T cells. Representative of 5 mice per group in at least n=2 independent experiments with similar results.

FIG. 21A shows cytotoxic activity of 1928ζ mutants compared to wild-type 1928ζ using an 18-h bioluminescence assay with FFL-expressing NALM6 cells as targets. Experiments were performed 1 week after expansion of effector cells on CD19⁺ target cells. Data are means±s.e.m. (n=4 independent experiments performed in triplicates). *P<0.05 (2¹: P=0.0273, 2⁻¹: P=0.0387, 2⁻²: P=0.0125), **P=0.0018 as calculated by two-tailed paired Student's t-test of average of triplicates. FIGS. 21B and 21C show Granzyme B (GrB) expression (n=4 independent experiments) on CD8+ CAR T cells (FIG. 21B) and cytokine secretion (FIG. 21C) of CD4+ and CD8+ CAR T cells upon 2nd stimulation with CD19-expressing target cells. All data are means±s.e.m. (IFNγ and IL2, n=4; TNFα, n=5 independent experiments). Unstimulated (Unstim.) wild-type 1928ζ cells were used as control. Significant differences compared to 1928ζ were determined by two-tailed paired Student's t-test.

FIGS. 22A-22D depict impact of ITAM location within 1928ζ CARs on T cell function and therapeutic potency. FIG. 22A shows cytotoxic activity as determined by 4-h ⁵¹Cr release assay 1 week after expansion of effector cells on irradiated 3T3-CD19 (data are means of n=2 independent experiments performed in triplicates). FIG. 22B shows cumulative cell counts of indicated CAR T cells upon weekly stimulation with CD19+ target cells (n=3 independent experiments). All data are means±s.e.m.; P values were calculated with two-tailed paired Student's t-test. FIG. 22C shows cytotoxic activity of D12 and D23 compared to wild-type 1928ζ as determined by 18-h bioluminescence assay with FFL-expressing NALM6 cells as targets. Experiments were performed 1 week after expansion of effector cells on CD19+ target cells. Data are means±s.e.m. (n=4 independent experiments performed in triplicates). P value was calculated by two-tailed paired Student's t-test of average of triplicates and showed no significant difference (P>0.05) between D12/D23 and wild-type 1928ζ for all E/T ratios. FIG. 22D shows NALM6-bearing mice were treated with 5×10⁴ CAR T cells. Kaplan-Meier analysis of survival of mice treated with wild-type 1928ζ or indicated 1928ζ mutants (n=10 mice per group). Control refers to untreated mice (n=6). P value was calculated by a one-sided log-rank Mantel-Cox test.

FIG. 23A shows Granzyme B (GrB) expression on CD8⁺ CAR T cells (n=5 independent experiments). FIG. 22B shows cytokine secretion of CD4⁺ and CD8⁺ CAR T cells upon second stimulation with CD19-expressing target cells. Unstimulated wild-type 1928ζ cells were used as control. All data are means±s.e.m. (IFNγ and IL2, n=4; TNFα, n=5 independent experiments). Each individual symbol indicates one sample. Significant differences compared to 1928ζ were determined by two-tailed paired Student's t-test.

FIG. 24A shows histogram and flow cytometric analysis of CAR expression 4 d after CAR gene integration into the TRAC locus. Representative of four independent experiments with similar results. FIG. 24B shows cell numbers of CD4+ and CD8+ CAR T cells. FIG. 24C shows percentage of CD8+ $T_{CM}$ (CD62L+CD45RA−) and flow cytometric analysis of CD62L/CD45RA expression on bone marrow CD8⁺ CAR T cells (representative of n=5 mice per group in one independent experiment). FIG. 24D shows ratio of CAR+IL7R+ to tumor cells and exemplary flow cytometric analysis of IL7R+ CAR T cells in the bone marrow of mice. FIG. 24E shows enumeration of CAR T cells in the spleen of mice. In FIGS. 24B-E, all data are means±s.e.m., two-tailed Mann-Whitney analysis was performed, n=5 mice per group. FIG. 24F shows cytotoxic activity of TRAC-1XX, TRAC-XX3 and wild-type TRAC-1928ζ (18-h bioluminescence assay with FFL-expressing NALM6 as targets). Experiments were performed 4 d post transduction, 1 week and 3 weeks after expansion with weekly CD19 antigen stimulations. Symbols demonstrate means of triplicates (one representative donor).

FIGS. 25A-25G depict in vivo T cell exhaustion of TRAC-1928ζ mutants compared to wild-type TRAC-1928ζ. FIG. 25A shows NALM6-bearing mice were treated with 1×10⁵ CAR T cells and euthanized at day 17 after infusion. FACS analysis of expression of exhaustion markers on CAR+ T cells, representative of n=5 mice per group in one independent experiment. FIGS. 25B-25G show NALM6-bearing mice were treated with 1×10⁵ TRAC-edited naive T cells. 16 days (FIGS. 25B and 25C) and 36 days (FIGS. 25E and 25G) after CAR administration, TRAC-1928ζ and TRAC-1XX cells from bone marrow and spleen were exposed to ex vivo stimulation with NALM6 or PMA/Ionomycin (Iono). Cytokine and granzyme B (GrB)/CD107a expression on CAR T cells as demonstrated by percentage of expression and flow cytometric analyses, representative for n=3 mice in two independent experiments (FIG. 25B) and for n=3 replicates (FIG. 25G). Expression of exhaustion markers PD1+LAG3+ on CAR T cells (FIG. 25D) and cytotoxic activity (FIG. 25F) of TRAC-1XX (day 36) after 10 h of co-culture with NALM6. All data are means±s.e.m., n=3 mice per group.

FIGS. 26A-26C show 16 and 36 d after administration of 1×10⁵ TRAC-1928ζ and TRAC-1XX, CARs were isolated from bone marrow and spleen. FIGS. 26A and 26B cell number of CAR T cells (FIG. 26A), central memory ($T_{CM}$: CD62L+CD45RA−), effector ($T_{EFF}$: CD62L-CD45RA+) and IL7R-expressing bone marrow CAR T cells (FIG. 26B). All data are means±s.e.m., n=3 mice per group. FIG. 26C shows representative flow cytometric analysis of CD62L/CD45RA expression on TRAC- 1928ζ and TRAC-1XX bone marrow CAR T cells at day 36 in one independent experiment (n=3 mice per group). FIGS. 26D-26G show NALM6-bearing mice were treated with $5 \times 10^5$ TRAC-edited naive T cells and were either rechallenged with NALM6 cells (n=5 mice per group) or no further rechallenge with tumor was performed (TRAC-1928ζ, n=6 mice; TRAC-1XX, n=7 mice). FIGS. 26D-26E show cell number of total CAR T cells (FIG. 26D), $T_{CM}$, $T_{EFF}$ and IL7R+ CAR T cells (FIG. 26E) in the spleen of treated mice 63 d post CAR administration (rechallenge: TRAC-1928ζ, n=4 mice; TRAC-1XX, n=5 mice. No rechallenge, n=5 mice per group). All data are means±s.e.m.; a two-tailed unpaired Student's t-test was used for statistical analysis. FIG. 26F shows FACS analysis of IL7R–, CD62L– and CD45RA-expression on TRAC-1928ζ and TRAC-1XX CAR T cells at day 63 post CAR infusion (representative for at least n=3 mice per group in one independent experiment). FIG. 26G shows expression of exhaustion markers PD1+ TIM3+LAG3+ on CAR T cells derived from the spleen (rechallenge: TRAC-1928ζ, n=4 mice; TRAC-1XX: n=5 mice. No rechallenge, n=5 mice per group). All data are means±s.e.m.; P value was determined by a two-tailed unpaired Student's t-test.

FIG. 27A shows principal component analysis (PCA) of global transcriptional profiles of CD8+ TRAC-1XX, TRAC-XX3 and TRAC-1928ζ after stimulation with CD19 target cells (left) and of sorted control T cell subsets (right): $T_N$, $T_{SCM}$ and $T_{EFF}$. Experiment was performed in technical triplicates for each CAR construct and in six replicates for each control subset. FIG. 27B shows representative GSEA enrichment plot (GSE10239), demonstrating downregulation of memory-relative to effector-related genes and naive-relative to effector-related genes in 1928ζ versus 1XX and in 1928ζ versus XX3 (n=3 mice per group). FIG. 27C shows heat map of 900 differentially expressed genes among CD8+ T cell subsets as described by Gattinoni et al (left) compared to differential gene expression of sorted control T cell subsets ($T_{EFF}$, $T_{SCM}$ and $T_N$).

FIG. 28A shows GSEA of a signature of the top 200 genes upregulated in exhausted CD8 T cells relative to naive or memory CD8 T cells as derived from GSE41867, demonstrating enrichment of exhaustion signature in TRAC-1928ζ versus TRAC-1XX or TRAC-XX3 and in the sorted control $T_{EFF}$ versus $T_N$ and $T_{SCM}$. Experiment was performed in technical triplicates for each CAR construct and in six replicates for each control subset. FIG. 28B shows gene ontology analysis demonstrating significantly enriched gene sets associated with inflammation, cytokine and chemokine signaling in 1928ζ versus XX3, 1XX versus XX3 and 1928ζ versus 1XX (n=3). Transcriptional analysis was performed after CAR gene integration into the TRAC locus of naive T cells and stimulation with CD19+ target cells. Results are shown in order of significance as $-\log_{10}$ (corrected P value). P values were determined by a one-tailed Fisher's exact test and the Benjamini-Hochberg method was used to correct for multiple hypotheses testing. FIG. 28C shows heat map of selected differentially expressed genes between CAR constructs related to inflammation, cytokine and chemokine activity. FIG. 28D shows flow cytometric analysis of T cell differentiation state on CD8+ CAR T cells after stimulation with CD19 antigen (representative for n=2 independent experiments with similar results).

FIGS. 29A and 29B show representative flow cytometric analysis of TRAC-1928ζ (FIG. 29A) compared to TRAC-1XX (FIG. 29B) on day 17 post CAR infusion. Placement of gating was based on FMO controls.

DETAILED DESCRIPTION OF THE INVENTION

Figure 1A:
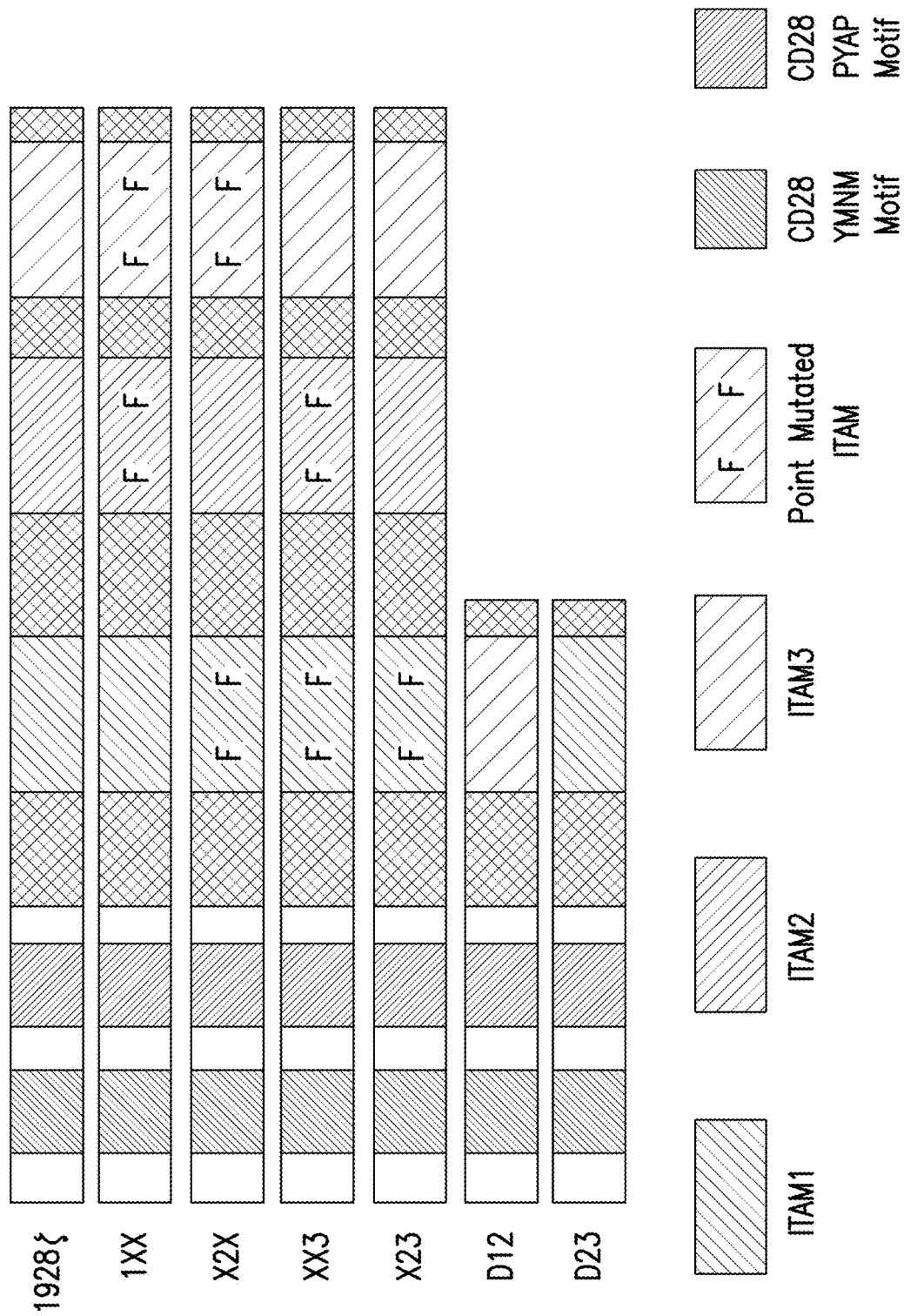
FIGS. 1A-1C depict cytoplasmic regions of wild-type, mutated and truncated 1928ζ(1928z) CARs.

The presently disclosed subject matter provides new CAR designs comprising a modified CD3ζ chain, and cells, including genetically modified immunoresponsive cells (e.g., T cells, NK cells, or CTL cells) comprising said CARs. The presently disclosed subject matter also provides methods of using such cells for inducing and/or enhancing an immune response to a target antigen, and/or treating and/or preventing a neoplasia or other diseases/disorders where an increase in an antigen-specific immune response is desired. The presently disclosed subject matter is based, at least in part, on the discovery that immunoresponsive cells comprising a presently disclosed CAR exhibited improved therapeutic potency (e.g., decreased cell exhaustion) compared to control cells which comprises conventional CARs.

1. Definitions

Unless defined otherwise, all technical and scientific terms used herein have the meaning commonly understood by a person skilled in the art. The following references provide one of skill with a general definition of many of the terms used in the presently disclosed subject matter: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold or within 2-fold, of a value.

By "activates an immunoresponsive cell" is meant induction of signal transduction or changes in protein expression in the cell resulting in initiation of an immune response. For example, when CD3 Chains cluster in response to ligand binding and immunoreceptor tyrosine-based inhibition motifs (ITAMs) a signal transduction cascade is produced. In certain embodiments, when an endogenous TCR or an exogenous CAR binds to an antigen, a formation of an immunological synapse occurs that includes clustering of many molecules near the bound receptor (e.g. CD4 or CD8, CD3γ/δ/ε/ζ, etc.). This clustering of membrane bound signaling molecules allows for ITAM motifs contained within the CD3 chains to become phosphorylated. This phosphorylation in turn initiates a T cell activation pathway ultimately activating transcription factors, such as NF-κB and AP-1. These transcription factors induce global gene expression of the T cell to increase IL-2 production for proliferation and expression of master regulator T cell proteins in order to initiate a T cell mediated immune response.

By "stimulates an immunoresponsive cell" is meant a signal that results in a robust and sustained immune response. In various embodiments, this occurs after immune cell (e.g., T-cell) activation or concomitantly mediated through receptors including, but not limited to, CD28, CD137 (4-1BB), OX40, CD40, CD27, CD40/My88, NKGD2 and ICOS. Receiving multiple stimulatory signals can be important to mount a robust and long-term T cell mediated immune response. T cells can quickly become inhibited and unresponsive to antigen. While the effects of these co-stimulatory signals may vary, they generally result in increased gene expression in order to generate long lived, proliferative, and anti-apoptotic T cells that robustly respond to antigen for complete and sustained eradication.

The term "antigen-recognizing receptor" as used herein refers to a receptor that is capable of activating an immune or immunoresponsive cell (e.g., a T-cell) in response to its binding to an antigen. Non-limiting examples of antigen-recognizing receptors include native or endogenous T cell receptors ("TCRs"), and chimeric antigen receptors ("CARs").

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983). As used herein, antibodies include whole native antibodies, bispecific antibodies; chimeric antibodies; Fab, Fab', single chain V region fragments (scFv), fusion polypeptides, and unconventional antibodies. In certain embodiments, an antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant ($C_H$) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. (1991) Sequences of Proteins of Immunological Interest, Fifth Edition, U.S. Department of Health and Human Services, NIH Publication No. 91-3242).

As used herein, the term "single-chain variable fragment" or "scFv" is a fusion protein of the variable regions of the heavy ($V_H$) and light chains ($V_L$) of an immunoglobulin covalently linked to form a $V_H$::$V_L$ heterodimer. The $V_H$ and $V_L$ are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278ζ 38):36740-7; Xie et al., Nat Biotech 1997 15(8):768-71; Ledbetter et al., Crit Rev Immunol 1997 17(5-6):427-55; Ho et al., BioChim Biophys Acta 2003 1638ζ 3):257-66).

As used herein, the term "affinity" is meant a measure of binding strength. Affinity can depend on the closeness of stereochemical fit between antibody combining sites and antigen determinants, on the size of the area of contact between them, and/or on the distribution of charged and hydrophobic groups. As used herein, the term "affinity" also includes "avidity", which refers to the strength of the antigen-antibody bond after formation of reversible complexes. Methods for calculating the affinity of an antibody for an antigen are known in the art, including, but not limited to, various antigen-binding experiments, e.g., functional assays (e.g., flow cytometry assay).

The term "chimeric antigen receptor" or "CAR" as used herein refers to a molecule comprising an extracellular antigen-binding domain that is fused to an intracellular signaling domain that is capable of activating or stimulating an immunoresponsive cell, and a transmembrane domain. In certain embodiments, the extracellular antigen-binding domain of a CAR comprises a scFv. The scFv can be derived from fusing the variable heavy and light regions of an antibody. Alternatively or additionally, the scFv may be derived from Fab's (instead of from an antibody, e.g., obtained from Fab libraries). In certain embodiments, the scFv is fused to the transmembrane domain and then to the intracellular signaling domain. In certain embodiments, the CAR is selected to have high binding affinity or avidity for the antigen.

As used herein, the term "nucleic acid molecules" include any nucleic acid molecule that encodes a polypeptide of interest or a fragment thereof. Such nucleic acid molecules need not be 100% homologous or identical with an endogenous nucleic acid sequence, but may exhibit substantial identity. Polynucleotides having "substantial identity" or "substantial homology" to an endogenous sequence are typically capable of hybridizing with at least one strand of a double-stranded nucleic acid molecule. By "hybridize" is meant a pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, e.g., less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, e.g., at least about 50% formamide. Stringent temperature conditions will ordinarily include temperatures of at least about 30° C., at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In certain embodiments, hybridization will occur at 30° C. in 750 mM NaCl, 75 mM trisodium citrate, and 1% SDS. In certain embodiments, hybridization will occur at 37° C. in 500 mM NaCl, 50 mM trisodium citrate, 1% SDS, 35% formamide, and 100 µg/ml denatured salmon sperm DNA (ssDNA). In certain embodiments, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate, e.g., less than about 15 mM NaCl and 1.5 mM trisodium citrate. Stringent temperature conditions for the wash steps will ordinarily include a temperature of at least about 25° C., of at least about 42° C., or of at least about 68° C. In certain embodiments, wash steps will occur at 25° C. in 30 mM NaCl, 3 mM trisodium citrate, and 0.1% SDS. In certain embodiments, wash steps will occur at 42° C. in 15 mM NaCl, 1.5 mM trisodium citrate, and 0.1% SDS. In certain embodiments, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" or "substantially homologous" is meant a polypeptide or nucleic acid molecule exhibiting at least about 50% homologous or identical to a reference amino acid sequence (for example, any one of the amino acid sequences described herein) or nucleic acid sequence (for example, any one of the nucleic acid sequences described herein). In certain embodiments, such a sequence is at least about 60%, at least about 65%, at least about 70%, at least about 75%, at least about 80%, at least about 85%, at least about 90%, at least about 95%, at least about 99%, or at least about 100% homologous or identical to the sequence of the amino acid or nucleic acid used for comparison.

Sequence identity can be measured by using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "analog" is meant a structurally related polypeptide or nucleic acid molecule having the function of a reference polypeptide or nucleic acid molecule.

The term "ligand" as used herein refers to a molecule that binds to a receptor. In certain embodiments, the ligand binds to a receptor on another cell, allowing for cell-to-cell recognition and/or interaction.

The term "constitutive expression" or "constitutively expressed" as used herein refers to expression or expressed under all physiological conditions.

By "disease" is meant any condition, disease or disorder that damages or interferes with the normal function of a cell, tissue, or organ, e.g., neoplasia, and pathogen infection of cell.

By "effective amount" is meant an amount sufficient to have a therapeutic effect. In certain embodiments, an "effective amount" is an amount sufficient to arrest, ameliorate, or inhibit the continued proliferation, growth, or metastasis (e.g., invasion, or migration) of a neoplasia.

By "enforcing tolerance" is meant preventing the activity of self-reactive cells or immunoresponsive cells that target transplanted organs or tissues.

By "endogenous" is meant a nucleic acid molecule or polypeptide that is normally expressed in a cell or tissue.

By "exogenous" is meant a nucleic acid molecule or polypeptide that is not endogenously present in a cell. The term "exogenous" would therefore encompass any recombinant nucleic acid molecule or polypeptide expressed in a cell, such as foreign, heterologous, and over-expressed nucleic acid molecules and polypeptides. By "exogenous" nucleic acid is meant a nucleic acid not present in a native wild-type cell; for example, an exogenous nucleic acid may vary from an endogenous counterpart by sequence, by position/location, or both. For clarity, an exogenous nucleic acid may have the same or different sequence relative to its native endogenous counterpart; it may be introduced by genetic engineering into the cell itself or a progenitor thereof, and may optionally be linked to alternative control sequences, such as a non-native promoter or secretory sequence.

By a "heterologous nucleic acid molecule or polypeptide" is meant a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

By "immunoresponsive cell" is meant a cell that functions in an immune response or a progenitor, or progeny thereof.

By "modulate" is meant positively or negatively alter. Exemplary modulations include a about 1%, about 2%, about 5%, about 10%, about 25%, about 50%, about 75%, or about 100% change.

By "increase" is meant to alter positively by at least about 5%. An alteration may be by about 5%, about 10%, about 25%, about 30%, about 50%, about 75%, about 100% or more.

By "reduce" is meant to alter negatively by at least about 5%. An alteration may be by about 5%, about 10%, about 25%, about 30%, about 50%, about 75%, or even by about 100%.

By "isolated cell" is meant a cell that is separated from the molecular and/or cellular components that naturally accompany the cell.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

The term "antigen-binding domain" as used herein refers to a domain capable of specifically binding a particular antigenic determinant or set of antigenic determinants present on a cell.

"Linker", as used herein, shall mean a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). In certain embodiments, the linker comprises a sequence set forth in GGGGSGGGGSGGGGS [SEQ ID NO: 66].

By "neoplasm" is meant a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasia can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasia include cancers, such as sarcomas, carcinomas, or plasmacytomas (malignant tumor of the plasma cells).

By "receptor" is meant a polypeptide, or portion thereof, present on a cell membrane that selectively binds one or more ligand.

By "recognize" is meant selectively binds to a target. A T cell that recognizes a tumor can expresses a receptor (e.g., a TCR or CAR) that binds to a tumor antigen.

By "reference" or "control" is meant a standard of comparison. For example, the level of scFv-antigen binding by a cell expressing a CAR and an scFv may be compared to the level of scFv-antigen binding in a corresponding cell expressing CAR alone.

By "secreted" is meant a polypeptide that is released from a cell via the secretory pathway through the endoplasmic reticulum, Golgi apparatus, and as a vesicle that transiently fuses at the cell plasma membrane, releasing the proteins outside of the cell.

By "signal sequence" or "leader sequence" is meant a peptide sequence (e.g., 5, 10, 15, 20, 25 or 30 amino acids) present at the N-terminus of newly synthesized proteins that directs their entry to the secretory pathway. Exemplary leader sequences include, but is not limited to, the L-2 signal sequence: MYRMQLLSCIALSLALVTNS [SEQ ID NO: 67] (human), MYSMQLASCVTLTLVLLVNS [SEQ ID NO: 68] (mouse); the kappa leader sequence: METPAQLLFLLLLWLPDTTG [SEQ ID NO: 69] (human), METDTLLLWVLLLWVPGSTG [SEQ ID NO: 70] (mouse); the CD8 leader sequence: MALPVTALLLPLALLLHAARP [SEQ ID NO: 71] (human); the truncated human CD8 signal peptide: MALPVTALLLPLALLLHA [SEQ ID NO: 72] (human); the albumin signal sequence: MKWVTFISLLFSSAYS [SEQ ID NO: 73](human); and the prolactin signal sequence: MDSKGSSQKGSRLLLLL-VVSNLLLCQGVVS [SEQ ID NO: 74] (human). In certain embodiments, a leader sequence can be an IgG signal peptide or a GM-CSF signal peptide. By "soluble" is meant a polypeptide that is freely diffusible in an aqueous environment (e.g., not membrane bound).

By "specifically binds" is meant a polypeptide or fragment thereof that recognizes and binds to a biological molecule of interest (e.g., a polypeptide), but which does not substantially recognize and bind other molecules in a sample, for example, a biological sample, which naturally includes a presently disclosed polypeptide.

The term "tumor antigen" as used herein refers to an antigen (e.g., a polypeptide) that is uniquely or differentially expressed on a tumor cell compared to a normal or non-IS neoplastic cell. In certain embodiments, a tumor antigen includes any polypeptide expressed by a tumor that is capable of activating or inducing an immune response via a CAR (e.g., CD19, MUC-16) or capable of suppressing an immune response via receptor-ligand binding (e.g., CD47, PD-L1/L2, B7.1/2).

The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys. The term "immunocompromised" as used herein refers to a subject who has an immunodeficiency. The subject is very vulnerable to opportunistic infections, infections caused by organisms that usually do not cause disease in a person with a healthy immune system, but can affect people with a poorly functioning or suppressed immune system.

Other aspects of the presently disclosed subject matter are described in the following disclosure and are within the ambit of the presently disclosed subject matter.

2. Chimeric Antigen Receptor

The present disclosure provides chimeric antigen receptors (CARs) that bind to an antigen of interest. The CAR can bind to a tumor antigen or a pathogen antigen.

2.1. Antigens

In certain embodiments, the CAR binds to a tumor antigen. Any tumor antigen (antigenic peptide) can be used in the tumor-related embodiments described herein. Sources of antigen include, but are not limited to, cancer proteins. The antigen can be expressed as a peptide or as an intact protein or portion thereof. The intact protein or a portion thereof can be native or mutagenized. Non-limiting examples of tumor antigens include carbonic anhydrase IX (CAIX), carcinoembryonic antigen (CEA), CD8, CD7, CD10, CD19, CD20, CD22, CD30, CD33, CLL1, CD34, CD38, CD41, CD44, CD49f, CD56, CD74, CD133, CD138, CD123, CD44V6, an antigen of a cytomegalovirus (CMV) infected cell (e.g., a cell surface antigen), epithelial glycoprotein-2 (EGP-2), epithelial glycoprotein-40 (EGP-40), epithelial cell adhesion molecule (EpCAM), receptor tyrosine-protein kinases erb-B2,3,4 (erb-B2,3,4), folate-binding protein (FBP), fetal acetylcholine receptor (AChR), folate receptor-α, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis Y (LeY), L1 cell adhesion molecule (L1CAM), melanoma antigen family A, 1 (MAGE-A1), Mucin 16 (MUC16), Mucin 1 (MUC1), Mesothelin (MSLN), ERBB2, MAGEA3, p53, MART1, GP100, Proteinase3 (PR1), Tyrosinase, Survivin, hTERT, EphA2, NKG2D ligands, cancer-testis antigen NY-ESO-1, oncofetal antigen (h5T4), prostate stem cell antigen (PSCA), prostate-specific membrane antigen (PSMA), ROR1, tumor-associated glycoprotein 72 (TAG-72), vascular endothelial growth factor R2 (VEGF-R2), and Wilms tumor protein (WT-1), BCMA, NKCS1, EGF1R, EGFR-VIII, CD99, CD70, ADGRE2, CCR1, LILRB2, PRAME CCR4, CD5, CD3, TRBC1, TRBC2, TIM-3, Integrin B7, ICAM-1, CD70, Tim3, CLEC12A and ERBB.

In certain embodiments, the CAR binds to a CD19 polypeptide. In certain embodiments, the CAR binds to a human CD19 polypeptide. In certain embodiments, the human CD19 polypeptide comprises the amino acid sequence set forth in SEQ ID NO: 75.

[SEQ ID NO: 75]
PEEPLVVKVEEGDNAVLQCLKGTSDGPTQQLTWSRESPLKPFLKLSLGLP

GLGIHMRPLAIWLFIFNVSQQMGGFYLCQPGPPSEKAWQPGWTVNVEGSG

ELFRWNVSDLGGLGCGLKNRSSEGPSSPSGKLMSPKLYVWAKDRPEIWEG

EPPCLPPRDSLNQSLSQDLTMAPGSTLWLSCGVPPDSVSRGPLSWTHVHP

KGPKSLLSLELKDDRPARDMWVMETGLLLPRATAQDAGKYYCHRGNLTMS

FHLEITARPVLWHWLLRTGGWK

In certain embodiments, the CAR binds to the extracellular domain of a CD19 protein.

In certain embodiments, the CAR binds to a pathogen antigen, e.g., for use in treating and/or preventing a pathogen infection or other infectious disease, for example, in an immunocompromised subject. Non-limiting examples of pathogen includes a virus, bacteria, fungi, parasite and protozoa capable of causing disease.

Non-limiting examples of viruses include, Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Naira viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Non-limiting examples of bacteria include *Pasteurella, Staphylococci, Streptococcus, Escherichia coli, Pseudomonas species*, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelli*.

In certain embodiments, the pathogen antigen is a viral antigen present in Cytomegalovirus (CMV), a viral antigen present in Epstein Barr Virus (EBV), a viral antigen present in Human Immunodeficiency Virus (HIV), or a viral antigen present in influenza virus.

2.2. Chimeric Antigen Receptor (CAR)

CARs are engineered receptors, which graft or confer a specificity of interest onto an immune effector cell. CARs can be used to graft the specificity of a monoclonal antibody onto a T cell; with transfer of their coding sequence facilitated by retroviral vectors.

There are three generations of CARs. "First generation" CARs are typically composed of an extracellular antigen-binding domain (e.g., a scFv), which is fused to a transmembrane domain, which is fused to cytoplasmic/intracellular signaling domain. "First generation" CARs can provide de novo antigen recognition and cause activation of both CD4$^+$ and CD8$^+$ T cells through their CD3ζ chain signaling domain in a single fusion molecule, independent of HLA-mediated antigen presentation. "Second generation" CARs add intracellular signaling domains from various co-stimulatory molecules (e.g., CD28, 4-1BB, ICOS, OX40, CD27, CD40/My88 and NKGD2) to the cytoplasmic tail of the CAR to provide additional signals to the T cell. "Second generation" CARs comprise those that provide both co-stimulation (e.g., CD28 or 4-1BB) and activation (CD3ζ). "Third generation" CARs comprise those that provide multiple co-stimulation (e.g., CD28 and 4-1BB) and activation (CD3ζ). In certain embodiments, the CAR is a second-generation CAR. In certain embodiments, the CAR comprises an extracellular antigen-binding domain that binds to an antigen, a transmembrane domain, and an intracellular signaling domain, wherein the intracellular signaling domain comprises a co-stimulatory signaling domain. In certain embodiments, the CAR further comprises a hinger/spacer region.

In certain non-limiting embodiments, the extracellular antigen-binding domain of the CAR (embodied, for example, an scFv or an analog thereof) binds to an antigen with a dissociation constant ($K_d$) of about $2 \times 10^{-7}$ M or less. In certain embodiments, the $K_d$ is about $2 \times 10^{-7}$ M or less, about $1 \times 10^{-7}$ M or less, about $9 \times 10^{-8}$ M or less, about $1 \times 10^{-8}$ M or less, about $9 \times 10^{-9}$ M or less, about $5 \times 10^{-9}$ M or less, about $4 \times 10^{-9}$ M or less, about $3 \times 10^{-9}$ M or less, about $2 \times 10^{-9}$ M or less, or about $1 \times 10^{-9}$ M or less. In certain non-limiting embodiments, the $K_d$ is about $3 \times 10^{-9}$ M or less. In certain non-limiting embodiments, the $K_d$ is from about $1 \times 10^{-9}$ M to about $3 \times 10^{-7}$ M. In certain non-limiting embodiments, the $K_d$ is from about $1.5 \times 10^{-9}$ M to about $3 \times 10^{-7}$ M. In certain non-limiting embodiments, the $K_d$ is from about $1.5 \times 10^{-9}$ M to about $2.7 \times 10^{-7}$ M. In certain non-limiting embodiments, the $K_d$ is from about $1 \times 10^{-4}$ M to about $1 \times 10^{-6}$ M. In certain non-limiting embodiments, the $K_d$ is from about $1 \times 10^{-13}$ M to about $1 \times 10^{-15}$ M.

Binding of the extracellular antigen-binding domain (for example, in an scFv or an analog thereof) can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or an scFv) specific for the complex of interest. For example, the scFv can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography. In certain embodiments, the extracellular antigen-binding domain of the CAR is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet).

2.2.1. Extracellular Antigen-Binding Domain of a CAR

In certain embodiments, the extracellular antigen-binding domain specifically binds to an antigen. In certain embodiments, the extracellular antigen-binding domain is an scFv. In certain embodiments, the scFv is a human scFv. In certain embodiments, the scFv is a humanized scFv. In certain embodiments, the scFv is a murine scFv. In certain embodiments, the extracellular antigen-binding domain is a Fab, which is optionally crosslinked. In certain embodiments, the extracellular antigen-binding domain is a F(ab)$_2$. In certain embodiments, any of the foregoing molecules may be comprised in a fusion protein with a heterologous sequence to form the extracellular antigen-binding domain. In certain embodiments, the scFv is identified by screening scFv phage library with an antigen-Fc fusion protein. The scFv can be derived from a mouse bearing human VL and/or VH genes. The scFv can also be substituted with a camelid Heavy chain (e.g., VHH, from camel, lama, etc.) or a partial natural ligand for a cell surface receptor. In certain embodiments, the antigen is a tumor antigen, e.g., one disclosed herein. In certain embodiments, the antigen is a pathogen antigen, e.g., one disclosed herein.

In certain embodiments, the extracellular antigen-binding domain is a murine scFv. In certain embodiments, the extracellular antigen-binding domain is a murine scFv that binds to a human CD19 polypeptide. In certain embodiments, the extracellular antigen-binding domain is a murine scFv, which comprises the amino acid sequence of SEQ ID NO: 84 and specifically binds to a human CD19 polypeptide (e.g., a human CD19 polypeptide comprising the amino acid sequence set forth in SEQ ID NO: 75). In certain embodiments, the nucleotide sequence encoding the amino acid sequence of SEQ ID NO: 84 is set forth in SEQ ID NO: 85. In certain embodiments, the murine scFv comprises a heavy chain variable region (V$_H$) comprising the amino acid sequence set forth in SEQ ID NO: 82. In certain embodiments, the murine scFV comprises a light chain variable region ($V_L$) comprising the amino acid sequence set forth in SEQ ID NO: 83. In certain embodiments, the murine scFv comprises $V_H$ comprising the amino acid sequence set forth in SEQ ID NO: 82 and a $V_L$ comprising the amino acid sequence set forth in SEQ ID NO: 83, optionally with (iii) a linker sequence, for example a linker peptide, between the $V_H$ and the $V_L$. In certain embodiments, the linker comprises amino acids having the sequence set forth in SEQ ID NO: 66. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 82. For example, the extracellular antigen-binding domain comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 82. In certain embodiments, the extracellular antigen-binding domain comprises a $V_H$ comprising the amino sequence set forth in SEQ ID NO: 82. In certain embodiments, the extracellular antigen-binding domain comprises a $V_L$ comprising an amino acid sequence that is at least about 80% (e.g., at least about 85%, at least about 90%, or at least about 95%) homologous to SEQ ID NO: 83. For example, the extracellular antigen-binding domain comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 83. In certain embodiments, the extracellular antigen-binding domain comprises a $V_L$ comprising the amino acid sequence set forth in SEQ ID NO: 83. certain embodiments, the extracellular antigen-binding domain comprises a $V_H$ comprising an amino acid sequence that is at least about 80% (e.g., at least about 85%, at least about 90%, or at least about 95%) homologous or identical to SEQ ID NO: 82, and a $V_L$ comprising an amino acid sequence that is at least about 80% (e.g., at least about 85%, at least about 90%, or at least about 95%) homologous or identical to SEQ ID NO: 83. In certain embodiments, the extracellular antigen-binding domain comprises a $V_H$ comprising the amino acid sequence set forth in SEQ ID NO: 82 and a $V_L$ comprising the amino acid sequence set forth in SEQ ID NO: 83. In certain embodiments, the extracellular antigen-binding domain comprises a $V_H$ CDR1 comprising the amino acid sequence set forth in SEQ ID NO: 76, or a conservative modification thereof, a $V_H$ CDR2 comprising the amino acid sequence set forth in SEQ ID NO: 77 or a conservative modification thereof, and a $V_H$ CDR3 comprising the amino acid sequence set forth in SEQ ID NO: 78, a conservative modification thereof. In certain embodiments, the extracellular antigen-binding domain comprises a $V_H$ CDR1 comprising the amino acid sequence set forth in SEQ ID NO: 76, a $V_H$ CDR2 comprising the amino acid sequence set forth in SEQ ID NO: 77, and a $V_H$ CDR3 comprising the amino acid sequence set forth in SEQ ID NO: 78. In certain embodiments, the extracellular antigen-binding domain comprises a $V_L$ CDR1 comprising the amino acid sequence set forth in SEQ ID NO: 79 or a conservative modification thereof, a $V_L$ CDR2 comprising the amino acid sequence set forth in SEQ ID NO: 80 or a conservative modification thereof, and a $V_L$ CDR3 comprising the amino acid sequence set forth in SEQ ID NO: 81 or a conservative modification thereof. In certain embodiments, the extracellular antigen-binding domain comprises a $V_L$ CDR1 comprising the amino acid sequence set forth in SEQ ID NO: 79, a $V_L$ CDR2 comprising the amino acid sequence set forth in SEQ ID NO: 80, and a $V_L$ CDR3 comprising the amino acid sequence set forth in SEQ ID NO: 81. In certain embodiments, the extracellular antigen-binding domain comprises a $V_H$ CDR1 comprising the amino acid sequence set forth in SEQ ID NO: 76 or a conservative modification thereof, a $V_H$ CDR2 comprising the amino acid sequence set forth in SEQ ID NO: 77 or a conservative modification thereof, a $V_H$ CDR3 comprising the amino acid sequence set forth in SEQ ID NO: 78, a conservative modification thereof, a $V_L$ CDR1 comprising the amino acid sequence set forth in SEQ ID NO: 79 or a conservative modification thereof, a $V_L$ CDR2 comprising the amino acid sequence set forth in SEQ ID NO: 80 or a conservative modification thereof, and a $V_L$ CDR3 comprising the amino acid sequence set forth in SEQ ID NO: 81 or a conservative modification thereof. In certain embodiments, the extracellular antigen-binding domain comprises a $V_H$ CDR1 comprising amino acids having the sequence set forth in SEQ ID NO:76, a $V_H$ CDR2 comprising the amino acid sequence set forth in SEQ ID NO: 77, a $V_H$ CDR3 comprising the amino acid sequence set forth in SEQ ID NO: 78, $V_L$ CDR1 comprising the amino acid sequence set forth in SEQ ID NO: 79, $V_L$ CDR2 comprising the amino acid sequence set forth in SEQ ID NO: 80 and a $V_L$ CDR3 comprising the amino acid sequence set forth in SEQ ID NO: 81.

TABLE 1

| anti-human CD19 scFv (SJ25C1) | | | |
|---|---|---|---|
| CDRs | 1 | 2 | 3 |
| $V_H$ a.a. | GYAFSS [SEQ ID NO: 76] | YPGDGD [SEQ ID NO: 77] | KTISSWDF [SEQ ID NO: 78] |
| $V_L$ a.a. | KASQNVGTNVA [SEQ ID NO: 79] | SATYRN [SEQ ID NO: 80] | QQYNRYPYT [SEQ ID NO: 81] |
| Full $V_H$ | EVKLQQSGAE LVRPGSSVKI SCKASGYAFS SYWMNWVKQR PGQGLEWIGQ IYPGDGDTNY NGKFKGQATL TADKSSSTAY MQLSGLTSED SAVYFCARKT ISSWDFYFD YWGQGTTVTV SS [SEQ ID NO: 82] | | |
| Full $V_L$ | DIELTQSPKF MSTSVGDRVS VTCKASQNVG TNVAWYQQKP GQSPKPLIYS ATYRNSGVPD RFTGSGSGTD FTLTITNVQS KDLADYFCQQ YNRYPYTSGG GTKLEIKR [SEQ ID NO: 83] | | |
| scFv | MALPVTALLL PLALLLHAEV KLQQSGAELV RPGSSVKISC KASGYAFSSY WMNWVKQRPG QGLEWIGQIY PGDGDTNYNG KFKGQATLTA DKSSSTAYMQ LSGLTSEDSA VYFCARKTIS SVVDFYFDYW GQGTTVTVSS GGGGSGGGGS GGGGSDIELT QSPKFMSTSV GDRVSVTCKA SQNVGTNVAW YQQKPGQSPK PLIYSATYRN SGVPDRFTGS GSGTDFTLTI TNVQSKDLAD YFCQQYNRYP YTSGGGTKLE IKR [SEQ ID NO: 85] | | |
| DNA | ATGGCTCTCCCAGTGACTGCCCTACTGCTTCCC CTAGCGCTTCTCCTGCATGCAGAGGTGAAGCTGC AGCAGTCTGGGGCTGAGCTGGTGAGGCCTGGGTC CTCAGTGAAGATTTCCTGCAAGGCTTCTGGCTAT GCATTCAGTAGCTACTGGATGAACTGGGTGAAGCA GAGGCCTGGACAGGGTCTTGAGTGGATTGGACAGA TTTATCCTGGAGATGGTGATACTAACTACAATGGA | | |

TABLE 1-continued anti-human CD19 scFv (SJ25C1)

| CDRs | 1 | 2 | 3 |
|---|---|---|---|
| | AAGTTCAAGGGTCAAGCCACACTGACTGCAGACAA | | |
| | ATCCTCCAGCACAGCCTACATGCAGCTCAGCGGCC | | |
| | TAACATCTGAGGACTCTGCGGTCTATTTCTGTGCA | | |
| | AGAAAGACCATTAGTTCGGTAGTAGATTTCTACTT | | |
| | TGACTACTGGGGCCAAGGGACCACGGTCACCGTCT | | |
| | CCTCAGGTGGAGGTGGATCAGGTGGAGGTGGATCT | | |
| | GGTGGAGGTGGATCTGACATTGAGCTCACCCAGTC | | |
| | TCCAAAATTCATGTCCACATCAGTAGGAGACAGGG | | |
| | TCAGCGTCACCTGCAAGGCCAGTCAGAATGTGGGT | | |
| | ACTAATGTAGCCTGGTATCAACAGAAACCAGGACA | | |
| | ATCTCCTAAACCACTGATTTACTCGGCAACCTACC | | |
| | GGAACAGTGGAGTCCCTGATCGCTTCACAGGCAGT | | |
| | GGATCTGGGACAGATTTCACTCTCACCATCACTAA | | |
| | CGTGCAGTCTAAAGACTTGGCAGACTATTTCTGTC | | |
| | AACAATATAACAGGTATCCGTACACGTCCGGAGGG | | |
| | GGGACCAAGCTGGAGATCAAACGG | | |
| | [SEQ ID NO: 85] | | |

As used herein, the term "a conservative sequence modification" refers to an amino acid modification that does not significantly affect or alter the binding characteristics of the presently disclosed CAR (e.g., the extracellular antigen-binding domain of the CAR) comprising the amino acid sequence. Conservative modifications can include amino acid substitutions, additions and deletions. Modifications can be introduced into the human scFv of the presently disclosed CAR by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (1) above) using the functional assays described herein. In certain embodiments, no more than one, no more than two, no more than three, no more than four, no more than five residues within a specified sequence or a CDR region are altered.

The $V_H$ and/or $V_L$ amino acid sequences having at least about 80%, at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homology or identity to a specific sequence (e.g., SEQ ID NOs: 82 and 83) may contain substitutions (e.g., conservative substitutions), insertions, or deletions relative to the specified sequence(s), but retain the ability to bind to a target antigen (e.g., CD19). In certain embodiments, a total of 1 to 10 amino acids are substituted, inserted, and/or deleted in a specific sequence (e.g., SEQ ID NOs: 82, and 83). In certain embodiments, substitutions, insertions, or deletions occur in regions outside the CDRs (e.g., in the FRs) of the extracellular antigen-binding domain. In certain embodiments, the extracellular antigen-binding domain comprises $V_H$ and/or $V_L$ sequence selected from the group consisting of SEQ ID NOs: 82, and 83, including post-translational modifications of that sequence (SEQ ID NO: 82 and 83).

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the amino acids sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the specified sequences (e.g., heavy and light chain variable region sequences of scFv m903, m904, m905, m906, and m900) disclosed herein. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

2.2.2. Transmembrane Domain of a CAR

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal are transmitted to the cell. In accordance with the presently disclosed subject matter, the transmembrane domain of the CAR can comprise a native or modified transmembrane domain of a CD8 polypeptide, a CD28 polypeptide, a CD3ζ polypeptide, a CD40 polypeptide, a 4-1BB polypeptide, an OX40 polypeptide, a CD84 polypeptide, a CD166 polypeptide, a CD8a polypeptide, a CD8b polypeptide, an ICOS polypeptide, an ICAM-1 polypeptide, a CTLA-4 polypeptide, a CD27 polypeptide, a CD40/My88 peptide, a NKGD2 peptide, a synthetic polypeptide (not based on a protein associated with the immune response), or a combination thereof.

CD8

In certain embodiments, the transmembrane domain comprises a CD8 polypeptide. In certain embodiments, the CD8 polypeptide comprises or has an amino acid sequence that is at least about 80%, at least about 85%, at least about 90%, at least about 95%, at least about 96%, at least about 97%, at least about 98%, at least about 99% or at least about 100% homologous or identical to the sequence having a NCBI Reference No: NP_001139345.1 (SEQ ID NO: 86) (homology herein may be determined using standard software such as BLAST or FASTA) as provided below, or fragments thereof, and/or may optionally comprise up to one or up to two or up to three conservative amino acid substitutions. In certain embodiments, the CD8 polypeptide comprises or has an amino acid sequence that is a consecutive portion of SEQ ID NO: 86 which is at least 20, or at least 30, or at least 40, or at least 50, and up to 235 amino acids in length. Alternatively or additionally, in non-limiting various embodiments, the CD8 polypeptide comprises or has an amino acid sequence of amino acids 1 to 235, 1 to 50, 50 to 100, 100 to 150, 150 to 200, or 200 to 235 of SEQ ID NO: 86. In certain embodiments, the CAR of the presently disclosed comprises a transmembrane domain comprising a CD8 polypeptide that comprises or has an amino acid sequence of amino acids 137 to 209 of SEQ ID NO: 86.

```
                                          [SEQ ID NO: 86]
MALPVTALLLPLALLLHAARPSQFRVSPLDRT

WNLGETVELKCQVLLSNPTSGCSWLFQPRGAA

ASPTFLLYLSQNKPKAAEGLDTQRFSGKRLGDT

FVLTLSDFRRENEGYYFCSALSNSIMYFSHFVP

VFLPAKPTTTPAPRPPTPAPTIASQPLSLRPEA

CRPAAGGAVHTRGLDFACDIYIWAPLAGTCGVL

LLSLVITLYCNHRNRRRVCKCPRPVVKSGDKPS

LSARYV
```

In certain embodiments, the CD8 polypeptide comprises or has an amino acid sequence that is at least about 80%, at least about 85%, at least about 90%, at least about 95%, at least about 96%, at least about 97%, at least about 98%, at least about 99% or at least about 100% homologous or identical to the sequence having a NCBI Reference No: AAA92533.1 (SEQ ID NO: 87) (homology herein may be determined using standard software such as BLAST or FASTA) as provided below, or fragments thereof, and/or may optionally comprise up to one or up to two or up to three conservative amino acid substitutions. In certain embodiments, the CD8 polypeptide comprises or has an amino acid sequence that is a consecutive portion of SEQ ID NO: 87 which is at least about 20, or at least about 30, or at least about 40, or at least about 50, or at least about 60, or at least about 70, or at least about 100, or at least about 200, and up to 247 amino acids in length. Alternatively or additionally, in non-limiting various embodiments, the CD8 polypeptide comprises or has an amino acid sequence of amino acids 1 to 247, 1 to 50, 50 to 100, 100 to 150, 150 to 200, 151 to 219, or 200 to 247 of SEQ ID NO: 87. In certain embodiments, the CAR of the presently disclosed comprises a transmembrane domain comprising a CD8 polypeptide that comprises or has an amino acid sequence of amino acids 151 to 219 of SEQ ID NO: 87.

```
                                          [SEQ ID NO: 87]
  1    MASPLTRELS  LNLLLMGESI  ILGSGEAKPQ

APELRIFPKK  MDAELGQKVD  LVCEVLGSVS

61    QGCSWLFQNS  SSKLPQPTFV  VYMASSHNKI

TWDEKLNSSK  LFSAVRDTNN  KYVLTLNKFS

121    KENEGYYFCS  VISNSVMYFS  SVVPVLQKVN

STTTKPVLRT  PSPVHPTGTS  QPQRPEDCRP

181    RGSVKGTGLD  FACDIYIWAP  LAGICVAPLL

SLIITLICYH  RSRKRVCKCP  RPLVRQEGKP

241    RPSEKIV
```

In certain embodiments, the CD8 polypeptide comprises or has the amino acid sequence set forth in SEQ ID NO: 88, which is provided below:

```
                                          [SEQ ID NO: 88]
STTTKPVLRTPSPVHPTGTSQPQRPEDCRPRGSVK

GTGLDFACDIYIWAPLAGICVALLLSLITTLICY
```

In accordance with the presently disclosed subject matter, a "CD8 nucleic acid molecule" refers to a polynucleotide encoding a CD8 polypeptide.

In certain embodiments, the CD8 nucleic acid molecule encoding the CD8 polypeptide having the amino acid sequence set forth in SEQ ID NO: 88 comprises or has nucleic acids having the sequence set forth in SEQ ID NO: 89 as provided below.

```
                                          [SEQ ID NO: 89]
TCTACTACTACCAAGCCAGTGCTGCGAACTCCCTCA

CCTGTGCACCCTACCGGGACATCTCAGCCCCAGAGA

CCAGAAGATTGTCGGCCCCGTGGCTCAGTGAAGGGG

ACCGGATTGGACTTCGCCTGTGATATTTACATCTGG

GCACCCTTGGCCGGAATCTGCGTGGCCCTTCTGCTG

TCCTTGATCATCACTCTCATCTGCTAC
```

CD28

In certain embodiments, the transmembrane domain of a presently disclosed CAR comprises a CD28 polypeptide. The CD28 polypeptide can have an amino acid sequence that is at least about 80%, at least about 85%, at least about 90%, at least about 95%, at least about 96%, at least about 97%, at least about 98%, at least about 99% or at least about 100% homologous or identical to the sequence having a NCBI Reference No: P10747 or NP_006130 (SEQ ID NO: 90), or fragments thereof, and/or may optionally comprise up to one or up to two or up to three conservative amino acid substitutions. In non-limiting certain embodiments, the CD28 polypeptide comprises or has an amino acid sequence that is a consecutive portion of SEQ ID NO: 90 which is at least 20, or at least 30, or at least 40, or at least 50, and up to 220 amino acids in length. Alternatively or additionally, in non-limiting various embodiments, the CD28 polypeptide comprises or has an amino acid sequence of amino acids 1 to 220, 1 to 50, 50 to 100, 100 to 150, 114 to 220, 150 to 200, or 200 to 220 of SEQ ID NO: 90. In certain embodiments, the CD28 polypeptide comprised in the transmembrane domain of a presently disclosed CAR comprises or has an amino acid sequence of amino acids 153 to 179 of SEQ ID NO: 90.

SEQ ID NO: 90 is provided below:

```
                                           [SEQ ID NO: 90]
  1    MLRLLLALNL  FPSIQVTGNK  ILVKQSPMLV

AYDNAVNLSC  KYSYNLFSRE  FRASLHKGLD

61    SAVEVCVVYG  NYSQQLQVYS  KTGFNCDGKL

GNESVTFYLQ  NLYVNQTDIY  FCKIEVMYPP

121    PYLDNEKSNG  TIIHVKGKHL  CPSPLFPGPS

KPFWVLVVVG  GVLACYSLLV  TVAFIIFWVR

181    SKRSRLLHSD  YMNMTPRRPG  PTRKHYQPYA

PPRDFAAYRS
```

In accordance with the presently disclosed subject matter, a "CD28 nucleic acid molecule" refers to a polynucleotide encoding a CD28 polypeptide. In certain embodiments, the CD28 nucleic acid molecule encoding the CD28 polypeptide having amino acids 153 to 179 of SEQ ID NO: 90 comprises or has nucleic acids having the sequence set forth in SEQ ID NO: 91 as provided below.

```
                                           [SEQ ID NO: 91]
     ttttgggtgctggtggtggttggtggagtcctggctt gctatagcttgctagtaacagtggcctttattatttt ctgggtg
```

In certain embodiments, the intracellular signaling domain of the CAR comprises a human CD28 transmembrane domain. The human CD28 transmembrane domain can comprise or have an amino acid sequence that is at least about 80%, at least about 85%, at least about 90%, at least about 95%, at least about 96%, at least about 97%, at least about 98%, at least about 99% or at least about 100% homologous or identical to SEQ ID NO: 92 or fragments thereof, and/or may optionally comprise up to one or up to two or up to three conservative amino acid substitutions. SEQ ID NO: 92 is provided below:

```
                                          [SEQ ID NO: 792]
     FWVLVVVGGV  LACYSLLVTV  AFIIFWV.
```

An exemplary nucleic acid sequence encoding the amino acid sequence of SEQ ID NO: 92 is set forth in SEQ ID NO: 93, which is provided below.

```
                                           [SEQ ID NO: 93]
     TTTTGGGTGCTGGTGGTGGTTGGTGGAGTCCTGG

CTTGCTATAGCTTGCTAGTAACAGTGGCCTTTAT

TATTTTCTGGGTG
```

CD84

In certain embodiments, the transmembrane domain of a presently disclosed CAR comprises a native or modified transmembrane domain of a CD84 polypeptide. The CD84 polypeptide can have an amino acid sequence that is at least about 80%, at least about 85%, at least about 90%, at least about 95%, at least about 96%, at least about 97%, at least about 98%, at least about 99% or at least about 100% homologous or identical to the sequence having a NCBI Reference No: NP_001171808.1 (SEQ ID No: 1), or fragments thereof, and/or may optionally comprise up to one or up to two or up to three conservative amino acid substitutions. In non-limiting certain embodiments, the CD84 polypeptide comprises or has an amino acid sequence that is a consecutive portion of SEQ ID NO: 1 which is at least 20, or at least 30, or at least 40, or at least 50, and up to 220 amino acids in length. Alternatively or additionally, in non-limiting various embodiments, the CD84 polypeptide comprises or has an amino acid sequence of amino acids 1 to 220, 1 to 50, 50 to 100, 100 to 150, 114 to 220, 150 to 200, or 200 to 220 of SEQ ID NO: 1. In certain embodiments, the CD84 polypeptide comprised in the transmembrane domain of a presently disclosed CAR comprises or has an amino acid sequence of amino acids 226 to 250 of SEQ ID NO: 1.

SEQ ID NO: 1 is provided below:

```
                                            [SEQ ID NO: 1]
  1    maqhhlwill  lclqtwpeaa  gkdseiftvn gilgesvtfp  vniqeprqvk  iiawtsktsv 61    ayvtpgdset  apvvtvthrn  yyerihalgp nynlvisdlr  medagdykad  intqadpytt 121    tkrynlqiyr  rlgkpkitqs  lmasvnstcn vtltcsveke  eknvtynwsp  lgeegnvlqi 181    fqtpedgelt  ytctagnpvs  nnsdsisarq lcadiamgfr  thhtgllsvl  amffllvlil 241    ssvflfrlfk  rrqgrifpeg  sclntftknp yaaskktiyt  yimasrntqp  aesriydeil 301    qskvlpskee  pvntvysevq  fadkmgkast qdskppgtss  yeivi
```

In accordance with the presently disclosed subject matter, a "CD84 nucleic acid molecule" refers to a polynucleotide encoding a CD84 polypeptide. In certain embodiments, the CD84 nucleic acid molecule encoding the CD84 polypeptide having amino acids 226 to 250 of SEQ ID NO: 1 comprises or has nucleic acids having the sequence set forth in SEQ ID NO: 2 as provided below.

```
                                           [SEQ ID NO: 2]
     TTGCTGAGCGTGCTGGCTATGTTCTTTCTGCTTGTT

CTCATTCTGTCTTCAGTGTTTTTGTTCCGTTTGTTC

AAG
```

CD166

In certain embodiments, the transmembrane domain of a presently disclosed CAR comprises a native or modified transmembrane domain of a CD166 polypeptide. The CD166 polypeptide can have an amino acid sequence that is at least about 80%, at least about 85%, at least about 90%, at least about 95%, at least about 96%, at least about 97%, at least about 98%, at least about 99% or at least about 100% homologous or identical to the sequence having a NCBI Reference No: NP_001618.2 (SEQ ID NO: 3), or fragments thereof, and/or may optionally comprise up to one or up to two or up to three conservative amino acid substitutions. In non-limiting certain embodiments, the CD166 polypeptide comprises or has an amino acid sequence that is a consecutive portion of SEQ ID NO: 3 which is at least 20, or at least 30, or at least 40, or at least 50, and up to 220 amino acids in length. Alternatively or additionally, in non-limiting various embodiments, the CD166 polypeptide comprises or has an amino acid sequence of amino acids 1 to 220, 1 to 50, 50 to 100, 100 to 150, 114 to 220, 150 to 200, or 200 to 220 of SEQ ID NO: 3. In certain embodiments, the CD166 polypeptide comprised in the transmembrane domain of a presently disclosed CAR comprises or has an amino acid sequence of amino acids 528 to 553 of SEQ ID NO: 3. In certain embodiments, the CD166 polypeptide comprised in the transmembrane domain of a presently disclosed CAR comprises or has an amino acid sequence of amino acids 528 to 549 of SEQ ID NO: 3.

SEQ ID NO: 3 is provided below:

```
                                            [SEQ ID NO: 3]
  1   meskgasscr  llfcllisat  vfrpglgwyt vnsaygdtii  iperldvpqn  lmfgkwkyek 61   pdgspvfiaf  rsstkksvqy  ddvpeykdrl nlsenytlsi  snarisdekr  fvcmlvtedn 121   vfeaptivkv  fkuskpeiv   skalfleteq lkklgdcise  dsypdgnitw  yrngkvlhpl 181   egavviifkk  emdpvtqlyt  mtstleyktt kadiqmpftc  svtyygpsgq  ktihseqavf 241   diyypteqvt  iqvlppknai  kegdnitlkc lgngnpppee  flfylpgqpe  girssntytl 301   tdvrrnatgd  ykcslidkks  miastaitvh yldlslnpsg  evtrqigdal  pvsctisasr 361   natvvwmkdn  irlrsspsfs  slhygdagny vcetalqeve  glkkreslt1  ivegkpqikm 421   tkktdpsgls  ktiichvegf  pkpaiqwtit gsgsvinqte  espyingryy  skiiispeen 481   vtltctaenq  lertvnslnv  saisipehde adeisdenre  kvndqakliv  givvglllaa 541   lvagvvywly  mkksktaskh  vnkdlgnmee nkkleennhk  tea
```

In accordance with the presently disclosed subject matter, a "CD166 nucleic acid molecule" refers to a polynucleotide encoding a CD166 polypeptide. In certain embodiments, the CD166 nucleic acid molecule encoding the CD166 polypeptide having amino acids 528 to 553 of SEQ ID NO: 3 comprises or has nucleic acids having the sequence set forth in SEQ ID NO: 4 as provided below.

```
                                            [SEQ ID NO: 4]
CTAATTGTGGGAATCGTTGTTGGTCTCCTCCTTGC

TGCCCTTGTTGCTGGTGTCGTCTACTGGCTGTACA

TGAAGAAG
```

CD8α

In certain embodiments, the transmembrane domain of a presently disclosed CAR comprises a native or modified transmembrane domain of a CD8a polypeptide. The CD8a polypeptide can have an amino acid sequence that is at least about 80%, at least about 85%, at least about 90%, at least about 95%, at least about 96%, at least about 97%, at least about 98%, at least about 99% or at least about 100% homologous or identical to the sequence having a NCBI Reference No: NP_001139345.1 (SEQ ID No: 5), or fragments thereof, and/or may optionally comprise up to one or up to two or up to three conservative amino acid substitutions. In non-limiting certain embodiments, the CD8a polypeptide comprises or has an amino acid sequence that is a consecutive portion of SEQ ID NO: 5 which is at least 20, or at least 30, or at least 40, or at least 50, and up to 220 amino acids in length. Alternatively or additionally, in non-limiting various embodiments, the CD8a polypeptide comprises or has an amino acid sequence of amino acids 1 to 220, 1 to 50, 50 to 100, 100 to 150, 114 to 220, 150 to 200, or 200 to 220 of SEQ ID NO: 5. In certain embodiments, the CD8a polypeptide comprised in the transmembrane domain of a presently disclosed CAR comprises or has an amino acid sequence of amino acids 183 to 207 of SEQ ID NO: 5.

SEQ ID NO: 5 is provided below:

```
                                            [SEQ ID NO: 5]
  1   malpvtalll  plalllhaar  psqfrvspld rtwnlgetve  lkcqvllsnp  tsgcswlfqp 61   rgaaasptfl  lylsqnkpka  aegldtqrfs gkrlgdtfvl  tlsdfrrene  gyyfcsalsn 121   simyfshfvp  vflpakpttt  paprpptpap tiasqplslr  peacrpaagg  avhtrgldfa 181   cdiyiwapla  gtcgvlllsl  vitlycnhrn rrrvckcprp  vvksgdkpsl  saryv
```

In accordance with the presently disclosed subject matter, a "CD8a nucleic acid molecule" refers to a polynucleotide encoding a CD8a polypeptide. In certain embodiments, the CD8a nucleic acid molecule encoding the CD8a polypeptide having amino acids 183 to 207 of SEQ ID NO: 5 comprises or has nucleic acids having the sequence set forth in SEQ ID NO: 6 as provided below.

```
                                            [SEQ ID NO: 6]
atctacatctgggcgcccttggccgggacttgtggg gtccttctcctgtcactggttatcaccctttactgc aac
```

CD8b

In certain embodiments, the transmembrane domain of a presently disclosed CAR comprises a native or modified transmembrane domain of a CD8b polypeptide. The CD8b polypeptide can have an amino acid sequence that is at least about 80%, at least about 85%, at least about 90%, at least about 95%, at least about 96%, at least about 97%, at least about 98%, at least about 99% or at least about 100% homologous or identical to the sequence having a NCBI Reference No: NP_742099.1 (SEQ ID No: 7), or fragments thereof, and/or may optionally comprise up to one or up to two or up to three conservative amino acid substitutions. In non-limiting certain embodiments, the CD8b polypeptide comprises or has an amino acid sequence that is a consecutive portion of SEQ ID NO: 7 which is at least 20, or at least 30, or at least 40, or at least 50, and up to 220 amino acids in length. Alternatively or additionally, in non-limiting various embodiments, the CD8b polypeptide comprises or has an amino acid sequence of amino acids 1 to 220, 1 to 50, 50 to 100, 100 to 150, 114 to 220, 150 to 200, or 200 to 220 of SEQ ID NO: 7. In certain embodiments, the CD8b polypeptide comprised in the transmembrane domain of a presently disclosed CAR comprises or has an amino acid sequence of amino acids 171 to 195 of SEQ ID NO: 7.

SEQ ID NO: 7 is provided below:

```
                                              [SEQ ID NO: 7]
  1 mrprlwllla aqltvlhgns vlqqtpayik vqtnkmvmls ceakislsnm riywlrqrqa 61 pssdshhefl alwdsakgti hgeeveqeki avfrdasrfi lnltsvkped sgiyfcmivg 121 speltfgkgt qlsvvdflpt taqptkkstl kkrvcrlprp etqkgplcsp itlgllvagv 181 lvllvslgva ihlccrrrra rlrfmkglrl hplekcsrmd y
```

In accordance with the presently disclosed subject matter, a "CD8b nucleic acid molecule" refers to a polynucleotide encoding a CD8b polypeptide. In certain embodiments, the CD8b nucleic acid molecule encoding the CD8b polypeptide having amino acids 171 to 195 of SEQ ID NO: 7 comprises or has nucleic acids having the sequence set forth in SEQ ID NO: 8 as provided below.

```
                                              [SEQ ID NO: 8]
ATCACCCTTGGCCTGCTGGTGGCTGGCGTCCTGGTTCTGCTGGTTTCCCT

GGGAGTGGCCATCCACCTGTGCTGC
```

ICOS

In certain embodiments, the transmembrane domain of a presently disclosed CAR comprises a native or modified transmembrane domain of an ICOS polypeptide. The ICOS polypeptide can have an amino acid sequence that is at least about 80%, at least about 85%, at least about 90%, at least about 95%, at least about 96%, at least about 97%, at least about 98%, at least about 99% or at least about 100% homologous or identical to the sequence having a NCBI Reference No: NP_036224.1 (SEQ ID No: 9), or fragments thereof, and/or may optionally comprise up to one or up to two or up to three conservative amino acid substitutions. In non-limiting certain embodiments, the ICOS polypeptide comprises or has an amino acid sequence that is a consecutive portion of SEQ ID NO: 9 which is at least 20, or at least 30, or at least 40, or at least 50, and up to 220 amino acids in length. Alternatively or additionally, in non-limiting various embodiments, the ICOS polypeptide comprises or has an amino acid sequence of amino acids 1 to 220, 1 to 50, 50 to 100, 100 to 150, 114 to 220, 150 to 200, or 200 to 220 of SEQ ID NO: 9. In certain embodiments, the ICOS polypeptide comprised in the transmembrane domain of a presently disclosed CAR comprises or has an amino acid sequence of amino acids 141 to 165 of SEQ ID NO: 9.

SEQ ID NO: 9 is provided below:

```
                                              [SEQ ID NO: 9]
  1 mksglwyffl fclrikvltg eingsanyem fifhnggvqi lckypdivqq fkmqllkggq 61 ilcdltktkg sgntvsiksl kfchsqlsnn sysfflynld hshanyyfcn lsifdpppfk 121 vtltggylhi yesqlccqlk fwlpigcaaf vvvcilgcil icwltkkkys ssvhdpngey 181 mfmravntak ksrltdvtl
```

In accordance with the presently disclosed subject matter, an "ICOS nucleic acid molecule" refers to a polynucleotide encoding an ICOS polypeptide. In certain embodiments, the ICOS nucleic acid molecule encoding the ICOS polypeptide having amino acids 141 to 165 of SEQ ID NO: 9 comprises or has nucleic acids having the sequence set forth in SEQ ID NO: 10 as provided below.

```
                                             [SEQ ID NO: 10]
TTCTGGTTACCCATAGGATGTGCAGCCTTTGTTGTAGTCTGCATTTTGGG

ATGCATACTTATTTGTTGGCTTACA
```

CTLA-4

In certain embodiments, the transmembrane domain of a presently disclosed CAR comprises a native or modified transmembrane domain of a CTLA-4 polypeptide. The CTLA-4 polypeptide can have an amino acid sequence that is at least about 80%, at least about 85%, at least about 90%, at least about 95%, at least about 96%, at least about 97%, at least about 98%, at least about 99% or at least about 100% homologous or identical to the sequence having a NCBI Reference No: NP_005205.2 (SEQ ID No: 11), or fragments thereof, and/or may optionally comprise up to one or up to two or up to three conservative amino acid substitutions. In non-limiting certain embodiments, the CTLA-4 polypeptide comprises or has an amino acid sequence that is a consecutive portion of SEQ ID NO: 11 which is at least 20, or at least 30, or at least 40, or at least 50, and up to 220 amino acids in length. Alternatively or additionally, in non-limiting various embodiments, the CTLA-4 polypeptide comprises or has an amino acid sequence of amino acids 1 to 220, 1 to 50, 50 to 100, 100 to 150, 114 to 220, 150 to 200, or 200 to 220 of SEQ ID NO: 11. In certain embodiments, the CTLA-4 polypeptide comprised in the transmembrane domain of a presently disclosed CAR comprises or has an amino acid sequence of amino acids 162 to 186 of SEQ ID NO: 11.

SEQ ID NO: 11 is provided below:

```
                                             [SEQ ID NO: 11]
  1 maclgfqrhk aqlnlatrtw pctllffllf ipvfckamhv aqpavvlass rgiasfvcey 61 aspgkatevr vtvlrqadsq vtevcaatym mgneltfldd sictgtssgn qvnitiqglr
```

```
121 amdtglyick velmypppyy lgigngtqiy vidpepcpds
    dfllwilaav ssglffysfl
181 ltayslskml kkrsplttgv yvkmpptepe cekqfqpyfi
    pin
```

In accordance with the presently disclosed subject matter, a "CTLA-4 nucleic acid molecule" refers to a polynucleotide encoding a CTLA-4 polypeptide. In certain embodiments, the CTLA-4 nucleic acid molecule encoding the CTLA-4 polypeptide having amino acids 162 to 186 of SEQ ID NO: 11 comprises or has nucleic acids having the sequence set forth in SEQ ID NO: 12 as provided below.

```
                                              [SEQ ID NO: 12]
TTCCTCCTCTGGATCCTTGCAGCAGTTAGTTCGGGGTTGTTTTTTATAG
CTTTCTCCTCACAGCTGTTTCTTTG
```

ICAM-1

In certain embodiments, the transmembrane domain of a presently disclosed CAR comprises a native or modified transmembrane domain of an ICAM-1 polypeptide. The ICAM-1 polypeptide can have an amino acid sequence that is at least about 80%, at least about 85%, at least about 90%, at least about 95%, at least about 96%, at least about 97%, at least about 98%, at least about 99% or at least about 100% homologous or identical to the sequence having a NCBI Reference No: NP_000192.2 (SEQ ID No: 13), or fragments thereof, and/or may optionally comprise up to one or up to two or up to three conservative amino acid substitutions. In non-limiting certain embodiments, the ICAM-1 polypeptide comprises or has an amino acid sequence that is a consecutive portion of SEQ ID NO: 13 which is at least 20, or at least 30, or at least 40, or at least 50, and up to 220 amino acids in length. Alternatively or additionally, in non-limiting various embodiments, the ICAM-1 polypeptide comprises or has an amino acid sequence of amino acids 1 to 220, 1 to 50, 50 to 100, 100 to 150, 114 to 220, 150 to 200, or 200 to 220 of SEQ ID NO: 13. In certain embodiments, the ICAM-1 polypeptide comprised in the transmembrane domain of a presently disclosed CAR comprises or has an amino acid sequence of amino acids 481 to 507 of SEQ ID NO: 13.

SEQ ID NO: 13 is provided below:

```
                                              [SEQ ID NO: 13]
  1 mapssprpal pallvllgal fpgpgnaqts vspskvilpr
    ggsvlvtcst scdqpkllgi
 61 etplpkkell lpgnnrkvye lsnvqedsqp mcysncpdgq
    staktfltvy wtpervelap
121 lpswqpvgkn ltlrcqvegg apranltvvl lrgekelkre
    pavgepaevt ttvlvrrdhh
181 ganfscrtel dlrpqglelf entsapyqlq tfvlpatppq
    lvsprvlevd tqgtvvcsld
241 glfpvseaqv hlalgdqrin ptvtygndsf sakasysvta
    edegtqrltc avilgngsge
301 tlqtvtiysf papnviltkp evsegtevtv kceahprakv
    tlngvpaqpl gpraqlllka
361 tpedngrsfs csatlevagq lihknqtrel rvlygprlde
    rdcpgnwtwp ensqqtpmcq
421 awgnplpelk clkdgtfplp igesvtvtrd legtylcrar
    stqgevtrkv tvnvlsprye
481 iviitvvaaa vimgtaglst ylynrqrkik kyrlqqaqkg
    tpmkpntqat pp
```

In accordance with the presently disclosed subject matter, an "ICAM-1 nucleic acid molecule" refers to a polynucleotide encoding an ICAM-1 polypeptide. In certain embodiments, the ICAM-1 nucleic acid molecule encoding the ICAM-1 polypeptide having amino acids 481 to 507 of SEQ ID NO: 13 comprises or has nucleic acids having the sequence set forth in SEQ ID NO: 14 as provided below.

```
                                              [SEQ ID NO: 14]
ATTGTCATCATCACTGTGGTAGCAGCCGCAGTCATAATGGGCACTGCAGG
CCTCAGCACGTACCTCTATAACCGCCAGCGG
```

2.2.3. Hinge Spacer Region

In certain non-limiting embodiments, a CAR can also comprise a hinge/spacer region that links the extracellular antigen-binding domain to the transmembrane domain. The hinge/spacer region can be flexible enough to allow the antigen binding domain to orient in different directions to facilitate antigen recognition. In certain non-limiting embodiments, the hinge/spacer region of the CAR can comprise a native or modified hinge region of a CD8 polypeptide, a CD28 polypeptide, a CD3ζ polypeptide, a CD40 polypeptide, a 4-1BB polypeptide, an OX40 polypeptide, a CD84 polypeptide, a CD166 polypeptide, a CD8a polypeptide, a CD8b polypeptide, an ICOS polypeptide, an ICAM-1 polypeptide, a CTLA-4 polypeptide, a CD27 polypeptide, a CD40/My88 peptide, a NKGD2 peptide, a synthetic polypeptide (not based on a protein associated with the immune response), or a combination thereof. The hinge/spacer region can be the hinge region from IgG1, or the $CH_2CH_3$ region of immunoglobulin and portions of CD3, a portion of a CD28 polypeptide (e.g., a portion of SEQ ID NO: 90), a portion of a CD8 polypeptide (e.g., a portion of SEQ ID NO: 86, or a portion of SEQ ID NO: 87), a variation of any of the foregoing which is at least about 80%, at least about 85%, at least about 90%, at least about 95%, or at least about 100% homologous or identical thereto, or a synthetic spacer sequence.

CD28

In certain embodiments, the hinge/spacer region of a presently disclosed CAR comprises a native or modified hinge region of a CD28 polypeptide as described herein. In certain embodiments, the CD28 polypeptide comprised in the hinge/spacer region of a presently disclosed CAR comprises or has an amino acid sequence of amino acids 114 to 152 of SEQ ID NO: 90. In certain embodiments, the CD28 nucleic acid molecule encoding the CD28 polypeptide having amino acids 114 to 152 of SEQ ID NO: 90 comprises or has nucleic acids having the sequence set forth in SEQ ID NO: 15 as provided below.

[SEQ ID NO: 15]
IEVMYPPPYLDNEKSNGTIIHVKGKHLCPSPLFPGPSKP

CD84

In certain embodiments, the hinge/spacer region of a presently disclosed CAR comprises a native or modified hinge region of a CD84 polypeptide as described herein. In certain embodiments, the CD84 polypeptide comprised in the hinge/spacer region of a presently disclosed CAR comprises or has an amino acid sequence of amino acids 187 to 225 of SEQ ID NO: 1. In certain embodiments, the CD84 nucleic acid molecule encoding the CD84 polypeptide having amino acids 187 to 225 of SEQ ID NO: 1 comprises or has nucleic acids having the sequence set forth in SEQ ID NO: 16 as provided below.

[SEQ ID NO: 16]
CAAGAGCTGACTTACACGTGTACAGCCCAGAACCCTGTCAGCAACAATTC

TGACTCCATCTCTGCCCGGCAGCTCTGTGCAGACATCGCAATGGGCTTCC

GTACTCACCACACCGGG

CD166

In certain embodiments, the hinge/spacer region of a presently disclosed CAR comprises a native or modified hinge region of a CD166 polypeptide as described herein. In certain embodiments, the CD166 polypeptide comprised in the hinge/spacer region of a presently disclosed CAR comprises or has amino acids 489 to 527 of SEQ ID NO:3. In certain embodiments, the CD166 nucleic acid molecule encoding the CD166 polypeptide having amino acids 489 to 527 of SEQ ID NO: 3 comprises or has nucleic acids having the sequence set forth in SEQ ID NO: 17 as provided below.

[SEQ ID NO: 17]
ACCAACTGGAGAGAACAGTAAACTCCTTGAATGTCTCTGCTATAAGTATT

CCAGAACACGATGAGGCAGACGAGATAAGTGATGAAAACAGAGAAAAGGT

GAATGACCAGGCAAAA

In certain embodiments, the CD166 polypeptide comprised in the hinge/spacer region of a presently disclosed CAR comprises or has amino acids 484 to 527 of SEQ ID NO:3. In certain embodiments, the CD166 polypeptide comprised in the hinge/spacer region of a presently disclosed CAR comprises or has amino acids 506 to 527 of SEQ ID NO:3. In certain embodiments, the CD166 polypeptide comprised in the hinge/spacer region of a presently disclosed CAR comprises or has amino acids 517 to 527 of SEQ ID NO:3. In certain embodiments, the CD166 polypeptide comprised in the hinge/spacer region of a presently disclosed CAR comprises or has the amino acid sequence set forth in SEQ ID NO: 109 or 110.

[SEQ ID NO: 109]
NQLERTVNSLNVPAISIPEHDEADEISDENREKVNDQAK

[SEQ ID NO: 110]
AAANQLERTVNSLNVSAISIPEHDEADEISDENREKVNDQAK

In certain embodiments, the CD166 polypeptide comprised in the hinge/spacer region and the transmembrane domain of a presently disclosed CAR comprises or has the amino acid sequence set forth in SEQ ID NO: 111, 112, 113, 114, 115, 116 or 117.

[SEQ ID NO: 111]
PEHDEADEISDENREKVNDQAKLIVGIVVGLLLAALVAGVVYWLYMKK

[SEQ ID NO: 112]
ENREKVNDQAKLIVGIVVGLLLAALVAGVVYWLYMKK

[SEQ ID NO: 113]
NQLERTVNSLNVPAISIPEHDEADEISDENREKVNDQAKLIVGIVVGLLL

AALVAGVVYWLYMKK

[SEQ ID NO: 114]
TCTAENQLERTVNSLNVSAISIPEHDEADEISDENREKVNDQAKLIVGIV

VGLLLAALVAGVVYWL

[SEQ ID NO: 115]
PEHDEADEISDENREKVNDQAKLIVGIVVGLLLAALVAGVVYWL

[SEQ ID NO: 116]
NQLERTVNSLNVSAISIPEHDEADEISDENREKVNDQAKLIVGIVVGLLL

AALVAGVVYWL

[SEQ ID NO: 117]
AAANQLERTVNSLNVSAISIPEHDEADEISDENREKVNDQAKLIVGIVVG

LLLAALVAGVVYWLYMKK

CD8a

In certain embodiments, the hinge/spacer region of a presently disclosed CAR comprises a native or modified hinge region of a CD8a polypeptide as described herein. In certain embodiments, the CD8a polypeptide comprised in the hinge/spacer region of a presently disclosed CAR comprises or has amino acids 137 to 182 of SEQ ID NO: 5. In certain embodiments, the CD8a nucleic acid molecule encoding the CD8a polypeptide having amino acids 137 to 182 of SEQ ID NO: 5 comprises or has nucleic acids having the sequence set forth in SEQ ID NO: 18 as provided below.

[SEQ ID NO: 18]
cccaccacgacgccagcgccgcgaccaccaacaccggcgcccaccatcgc gtcgcagcccctgtccctgcgcccagaggcgtgccggccagcggcggggg gcgcagtgcacacgaggggctggacttcgcctgtgat CD8b In certain embodiments, the hinge/spacer region of a presently disclosed CAR comprises a native or modified hinge region of a CD8b polypeptide as described herein. In certain embodiments, the CD8b polypeptide comprised in the hinge/spacer region of a presently disclosed CAR comprises or has amino acids 132 to 170 of SEQ ID NO: 7. In certain embodiments, the CD8b nucleic acid molecule encoding the CD8b polypeptide having amino acids 132 to 170 of SEQ ID NO: 7 comprises or has nucleic acids having the sequence set forth in SEQ ID NO: 19 as provided below.

[SEQ ID NO: 19]
CTGAGTGTGGTTGATTTCCTTCCCACCACTGCCCAGCCCACCAAGAAGTC

CACCCTCAAGAAGAGAGTGTGCCGGTTACCCAGGCCAGAGACCCAGAAGG

GCCCACTTTGTAGCCCC

ICOS

In certain embodiments, the hinge/spacer region of a presently disclosed CAR comprises a native or modified hinge region of an ICOS polypeptide as described herein. In certain embodiments, the ICOS polypeptide comprised in the hinge/spacer region of a presently disclosed CAR comprises or has amino acids 102 to 140 of SEQ ID NO: 9. In certain embodiments, the ICOS nucleic acid molecule encoding the ICOS polypeptide having amino acids 102 to 140 of SEQ ID NO: 9 comprises or has nucleic acids having the sequence set forth in SEQ ID NO: 20 as provided below.

```
                                          [SEQ ID NO: 20]
    tctcatgccaactattacttctgcaacctatcaa tttttgatcctcctccttttaaagtaactcttac aggaggatatttgcatatttatgaatcacaactt tgttgccagctgaag
```

CTLA-4

In certain embodiments, the hinge/spacer region of a presently disclosed CAR comprises a native or modified hinge region of a CTLA-4 polypeptide as described herein. In certain embodiments, the CTLA-4 polypeptide comprised in the hinge/spacer region of a presently disclosed CAR comprises or has amino acids 123 to 161 of SEQ ID NO: 11. In certain embodiments, the CTLA-4 nucleic acid molecule encoding the CTLA-4 polypeptide having amino acids 123 to 161 of SEQ ID NO: 11 comprises or has nucleic acids having the sequence set forth in SEQ ID NO: 21 as provided below.

```
                                          [SEQ ID NO: 21]
    GACACGGGACTCTACATCTGCAAGGTGGAGCTCATG

TACCCACCGCCATACTACCTGGGCATAGGCAACGGA

ACCCAGATTTATGTAATTGATCCAGAACCGTGCCCA

GATTCTGAC
```

ICAM-1

In certain embodiments, the hinge/spacer region of a presently disclosed CAR comprises a native or modified hinge region of a ICAM-1 polypeptide as described herein. In certain embodiments, the ICAM-1 polypeptide comprised in the hinge/spacer region of a presently disclosed CAR comprises or has amino acids 442 to 480 of SEQ ID NO: 13. In certain embodiments, the ICAM-1 nucleic acid molecule encoding the ICAM-1 polypeptide having amino acids 442 to 480 of SEQ ID NO: 13 comprises or has nucleic acids having the sequence set forth in SEQ ID NO: 22 as provided below.

```
                                          [SEQ ID NO: 22]
    GGGGAATCAGTGACTGTCACTCGAGATCTTGAGGGC

ACCTACCTCTGTCGGGCCAGGAGCACTCAAGGGGAGG

TCACCCGCAAGGTGACCGTGAATGTGCTCTCCCCCG

GTATGAG
```

In certain embodiments, a presently disclosed CAR comprises a hinge/spacer region. In certain embodiments, the hinge/spacer region is positioned between the extracellular antigen-binding domain and the transmembrane domain. In certain embodiments, the hinge/spacer region comprises a CD8 polypeptide, a CD28 polypeptide, a CD3ζ polypeptide, a CD4 polypeptide, a 4-1BB polypeptide, an OX40 polypeptide, a CD166 polypeptide, a CD8a polypeptide, a CD8b polypeptide, an ICOS polypeptide, an ICAM-1 polypeptide, a CTLA-4 polypeptide, a CD27 polypeptide, a CD40/My88 peptide, a NKGD2 peptide, a synthetic polypeptide (not based on a protein associated with the immune response), or a combination thereof. In certain embodiments, the transmembrane domain comprises a CD8 polypeptide, a CD28 polypeptide, a CD3ζ polypeptide, a CD4 polypeptide, a 4-1BB polypeptide, an OX40 polypeptide, a CD166 polypeptide, a CD8a polypeptide, a CD8b polypeptide, an ICOS polypeptide, an ICAM-1 polypeptide, a CTLA-4 polypeptide, a CD27 polypeptide, a CD40/My88 peptide, a NKGD2 peptide, a synthetic polypeptide (not based on a protein associated with the immune response), or a combination thereof.

In certain embodiments, the transmembrane domain and the hinge/spacer region are derived from the same molecule. In certain embodiments, the transmembrane domain and the hinge/spacer region are derived from different molecules. In certain embodiments, the hinge/spacer region of the CAR comprises a CD28 polypeptide and the transmembrane domain of the CAR comprises a CD28 polypeptide. In certain embodiments, the hinge/spacer region of the CAR comprises a CD28 polypeptide and the transmembrane domain of the CAR comprises a CD28 polypeptide. In certain embodiments, the hinge/spacer region of the CAR comprises a CD84 polypeptide and the transmembrane domain of the CAR comprises a CD84 polypeptide. In certain embodiments, the hinge/spacer region of the CAR comprises a CD166 polypeptide and the transmembrane domain of the CAR comprises a CD166 polypeptide. In certain embodiments, the hinge/spacer region of the CAR comprises a CD8a polypeptide and the transmembrane domain of the CAR comprises a CD8a polypeptide. In certain embodiments, the hinge/spacer region of the CAR comprises a CD8b polypeptide and the transmembrane domain of the CAR comprises a CD8b polypeptide. In certain embodiments, the hinge/spacer region of the CAR comprises a CD28 polypeptide and the transmembrane domain of the CAR comprises an ICOS polypeptide.

2.2.4. Intracellular Signaling Domain of a CAR

In certain non-limiting embodiments, an intracellular signaling domain of the CAR comprises a CD3ζ polypeptide, which can activate or stimulate a cell (e.g., a cell of the lymphoid lineage, e.g., a T cell). Wild type ("native") CD3ζ comprises three immunoreceptor tyrosine-based activation motifs ("ITAMs") (e.g., ITAM1, ITAM2 and ITAM3), three basic-rich stretch (BRS) regions (BRS1, BRS2 and BRS3), and transmits an activation signal to the cell (e.g., a cell of the lymphoid lineage, e.g., a T cell) after antigen is bound. The intracellular signaling domain of the native CD3ζ-chain is the primary transmitter of signals from endogenous TCRs. CD3ζ, as used in embodiments herein, is not native CD3ζ but is a modified CD3ζ. In certain embodiments, the modified CD3ζ polypeptide comprises or has an amino acid sequence that is at least about 80%, at least about 85%, at least about 90%, at least about 95%, at least about 96%, at least about 97%, at least about 98%, or at least about 99%, at least about 100% homologous or identical to the sequence having a NCBI Reference No: NP_932170 (SEQ ID No: 94), or fragments thereof. In certain non-limiting embodiments, the modified CD3ζ polypeptide comprises or has an amino acid sequence that is a consecutive portion of SEQ ID NO: 94, which is at least 20, or at least 30, or at least 40, or at least 50, or at least 100, or at least 110, or at least 113, and up to 163 amino acids in length. Alternatively or additionally, in non-limiting various embodiments, the modified CD3ζ polypeptide comprises or has an amino acid sequence of amino acids 1 to 50, 50 to 100, 100 to 150, 50 to 164, 55 to 164, or 150 to 164 of SEQ ID NO: 94. In certain embodiments, the modified CD3ζ polypeptide comprises or has an amino acid sequence of amino acids 52 to 164 of SEQ ID NO: 94.

SEQ ID NO: 94 is provided below:

```
                                        [SEQ ID NO: 94]
  1 MKWKALFTAA ILQAQLPITE AQSFGLLDPK

LCYLLDGILF IYGVILTALF LRVKFSRSAD

61 APAYQQGQNQ LYNELNLGRR EEYDVLDKRR

GRDPEMGGKP QRRKNPQEGL YNELQKDKMA

121 EAYSEIGMKG ERRRGKGHDG LYQGLSTATK

DTYDALHMQA LPPR
```

In certain embodiments, the intracellular signaling domain of the CAR comprises a modified human CD3ζ polypeptide. The modified human CD3ζ polypeptide can comprise or have an amino acid sequence that is at least about 80%, at least about 85%, at least about 90%, at least about 95%, at least about 96%, at least about 97%, at least about 98%, or at least about 99%, at least about 100% homologous or identical to SEQ ID NO: 95 or fragments thereof, and/or may optionally comprise up to one or up to two or up to three conservative amino acid substitutions. SEQ ID NO: 95 is provided below:

```
                                        [SEQ ID NO: 95]
    RVKFSRSADA PAYQQGQNQL YNELNLGRRE

EYDVLDKRRG RDPEMGGKPR RKNPQEGLYN

ELQKDKMAEA YSEIGMKGER RRGKGHDGLY

QGLSTATKDT YDALHMQALP PR.
```

An exemplary nucleic acid sequence encoding the amino acid sequence of SEQ ID NO: 95 is set forth in SEQ ID NO: 96, which is provided below.

```
                                        [SEQ ID NO: 96]
    AGAGTGAAGTTCAGCAGGAGCGCAGACGCCCCCGCGT

ACCAGCAGGGCCAGAACCAGCTCTATAACGAGCTCAA

TCTAGGACGAAGAGAGGAGTACGATGTTTTGGACAAG

AGACGTGGCCGGGACCCTGAGATGGGGGGAAAGCCGA

GAAGGAAGAACCCTCAGGAAGGCCTGTACAATGAACT

GCAGAAAGATAAGATGGCGGAGGCCTACAGTGAGATT

GGGATGAAAGGCGAGCGCCGGAGGGGCAAGGGGCACG

ATGGCCTTTACCAGGGTCTCAGTACAGCCACCAAGGA

CACCTACGACGCCCTTCACATGCAGGCCCTGCCCCCT

CGC
```

Immunoreceptor Tyrosine-Based Activation Motifs (ITAMs)

In certain non-limiting embodiments, the intracellular signaling domain of the CAR comprises a modified CD3ζ polypeptide comprising one, two or three ITAMs. In certain embodiments, the modified CD3ζ polypeptide comprises a native ITAM1 comprising the amino acid sequence set forth in SEQ ID NO: 23.

```
                                        [SEQ ID NO: 23]
    QNQLYNELNLGRREEYDVLDKR
```

An exemplary nucleic acid sequence encoding the amino acid sequence of SEQ ID NO: 23 is set forth in SEQ ID NO: 24, which is provided below.

```
                                        [SEQ ID NO: 24]
    cagaaccagctctataacgagctcaatctagga cgaagagaggagtacgatgttttggacaagaga
```

In certain embodiments, the modified CD3ζ polypeptide comprises an ITAM1 variant comprising one or more loss-of-function mutations. In certain embodiments, the modified CD3ζ polypeptide has an ITAM1 variant comprising two loss-of-function mutations. In certain embodiments, the loss of function mutation comprises a mutation of a tyrosine residue in ITAM1. In certain embodiments, the ITAM1 variant consisting of two loss-of-function mutations comprises the amino acid sequence set forth in SEQ ID NO: 25, which is provided below.

```
                                        [SEQ ID NO: 25]
    QNQLFNELNLGRREEFDVLDKR
```

An exemplary nucleic acid sequence encoding the amino acid sequence of SEQ ID NO: 25 is set forth in SEQ ID NO: 26, which is provided below.

```
                                        [SEQ ID NO: 26]
    cagaaccagctctTtaacgagctcaatctagga cgaagagaggagtTcgatgttttggacaagaga
```

In certain embodiments, the modified CD3ζ polypeptide comprises a native ITAM2 comprising the amino acid sequence set forth in SEQ ID NO: 27, which is provided below.

```
                                        [SEQ ID NO: 27]
    QEGLYNELQKDKMAEAYSEIGMK
```

An exemplary nucleic acid sequence encoding the amino acid sequence of SEQ ID NO: 27 is set forth in SEQ ID NO: 28, which is provided below.

```
                                        [SEQ ID NO: 28]
    caggaaggcctgtacaatgaactgcagaaagataa gatggcggaggcctacagtgagattgggatgaaa
```

In certain embodiments, the modified CD3ζ polypeptide comprises an ITAM2 variant comprising one or more loss-of-function mutations. In certain embodiments, the modified CD3ζ polypeptide has an ITAM2 variant comprising two loss-of-function mutations. In certain embodiments, the loss of function mutation comprises a mutation of a tyrosine residue in ITAM2. In certain embodiments, the ITAM2 variant consisting of two loss-of-function mutations comprises the amino acid sequence set forth in SEQ ID NO: 29, which is provided below.

[SEQ ID NO: 29]
QEGLFNELQKDKMAEAFSEIGMK

An exemplary nucleic acid sequence encoding the amino acid sequence of SEQ ID NO: 29 is set forth in SEQ ID NO: 30, which is provided below.

[SEQ ID NO: 30]
caggaaggcctgtTcaatgaactgcagaaagataa gatggcggaggcctTcagtgagattgggatgaaa In certain embodiments, the modified CD3ζ polypeptide comprises a native ITAM3 comprising the amino acid sequence set forth in SEQ ID NO: 31, which is provided below.

[SEQ ID NO: 31]
HDGLYQGLSTATKDTYDALHMQ

An exemplary nucleic acid sequence encoding the amino acid sequence of SEQ ID NO: 131 is set forth in SEQ ID NO: 32, which is provided below.

[SEQ ID NO: 32]
cacgatggcctttaccagggtctcagtacagccaccaaggacacctacg acgcccttcacatgcag In certain embodiments, the modified CD3ζ polypeptide comprises an ITAM3 variant comprising one or more loss-of-function mutations. In certain embodiments, the modified CD3ζ polypeptide has an ITAM3 variant comprising two loss-of-function mutations. In certain embodiments, the loss of function mutation comprises a mutation of a tyrosine residue in ITAM3. In certain embodiments, the ITAM3 variant consisting of two loss-of-function mutations comprises the amino acid sequence set forth in SEQ ID NO: 33, which is provided below.

[SEQ ID NO: 33]
HDGLFQGLSTATKDTFDALHMQ

An exemplary nucleic acid sequence encoding the amino acid sequence of SEQ ID NO: 33 is set forth in SEQ ID NO: 34, which is provided below.

[SEQ ID NO: 34]
cacgatggcctttTccaggggctcagtacagccaccaaggacacctTcga cgcccttcacatgcag In certain embodiments, the intracellular signaling domain of the CAR comprises a modified CD3ζ polypeptide comprising or consisting essentially of or consisting of an ITAM1 variant comprising one or more loss-of-function mutations, an ITAM2 variant comprising one or more loss-of-function mutations, an ITAM3 variant comprising one or more loss-of-function mutations, or a combination thereof. In certain embodiments, the intracellular signaling domain of the CAR comprises a modified CD3ζ polypeptide comprising an ITAM2 variant comprising one or more (e.g., two) loss-of-function mutations and an ITAM3 variant comprising one or more (e.g., two) loss-of-function mutations. In certain embodiments, the intracellular signaling domain of the CAR comprises a modified CD3ζ polypeptide comprising a native ITAM1, an ITAM2 variant comprising two loss-of-function mutations and an ITAM3 variant comprising two loss-of-function mutations. In certain embodiments, the intracellular signaling domain of the CAR comprises a modified CD3ζ polypeptide comprising a native ITAM1 having the amino acid sequence set forth in SEQ ID NO: 23, an ITAM2 variant having the amino acid sequence set forth in SEQ ID NO: 29 and an ITAM3 variant having the amino acid sequence set forth in SEQ ID NO: 33(e.g., a construct designated as "1XX").

In certain embodiments, the intracellular signaling domain of the CAR comprises a modified CD3ζ polypeptide comprising an ITAM1 variant comprising one or more (e.g., two) loss-of-function mutations and an ITAM3 variant comprising one or more (e.g., two) loss-of-function mutations. In certain embodiments, the intracellular signaling domain of the CAR comprises a modified CD3ζ polypeptide comprising an ITAM1 variant comprising two loss-of-function mutations, a native ITAM2, and an ITAM3 variant comprising two loss-of-function mutations. In certain embodiments, the intracellular signaling domain of the CAR comprises a modified CD3ζ polypeptide comprising an ITAM1 variant having the amino acid sequence set forth in SEQ ID NO: 25, a native ITAM2 having the amino acid sequence set forth in SEQ ID NO: 27 and an ITAM3 variant having the amino acid sequence set forth in SEQ ID NO: 33 (e.g., a construct designated as "X2X").

In certain embodiments, the intracellular signaling domain of the CAR comprises a modified CD3ζ polypeptide comprising an ITAM1 variant comprising one or more (e.g., two) loss-of-function mutations and an ITAM2 variant comprising one or more (e.g., two) loss-of-function mutations. In certain embodiments, the intracellular signaling domain of the CAR comprises a modified CD3ζ polypeptide comprising an ITAM1 variant comprising two loss-of-function mutations, an ITAM2 variant comprising two loss-of-function mutations, and a native ITAM3. In certain embodiments, the intracellular signaling domain of the CAR comprises a modified CD3ζ polypeptide comprising an ITAM1 variant having the amino acid sequence set forth in SEQ ID NO: 25, an ITAM2 variant having the amino acid sequence set forth in SEQ ID NO: 29 and a native ITAM3 having the amino acid sequence set forth in SEQ ID NO: 31 (e.g., a construct designated as "XX3").

In certain embodiments, the intracellular signaling domain of the CAR comprises a modified CD3ζ polypeptide comprising an ITAM1 variant comprising one or more (e.g., two) loss-of-function mutations. In certain embodiments, the intracellular signaling domain of the CAR comprises a modified CD3ζ polypeptide comprising an ITAM1 variant comprising two loss-of-function mutations, a native ITAM2, and a native ITAM3. In certain embodiments, the intracellular signaling domain of the CAR comprises a modified CD3ζ polypeptide comprising an ITAM1 variant having the amino acid sequence set forth in SEQ ID NO: 27, a native ITAM2 having the amino acid sequence set forth in SEQ ID NO: 29 and a native ITAM3 having the amino acid sequence set forth in SEQ ID NO: 31 (e.g., a construct designated as "X23").

In certain embodiments, the intracellular signaling domain of the CAR comprises a modified CD3ζ polypeptide comprising a native ITAM1, a native ITAM2, and an ITAM3 variant comprising one or more (e.g., two) loss-of-function mutations. In certain embodiments, the intracellular signaling domain of the CAR comprises a modified CD3ζ polypeptide comprising a native ITAM1, a native ITAM2, and an ITAM1 variant comprising two loss-of-function mutations.

In certain embodiments, the intracellular signaling domain of the CAR comprises a modified CD3ζ polypeptide comprising a native ITAM1 having the amino acid sequence set forth in SEQ ID NO: 23, a native ITAM2 having the amino acid sequence set forth in SEQ ID NO: 27 and an ITAM3 variant having the amino acid sequence set forth in SEQ ID NO: 33 (e.g., a construct designated as "12X").

In certain embodiments, the intracellular signaling domain of the CAR comprises a modified CD3ζ polypeptide comprising a native ITAM1, an ITAM2 variant comprising one or more (e.g., two) loss-of-function mutations, and a native ITAM3. In certain embodiments, the intracellular signaling domain of the CAR comprises a modified CD3ζ polypeptide comprising a native ITAM1, an ITAM2 variant comprising two loss-of-function mutations, and a native ITAM3. In certain embodiments, the intracellular signaling domain of the CAR comprises a modified CD3ζ polypeptide comprising a native ITAM1 having the amino acid sequence set forth in SEQ ID NO: 23, an ITAM2 variant having the amino acid sequence set forth in SEQ ID NO: 29 and a native ITAM3 variant having the amino acid sequence set forth in SEQ ID NO: 31 (e.g., a construct designated as "1X3").

In certain embodiments, the intracellular signaling domain of the CAR comprises a modified CD3ζ polypeptide comprising a deletion of one or two ITAMs. In certain embodiments, the modified CD3ζ polypeptide comprises a deletion of ITAM1 and ITAM2, e.g., the modified CD3ζ polypeptide comprises a native ITAM3 or a ITAM3 variant, and does not comprise an ITAM1 or an ITAM2. In certain embodiments, the modified CD3ζ polypeptide comprises a native ITAM3 having the amino acid sequence set forth in SEQ ID NO: 31, and does not comprise an ITAM1 (native or modified), or an ITAM2 (native or modified) (e.g., D12).

In certain embodiments, the modified CD3ζ polypeptide comprises a deletion of ITAM2 and ITAM3, e.g., the modified CD3ζ polypeptide comprises a native ITAM1 or a ITAM1 variant, and does not comprise an ITAM2 or an ITAM3. In certain embodiments, the modified CD3ζ polypeptide comprises a native ITAM1 having the amino acid sequence set forth in SEQ ID NO: 23, and does not comprise an ITAM2 (native or modified), or an ITAM3 (native or modified) (e.g., D23).

In certain embodiments, the modified CD3ζ polypeptide comprises a deletion of ITAM1 and ITAM3, e.g., the modified CD3ζ polypeptide comprises a native ITAM2 or a ITAM2 variant, and does not comprise an ITAM1 or an ITAM3. In certain embodiments, the modified CD3ζ polypeptide comprises a native ITAM2 having the amino acid sequence set forth in SEQ ID NO: 27, and does not comprise an ITAM1 (native or modified), or an ITAM3 (native or modified) (e.g., D13).

In certain embodiments, the modified CD3ζ polypeptide comprises a deletion of ITAM1, e.g., the modified CD3ζ polypeptide comprises a native ITAM2 or an ITAM2 variant, and a native ITAM3 or an ITAM3 variant, and does not comprise an ITAM1 (native or modified).

In certain embodiments, the modified CD3ζ polypeptide comprises a deletion of ITAM2, e.g., the modified CD3ζ polypeptide comprises a native ITAM1 or an ITAM1 variant, and a native ITAM3 or an ITAM3 variant, and does not comprise an ITAM2 (native or modified).

In certain embodiments, the modified CD3ζ polypeptide comprises a deletion of ITAM3, e.g., the modified CD3ζ polypeptide comprises a native ITAM1 or an ITAM1 variant, and a native ITAM2 or an ITAM2 variant, and does not comprise an ITAM3 (native or modified).

Basic-Rich Stretch (BRS) Region

In certain non-limiting embodiments, the intracellular signaling domain of the CAR comprises a modified CD3ζ polypeptide comprising one, two or three BRS regions (i.e., BRS1, BRS2, and BRS3). The BRS region can be a native BRS or a modified BRS (e.g., a BRS variant). In certain embodiments, the modified CD3ζ polypeptide comprises a native BRS1 region comprising the amino acid sequence set forth in SEQ ID NO: 35, which is provided below.

```
                                            [SEQ ID NO: 35]
         KRRGR
```

An exemplary nucleic acid sequence encoding the amino acid sequence of SEQ ID NO: 35 is set forth in SEQ ID NO: 36, which is provided below.

```
                                            [SEQ ID NO: 36]
         aagagacgtggccgg
```

In certain embodiments, the modified CD3ζ polypeptide comprises a BRS1 variant comprising one or more loss-of-function mutations.

In certain embodiments, the modified CD3ζ polypeptide comprises a native BRS2 comprising the amino acid sequence set forth in SEQ ID NO: 37.

```
                                            [SEQ ID NO: 37]
         KPRRK
```

An exemplary nucleic acid sequence encoding the amino acid sequence of SEQ ID NO: 37 is set forth in SEQ ID NO: 38, which is provided below.

```
                                            [SEQ ID NO: 38]
         aagccgagaaggaag
```

In certain embodiments, the modified CD3ζ polypeptide comprises a BRS2 variant comprising one or more loss-of-function mutations.

In certain embodiments, the modified CD3ζ polypeptide comprises a native BRS3 comprising the amino acid sequence set forth in SEQ ID NO: 39.

```
                                            [SEQ ID NO: 39]
         KGERRRGK
```

An exemplary nucleic acid sequence encoding the amino acid sequence of SEQ ID NO: 39 is set forth in SEQ ID NO: 40, which is provided below.

```
                                            [SEQ ID NO: 40]
         aaaggcgagcgccggaggggcaag
```

In certain embodiments, the modified CD3ζ polypeptide comprises a BRS3 variant comprising one or more loss-of-function mutations.

In certain embodiments, the intracellular signaling domain of the CAR comprises a modified CD3ζ polypeptide comprising all three BRS regions, i.e., a BRS1 region, a BRS2 region, and a BRS3 region. In certain embodiments, the intracellular signaling domain of the CAR comprises a modified CD3ζ polypeptide comprising a native BRS1, a native BRS2, and a native BRS3. In certain embodiments, the intracellular signaling domain of the CAR comprises a modified CD3ζ polypeptide comprising a native BRS1 having the amino acid sequence set forth in SEQ ID NO: 35, a native BRS2 having the amino acid sequence set forth in SEQ ID NO: 37, and a native BRS3 having the amino acid sequence set forth in SEQ ID NO: 39, e.g., the modified CD3ζ polypeptide comprised in construct 1XX.

In certain embodiments, the intracellular signaling domain of the CAR comprises a modified CD3ζ polypeptide comprising one or two but not all three BRS regions. In certain embodiments, the modified CD3ζ polypeptide comprises a BRS1 region and a BRS2 region, and does not comprise a BRS3 region. In certain embodiments, the modified CD3ζ polypeptide comprises a BRS1 region and a BRS3 region, and does not comprise a BRS2 region. In certain embodiments, the modified CD3ζ polypeptide comprises a BRS2 region and a BRS3 region, and does not comprise a BRS1 region.

In certain embodiments, the modified CD3ζ polypeptide comprises a BRS1 region, and does not comprise a BRS2 region or a BRS3 region. In certain embodiments, the modified CD3ζ polypeptide comprises a native BRS1 having the amino acid sequence set forth in SEQ ID NO: 35, and does not comprise a BRS2 region or a BRS3 region, e.g., the modified CD3ζ polypeptide comprised in construct D23. In certain embodiments, the modified CD3ζ polypeptide comprises a BRS2 region, and does not comprise a BRS1 region or BRS3 region. In certain embodiments, the modified CD3ζ polypeptide comprises a BRS3 region, and does not comprise a BRS1 region or a BRS2 region.

In certain embodiments, the modified CD3ζ polypeptide does not comprise a BRS region (native or modified BRS1, BRS2 or BRS3), e.g., all three BRSs are deleted, e.g., the modified CD3ζ polypeptide comprised in construct D12.

In certain non-limiting embodiments, the CAR comprises an extracellular antigen-binding domain, a transmembrane domain, and an intracellular signaling domain comprising a modified CD3ζ polypeptide, wherein the modified CD3ζ polypeptide lacks all or part of immunoreceptor tyrosine-based activation motifs (ITAMs), wherein the ITAMs are ITAM1, ITAM2, and ITAM3. In certain embodiments, the modified CD3ζ polypeptide lacks ITAM2 or a portion thereof. In certain embodiments, the modified CD3ζ polypeptide further lacks ITAM3 or a portion thereof. In certain embodiments, the modified CD3ζ polypeptide further lacks ITAM1 or a portion thereof. In certain embodiments, the modified CD3ζ polypeptide lacks ITAM1 or a portion thereof. In certain embodiments, the modified CD3ζ polypeptide further lacks ITAM3 or a portion thereof. In certain embodiments, the modified CD3ζ polypeptide lacks ITAM3 or a portion thereof. In certain embodiments, the modified CD3ζ polypeptide lacks all or part of basic-rich stretch (BRS) regions, wherein the BRS regions are BRS1, BRS2, and BRS3. In certain embodiments, the modified CD3ζ polypeptide lacks BRS2 or a portion thereof. In certain embodiments, the modified CD3ζ polypeptide further lacks BRS3 or a portion thereof. In certain embodiments, the modified CD3ζ polypeptide further lacks BRS1 or a portion thereof. In certain embodiments, the modified CD3ζ polypeptide lacks BRS1 or a portion thereof. In certain embodiments, the modified CD3ζ polypeptide further lacks BRS3 or a portion thereof. In certain embodiments, the modified CD3ζ polypeptide lacks BRS3 or a portion thereof. In certain embodiments, the modified CD3ζ polypeptide lacks BRS1 or portion thereof, BRS2 or portion thereof, and BRS3 or a portion thereof. In certain embodiments, the modified CD3ζ polypeptide lacks ITAM2, ITAM3, BRS2, and BRS3. In certain embodiments, the CAR comprises the amino acid sequence set forth in SEQ ID NO: 45 or SEQ ID NO: 47. In certain embodiments, the CAR comprises an extracellular antigen-binding domain, a transmembrane domain, and an intracellular signaling domain comprising a modified CD3ζ polypeptide, wherein the modified CD3ζ polypeptide lacks all or part of basic-rich stretch (BRS) regions, wherein the BRS regions are BRS1, BRS2, and BRS3. In certain embodiments, the CAR comprises an extracellular antigen-binding domain, a transmembrane domain, and an intracellular signaling domain comprising a modified CD3ζ polypeptide, wherein the modified CD3ζ polypeptide comprises a BRS variant selected from a BRS1 variant, a BRS2 variant, and a BRS3 variant, wherein the BRS variant comprises one or more loss-of-function mutations.

Co-Stimulatory Signaling Region

In certain non-limiting embodiments, an intracellular signaling domain of the CAR further comprises at least a co-stimulatory signaling region. In certain embodiments, the co-stimulatory signaling region comprises at least one co-stimulatory molecule, which can provide optimal lymphocyte activation.

As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a DAP-10 polypeptide, a CD27 peptide, a CD40/My88 peptide, a NKGD2 peptide or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. Co-stimulatory ligands, include, but are not limited to CD80, CD86, CD70, OX40L, and 4-1BBL. As one example, a 4-1BB ligand (i.e., 4-1BBL) may bind to 4-1BB (also known as "CD137") for providing an intracellular signal that in combination with a CAR signal induces an effector cell function of the CAR$^+$ T cell. CARs comprising an intracellular signaling domain that comprises a co-stimulatory signaling region comprising 4-1BB, ICOS or DAP-10 are disclosed in U.S. Pat. No. 7,446,190, which is herein incorporated by reference in its entirety.

In certain embodiments, the intracellular signaling domain of the CAR comprises a co-stimulatory signaling region that comprises a CD28 polypeptide. The CD28 polypeptide can comprise or have an amino acid sequence that is at least about 80%, at least about 85%, at least about 90%, at least about 95%, at least about 96%, at least about 97%, at least about 98%, or at least about 99%, at least about 100% homologous or identical to the sequence having a NCBI Reference No: P10747 or NP_006130 (SEQ ID NO: 90), or fragments thereof, and/or may optionally comprise up to one or up to two or up to three conservative amino acid substitutions. In non-limiting certain embodiments, the CD28 polypeptide comprises or has an amino acid sequence that is a consecutive portion of SEQ ID NO: 90 which is at least 20, or at least 30, or at least 40, or at least 50, and up to 220 amino acids in length. Alternatively or additionally, in non-limiting various embodiments, the CD28 polypeptide comprises or has an amino acid sequence of amino acids 1 to 220, 1 to 50, 50 to 100, 100 to 150, 114 to 220, 150 to 200, or 200 to 220 of SEQ ID NO: 90. In certain embodiments, the intracellular signaling domain of the CAR comprises a co-stimulatory signaling region that comprises a CD28 polypeptide comprising or having an amino acid sequence of amino acids 180 to 220 of SEQ ID NO: 90.

In certain embodiments, the CD28 polypeptide comprises or has an amino acid sequence that is at least about 80%, at least about 85%, at least about 90%, at least about 95%, at least about 96%, at least about 97%, at least about 98%, or at least about 99%, at least about 100% homologous or identical to the sequence having a NCBI Reference No: NP_031668.3 (SEQ ID NO: 97), or fragments thereof, and/or may optionally comprise up to one or up to two or up to three conservative amino acid substitutions. In non-limiting certain embodiments, the CD28 polypeptide comprises or has an amino acid sequence that is a consecutive portion of SEQ ID NO: 97 which is at least about 20, or at least about 30, or at least about 40, or at least about 50, and up to 218 amino acids in length. Alternatively or additionally, in non-limiting various embodiments, the CD28 polypeptide comprises or has an amino acid sequence of amino acids 1 to 218, 1 to 50, 50 to 100, 100 to 150, 114 to 220, 150 to 200, 178 to 218, or 200 to 220 of SEQ ID NO: 97. In certain embodiments, the co-stimulatory signaling region of a presently disclosed CAR comprises a CD28 polypeptide that comprises or has the amino acids 178 to 218 of SEQ ID NO: 97.

SEQ ID NO: 97 is provided below:

```
                                           [SEQ ID NO: 97]
  1    MTLRLLFLAL NFFSVQVTEN KILVKQSPLL VVDSNEVSLS

CRYSYNLLAK EFRASLYKGV

61    NSDVEVCVGN GNFTYQPQFR SNAEFNCDGD FDNETVTFRL

WNLHVNHTDI YFCKIEFMYP

121    PPYLDNERSN GTIIHIKEKH LCHTQSSPKL FWALVVVAGV

LFCYGLLVTV ALCVIWTNSR

181    RNRLLQSDYM NMTPRRPGLT RKPYQPYAPA RDFAAYRP
```

In accordance with the presently disclosed subject matter, a "CD28 nucleic acid molecule" refers to a polynucleotide encoding a CD28 polypeptide. In certain embodiments, a CD28 nucleic acid molecule that encodes a CD28 polypeptide comprised in the co-stimulatory signaling region of a presently disclosed CAR (e.g., amino acids 178 to 218 of SEQ ID NO: 97) comprises or has a nucleotide sequence set forth in SEQ ID NO: 98, which is provided below.

```
                                           [SEQ ID NO: 98]
aat agtagaagga acagactcct tcaaagtgac tacatgaaca tgactccccg gaggcctggg ctcactcgaa agccttacca gccctacgcc cctgccagag actttgcagc gtaccgcccc
```

In certain embodiments, the intracellular signaling domain of the CAR comprises a murine intracellular signaling domain of CD28. The murine intracellular signaling domain of CD28 can comprise or have an amino acid sequence that is at least about 80%, at least about 85%, at least about 90%, at least about 95%, at least about 96%, at least about 97%, at least about 98%, or at least about 99%, at least about 100% homologous or identical to SEQ ID NO: 99 or fragments thereof, and/or may optionally comprise up to one or up to two or up to three conservative amino acid substitutions. SEQ ID NO: 99 is provided below:

```
                                           [SEQ ID NO: 99]
     NSRRNRLLQS DYMNMTPRRP GLTRKPYQPY APARDFAAYR P.
```

An exemplary nucleic acid sequence encoding the amino acid sequence of SEQ ID NO: 99 is set forth in SEQ ID NO: 100, which is provided below.

```
                                           [SEQ ID NO: 100]
AATAGTAGAAGGAACAGACTCCTTCAAAGTGACTACATGAACATGACTCC

CCGGAGGCCTGGGCTCACTCGAAAGCCTTACCAGCCCTACGCCCCTGCCA

GAGACTTTGCAGCGTACCGCCCC
```

In certain embodiments, the intracellular signaling domain of the CAR comprises a human intracellular signaling domain of CD28. The human intracellular signaling domain of CD28 can comprise or have an amino acid sequence that is at least about 80%, at least about 85%, at least about 90%, at least about 95%, at least about 96%, at least about 97%, at least about 98%, or at least about 99%, at least about 100% homologous or identical to SEQ ID NO: 101 or fragments thereof, and/or may optionally comprise up to one or up to two or up to three conservative amino acid substitutions. SEQ ID NO: 101 is provided below:

```
                                           [SEQ ID NO: 101]
     RSKRSRLLHS DYMNMTPRRP GPTRKHYQPY APPRDFAAYR S.
```

An exemplary nucleic acid sequence encoding the amino acid sequence of SEQ ID NO: 70 is set forth in SEQ ID NO: 102, which is provided below.

```
                                           [SEQ ID NO: 102]
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC
```

In certain embodiments, the intracellular signaling domain of the CAR comprises a de-immunized human intracellular signaling domain of CD28. The de-immunized human intracellular signaling domain of CD28 can comprise or have an amino acid sequence that is at least about 80%, at least about 85%, at least about 90%, at least about 95%, at least about 96%, at least about 97%, at least about 98%, or at least about 99%, at least about 100% homologous or identical to SEQ ID NO: 108 or fragments thereof, and/or may optionally comprise up to one or up to two or up to three conservative amino acid substitutions. SEQ ID NO: 108 is provided below:

```
                                           [SEQ ID NO: 108]
     RSKRSRLLHS DYMNMTPRRP GPTRKHYQPY APPRDFAAYR K
```

In certain embodiments, the intracellular signaling domain of the CAR comprises a co-stimulatory signaling region that comprises two co-stimulatory molecules, e.g., co-stimulatory signaling regions of CD28 and 4-1BB or co-stimulatory signaling regions of CD28 and OX40.

4-1BB can act as a tumor necrosis factor (TNF) ligand and have stimulatory activity. The 4-1BB polypeptide can comprise or have an amino acid sequence that is at least about 80%, at least about 85%, at least about 90%, at least about 95%, at least about 96%, at least about 97%, at least about 98%, or at least about 99%, at least about 100% homologous or identical to the sequence having a NCBI Reference No: P41273 or NP_001552 (SEQ ID NO: 103) or fragments thereof, and/or may optionally comprise up to one or up to two or up to three conservative amino acid substitutions.

SEQ ID NO: 103 is provided below:

```
                                              [SEQ ID NO: 103]
  1 MGNSCYNIVA TLLLVLNFER TRSLQDPCSN CPAGTFCDNN
    RNQICSPCPP NSFSSAGGQR

61 TCDICRQCKG VFRTRKECSS TSNAECDCTP GFHCLGAGCS
    MCEQDCKQGQ ELTKKGCKDC

121 CFGTFNDQKR GICRPWTNCS LDGKSVLVNG TKERDVVCGP
    SPADLSPGAS SVTPPAPARE

181 PGHSPQIISF FLALTSTALL FLLFFLTLRF SVVKRGRKKL
    LYIFKQPFMR PVQTTQEEDG

241 CSCRFPEEEE GGCEL
```

In accordance with the presently disclosed subject matter, a "4-1BB nucleic acid molecule" refers to a polynucleotide encoding a 4-1BB polypeptide.

In certain embodiments, the intracellular signaling domain of the CAR comprises a intracellular signaling domain of 4-1BB. The intracellular signaling domain of 4-1BB can comprise or have an amino acid sequence that is at least about 80%, at least about 85%, at least about 90%, at least about 95%, at least about 96%, at least about 97%, at least about 98%, or at least about 99%, at least about 100% homologous or identical to SEQ ID NO: 104 or fragments thereof, and/or may optionally comprise up to one or up to two or up to three conservative amino acid substitutions. SEQ ID NO: 104 is provided below:

```
                                              [SEQ ID NO: 104]
KRGRKKLLYI FKQPFMRPVQ TTQEEDGCSC RFPEEEEGGC EL.
```

An exemplary nucleic acid sequence encoding the amino acid sequence of SEQ ID NO: 104 is set forth in SEQ ID NO: 105, which is provided below.

```
                                              [SEQ ID NO: 105]
AAACGGGGCAGAAAGAAACTCCTGTATATATTCAAACAACCATTTATGAGA

CCAGTACAAACTACTCAAGAGGAAGATGGCTGTAGCTGCCGATTTCCAGAA

GAAGAAGAAGGAGGATGTGAACTG
```

An OX40 polypeptide can comprise or have an amino acid sequence that is at least about 80%, at least about 85%, at least about 90%, at least about 95%, at least about 96%, at least about 97%, at least about 98%, or at least about 99%, at least about 100% homologous or identical to the sequence having a NCBI Reference No: P43489 or NP_003318 (SEQ ID NO: 106), or fragments thereof, and/or may optionally comprise up to one or up to two or up to three conservative amino acid substitutions.

SEQ ID NO: 106 is provided below:

```
                                              [SEQ ID NO: 106]
  1 MCVGARRLGR GPCAALLLLG LGLSTVTGLH CVGDTYPSND
    RCCHECRPGN GMVSRCSRSQ

61 NTVCRPCGPG FYNDVVSSKP CKPCTWCNLR SGSERKQLCT
    ATQDTVCRCR AGTQPLDSYK

121 PGVDCAPCPP GHFSPGDNQA CKPWTNCTLA GKHTLQPASN
    SSDAICEDRD PPATQPQETQ

181 GPPARPITVQ PTEAWPRTSQ GPSTRPVEVP GGRAVAAILG
    LGLVLGLLGP LAILLALYLL

241 RRDQRLPPDA HKPPGGGSFR TPIQEEQADA HSTLAKI
```

In accordance with the presently disclosed subject matter, an "OX40 nucleic acid molecule" refers to a polynucleotide encoding an OX40 polypeptide.

An ICOS polypeptide can comprise or have an amino acid sequence that is at least about 80%, at least about 85%, at least about 90%, at least about 95%, at least about 96%, at least about 97%, at least about 98%, or at least about 99%, at least about 100% homologous or identical homologous to the sequence having a NCBI Reference No: NP_036224 (SEQ ID NO: 65) or fragments thereof, and/or may optionally comprise up to one or up to two or up to three conservative amino acid substitutions.

SEQ ID NO: 65 is provided below:

```
                                              [SEQ ID NO: 65]
  1 MKSGLWYFFL FCLRIKVLTG EINGSANYEM FIFHNGGVQI
    LCKYPDIVQQ FKMQLLKGGQ

61 ILCDLIKTKG SGNTVSIKSL KFCHSQLSNN SVSFFLYNLD
    HSHANYYFCN LSIFDPPPFK

121 VTLIGGYLHI YESQLCCQLK FWLPIGCAAF VVVCILGCIL
    ICWLTKKKYS SSVHDPNGEY

181 MFMRAVNTAK KSRLTDVTL
```

In accordance with the presently disclosed subject matter, an "ICOS nucleic acid molecule" refers to a polynucleotide encoding an ICOS polypeptide.

In certain embodiments, a presently disclosed CAR further comprises an inducible promoter, for expressing nucleic acid sequences in human cells. Promoters for use in expressing CAR genes can be a constitutive promoter, such as ubiquitin C (UbiC) promoter.

In certain embodiments, mutation sites and/or junction between domains/motifs/regions of the CAR derived from different proteins are de-immunized. Immunogenicity of junctions between different CAR moieties can be predicted using NetMHC 4.0 Server. For each peptide containing at least one amino acid from next moiety, binding affinity to HLA A, B and C, for all alleles, can be predicted. A score of immunogenicity of each peptide can be assigned for each peptide. Immunogenicity score can be calculated using the formula Immunogenicity score=$[(50-\text{binding affinity})*\text{HLA frequency}]_n$. n is the number of prediction for each peptide.

1928z WT Construct

In certain embodiments, a presently disclosed CAR comprises an extracellular antigen-binding domain that binds to a CD19 polypeptide (e.g., a human CD19 polypeptide), a transmembrane domain and a hinge/spacer region derived from a CD28 polypeptide, an intracellular signaling domain comprising a modified CD3ζ polypeptide (e.g., a modified human CD3ζ polypeptide) comprising a native ITAM1, a native ITAM2, a native ITAM3, a native BRS1, a native BRS2, and a native BRS3, and a co-stimulatory signaling region comprising a CD28 polypeptide (e.g., a human CD28 polypeptide). In certain embodiments, the CAR is designated as "1928z WT". In certain embodiments, the CAR (e.g., 1928z WT) comprises an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 41, which is provided below. SEQ ID NO: 41 includes a CD8 leader sequence at amino acids 1 to 18, and is able to bind to CD19 (e.g., human CD19).

[SEQ ID NO: 41]
MALPVTALLLPLALLLHAEVKLQQSGAELVRPGSSVKISCKASGYAFSSYW
MNWVKQRPGQGLEWIGQIYPGDGDTNYNGKFKGQATLTADKSSSTAYMQLS
GLTSEDSAVYFCARKTISSVVDFYFDYWGQGTTVTVSSGGGGSGGGGSGGG
GSDIELTQSPKFMSTSVGDRVSVTCKASQNVGTNVAWYQQKPGQSPKPLIY
SATYRNSGVPDRFTGSGSGTDFTLTITNVQSKDLADYFCQQYNRYPYTSGG
GTKLEIKRAAAIEVMYPPPYLDNEKSNGTIIHVKGKHLCPSPLFPGPSKPF
WVLVVVGGVLACYSLLVTVAFIIFWVRSKRSRLLHSDYMNMTPRRPGPTRK
HYQPYAPPRDFAAYRSRVKFSRSADAPAYQQGQNQLYNELNLGRREEYDVL
DKRRGRDPEMGGKPRRKNPQEGLYNELQKDKMAEAYSEIGMKGERRRGKGH
DGLYQGLSTATKDTYDALHMQALPPR

An exemplary nucleic acid sequence encoding the amino acid sequence of SEQ ID NO: 41 is set forth in SEQ ID NO: 42, which is provided below.

[SEQ ID NO: 42]
atggctctcccagtgactgccctactgcttcccctagcgcttctcctgcat gcagaggtgaagctgcagcagtctggggctgagctggtgaggcctgggtcc tcagtgaagatttcctgcaaggcttctggctatgcattcagtagctactgg atgaactgggtgaagcagaggcctggacagggtcttgagtggattggacag atttatcctggagatggtgatactaactacaatggaaagttcaagggtcaa gccacactgactgcagacaaatcctccagcacagcctacatgcagctcagc ggcctaacatctgaggactctgcggtctatttctgtgcaagaaagaccatt agttcggtagtagatttctactttgactactgggccaagggaccacggtc accgtctcctcaggtggaggtggatcaggtggaggtggatctggtggaggt ggatctgacattgagctcacccagtctccaaaattcatgtccacatcagta ggagacagggtcagcgtcacctgcaaggccagtcagaatgtgggtactaat gtagcctggtatcaacagaaaccaggacaatctcctaaaccactgatttac tcggcaacctaccggaacagtggagtccctgatcgcttcacaggcagtgga tctgggacagatttcactctcaccatcactaacgtgcagtctaaagacttg gcagactatttctgtcaacaatataacaggtatccgtacacgtccggaggg gggaccaagctggagatcaaacgggcggccgcaattgaagttatgtatcct cctcttacctagacaatgagaagagcaatggaaccattatccatgtgaaa gggaaacacctttgtccaagtcccctatttcccggaccttctaagcccttt tgggtgctggtggtggttggtggagtcctggcttgctatagcttgctagta acagtggcctttattattttctgggtgaggagtaagaggagcaggctcctg cacagtgactacatgaacatgactccccgccgccccgggccacccgcaag cattaccagccctatgccccaccacgcgacttcgcagcctatcgctccaga gtgaagttcagcaggagcgcagacgcccccgcgtaccagcagggccagaac -continued cagctctataacgagctcaatctaggacgaagagaggagtacgatgttttg gacaagagacgtggccgggacccctgagatgggggaaagccgagaaggaag aaccctcaggaaggcctgtacaatgaactgcagaaagataagatggcggag gcctacagtgagattgggatgaaaggcgagcgccggaggggcaaggggcac gatggcctttaccagggtctcagtacagccaccaaggacacctacgacgcc cttcacatgcaggccctgcccctcgctaa 1XX Construct In certain embodiments, a presently disclosed CAR comprises an extracellular antigen-binding domain that binds to a CD19 polypeptide (e.g., a human CD19 polypeptide), a transmembrane domain and a hinge/spacer region derived from a CD28 polypeptide, an intracellular signaling domain comprising a modified CD3ζ polypeptide (e.g., a modified human CD3ζ polypeptide) comprising a native ITAM1, a native BRS1, a native BRS2, a native BRS3, an ITAM2 variant having two loss-of-function mutations, and an ITAM3 variant having two loss-of-function mutations, and a co-stimulatory signaling region comprising a CD28 polypeptide (e.g., a human CD28 polypeptide). In certain embodiments, the CAR is designated as "1XX". In certain embodiments, the CAR (e.g., 1XX) comprises an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 43, which is provided below. SEQ ID NO: 43 includes a CD8 leader sequence at amino acids 1 to 18, and is able to bind to CD19 (e.g., human CD19).

[SEQ ID NO: 43]
MALPVTALLLPLALLLHAEVKLQQSGAELVRPGSSVKISCKASGYAFSSYW
MNWVKQRPGQGLEWIGQIYPGDGDTNYNGKFKGQATLTADKSSSTAYMQLS
GLTSEDSAVYFCARKTISSVVDFYFDYWGQGTTVTVSSGGGGSGGGGSGGG
GSDIELTQSPKFMSTSVGDRVSVTCKASQNVGTNVAWYQQKPGQSPKPLIY
SATYRNSGVPDRFTGSGSGTDFTLTITNVQSKDLADYFCQQYNRYPYTSGG
GTKLEIKRAAAIEVMYPPPYLDNEKSNGTIIHVKGKHLCPSPLFPGPSKPF
WVLVVVGGVLACYSLLVTVAFIIFWVRSKRSRLLHSDYMNMTPRRPGPTRK
HYQPYAPPRDFAAYRSRVKFSRSADAPAYQQGQNQLYNELNLGRREEYDVL
DKRRGRDPEMGGKPRRKNPQEGLFNELQKDKMAEAFSEIGMKGERRRGKGH
DGLFQGLSTATKDTFDALHMQALPPR

An exemplary nucleic acid sequence encoding the amino acid sequence of SEQ ID NO: 43 is set forth in SEQ ID NO: 44, which is provided below.

[SEQ ID NO: 44]
atggctctcccagtgactgccctactgcttcccctagcgcttctcctgcat gcagaggtgaagctgcagcagtctggggctgagctggtgaggcctgggtcc tcagtgaagatttcctgcaaggcttctggctatgcattcagtagctactgg atgaactgggtgaagcagaggcctggacagggtcttgagtggattggacag atttatcctggagatggtgatactaactacaatggaaagttcaagggtcaa

```
gccacactgactgcagacaaatcctccagcacagcctacatgcagctcagc ggcctaacatctgaggactctgcggtctatttctgtgcaagaaagaccatt agttcggtagtagatttctactttgactactggggccaagggaccacggtc accgtctcctcaggtggaggtggatcaggtggaggtggatctggtggaggt ggatctgacattgagctcacccagtctccaaaattcatgtccacatcagta ggagacagggtcagcgtcacctgcaaggccagtcagaatgtgggtactaat gtagcctggtatcaacagaaaccaggacaatctcctaaaccactgatttac tcggcaacctaccggaacagtggagtccctgatcgcttcacaggcagtgga tctgggacagatttcactctcaccatcactaacgtgcagtctaaagacttg gcagactatttctgtcaacaatataacaggtatccgtacacgtccggaggg gggaccaagctggagatcaaacgggcggccgcaattgaagttatgtatcct cctccttacctagacaatgagaagagcaatggaaccattatccatgtgaaa gggaaacacctttgtccaagtcccctatttcccggaccttctaagcccttt tgggtgctggtggtggttggtggagtcctggcttgctatagcttgctagta acagtggcctttattattttctgggtgaggagtaagaggagcaggctcctg cacagtgactacatgaacatgactccccgccgccccgggcccacccgcaag cattaccagccctatgccccaccacgcgacttcgcagcctatcgctccaga gtgaagttcagcaggagcgcagacgcccccgcgtaccagcagggccagaac cagctctataacgagctcaatctaggacgaagagaggagtacgatgttttg gacaagagacgtggccgggaccctgagatgggggaaagccgagaaggaag aaccctcaggaaggcctgtTcaatgaactgcagaaagataagatggcggag gcctTcagtgagattgggatgaaaggcgagcgccggaggggcaaggggcac gatggcctttTccaggggctcagtacagccaccaaggacacctTcgacgcc cttcacatgcaggccctgccccctcgctaa
```

D12 Construct

In certain embodiments, a presently disclosed CAR comprises an extracellular antigen-binding domain that binds to a CD19 polypeptide (e.g., a human CD19 polypeptide), a transmembrane domain and a hinge/spacer region derived from a CD28 polypeptide, an intracellular signaling domain comprising a modified CD3ζ polypeptide (e.g., a modified human CD3ζ polypeptide), and a co-stimulatory signaling region comprising a CD28 polypeptide (e.g., a human CD28 polypeptide), wherein the modified CD3ζ polypeptide comprises a native ITAM3 and does not comprise an ITAM1 (native or modified), an ITAM2 (native or modified), a BRS1 (native or modified), a BRS2 (native or modified), or a BRS3 (native or modified). In certain embodiments, the CAR is designated as "D12". In certain embodiments, the CAR (e.g., D12) comprises an amino acid sequence that is at least about 85%, about 90%, about 95%, about 96%, about 97%, about 98%, about 99% or about 100% homologous to the amino acid sequence set forth in SEQ ID NO: 45, which is provided below. SEQ ID NO: 45 includes a CD8 leader sequence at amino acids 1 to 18, and is able to bind to CD19 (e.g., human CD19).

```
                                          [SEQ ID NO: 45]
MALPVTALLLPLALLLHAEVKLQQSGAELVRPGSSVKISCKASGYAFSSYW

MNWVKQRPGQGLEWIGQIYPGDGDTNYNGKFKGQATLTADKSSSTAYMQLS

GLTSEDSAVYFCARKTISSVVDFYFDYWGQGTTVTVSSGGGGSGGGGSGGG

GSDIELTQSPKFMSTSVGDRVSVTCKASQNVGTNVAWYQQKPGQSPKPLIY

SATYRNSGVPDRFTGSGSGTDFTLTITNVQSKDLADYFCQQYNRYPYTSGG

GTKLEIKRAAAIEVMYPPPYLDNEKSNGTIIHVKGKHLCPSPLFPGPSKPF

WVLVVVGGVLACYSLLVTVAFIIFWVRSKRSRLLHSDYMNMTPRRPGPTRK

HYQPYAPPRDFAAYRSRVKFSRSADAPAYQQGHDGLYQGLSTATKDTYDAL

HMQALPPR
```

An exemplary nucleic acid sequence encoding the amino acid sequence of SEQ ID NO: 45 is set forth in SEQ ID NO: 46, which is provided below.

```
                                          [SEQ ID NO: 46]
atggctctcccagtgactgccctactgcttccctagcgcttctcctgcat gcagaggtgaagctgcagcagtctggggctgagctggtgaggcctgggtcc tcagtgaagatttcctgcaaggcttctggctatgcattcagtagctactgg atgaactgggtgaagcagaggcctggacagggtcttgagtggattggacag atttatcctggagatggtgatactaactacaatggaaagttcaagggtcaa gccacactgactgcagacaaatcctccagcacagcctacatgcagctcagc ggcctaacatctgaggactctgcggtctatttctgtgcaagaaagaccatt agttcggtagtagatttctactttgactactggggccaagggaccacggtc accgtctcctcaggtggaggtggatcaggtggaggtggatctggtggaggt ggatctgacattgagctcacccagtctccaaaattcatgtccacatcagta ggagacagggtcagcgtcacctgcaaggccagtcagaatgtgggtactaat gtagcctggtatcaacagaaaccaggacaatctcctaaaccactgatttac tcggcaacctaccggaacagtggagtccctgatcgcttcacaggcagtgga tctgggacagatttcactctcaccatcactaacgtgcagtctaaagacttg gcagactatttctgtcaacaatataacaggtatccgtacacgtccggaggg gggaccaagctggagatcaaacgggcggccgcaattgaagttatgtatcct cctccttacctagacaatgagaagagcaatggaaccattatccatgtgaaa gggaaacacctttgtccaagtcccctatttcccggaccttctaagcccttt tgggtgctggtggtggttggtggagtcctggcttgctatagcttgctagta acagtggcctttattattttctgggtgaggagtaagaggagcaggctcctg cacagtgactacatgaacatgactccccgccgccccgggcccacccgcaag cattaccagccctatgccccaccacgcgacttcgcagcctatcgctccaga gtgaagttcagcaggagcgcagacgcccccgcgtaccagcagggccacgat ggcctttaccaggggctcagtacagccaccaaggacacctacgacgccctt cacatgcaggccctgccccctcgctaa
```

D23 Construct

In certain embodiments, a presently disclosed CAR comprises an extracellular antigen-binding domain that binds to a CD19 polypeptide (e.g., human CD19 polypeptide), a transmembrane domain and a hinge/spacer region derived from a CD28 polypeptide, an intracellular signaling domain comprising a modified CD3ζ polypeptide (e.g., a modified human CD3ζ polypeptide) comprising ITAM1, BRS1 and a deletion of ITAM2, ITAM3, BRS2 and BRS3, and a co-stimulatory signaling region comprising a CD28 polypeptide (e.g., a human CD28 polypeptide), wherein the modified CD3ζ polypeptide comprises a native ITAM1 and a native BRS1, and does not comprise an ITAM2 (native or modified), an ITAM3 (native or modified), a BRS2 (native or modified), or a BRS3 (native or modified). In certain embodiments, the CAR is designated as "D23". In certain embodiments, the CAR (e.g., D23) comprises an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 47, which is provided below. SEQ ID NO: 47 includes a CD8 sequence at amino acids 1 to 18, and is able to bind to CD19 (e.g., human CD19).

[SEQ ID NO: 47]
MALPVTALLLPLALLLHAEVKLQQSGAELVRPGSSVKISCKASGYAFSSYW

MNWVKQRPGQGLEWIGQIYPGDGDTNYNGKFKGQATLTADKSSSTAYMQLS

GLTSEDSAVYFCARKTISSVVDFYFDYWGQGTTVTVSSGGGGSGGGGSGGG

GSDIELTQSPKFMSTSVGDRVSVTCKASQNVGTNVAWYQQKPGQSPKPLIY

SATYRNSGVPDRFTGSGSGTDFTLTITNVQSKDLADYFCQQYNRYPYTSGG

GTKLEIKRAAAIEVMYPPPYLDNEKSNGTIIHVKGKHLCPSPLFPGPSKPF

WVLVVVGGVLACYSLLVTVAFIIFWVRSKRSRLLHSDYMNMTPRRPGPTRK

HYQPYAPPRDFAAYRSRVKFSRSADAPAYQQGQNQLYNELNLGRREEYDVL

DKRRGRDP

An exemplary nucleic acid sequence encoding the amino acid sequence of SEQ ID NO: 47 is set forth in SEQ ID NO: 48, which is provided below.

[SEQ ID NO: 48]
atggctctcccagtgactgccctactgcttcccctagcgcttctcctgcat gcagaggtgaagctgcagcagtctggggctgagctggtgaggcctggtcc tcagtgaagatttcctgcaaggcttctggctatgcattcagtagctactgg atgaactgggtgaagcagaggcctggacagggtcttgagtggattggacag atttatcctggagatggtgatactaactacaatggaaagttcaagggtcaa gccacactgactgcagacaaatcctccagcacagcctacatgcagctcagc ggcctaacatctgaggactctgcggtctatttctgtgcaagaaagaccatt agttcggtagtagatttctactttgactactggggccaagggaccacggtc accgtctcctcaggtggaggtggatcaggtggaggtggatctggtggaggt ggatctgacattgagctcacccagtctccaaaattcatgtccacatcagta ggagacagggtcagcgtcacctgcaaggccagtcagaatgtgggtactaat gtagcctggtatcaacagaaaccaggacaatctcctaaaccactgatttac tcggcaacctaccggaacagtggagtccctgatcgcttcacaggcagtgga tctgggacagatttcactctcaccatcactaacgtgcagtctaaagacttg gcagactattctgtcaacaatataacaggtatccgtacacgtccggaggg gggaccaagctggagatcaaacgggcggccgcaattgaagttatgtatcct cctccttacctagacaatgagaagagcaatggaaccattatccatgtgaaa gggaaacacctttgtccaagtcccctatttcccggaccttctaagcccttt tgggtgctggtggtggttggtggagtcctggcttgctatagcttgctagta acagtggcctttattattttctgggtgaggagtaagaggagcaggctcctg cacagtgactacatgaacatgactccccgccgccccgggcccacccgcaag cattaccagccctatgcccaccacgcgacttcgcagcctatcgctccaga gtgaagttcagcaggagcgcagacgccccgcgtaccagcagggccagaac cagctctataacgagctcaatctaggacgaagagaggagtacgatgttttg gacaagagacgtggccgggacccttaa XX3 Construct In certain embodiments, a presently disclosed CAR comprises an extracellular antigen-binding domain that binds to a CD19 polypeptide (e.g., a human CD19 polypeptide), a transmembrane domain and a hinge/spacer region derived from a CD28 polypeptide, an intracellular signaling domain comprising a modified CD3ζ polypeptide (e.g., a modified human CD3ζ polypeptide) comprising a native ITAM3, a native BRS1, a native BRS2, a native BRS3, an ITAM1 variant having two loss-of-function mutations, and an ITAM2 variant having two loss-of-function mutations, and a co-stimulatory signaling region comprising a CD28 polypeptide (e.g., a human CD28 polypeptide). In certain embodiments, the CAR is designated as "XX3". In certain embodiments, the CAR (e.g., XX3) comprises an amino acid sequence that is at least about 85%, about 90%, about 95%, about 96%, about 97%, about 98%, about 99% or about 100% homologous to the amino acid sequence set forth in SEQ ID NO: 49, which is provided below. SEQ ID NO: 49 includes a CD8 leader sequence at amino acids 1 to 18, and is able to bind to CD19 (e.g., human CD19).

[SEQ ID NO: 49]
MALPVTALLLPLALLLHAEVKLQQSGAELVRPGSSVKISCKASGYAFSSYW

MNWVKQRPGQGLEWIGQIYPGDGDTNYNGKFKGQATLTADKSSSTAYMQLS

GLTSEDSAVYFCARKTISSVVDFYFDYWGQGTTVTVSSGGGGSGGGGSGGG

GSDIELTQSPKFMSTSVGDRVSVTCKASQNVGTNVAWYQQKPGQSPKPLIY

SATYRNSGVPDRFTGSGSGTDFTLTITNVQSKDLADYFCQQYNRYPYTSGG

GTKLEIKRAAAIEVMYPPPYLDNEKSNGTIIHVKGKHLCPSPLFPGPSKPF

WVLVVVGGVLACYSLLVTVAFIIFWVRSKRSRLLHSDYMNMTPRRPGPTRK

HYQPYAPPRDFAAYRSRVKFSRSADAPAYQQGQNQLFNELNLGRREEFDVL

DKRRGRDPEMGGKPRRKNPQEGLFNELQKDKMAEAFSEIGMKGERRRGKGH

DGLYQGLSTATKDTYDALHMQALPPR

An exemplary nucleic acid sequence encoding the amino acid sequence of SEQ ID NO: 49 is set forth in SEQ ID NO: 50, which is provided below.

[SEQ ID NO: 50]
atggctctcccagtgactgccctactgcttcccctagcgcttctcctg catgcagaggtgaagctgcagcagtctggggctgagctggtgaggcct -continued

```
gggtcctcagtgaagatttcctgcaaggcttctggctatgcattcagt agctactggatgaactgggtgaagcagaggcctggacagggtcttgag tggattggacagatttatcctggagatggtgatactaactacaatgga aagttcaagggtcaagccacactgactgcagacaaatcctccagcaca gcctacatgcagctcagcggcctaacatctgaggactctgcggtctat ttctgtgcaagaaagaccattagttcggtagtagatttctactttgac tactggggccaagggaccacggtcaccgtctcctcaggtggaggtgga tcaggtggaggtggatctggtggaggtggatctgacattgagctcacc cagtctccaaaattcatgtccacatcagtaggagacagggtcagcgtc acctgcaaggccagtcagaatgtgggtactaatgtagcctggtatcaa cagaaaccaggacaatctcctaaaccactgatttactcggcaacctac cggaacagtggagtccctgatcgcttcacaggcagtggatctgggaca gatttcactctcaccatcactaacgtgcagtctaaagacttggcagac tatttctgtcaacaatataacaggtatccgtacacgtccggagggggg accaagctggagatcaaacgggcggccgcaattgaagttatgtatcct cctccttacctagacaatgagaagagcaatggaaccattatccatgtg aaagggaaacacctttgtccaagtccctatttcccggaccttctaag cccttttgggtgctggtggtggttggtggagtcctggcttgctatagc ttgctagtaacagtggcctttattattttctgggtgaggagtaagagg agcaggctcctgcacagtgactacatgaacatgactccccgccgcccc gggcccacccgcaagcattaccagccctatgccccaccacgcgacttc gcagcctatcgctccagagtgaagttcagcaggagcgcagacgccccc gcgtaccagcagggccagaaccagctctTtaacgagctcaatctagga cgaagagaggagtTcgatgttttggacaagagacgtggccgggaccct gagatgggggaaagccgagaaggaagaaccctcaggaaggcctgtTc aatgaactgcagaaagataagatggcggaggcctTcagtgagattggg atgaaagcgagcgccgaggggcaaggggcacgatggcctttaccag ggtctcagtacagccaccaaggacacctacgacgccttcacatgcag gccctgccccctcgctaa
```

X23 Construct

In certain embodiments, a presently disclosed CAR comprises an extracellular antigen-binding domain that binds to a CD19 polypeptide (e.g., a human CD19 polypeptide), a transmembrane domain and a hinge/spacer region derived from a CD28 polypeptide, an intracellular signaling domain comprising a modified CD3ζ polypeptide (e.g., a modified human CD3ζ polypeptide) comprising a native ITAM2, a native ITAM3, a native BRS1, a native BRS2, a native BRS3, and an ITAM1 variant having two loss-of-function mutations, and a co-stimulatory signaling region comprising a CD28 polypeptide (e.g., a human CD28 polypeptide). In certain embodiments, the CAR is designated as "X23". In certain embodiments, the CAR (e.g., X23) comprises an amino acid sequence that is at least about 85%, about 90%, about 95%, about 96%, about 97%, about 98%, about 99% or about 100% homologous to the amino acid sequence set forth in SEQ ID NO: 51, which is provided below. SEQ ID NO: 51 includes a CD8 leader sequence at amino acids 1 to 18, and is able to bind to CD19 (e.g., human CD19).

[SEQ ID NO: 51]
MALPVTALLLPLALLLHAEVKLQQSGAELVRPGSSVKISCKASGYAFS

SYWMNWVKQRPGQGLEWIGQIYPGDGDTNYNGKFKGQATLTADKSSST

AYMQLSGLTSEDSAVYFCARKTISSVVDFYFDYWGQGTTVTVSSGGGG

SGGGGSGGGGSDIELTQSPKFMSTSVGDRVSVTCKASQNVGTNVAWYQ

QKPGQSPKPLIYSATYRNSGVPDRFTGSGSGTDFTLTITNVQSKDLAD

YFCQQYNRYPYTSGGGTKLEIKRAAAIEVMYPPPYLDNEKSNGTIIHV

KGKHLCPSPLFPGPSKPFWVLVVVGGVLACYSLLVTVAFIIFWVRSKR

SRLLHSDYMNMTPRRPGPTRKHYQPYAPPRDFAAYRSRVKFSRSADAP

AYQQGQNQLFNELNLGRREEFDVLDKRRGRDPEMGGKPRRKNPQEGLY

NELQKDKMAEAYSEIGMKGERRRGKGHDGLYQGLSTATKDTYDALHMQ

ALPPR

An exemplary nucleic acid sequence encoding the amino acid sequence of SEQ ID NO: 51 is set forth in SEQ ID NO: 52, which is provided below.

[SEQ ID NO: 52]
```
atggctctcccagtgactgccctactgcttccccctagcgcttctcctg catgcagaggtgaagctgcagcagtctggggctgagctggtgaggcct gggtcctcagtgaagatttcctgcaaggcttctggctatgcattcagt agctactggatgaactgggtgaagcagaggcctggacagggtcttgag tggattggacagatttatcctggagatggtgatactaactacaatgga aagttcaagggtcaagccacactgactgcagacaaatcctccagcaca gcctacatgcagctcagcggcctaacatctgaggactctgcggtctat ttctgtgcaagaaagaccattagttcggtagtagatttctactttgac tactggggccaagggaccacggtcaccgtctcctcaggtggaggtgga tcaggtggaggtggatctggtggaggtggatctgacattgagctcacc cagtctccaaaattcatgtccacatcagtaggagacagggtcagcgtc acctgcaaggccagtcagaatgtgggtactaatgtagcctggtatcaa cagaaaccaggacaatctcctaaaccactgatttactcggcaacctac cggaacagtggagtccctgatcgcttcacaggcagtggatctgggaca gatttcactctcaccatcactaacgtgcagtctaaagacttggcagac tatttctgtcaacaatataacaggtatccgtacacgtccggagggggg accaagctggagatcaaacgggcggccgcaattgaagttatgtatcct cctccttacctagacaatgagaagagcaatggaaccattatccatgtg aaagggaaacacctttgtccaagtccctatttcccggaccttctaag cccttttgggtgctggtggtggttggtggagtcctggcttgctatagc ttgctagtaacagtggcctttattattttctgggtgaggagtaagagg agcaggctcctgcacagtgactacatgaacatgactccccgccgcccc gggcccacccgcaagcattaccagccctatgccccaccacgcgacttc gcagcctatcgctccagagtgaagttcagcaggagcgcagacgccccc
```

```
gcgtaccagcagggccagaaccagctctTtaacgagctcaatctagga cgaagagaggagtTcgatgttttggacaagagacgtggccgggaccct gagatgggggaaagccgagaaggaagaaccctcaggaaggcctgtac aatgaactgcagaaagataagatggcggaggcctacagtgagattggg atgaaggcgagcgccggaggggcaaggggcacgatggcctttaccag ggtctcagtacagccaccaaggacacctacgacgccttcacatgcag gccctgccccctcgctaa
```

X2X Construct

In certain embodiments, a presently disclosed CAR comprises an extracellular antigen-binding domain that binds to a CD19 polypeptide (e.g., a human CD19 polypeptide), a transmembrane domain and a hinge/spacer region derived from a CD28 polypeptide, an intracellular signaling domain comprising a modified CD3ζ polypeptide (e.g., a modified human CD3ζ polypeptide) comprising a native ITAM2, a native BRS1, a native BRS2, a native BRS3, an ITAM1 variant having two loss-of-function mutations, and an ITAM3 variant having two loss-of-function mutations, and a co-stimulatory signaling region comprising a CD28 polypeptide (e.g., a human CD28 polypeptide). In certain embodiments, the CAR is designated as "X2X". In certain embodiments, the CAR (e.g., X2X) comprises an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 53, which is provided below. SEQ ID NO: 53 includes a CD8 leader sequence at amino acids 1 to 18, and is able to bind to CD19 (e.g., human CD19).

[SEQ ID NO: 53]
```
MALPVTALLLPLALLLHAEVKLQQSGAELVRPGSSVKISCKASGYAFS

SYWMNWVKQRPGQGLEWIGQIYPGDGDTNYNGKFKGQATLTADKSSST

AYMQLSGLTSEDSAVYFCARKTISSVVDFYFDYWGQGTTVTVSSGGGG

SGGGGSGGGGSDIELTQSPKFMSTSVGDRVSVTCKASQNVGTNVAWYQ

QKPGQSPKPLIYSATYRNSGVPDRFTGSGSGTDFTLTITNVQSKDLAD

YFCQQYNRYPYTSGGGTKLEIKRAAAIEVMYPPPYLDNEKSNGTIIHV

KGKHLCPSPLFPGPSKPFWVLVVVGGVLACYSLLVTVAFIIFWVRSKR

SRLLHSDYMNMTPRRPGPTRKHYQPYAPPRDFAAYRSRVKFSRSADAP

AYQQGQNQLFNELNLGRREEFDVLDKRRGRDPEMGGKPRRKNPQEGLY

NELQKDKMAEAYSEIGMKGERRRGKGHDGLFQGLSTATKDTFDALHMQ

ALPPR
```

An exemplary nucleic acid sequence encoding the amino acid sequence of SEQ ID NO: 53 is set forth in SEQ ID NO: 54, which is provided below.

[SEQ ID NO: 54]
```
atggctctcccagtgactgccctactgcttcccctagcgcttctcctg catgcagaggtgaagctgcagcagtctggggctgagctggtgaggcct gggtcctcagtgaagatttcctgcaaggcttctggctatgcattcagt agctactggatgaactgggtgaagcagaggcctggacagggtcttgag tggattggacagatttatcctggagatggtgatactaactacaatgga aagttcaagggtcaagccacactgactgcagacaaatcctccagcaca gcctacatgcagctcagcggcctaacatctgaggactctgcggtctat ttctgtgcaagaaagaccattagttcggtagtagatttctactttgac tactggggccaagggaccacggtcaccgtctcctcaggtggaggtgga tcaggtggaggtggatctggtggaggtggatctgacattgagctcacc cagtctccaaaattcatgtccacatcagtaggagacagggtcagcgtc acctgcaaggccagtcagaatgtgggtactaatgtagcctggtatcaa cagaaaccaggacaatctcctaaaccactgatttactcggcaacctac cggaacagtggagtccctgatcgcttcacaggcagtggatctgggaca gatttcactctcaccatcactaacgtgcagtctaaagacttggcagac tatttctgtcaacaatataacaggtatccgtacacgtccggaggggg accaagctggagatcaaacgggcggccgcaattgaagttatgtatcct cctccttacctagacaatgagaagagcaatggaaccattatccatgtg aaagggaaacacctttgtccaagtcccctatttcccggaccttctaag ccctttgggtgctggtggtggttggtggagtcctggcttgctatagc ttgctagtaacagtggcctttattattttctgggtgaggagtaagagg agcaggctcctgcacagtgactacatgaacatgactcccgccgcccc gggcccacccgcaagcattaccagccctatgccccaccacgcgacttc gcagcctatcgctccagagtgaagttcagcaggagcgcagacgccccc gcgtaccagcagggccagaaccagctctTtaacgagctcaatctagga cgaagagaggagtTcgatgttttggacaagagacgtggccgggaccct gagatgggggaaagccgagaaggaagaaccctcaggaaggcctgtac aatgaactgcagaaagataagatggcggaggcctacagtgagattggg atgaaggcgagcgccggaggggcaaggggcacgatggcctttTccag gggctcagtacagccaccaaggacacctTcgacgccttcacatgcag gccctgccccctcgctaa
```

12X Construct

In certain embodiments, a presently disclosed CAR comprises an extracellular antigen-binding domain that binds to a CD19 polypeptide (e.g., a human CD19 polypeptide), a transmembrane domain and a hinge/spacer region derived from a CD28 polypeptide, an intracellular signaling domain comprising a modified CD3ζ polypeptide (e.g., a modified human CD3ζ polypeptide) comprising a native ITAM1, a native ITAM2, a native BRS1, a native BRS2, a native BRS3, and an ITAM3 variant having two loss-of-function mutations, and a co-stimulatory signaling region comprising a CD28 polypeptide (e.g., a human CD28 polypeptide). In certain embodiments, the CAR is designated as "12X". In certain embodiments, the CAR (e.g., 12X) comprises an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 55, which is provided below. SEQ ID NO: 55 includes a CD8 leader sequence at amino acids 1 to 18, and is able to bind to CD19 (e.g., human CD19).

[SEQ ID NO: 55]
MALPVTALLLPLALLLHAEVKLQQSGAELVRPGSSVKISCKASGYAFS

SYWMNWVKQRPGQGLEWIGQIYPGDGDTNYNGKFKGQATLTADKSSST

AYMQLSGLTSEDSAVYFCARKTISSVVDFYFDYWGQGTTVTVSSGGGG

SGGGGSGGGGSDIELTQSPKFMSTSVGDRVSVTCKASQNVGTNVAWYQ

QKPGQSPKPLIYSATYRNSGVPDRFTGSGSGTDFTLTITNVQSKDLAD

YFCQQYNRYPYTSGGGTKLEIKRAAAIEVMYPPPYLDNEKSNGTIIHV

KGKHLCPSPLFPGPSKPFWVLVVVGGVLACYSLLVTVAFIIFWVRSKR

SRLLHSDYMNMTPRRPGPTRKHYQPYAPPRDFAAYRSRVKFSRSADAP

AYQQGQNQLYNELNLGRREEYDVLDKRRGRDPEMGGKPRRKNPQEGLY

NELQKDKMAEAYSEIGMKGERRRGKGHDGLFQGLSTATKDTFDALHMQ

ALPPR

An exemplary nucleic acid sequence encoding the amino acid sequence of SEQ ID NO: 55 is set forth in SEQ ID NO: 56, which is provided below.

[SEQ ID NO: 56]
atggctctcccagtgactgccctactgcttcccctagcgcttctcctg catgcagaggtgaagctgcagcagtctggggctgagctggtgaggcct gggtcctcagtgaagatttcctgcaaggcttctggctatgcattcagt agctactggatgaactgggtgaagcagaggcctggacagggtcttgag tggattggacagatttatcctggagatggtgatactaactacaatgga aagttcaagggtcaagccacactgactgcagacaaatcctccagcaca gcctacatgcagctcagcggcctaacatctgaggactctgcggtctat ttctgtgcaagaaagaccattagttcggtagtagatttctactttgac tactggggccaagggaccacggtcaccgtctcctcaggtggaggtgga tcaggtggaggtggatctggtggaggtggatctgacattgagctcacc cagtctccaaaattcatgtccacatcagtaggagacagggtcagcgtc acctgcaaggccagtcagaatgtgggtactaatgtagcctggtatcaa cagaaaccaggacaatctcctaaaccactgatttactcggcaacctac cggaacagtggagtccctgatcgcttcacaggcagtggatctgggaca gatttcactctcaccatcactaacgtgcagtctaaagacttggcagac tatttctgtcaacaatataacaggtatccgtacacgtccggagggggg accaagctggagatcaaacgggcggccgcaattgaagttatgtatcct cctcctacctagacaatgagaagagcaatggaaccattatccatgtg aaagggaaacacctttgtccaagtccctatttcccggaccttctaag ccctttggtgctggtggtggttggtggagtcctggcttgctatagc ttgctagtaacagtggcctttattattttctgggtgaggagtaagagg agcaggctcctgcacagtgactacatgaacatgactccccgccgccc gggcccacccgcaagcattaccagccctatgccccaccacgcgacttc gcagcctatcgctccagagtgaagttcagcaggagcgcagacgccccc gcgtaccagcagggccagaaccagctctataacgagctcaatctagga cgaagagaggagtacgatgttttggacaagagacgtggccgggaccct gagatggggggaaagccgagaaggaagaaccctcaggaaggcctgtac aatgaactgcagaaagataagatggcggaggcctacagtgagattggg atgaaaggcgagcgccggaggggcaaggggcacgatggcctttTccag gggctcagtacagccaccaaggacacctTcgacgcccttcacatgcag gccctgccccctcgctaa D3 Construct In certain embodiments, a presently disclosed CAR comprises an extracellular antigen-binding domain that binds to a CD19 polypeptide (e.g., human CD19 polypeptide), a transmembrane domain and a hinge/spacer region derived from a CD28 polypeptide, an intracellular signaling domain comprising a modified CD3ζ polypeptide (e.g., a modified human CD3ζ polypeptide) comprising ITAM1, ITAM2, BRS1, BRS2, and a deletion of ITAM3 and a portion of BRS3, and a co-stimulatory signaling region comprising a CD28 polypeptide (e.g., a human CD28 polypeptide), wherein the modified CD3ζ polypeptide comprises a native ITAM1, a native ITAM2, a native BRS1 and a native BRS2, and does not comprise an ITAM3 (native or modified) or a native BRS3. In certain embodiments, the CAR is designated as "D3". In certain embodiments, the CAR (e.g., D3) comprises an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 57, which is provided below. SEQ ID NO: 57 includes a CD8 leader sequence at amino acids 1 to 18, and is able to bind to CD19 (e.g., human CD19).

[SEQ ID NO: 57]
MALPVTALLLPLALLLHAEVKLQQSGAELVRPGSSVKISCKASGYAFS

SYWMNWVKQRPGQGLEWIGQIYPGDGDTNYNGKFKGQATLTADKSSST

AYMQLSGLTSEDSAVYFCARKTISSVVDFYFDYWGQGTTVTVSSGGGG

SGGGGSGGGGSDIELTQSPKFMSTSVGDRVSVTCKASQNVGTNVAWYQ

QKPGQSPKPLIYSATYRNSGVPDRFTGSGSGTDFTLTITNVQSKDLAD

YFCQQYNRYPYTSGGGTKLEIKRAAAIEVMYPPPYLDNEKSNGTIIHV

KGKHLCPSPLFPGPSKPFWVLVVVGGVLACYSLLVTVAFIIFWVRSKR

SRLLHSDYMNMTPRRPGPTRKHYQPYAPPRDFAAYRSRVKFSRSADAP

AYQQGQNQLYNELNLGRREEYDVLDKRRGRDPEMGGKPRRKNPQEGLY

NELQKDKMAEAYSEIGMKGERRR

An exemplary nucleic acid sequence encoding the amino acid sequence of SEQ ID NO: 57 is set forth in SEQ ID NO: 58, which is provided below.

[SEQ ID NO: 58]
atggctctcccagtgactgccctactgcttcccctagcgcttctcctg catgcagaggtgaagctgcagcagtctggggctgagctggtgaggcct -continued
```
gggtcctcagtgaagatttcctgcaaggcttctggctatgcattcagt agctactggatgaactgggtgaagcagaggcctggacagggtcttgag tggattggacagatttatcctggagatggtgatactaactacaatgga aagttcaagggtcaagccacactgactgcagacaaatcctccagcaca gcctacatgcagctcagcggcctaacatctgaggactctgcggtctat ttctgtgcaagaaagaccattagttcggtagtagatttctactttgac tactggggccaagggaccacggtcaccgtctcctcaggtggaggtgga tcaggtggaggtggatctggtggaggtggatctgacattgagctcacc cagtctccaaaattcatgtccacatcagtaggagacagggtcagcgtc acctgcaaggccagtcagaatgtgggtactaatgtagcctggtatcaa cagaaaccaggacaatctcctaaaccactgatttactcggcaacctac cggaacagtggagtccctgatcgcttcacaggcagtggatctgggaca gatttcactctcaccatcactaacgtgcagtctaaagacttggcagac tatttctgtcaacaatataacaggtatccgtacacgtccggaggggg accaagctggagatcaaacgggcggccgcaattgaagttatgtatcct cctccttacctagacaatgagaagagcaatggaaccattatccatgtg aaagggaaacacctttgtccaagtccctatttcccggaccttctaag ccctttgggtgctggtggtggttggtggagtcctggcttgctatagc ttgctagtaacagtggcctttattattttctgggtgaggagtaagagg agcaggctcctgcacagtgactacatgaacatgactccccgccgccc gggcccaccgcaagcattaccagccctatgccccaccacgcgacttc gcagcctatcgctccagagtgaagttcagcaggagcgcagacgccccc gcgtaccagcagggccagaaccagctctataacgagctcaatctagga cgaagagaggagtacgatgttttggacaagagacgtggccgggaccct gagatggggggaaagccgagaaggaagaaccctcaggaaggcctgtac aatgaactgcagaaagataagatggcggaggcctacagtgagattggg atgaaaggcgagcgccggaggtaa
```

19-166-28z Construct

In certain embodiments, a presently disclosed CAR comprises an extracellular antigen-binding domain that binds to a CD19 polypeptide (e.g., a human CD19 polypeptide), a transmembrane domain and a hinge/spacer region derived from a CD166 polypeptide, an intracellular signaling domain comprising a modified CD3ζ polypeptide (e.g., a modified human CD3ζ polypeptide) comprising a native ITAM1, a native ITAM2, a native ITAM3, a native BRS1, a native BRS2, and a native BRS3, and a co-stimulatory signaling region comprising a CD28 polypeptide (e.g., a human CD28 polypeptide). In certain embodiments, the CAR is designated as "19-166-28z". In certain embodiments, the CAR (e.g., 19-166-28z) comprises an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 59, which is provided below. SEQ ID NO: 59 includes a CD8 leader sequence at amino acids 1 to 18, and is able to bind to CD19 (e.g., human CD19).

[SEQ ID NO: 59]
```
MALPVTALLLPLALLLHAEVKLQQSGAELVRPGSSVKISCKASGYAFS

SYWMNWVKQRPGQGLEWIGQIYPGDGDTNYNGKFKGQATLTADKSSST

AYMQLSGLTSEDSAVYFCARKTISSVVDFYFDYWGQGTTVTVSSGGGG

SGGGGSGGGGSDIELTQSPKFMSTSVGDRVSVTCKASQNVGTNVAWYQ

QKPGQSPKPLIYSATYRNSGVPDRFTGSGSGTDFTLTITNVQSKDLAD

YFCQQYNRYPYTSGGGTKLEIKRNQLERTVNSLNVSAISIPEHDEADE

ISDENREKVNDQAKLIVGIVVGLLLAALVAGVVYWLYMKKRSKRSRLL

HSDYMNMTPRRPGPTRKHYQPYAPPRDFAAYRKRVKFSRSADAPAYQQ

GQNQLYNELNLGRREEYDVLDKRRGRDPEMGGKPRRKNPQEGLYNELQ

KDKMAEAYSEIGMKGERRRGKGHDGLYQGLSTATKDTYDALHMQALPP

R
```

An exemplary nucleic acid sequence encoding the amino acid sequence of SEQ ID NO: 59 is set forth in SEQ ID NO: 60, which is provided below.

[SEQ ID NO: 60]
```
atggctctcccagtgactgccctactgcttcccctagcgcttctcctg catgcagaggtgaagctgcagcagtctggggctgagctggtgaggcct gggtcctcagtgaagatttcctgcaaggcttctggctatgcattcagt agctactggatgaactgggtgaagcagaggcctggacagggtcttgag tggattggacagatttatcctggagatggtgatactaactacaatgga aagttcaagggtcaagccacactgactgcagacaaatcctccagcaca gcctacatgcagctcagcggcctaacatctgaggactctgcggtctat ttctgtgcaagaaagaccattagttcggtagtagatttctactttgac tactggggccaagggaccacggtcaccgtctcctcaggtggaggtgga tcaggtggaggtggatctggtggaggtggatctgacattgagctcacc cagtctccaaaattcatgtccacatcagtaggagacagggtcagcgtc acctgcaaggccagtcagaatgtgggtactaatgtagcctggtatcaa cagaaaccaggacaatctcctaaaccactgatttactcggcaacctac cggaacagtggagtccctgatcgcttcacaggcagtggatctgggaca gatttcactctcaccatcactaacgtgcagtctaaagacttggcagac tatttctgtcaacaatataacaggtatccgtacacgtccggaggggg accaagctggagatcaaacggAACCAACTGGAGAGAACAGTAAACTCC

TTGAATGTCTCTGCTATAAGTATTCCAGAACACGATGAGGCAGACGAG

ATAAGTGATGAAAACAGAGAAAAGGTGAATGACCAGGCAAAACTAATT

GTGGGAATCGTTGTTGGTCTCCTCCTTGCTGCCCTTGTTGCTGGTGTC

GTCTACTGGCTGTACATGAAGAAGgagtaagaggagcaggctcctg cacagtgactacatgaacatgactccccgccgccccgggcccaccgc aagcattaccagccctatgccccaccacgcgacttcgcagcctatcgc aaaagagtgaagttcagcaggagcgcagacgccccgcgtaccagcag ggccagaaccagctctataacgagctcaatctaggacgaagagaggag tacgatgttttggacaagagacgtggccgggaccctgagatgggggga
```

```
aagccgagaaggaagaaccctcaggaaggcctgtacaatgaactgcag aaagataagatggcggaggcctacagtgagattgggatgaaaggcgag cgccggaggggcaagggcacgatggcctttaccagggtctcagtaca gccaccaaggacacctacgacgccttcacatgcaggccctgcccct cgctaa
```

19-166-28z 1XX Construct

In certain embodiments, a presently disclosed CAR comprises an extracellular antigen-binding domain that binds to a CD19 polypeptide (e.g., a human CD19 polypeptide), a transmembrane domain and a hinge/spacer region derived from a CD166 polypeptide, an intracellular signaling domain comprising a modified CD3ζ polypeptide (e.g., a modified human CD3ζ polypeptide) comprising a native ITAM1, a native BRS1, a native BRS2, a native BRS3, an ITAM2 variant having two loss-of-function mutations, and an ITAM3 variant having two loss-of-function mutations, and a co-stimulatory signaling region comprising a CD28 polypeptide (e.g., a human CD28 polypeptide). In certain embodiments, the CAR is designated as "19-166-28z 1XX". In certain embodiments, the CAR (e.g., 19-166-28z 1XX) comprises an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 61, which is provided below. SEQ ID NO: 61 includes a CD8 leader sequence at amino acids 1 to 18, and is able to bind to CD19 (e.g., human CD19).

```
[SEQ ID NO: 61]
MALPVTALLLPLALLLHAEVKLQQSGAELVRPGSSVKISCKASGYAFS

SYWMNWVKQRPGQGLEWIGQIYPGDGDTNYNGKFKGQATLTADKSSST

AYMQLSGLTSEDSAVYFCARKTISSVVDFYFDYWGQGTTVTVSSGGGG

SGGGGSGGGGSDIELTQSPKFMSTSVGDRVSVTCKASQNVGTNVAWYQ

QKPGQSPKPLIYSATYRNSGVPDRFTGSGSGTDFTLTITNVQSKDLAD

YFCQQYNRYPYTSGGGTKLEIKRNQLERTVNSLNVSAISIPEHDEADE

ISDENREKVNDQAKLIVGIVVGLLLAALVAGVVYWLYMKKRSKRSRLL

HSDYMNMTPRRPGPTRKHYQPYAPPRDFAAYRKRVKFSRSADAPAYQQ

GQNQLYNELNLGRREEYDVLDKRRGRDPEMGGKPRRKNPQEGLFNELQ

KDKMAEAFSEIGMKGERRRGKGHDGLFQGLSTATKDTFDALHMQALPP

R
```

An exemplary nucleic acid sequence encoding the amino acid sequence of SEQ ID NO: 61 is set forth in SEQ ID NO: 62, which is provided below.

```
[SEQ ID NO: 62]
atggctctcccagtgactgccctactgcttcccctagcgcttctcctg catgcagaggtgaagctgcagcagtctggggctgagctggtgaggcct gggtcctcagtgaagatttcctgcaaggcttctggctatgcattcagt agctactggatgaactgggtgaagcagaggcctggacagggtcttgag tggattggacagatttatcctggagatggtgatactaactacaatgga aagttcaagggtcaagccacactgactgcagacaaatcctccagcaca gcctacatgcagctcagcggcctaacatctgaggactctgcggtctat ttctgtgcaagaaagaccattagttcggtagtagatttctactttgac tactggggccaagggaccacggtcaccgtctcctcaggtggaggtgga tcaggtggaggtggatctggtggaggtggatctgacattgagctcacc cagtctccaaaattcatgtccacatcagtaggagacagggtcagcgtc acctgcaaggccagtcagaatgtgggtactaatgtagcctggtatcaa cagaaaccaggacaatctcctaaaccactgatttactcggcaacctac cggaacagtggagtccctgatcgcttcacaggcagtggatctgggaca gatttcactctcaccatcactaacgtgcagtctaaagacttggcagac tatttctgtcaacaatataacaggtatccgtacacgtccggaggggggg accaagctggagatcaaacggAACCAACTGGAGAGAACAGTAAACTCC

TTGAATGTCTCTGCTATAAGTATTCCAGAACACGATGAGGCAGACGAG

ATAAGTGATGAAAACAGAGAAAAGGTGAATGACCAGGCAAAACTAATT

GTGGGAATCGTTGTTGGTCTCCTCCTTGCTGCCCTTGTTGCTGGTGTC

GTCTACTGGCTGTACATGAAGAAGaggagtaagaggagcaggctcctg cacagtgactacatgaacatgactccccgccgccccgggcccacccgc aagcattaccagcccctatgccccaccacgcgacttcgcagcctatcgc aaaagagtgaagttcagcaggagcgcagaCGccccgcgtaccagcag ggccagaaccagctctataacgagctcaatctaggacgaagagaggag tacgatgttttggacaagagacgtggccgggaccctgagatgggggga aagccgagaaggaagaaccctcaggaaggcctgtTcaatgaactgcag aaagataagatggcggaggcctTcagtgagattgggatgaaaggcgag cgccggaggggcaagggcacgatggcctttTccagggtctcagtaca gccaccaaggacacctTcgacgcccttcacatgcaggccctgcccct cgctaa
```

19-166-28z D23 Construct

In certain embodiments, a presently disclosed CAR comprises an extracellular antigen-binding domain that binds to a CD19 polypeptide (e.g., human CD19 polypeptide), a transmembrane domain and a hinge/spacer region derived from a CD166 polypeptide, an intracellular signaling domain comprising a modified CD3ζ polypeptide (e.g., a modified human CD3ζ polypeptide) comprising ITAM1, BRS1 and a deletion of ITAM2, ITAM3, BRS2 and BRS3, and a co-stimulatory signaling region comprising a CD28 polypeptide (e.g., a human CD28 polypeptide), wherein the modified CD3ζ polypeptide comprises a native ITAM1 and a native BRS1, and does not comprise an ITAM2 (native or modified), an ITAM3 (native or modified), a BRS2 (native or modified), or a BRS3 (native or modified). In certain embodiments, the CAR is designated as "19-166-28z D23". In certain embodiments, the CAR (e.g., 19-166-28z D23) comprises an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 63, which is provided below. SEQ ID NO: 63 includes a CD8 leader sequence at amino acids 1 to 18, and is able to bind to CD19 (e.g., human CD19).

[SEQ ID NO: 63]
MALPVTALLLPLALLLHAEVKLQQSGAELVRPGSSVKISCKASGYAFS

SYWMNWVKQRPGQGLEWIGQIYPGDGDTNYNGKFKGQATLTADKSSST

AYMQLSGLTSEDSAVYFCARKTISSVVDFYFDYWGQGTTVTVSSGGGG

SGGGGSGGGGSDIELTQSPKFMSTSVGDRVSVTCKASQNVGTNVAWYQ

QKPGQSPKPLIYSATYRNSGVPDRFTGSGSGTDFTLTITNVQSKDLAD

YFCQQYNRYPYTSGGGTKLEIKRNQLERTVNSLNVSAISIPEHDEADE

ISDENREKVNDQAKLIVGIVVGLLLAALVAGVVYWLYMKKRSKRSRLL

HSDYMNMTPRRPGPTRKHYQPYAPPRDFAAYRKRVKFSRSADAPAYQQ

GQNQLYNELNLGRREEYDVLDKRRGRDP

An exemplary nucleic acid sequence encoding the amino acid sequence of SEQ ID NO: 63 is set forth in SEQ ID NO: 64, which is provided below.

[SEQ ID NO: 64]
atggctctcccagtgactgccctactgcttcccctagcgcttctcctg catgcagaggtgaagctgcagcagtctggggctgagctggtgaggcct gggtcctcagtgaagatttcctgcaaggcttctggctatgcattcagt agctactggatgaactgggtgaagcagaggcctggacagggtcttgag tggattggacagatttatcctggagatggtgatactaactacaatgga aagttcaagggtcaagccacactgactgcagacaaatcctccagcaca gcctacatgcagctcagcggcctaacatctgaggactctgcggtctat ttctgtgcaagaaagaccattagttcggtagtagatttctactttgac tactggggccaagggaccacggtcaccgtctcctcaggtggaggtgga tcaggtggaggtggatctggtggaggtggatctgacattgagctcacc cagtctccaaaattcatgtccacatcagtaggagacagggtcagcgtc acctgcaaggccagtcagaatgtgggtactaatgtagcctggtatcaa cagaaaccaggacaatctcctaaaccactgatttactcggcaacctac cggaacagtggagtccctgatcgcttcacaggcagtggatctgggaca gatttcactctcaccatcactaacgtgcagtctaaagacttggcagac tatttctgtcaacaatataacaggtatccgtacacgtccggaggggg accaagctggagatcaaacggAACCAACTGGAGAGAACAGTAAACTCC

TTGAATGTCTCTGCTATAAGTATTCCAGAACACGATGAGGCAGACGAG

ATAAGTGATGAAAACAGAGAAAAGGTGAATGACCAGGCAAAACTAATT

GTGGGAATCGTTGTTGGTCTCCTCCTTGCTGCCCTTGTTGCTGGTGTC

GTCTACTGGCTGTACATGAAGAAGaggagtaagaggagcaggctcctg cacagtgactacatgaacatgactccccgccgccccgggccaccgc aagcattaccagccctatgccccaccacgcgacttcgcagcctatcgc aaaagagtgaagttcagcaggagcgcagaCGccccgcgtaccagcag ggccagaaccagctctataacgagctcaatctaggacgaagagaggag tacgatgttttggacaagagacgtggccgggacccttaa 3. Immunoresponsive Cells The presently disclosed subject matter provides immunoresponsive cells comprising one or more CARs disclosed herein. In certain embodiments, the CAR is capable of activating the immunoresponsive cell. In certain embodiments, the CAR is expressed from an endogenous locus (e.g., TRAC).

In certain embodiments, the immunoresponsive cells comprising one or more presently disclosed CAR exhibit improved therapeutic potency compared to control cells. In certain embodiments, the immunoresponsive cells comprising one or more presently disclosed CAR exhibit similar cytolytic effects compared to control cells. In certain embodiments, the immunoresponsive cells comprising one or more presently disclosed CAR exhibit increased cell accumulation when administered to a subject compared to control cells. In certain embodiments, the immunoresponsive cells comprising one or more presently disclosed CAR exhibit decreased cell exhaustion when administered to a subject compared to control cells. Immunoresponsive cell exhaustion markers include, but are not limited to, TIM3, LAG3, and PD1. In certain embodiments, the immunoresponsive cells comprising a presently disclosed CAR maintains a higher contingent of memory immune cells when administered to a subject compared to control cells. Memory immune cell markers include, but are not limited to, CD62L and CD45RA. In certain embodiments, the immunoresponsive cells comprising one or more presently disclosed CAR secrete similar levels of cytokines compared to control cells. In certain embodiments, the cytokines secreted by the immunoresponsive cells include, but are not limited to, TNFα, IFNγ and IL2. In certain embodiments, the control cells comprise a CAR comprising an intracellular signaling domain that comprises a modified CD3ζ polypeptide, wherein the modified CD3ζ polypeptide comprises all native ITAM1-3 and all native BRS1-3.

3.1 Immunoresponsive Cells Comprising Two or More CARs

In certain embodiments, the immunoresponsive cell comprises two or more CARs. In certain embodiments, at least one of the two or more CARs is a CAR disclosed herein. In certain embodiments, the immunoresponsive cell comprises two CARs. In certain embodiments, the immunoresponsive cell comprises three CARs.

In certain embodiments, the immunoresponsive cell comprises a) a first CAR comprising a first extracellular antigen-binding domain that binds to a first antigen, a first transmembrane domain, and a first intracellular signaling domain comprising modified CD3ζ polypeptide (e.g., one modified CD3ζ polypeptide disclosed herein); and b) a second CAR comprising a second extracellular antigen-binding domain that binds to a second antigen, a second transmembrane domain, and a second intracellular signaling domain. In certain embodiments, the first CAR further comprises a first hinge/spacer region. In certain embodiments, the second CAR further comprises a second hinge/spacer region.

In certain embodiments, the second intracellular signaling domain comprises a modified CD3ζ polypeptide (e.g., one modified CD3ζ polypeptide disclosed herein). In certain embodiments, the second intracellular signaling domain comprises a native CD3ζ polypeptide. In certain embodiments, the modified CD3ζ polypeptide comprised in the second intracellular signaling domain is the same as the modified CD3ζ polypeptide comprised in the first intracellular signaling domain. In certain embodiments, the modified CD3ζ polypeptide comprised in the second intracellular signaling domain is different from the modified CD3ζ polypeptide comprised in the first intracellular signaling domain. In certain embodiments, the modified CD3ζ polypeptides are selected from the group consisting of CD3ζ polypeptides comprising one native ITAM, CD3ζ polypeptides comprising two native ITAMs, CD3ζ polypeptides comprising three native ITAMs, CD3ζ polypeptides comprising one ITAM variant disclosed herein, CD3ζ polypeptides comprising two ITAM variants disclosed herein, CD3ζ polypeptides comprising one native BRS region, CD3ζ polypeptides comprising two native BRS regions, CD3ζ polypeptides comprising three native BRS regions, CD3ζ polypeptides that lack all or part of ITAM1, ITAM2, ITAM3 and/or any portion thereof, and any combination thereof.

In certain embodiments, the two or more CARs comprised in the immunoresponsive cell are different (e.g., the first CAR is different from the second CAR). In certain embodiments, the two or more CARs comprised in the immunoresponsive cell are the same (e.g., the first CAR is same as the second CAR).

In certain embodiments, the two or more CARs bind to different antigens (e.g., the first antigen is different from the second antigen).

In certain embodiments, the two or more CARs comprise different intracellular signaling domains (e.g., the first intracellular signaling domain is different from the second intracellular signaling domain). In certain embodiments, the two or more CARs comprise the same intracellular signaling domain (e.g., the first intracellular signaling domain is the same as the second intracellular signaling domain).

In certain embodiments, the intracellular signaling domains of the two or more CARs comprise different co-stimulatory signaling regions. In certain embodiments, the co-stimulatory signaling regions are selected from the group consisting of a CD28 polypeptide, a 4-1BB polypeptide, an OX40 polypeptide, an ICOS polypeptide, a DAP-10 polypeptide, a CD27 peptide, a CD40/My88 peptide, a NKGD2 peptide, and combinations thereof. In certain embodiments, the intracellular signaling domains of the two or more CARs comprise the same co-stimulatory signaling region.

In certain embodiments, the immunoresponsive cell comprises two, three or more presently disclosed CARs. In certain embodiments, wherein each of the intracellular signaling domains of the CARs is independently selected from the group consisting of the intracellular signaling domains of 1928ζ, 19ζ, 1XX, X2X, XX3, X23, 12X, D3, D12 and D23.

Selection of the CARs comprised in the cell can depend on the densities of the antigens targeted by the CARs, the sum of all ITAMs, the distance between each ITAM, the transmembrane domain of CARs, and/or the co-stimulatory signaling domain of CARs, as the above can determine the strength of the activation signals produced by each CAR.

In certain embodiments, the immunoresponsive cell comprises two CARs, wherein the first CAR comprises a first intracellular signaling domain, and the second CAR comprises a second intracellular signaling domain. In certain embodiments, each of the first and second intracellular signaling domains are selected from the group consisting of the intracellular signaling domains of 1928ζ, 19ζ, 1XX, X2X, XX3, 12X, X23, D3, D12 and D23.

In certain embodiments, the first intracellular signaling domain is the same as the second intracellular signaling domain. In certain embodiments, each of the first and second intracellular signaling domains is the intracellular signaling domain of 1XX. In certain embodiments, the first intracellular signaling domain and the second intracellular signaling domain are the intracellular signaling domain of 1XX and the intracellular signaling domains of D23. In certain embodiments, the first intracellular signaling domain and the second intracellular signaling domain are the intracellular signaling domain of 1XX and the intracellular signaling domain of XX3. In certain embodiments, the first intracellular signaling domain and the second intracellular signaling domain are the intracellular signaling domain of D23 and the intracellular signaling domain of XX3. In certain embodiments, the first intracellular signaling domain and the second intracellular signaling domain are the intracellular signaling domain of 1XX and the intracellular signaling domain of X2X. In certain embodiments, the first intracellular signaling domain and the second intracellular signaling domain are the intracellular signaling domain of 1XX and the intracellular signaling domain of D12. In certain embodiments, the first intracellular signaling domain and the second intracellular signaling domain are the intracellular signaling domain of 1XX and the intracellular signaling domain of 12X. In certain embodiments, the first intracellular signaling domain and the second intracellular signaling domain are the intracellular signaling domain of 1XX and the intracellular signaling domain of D3. In certain embodiments, the first intracellular signaling domain and the second intracellular signaling domain are the intracellular signaling domain of X2X and the intracellular signaling domain of X2X. In certain embodiments, the first intracellular signaling domain and the second intracellular signaling domain are the intracellular signaling domain of 1928z and the intracellular signaling domain of 1XX.

In certain embodiments, the first intracellular signaling domain comprises or has an ITAM2 variant and an ITAM3 variant, and the second intracellular signaling domain comprises or has a deletion of ITAM2 or a portion thereof and a deletion of ITAM3 or a portion thereof. In certain embodiments, the first intracellular signaling domain comprises or has an ITAM2 variant and an ITAM3 variant, and the second intracellular signaling domain comprises or has an ITAM1 variant and an ITAM2 variant.

In certain embodiments, the sum of native ITAMs comprised in the two CARs is no more than about five, no more than about four, no more than about three, or no more than about two.

In certain embodiments, the immunoresponsive cell comprises three CARs, wherein the first CAR comprises a first intracellular signaling domain, the second CAR comprises a second intracellular signaling domain, and the third CAR comprises a third intracellular signaling domain. In certain embodiments, each of the first, second and third intracellular signaling domains is independently selected from the group consisting of the intracellular signaling domains of 1928ζ, 19ζ, 1XX, X2X, XX3, X23, 12X, D3 D12 and D23.

In certain embodiments, the first intracellular signaling domain, the second intracellular signaling domain, and the third intracellular signaling domain are the intracellular signaling domain of 1XX, the intracellular signaling domain of D23, and the intracellular signaling domain of XX3. In certain embodiments, the first intracellular signaling domain, the second intracellular signaling domain, and the third intracellular signaling domain are the intracellular signaling domain of D23, the intracellular signaling domain of D23, and the intracellular signaling domain of XX3. In certain embodiments, the first intracellular signaling domain, the second intracellular signaling domain, and the third intracellular signaling domain are the intracellular signaling domains of D23, the intracellular signaling domain of XX3, and the intracellular signaling domain of XX3. In certain embodiments the first intracellular signaling domain, the second intracellular signaling domain, and the third intracellular signaling domain are the intracellular signaling domain of XX3, the intracellular signaling domain of XX3, and the intracellular signaling domain of XX3. In certain embodiments the first intracellular signaling domain, the second intracellular signaling domain, and the third intracellular signaling domain are the intracellular signaling domain of 1XX, the intracellular signaling domain of 1XX, and the intracellular signaling domain of 1XX. In certain embodiments, the first intracellular signaling domain, the second intracellular signaling domain, and the third intracellular signaling domain are the intracellular signaling domain of 1XX, the intracellular signaling domain of X2X, and the intracellular signaling domain of X2X. In certain embodiments, the first intracellular signaling domain, the second intracellular signaling domain, and the third intracellular signaling domain are the intracellular signaling domain of 1XX, the intracellular signaling domain of 1XX, and the intracellular signaling domain of X2X. In certain embodiments, the first intracellular signaling domain, the second intracellular signaling domain, and the third intracellular signaling domain are the intracellular signaling domain of 1XX, the intracellular signaling domain of 1XX, and the intracellular signaling domain of D12. In certain embodiments, the first intracellular signaling domain, the second intracellular signaling domain, and the third intracellular signaling domain are the intracellular signaling domain of 1XX, the intracellular signaling domain of 1XX, and the intracellular signaling domain of D23. In certain embodiments, the first intracellular signaling domain, the second intracellular signaling domain, and the third intracellular signaling domain are the intracellular signaling domain of 1XX, the intracellular signaling domain of 1XX, and the intracellular signaling domain of 12X. In certain embodiments, the first intracellular signaling domain, the second intracellular signaling domain, and the third intracellular signaling domain are the intracellular signaling domain of 1XX, the intracellular signaling domain of 1XX, and the intracellular signaling domain of D3. In certain embodiments, the first intracellular signaling domain, the second intracellular signaling domain, and the third intracellular signaling domain are the intracellular signaling domain of X2X, the intracellular signaling domain of X2X, and the intracellular signaling domain of X2X.

In certain embodiments, the first intracellular signaling domain comprises or has an ITAM2 variant and an ITAM3 variant, the second intracellular signaling domain comprises or has a deletion of ITAM2 or a portion thereof and a deletion of ITAM3 or a portion thereof, and the third intracellular signaling domain comprises or has an ITAM1 variant and an ITAM2 variant. In certain embodiments, the first intracellular signaling domain comprises or has a deletion of ITAM2 or a portion thereof and a deletion of ITAM3 or a portion thereof, the second intracellular signaling domain comprises or has a deletion of ITAM2 or a portion thereof and a deletion of ITAM3 or a portion thereof, and the third intracellular signaling domain comprises or has an ITAM1 variant and an ITAM2 variant. In certain embodiments, the first intracellular signaling domain comprises or has a deletion of ITAM2 or a portion thereof and a deletion of ITAM3 or a portion thereof, the second intracellular signaling domain comprises or has an ITAM1 variant and an ITAM2 variant, and the third intracellular signaling domain comprises or has an ITAM1 variant and an ITAM2 variant. In certain embodiments, the first intracellular signaling domain comprises or has an ITAM1 variant and an ITAM2 variant, the second intracellular signaling domain comprises or has an ITAM1 variant and an ITAM2 variant, and the third intracellular signaling domain comprises or has an ITAM1 variant and an ITAM2 variant.

In certain embodiments, the sum of native ITAMs comprised in the three CARs is no more than about five, no more than about four, no more than about three.

In certain embodiments, the targets of the CARs are different from each other.

3.1 Types of Immunoresponsive Cells

The immunoresponsive cells of the presently disclosed subject matter can be cells of the lymphoid lineage. The lymphoid lineage, comprising B, T and natural killer (NK) cells, provides for the production of antibodies, regulation of the cellular immune system, detection of foreign agents in the blood, detection of cells foreign to the host, and the like. Non-limiting examples of immunoresponsive cells of the lymphoid lineage include T cells, Natural Killer (NK) cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, helper T cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells, Regulatory T cells (also known as suppressor T cells), Natural killer T cells, Mucosal associated invariant T cells, and γδ T cells. Cytotoxic T cells (CTL or killer T cells) are a subset of T lymphocytes capable of inducing the death of infected somatic or tumor cells. A patient's own T cells may be genetically modified to target specific antigens through the introduction of a CAR. In certain embodiments, the immunoresponsive cell is a T cell. The T cell can be a $CD4^+$ T cell or a $CD8^+$ T cell. In certain embodiments, the T cell is a $CD4^+$ T cell. In certain embodiments, the T cell is a $CD8^+$ T cell.

Natural killer (NK) cells can be lymphocytes that are part of cell-mediated immunity and act during the innate immune response. NK cells do not require prior activation in order to perform their cytotoxic effect on target cells.

Types of human lymphocytes of the presently disclosed subject matter include, without limitation, peripheral donor lymphocytes, e.g., those disclosed in Sadelain, M., et al. 2003 *Nat Rev Cancer* 3:35-45 (disclosing peripheral donor lymphocytes genetically modified to express CARs), in Morgan, R. A., et al. 2006 *Science* 314:126-129 (disclosing peripheral donor lymphocytes genetically modified to express a full-length tumor antigen-recognizing T cell receptor complex comprising the α and β heterodimer), in Panelli, M. C., et al. 2000 *J Immunol* 164:495-504; Panelli, M. C., et al. 2000 *J Immunol* 164:4382-4392 (disclosing lymphocyte cultures derived from tumor infiltrating lymphocytes (TILs) in tumor biopsies), and in Dupont, J., et al. 2005 *Cancer Res* 65:5417-5427; Papanicolaou, G. A., et al. 2003 *Blood* 102:2498-2505 (disclosing selectively in vitro-expanded antigen-specific peripheral blood leukocytes employing artificial antigen-presenting cells (AAPCs) or pulsed dendritic cells). The immunoresponsive cells (e.g., T cells) can be autologous, non-autologous (e.g., allogeneic), or derived in vitro from engineered progenitor or stem cells.

The presently disclosed immunoresponsive cells are capable of modulating the tumor microenvironment. Tumors have a microenvironment that is hostile to the host immune response involving a series of mechanisms by malignant cells to protect themselves from immune recognition and elimination. This "hostile tumor microenvironment" comprises a variety of immune suppressive factors including infiltrating regulatory $CD4^+$ T cells (Tregs), myeloid derived suppressor cells (MDSCs), tumor associated macrophages (TAMs), immune suppressive cytokines including TGF-β, and expression of ligands targeted to immune suppressive receptors expressed by activated T cells (CTLA-4 and PD-1). These mechanisms of immune suppression play a role in the maintenance of tolerance and suppressing inappropriate immune responses, however within the tumor microenvironment these mechanisms prevent an effective anti-tumor immune response. Collectively these immune suppressive factors can induce either marked anergy or apoptosis of adoptively transferred CAR modified T cells upon encounter with targeted tumor cells.

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. mAbs are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. In certain embodiments, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). In certain embodiments, the cells are collected in a medium comprising 2% fetal calf serum (FCS) or 0.2% bovine serum albumin (BSA) or any other suitable, e.g., sterile, isotonic medium.

4. Vectors

Genetic modification of an immunoresponsive cell (e.g., a T cell or a NK cell) can be accomplished by transducing a substantially homogeneous cell composition with a recombinant DNA construct. In certain embodiments, a retroviral vector (either gamma-retroviral or lentiviral) is employed for the introduction of the DNA construct into the cell. For example, a polynucleotide encoding a CAR can be cloned into a retroviral vector and expression can be driven from its endogenous promoter, from the retroviral long terminal repeat, or from a promoter specific for a target cell type of interest. Non-viral vectors may be used as well.

For initial genetic modification of an immunoresponsive cell to include a CAR, a retroviral vector is generally employed for transduction, however any other suitable viral vector or non-viral delivery system can be used. The CAR can be constructed with an auxiliary molecule (e.g., a cytokine) in a single, multicistronic expression cassette, in multiple expression cassettes of a single vector, or in multiple vectors. Examples of elements that create polycistronic expression cassette include, but is not limited to, various viral and non-viral Internal Ribosome Entry Sites (IRES, e.g., FGF-1 IRES, FGF-2 IRES, VEGF IRES, IGF-II IRES, NF-κB IRES, RUNX1 IRES, p53 IRES, hepatitis A IRES, hepatitis C IRES, pestivirus IRES, aphthovirus IRES, picornavirus IRES, poliovirus IRES and encephalomyocarditis virus IRES) and cleavable linkers (e.g., 2A peptides, e.g., P2A, T2A, E2A and F2A peptides). In certain embodiments, any vector or CAR disclosed herein can comprise a P2A peptide comprising the amino acid sequence of GSGATNFSLLKQAGDVEENPGP (SEQ ID NO: 107). Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Nat. Acad. Sci. USA* 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J Clin. Invest.* 89:1817.

Other transducing viral vectors can be used to modify an immunoresponsive cell. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272: 263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; LeGal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for genetic modification of an immunoresponsive cell. For example, a nucleic acid molecule can be introduced into an immunoresponsive cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by microinjection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases, CRISPR). Transient expression may be obtained by RNA electroporation.

Clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, contains the RNA used by Cas9 to guide it to the correct section of host DNA along with a region that binds to tracrRNA (generally in a hairpin loop form) forming an active complex with Cas9), trans-activating crRNA (tracrRNA, binds to crRNA and forms an active complex with Cas9), and an optional section of DNA repair template (DNA that guides the cellular repair process allowing insertion of a specific DNA sequence). CRISPR/Cas9 often employs a plasmid to transfect the target cells. The crRNA needs to be designed for each application as this is the sequence that Cas9 uses to identify and directly bind to the target DNA in a cell. The repair template carrying CAR expression cassette need also be designed for each application, as it must overlap with the sequences on either side of the cut and code for the insertion sequence. Multiple crRNA's and the tracrRNA can be packaged together to forma single-guide RNA (sgRNA). This sgRNA can be joined together with the Cas9 gene and made into a plasmid in order to be transfected into cells.

A zinc-finger nuclease (ZFN) is an artificial restriction enzyme, which is generated by combining a zinc finger DNA-binding domain with a DNA-cleavage domain. A zinc finger domain can be engineered to target specific DNA sequences which allows a zinc-finger nuclease to target desired sequences within genomes. The DNA-binding domains of individual ZFNs typically contain a plurality of individual zinc finger repeats and can each recognize a plurality of basepairs. The most common method to generate new zinc-finger domain is to combine smaller zinc-finger "modules" of known specificity. The most common cleavage domain in ZFNs is the non-specific cleavage domain from the type IIs restriction endonuclease FokI. Using the endogenous homologous recombination (HR) machinery and a homologous DNA template carrying CAR expression cassette, ZFNs can be used to insert the CAR expression cassette into genome. When the targeted sequence is cleaved by ZFNs, the HR machinery searches for homology between the damaged chromosome and the homologous DNA template, and then copies the sequence of the template between the two broken ends of the chromosome, whereby the homologous DNA template is integrated into the genome.

Transcription activator-like effector nucleases (TALEN) are restriction enzymes that can be engineered to cut specific sequences of DNA. TALEN system operates on almost the same principle as ZFNs. They are generated by combining a transcription activator-like effectors DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in genome.cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

5. Genome Editing Methods

Any targeted genome editing methods can be used to place presently disclosed CARs at one or more endogenous gene loci of a presently disclosed immunoresponsive cell. In certain embodiments, a CRISPR system is used to deliver presently disclosed CARs to one or more endogenous gene loci of a presently disclosed immunoresponsive cell. In certain embodiments, zinc-finger nucleases are used to deliver presently disclosed CARs to one or more endogenous gene loci of a presently disclosed immunoresponsive cell. In certain embodiments, a TALEN system is used to deliver presently disclosed CARs to one or more endogenous gene loci of a presently disclosed immunoresponsive cell.

Methods for delivering the genome editing agents/systems can vary depending on the need. In certain embodiments, the components of a selected genome editing method are delivered as DNA constructs in one or more plasmids. In certain embodiments, the components are delivered via viral vectors. Common delivery methods include but is not limited to, electroporation, microinjection, gene gun, impalefection, hydrostatic pressure, continuous infusion, sonication, magnetofection, adeno-associated viruses, envelope protein pseudotyping of viral vectors, replication-competent vectors cis and trans-acting elements, herpes simplex virus, and chemical vehicles (e.g., oligonucleotides, lipoplexes, polymersomes, polyplexes, dendrimers, inorganic Nanoparticles, and cell-penetrating peptides).

Placement of a presently disclosed CAR can be made at any endogenous gene locus. In certain embodiments, the endogenous gene locus is a TRAC locus, a TRBC locus or a TRGC locus. In certain embodiments, the endogenous gene locus is a TRAC locus. In certain embodiments, the placement of the CAR disrupts or abolishes the endogenous expression of a TCR.

6. Polypeptides and Analogs

Also included in the presently disclosed subject matter are a CD19, CD8, CD28, CD3ζ, CD40, 4-1BB, OX40, CD84, CD166, CD8a, CD8b, ICOS, ICAM-1, CD27, MY88, NKGD2 and CTLA-4 polypeptides or fragments thereof that are modified in ways that enhance their anti-neoplastic activity when expressed in an immunoresponsive cell. The presently disclosed subject matter provides methods for optimizing an amino acid sequence or nucleic acid sequence by producing an alteration in the sequence. Such alterations may include certain mutations, deletions, insertions, or post-translational modifications. The presently disclosed subject matter further includes analogs of any naturally-occurring polypeptide disclosed herein (including, but not limited to, CD19, CD8, CD28, CD3ζ, CD40, 4-1BB, OX40, CD27, CD40/My88, NKGD2, CD84, CD166, CD8a, CD8b, ICOS, ICAM-1, and CTLA-4). Analogs can differ from a naturally-occurring polypeptide disclosed herein by amino acid sequence differences, by post-translational modifications, or by both. Analogs can exhibit at least about 85%, about 90%, about 91%, about 92%, about 93%, about 94%, about 95%, about 96%, about 97%, about 98%, about 99% or more homologous to all or part of a naturally-occurring amino, acid sequence of the presently disclosed subject matte. The length of sequence comparison is at least 5, 10, 15 or 20 amino acid residues, e.g., at least 25, 50, or 75 amino acid residues, or more than 100 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amina acids, e.g., D-amino acids or non-naturally occurring or synthetic amino acids, e.g., .beta. or .gamma. amino acids.

In addition to full-length polypeptides, the presently disclosed subject matter also provides fragments of any one of the polypeptides or peptide domains disclosed herein. As used herein, the term "a fragment" means at least 5, 10, 13, or 15 amino acids. In certain embodiments, a fragment comprises at least 20 contiguous amino acids, at least 30 contiguous amino acids, or at least 50 contiguous amino acids. In certain embodiments, a fragment comprises at least 60 to 80, 100, 200, 300 or more contiguous amino acids. Fragments can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein disclosed herein. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. In certain embodiments, the protein analogs are relatively resistant to in vivo degradation, resulting in a more prolonged therapeutic effect upon administration. Assays for measuring functional activity include, but are not limited to, those described in the Examples below.

7. Administration

Compositions comprising the presently disclosed immunoresponsive cells can be provided systemically or directly to a subject for inducing and/or enhancing an immune response to an antigen and/or treating and/or preventing a neoplasm, pathogen infection, or infectious disease. In certain embodiments, the presently disclosed immunoresponsive cells or compositions comprising thereof are directly injected into an organ of interest (e.g., an organ affected by a neoplasia). Alternatively, the presently disclosed immunoresponsive cells or compositions comprising thereof are provided indirectly to the organ of interest, for example, by administration into the circulatory system (e.g., the tumor vasculature). Expansion and differentiation agents can be provided prior to, during or after administration of the cells or compositions to increase production of T cells, NK cells, or CTL cells in vitro or in vivo.

The presently disclosed immunoresponsive cells can be administered in any physiologically acceptable vehicle, normally intravascularly, although they may also be introduced into bone or other convenient site where the cells may find an appropriate site for regeneration and differentiation (e.g., thymus). Usually, at least about $1 \times 10^5$ cells will be administered, eventually reaching about $1 \times 10^{10}$ or more. The presently disclosed immunoresponsive cells can comprise a purified population of cells. Those skilled in the art can readily determine the percentage of the presently disclosed immunoresponsive cells in a population using various well-known methods, such as fluorescence activated cell sorting (FACS). Suitable ranges of purity in populations comprising the presently disclosed immunoresponsive cells are about 50% to about 55%, about 5% to about 60%, and about 65% to about 70%. In certain embodiments, the purity is about 70% to about 75%, about 75% to about 80%, or about 80% to about 85%. In certain embodiments, the purity is about 85% to about 90%, about 90% to about 95%, and about 95% to about 100%. Dosages can be readily adjusted by those skilled in the art (e.g., a decrease in purity may require an increase in dosage). The cells can be introduced by injection, catheter, or the like.

The presently disclosed compositions can be pharmaceutical compositions comprising the presently disclosed immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition of the presently disclosed subject matter (e.g., a pharmaceutical composition comprising a presently disclosed immunoresponsive cell), it can be formulated in a unit dosage injectable form (solution, suspension, emulsion).

8. Formulations

Compositions comprising the presently disclosed immunoresponsive cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the genetically modified immunoresponsive cells in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the presently disclosed subject matter, however, any vehicle, diluent, or additive used would have to be compatible with the genetically modified immunoresponsive cells or their progenitors.

The compositions can be isotonic, i.e., they can have the same osmotic pressure as blood and lacrimal fluid. The desired isotonicity of the compositions may be accomplished using sodium chloride, or other pharmaceutically acceptable agents such as dextrose, boric acid, sodium tartrate, propylene glycol or other inorganic or organic solutes. Sodium chloride can be particularly for buffers containing sodium ions.

Viscosity of the compositions, if desired, can be maintained at the selected level using a pharmaceutically acceptable thickening agent. For example, methylcellulose is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

The quantity of cells to be administered will vary for the subject being treated. In a one embodiment, between about $10^4$ and about $10^{10}$, between about $10^5$ and about $10^9$, or between about $10^6$ and about $10^8$ of the presently disclosed immunoresponsive cells are administered to a human subject. More effective cells may be administered in even smaller numbers. In certain embodiments, at least about $1 \times 10^8$, about $2 \times 10^8$, about $3 \times 10^8$, about $4 \times 10^8$, or about $5 \times 10^8$ of the presently disclosed immunoresponsive cells are administered to a human subject. In certain embodiments, between about $1 \times 10^7$ and $5 \times 10^8$ of the presently disclosed immunoresponsive cells are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods. Typically, any additives (in addition to the active cell(s) and/or agent(s)) are present in an amount of 0.001 to 50% (weight) solution in phosphate buffered saline, and the active ingredient is present in the order of micrograms to milligrams, such as about 0.0001 to about 5 wt %, about 0.0001 to about 1 wt %, about 0.0001 to about 0.05 wt % or about 0.001 to about 20 wt %, about 0.01 to about 10 wt %, or about 0.05 to about 5 wt %. For any composition to be administered to an animal or human, the followings can be determined: toxicity such as by determining the lethal dose (LD) and LD50 in a suitable animal model e.g., rodent such as mouse; the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

9. Methods of Treatment

The presently disclosed subject matter provides methods for inducing and/or increasing an immune response in a subject in need thereof. The presently disclosed immunoresponsive cells and compositions comprising thereof can be used for treating and/or preventing a neoplasm in a subject. The presently disclosed immunoresponsive cells and compositions comprising thereof can be used for prolonging the survival of a subject suffering from a neoplasm. The presently disclosed immunoresponsive cells and compositions comprising thereof can also be used for treating and/or preventing a pathogen infection or other infectious disease in a subject, such as an immunocompromised human subject. In certain embodiments, immunoresponsive cells comprising a CAR disclosed herein can be used to treat a subject having a relapse of a disease, wherein the subject received treatment which leads to residual tumor cells. In certain embodiments, the residual tumor cells have low density of a target molecule on the surface of the tumor cells. In certain embodiments, a target molecule having low density on the cell surface has below about 10000 molecules per cell, below about 8000 molecules per cell, below about 6000 molecules per cell, below about 4000 molecules per cell, below about 2000 molecules per cell, below about 1000 molecules per cell, below about 500 molecules per cell, below about 200 molecules per cell, or below about 100 molecules per cell, In certain embodiments, a target molecule having low density on the cell surface has between about 4000 to about 2000 molecules per cell or between about 2000 to about 1000 molecules per cell. In certain embodiments, immunoresponsive cells comprising a CAR disclosed herein can be used to treat a subject having a relapse of a disease, wherein the subject received immunoresponsive cells (e.g., T cells) comprising a CAR comprising an intracellular signaling domain that comprises a co-stimulatory signaling domain comprising a 4-1BB polypeptide (e.g., a 4-1BBz CAR). In certain embodiments, the tumor cells have a low density of a tumor specific antigen on the surface of the tumor cells. In certain embodiments, the disease is CD19$^+$ ALL. In certain embodiments, the tumor cells have a low density of CD19 on the tumor cells. Such methods comprise administering the presently disclosed immunoresponsive cells in an amount effective or a composition (e.g., pharmaceutical composition) comprising thereof to achieve the desired effect, alleviation of an existing condition or prevention of recurrence. For treatment, the amount administered is an amount effective in producing the desired effect. An effective amount can be provided in one or a series of administrations. An effective amount can be provided in a bolus or by continuous perfusion.

An "effective amount" (or, "therapeutically effective amount") is an amount sufficient to effect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

For adoptive immunotherapy using antigen-specific T cells, cell doses in the range of about $10^6$-$10^{10}$ (e.g., about $10^9$) are typically infused. Upon administration of the presently disclosed cells into the host and subsequent differentiation, T cells are induced that are specifically directed against the specific antigen. The immunoresponsive cells can be administered by any method known in the art including, but not limited to, intravenous, subcutaneous, intranodal, intratumoral, intrathecal, intrapleural, intraperitoneal and directly to the thymus.

The presently disclosed subject matter provides methods for treating and/or preventing a neoplasm in a subject. The method can comprise administering an effective amount of the presently disclosed immunoresponsive cells or a composition comprising thereof to a subject having a neoplasm.

Non-limiting examples of neoplasia include blood cancers (e.g. leukemias, lymphomas, and myelomas), ovarian cancer, breast cancer, bladder cancer, brain cancer, colon cancer, intestinal cancer, liver cancer, lung cancer, pancreatic cancer, prostate cancer, skin cancer, stomach cancer, glioblastoma, throat cancer, melanoma, neuroblastoma, adenocarcinoma, glioma, soft tissue sarcoma, and various carcinomas (including prostate and small cell lung cancer). Suitable carcinomas further include any known in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolarcarcinoma, epithelial adenocarcinoma, and liver metastases thereof, lymphangiosarcoma, lymphangioendotheliosarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bile duct carcinoma, choriocarcinoma, seminoma, embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, and heavy chain disease, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas. In certain embodiments, the neoplasia is selected from the group consisting of blood cancers (e.g. leukemias, lymphomas, and myelomas), ovarian cancer, prostate cancer, breast cancer, bladder cancer, brain cancer, colon cancer, intestinal cancer, liver cancer, lung cancer, pancreatic cancer, prostate cancer, skin cancer, stomach cancer, glioblastoma, and throat cancer. In certain embodiments, the presently disclosed immunoresponsive cells and compositions comprising thereof can be used for treating and/or preventing blood cancers (e.g., leukemias, lymphomas, and myelomas) or ovarian cancer, which are not amenable to conventional therapeutic interventions.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Suitable human subjects for therapy typically comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition is administered to these subjects to elicit an anti-tumor response, with the objective of palliating their condition.

Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group." These are individuals who have had a history of neoplasia, but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor has invaded neighboring tissues, or who show involvement of lymph nodes.

Another group have a genetic predisposition to neoplasia but have not yet evidenced clinical signs of neoplasia. For instance, women testing positive for a genetic mutation associated with breast cancer, but still of childbearing age, can wish to receive one or more of the immunoresponsive cells described herein in treatment prophylactically to prevent the occurrence of neoplasia until it is suitable to perform preventive surgery.

Additionally, the presently disclosed subject matter provides methods for treating and/or preventing a pathogen infection (e.g., viral infection, bacterial infection, fungal infection, parasite infection, or protozoal infection) in a subject, e.g., in an immunocompromised subject. The method can comprise administering an effective amount of the presently disclosed immunoresponsive cells or a composition comprising thereof to a subject having a pathogen infection. Exemplary viral infections susceptible to treatment include, but are not limited to, Cytomegalovirus (CMV), Epstein Barr Virus (EBV), Human Immunodeficiency Virus (HIV), and influenza virus infections.

Further modification can be introduced to the presently disclosed immunoresponsive cells (e.g., T cells) to avert or minimize the risks of immunological complications (known as "malignant T-cell transformation"), e.g., graft versus-host disease (GvHD), or when healthy tissues express the same target antigens as the tumor cells, leading to outcomes similar to GvHD. A potential solution to this problem is engineering a suicide gene into the presently disclosed immunoresponsive cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T cell elimination by administering anti-EGFR monoclonal antibody (e.g., cetuximab). EGFRt can be covalently joined to the upstream of a presently disclosed CAR. The suicide gene can be included within the vector comprising nucleic acids encoding a presently disclosed CAR. In this way, administration of a prodrug designed to activate the suicide gene (e.g., a prodrug (e.g., AP1903 that can activate iCasp-9) during malignant T-cell transformation (e.g., GVHD) triggers apoptosis in the suicide gene-activated CAR-expressing T cells. The incorporation of a suicide gene into the a presently disclosed CAR gives an added level of safety with the ability to eliminate the majority of CAR T cells within a very short time period. A presently disclosed immunoresponsive cell (e.g., a T cell) incorporated with a suicide gene can be pre-emptively eliminated at a given timepoint post CAR T cell infusion, or eradicated at the earliest signs of toxicity.

10. Kits

The presently disclosed subject matter provides kits for inducing and/or enhancing an immune response and/or treating and/or preventing a neoplasm or a pathogen infection in a subject. In certain embodiments, the kit comprises an effective amount of presently disclosed immunoresponsive cells or a pharmaceutical composition comprising thereof. In certain embodiments, the kit comprises a sterile container; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In certain non-limiting embodiments, the kit includes an isolated nucleic acid molecule encoding a presently disclosed CAR that is directed toward an antigen of interest in expressible form, which may optionally be comprised in one or more vectors.

If desired, the immunoresponsive cells and/or nucleic acid molecules are provided together with instructions for administering the cells or nucleic acid molecules to a subject having or at risk of developing a neoplasia or pathogen or immune disorder. The instructions generally include information about the use of the composition for the treatment and/or prevention of a neoplasm or a pathogen infection. In certain embodiments, the instructions include at least one of the following: description of the therapeutic agent; dosage schedule and administration for treatment or prevention of a neoplasia, pathogen infection, or immune disorder or symptoms thereof; precautions; warnings; indications; counter-indications; over-dosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides disclosed herein, and, as such, may be considered in making and practicing the presently disclosed subject matter. Particularly useful techniques for particular embodiments will be discussed in the sections that follow.

The following examples are put forth so as to provide those of ordinary skill in the art with a complete disclosure and description of how to make and use the presently

Example 1

Introduction

Multiple ITAMs in CD3ζ and TCR complex have been proposed to amplify TCR signals (PMID: 20516133). Meanwhile, CD28 provides a quantitative support for TCR signaling (PMID: 14647476). Therefore, the number and type of signaling domains matter in TCR signaling. In human T cells, CD28 and TCR/CD3ζ are expressed at ~$6 \times 10^4$ and ~$2 \times 10^4$ molecules per cell (PMID: 14647476). Therefore, three molecules of CD28 can provide signaling support for one molecule of TCR/CD3ζ, which has three ITAMs. However, the second-generation CAR 1928z has the design of fused CD28 and CD3ζ cytosolic domains, fixing the stoichiometry ratio of them to be one. With superior abilities of killing and proliferation, 1928z CAR allows fast elimination of CD19 bearing cells in vitro, in mouse models and in patients. However, improvement of current 1928z CAR is necessary to overcome some issues in the clinical trials. One issues is cytokine release syndrome (CRS), characterized by massive synchronized T cell activation and the release of large amount of cytokines. Even though the mechanism of CRS is still elusive, it can be related to excessive signaling of 1928z CAR T cells. Another issue is exhaustion and persistence of CAR T cells. 1928z CAR T cells were found to exist in low numbers and/or in a dysfunctional state expressing exhaustion markers, such as PD-1, weeks or months after infusion, which may account for some cases of relapse. It is hypothesized that exhaustion is linked to excessive activation (PMID: 26331345), which may be attributed to intrinsic properties due to the design of 1928z CAR.

Comparing 1928z CAR signaling to TCR signaling, some major differences due to the fusion of two cytosolic domains are obvious. First, in the CAR, CD28 signaling domain is in cis with CD3ζ signaling domain, while CD28 is recruited into synapse and co-localized with CD3ζ in trans. Second, CD28 activation is concurrent with CD3ζ activation in CAR while CD28 costimulation is seconds after TCR ligation. Third, three CD28 molecules help one TCR while the ratio is one to one in CAR. The first two differences are not easy to modify under the current CAR design but the third difference might be addressed by balancing the costimulation signal and activation signal, which may help to solve the existing problem of overstimulation. The CD28/CD3; ratio cannot be changed directly due to the fusion design, but the number of ITAMs in CD3ζ can be mutated to mimic the ratio in TCR signaling. The three ITAMs in CD3ζ differ in their primary amino acid sequence as well as their positions relative to the plasma membrane (namely ITAM1, ITAM2, ITAM3 from membrane proximal to distal) and therefore their ability of being phosphorylated by Lck or binding to ZAP70 upon phosphorylation are different (PMID: 23555234). A previous study of CD28-based ErbB2 CAR with only one ITAM at second position showed reduced apoptosis in vitro (PMID:19843940), but further CAR characterization and in vivo studies were still missing. Therefore, novel CARS based on the 1928z CAR-design was designed, which introduced defined ITAM numbers and positions in order to evaluate their functionality, especially in terms of the above-mentioned issues, including their impact on aT cell persistence, differentiation, exhaustion and anti-tumor activity. How each ITAM coupled to CD28 signaling in the 1928z CAR context affects the overall CAR function in vitro and in vivo was analyzed. ITAM1 coupled to CD28 was not only better than ITAM2 or ITAM3 coupled to CD28, but more importantly better than the original 1928z CAR in terms of in vivo anti-tumor efficacy, making it a great candidate for clinical applications. All studies were performed in human peripheral blood T cells.

Results

Figure 1B:
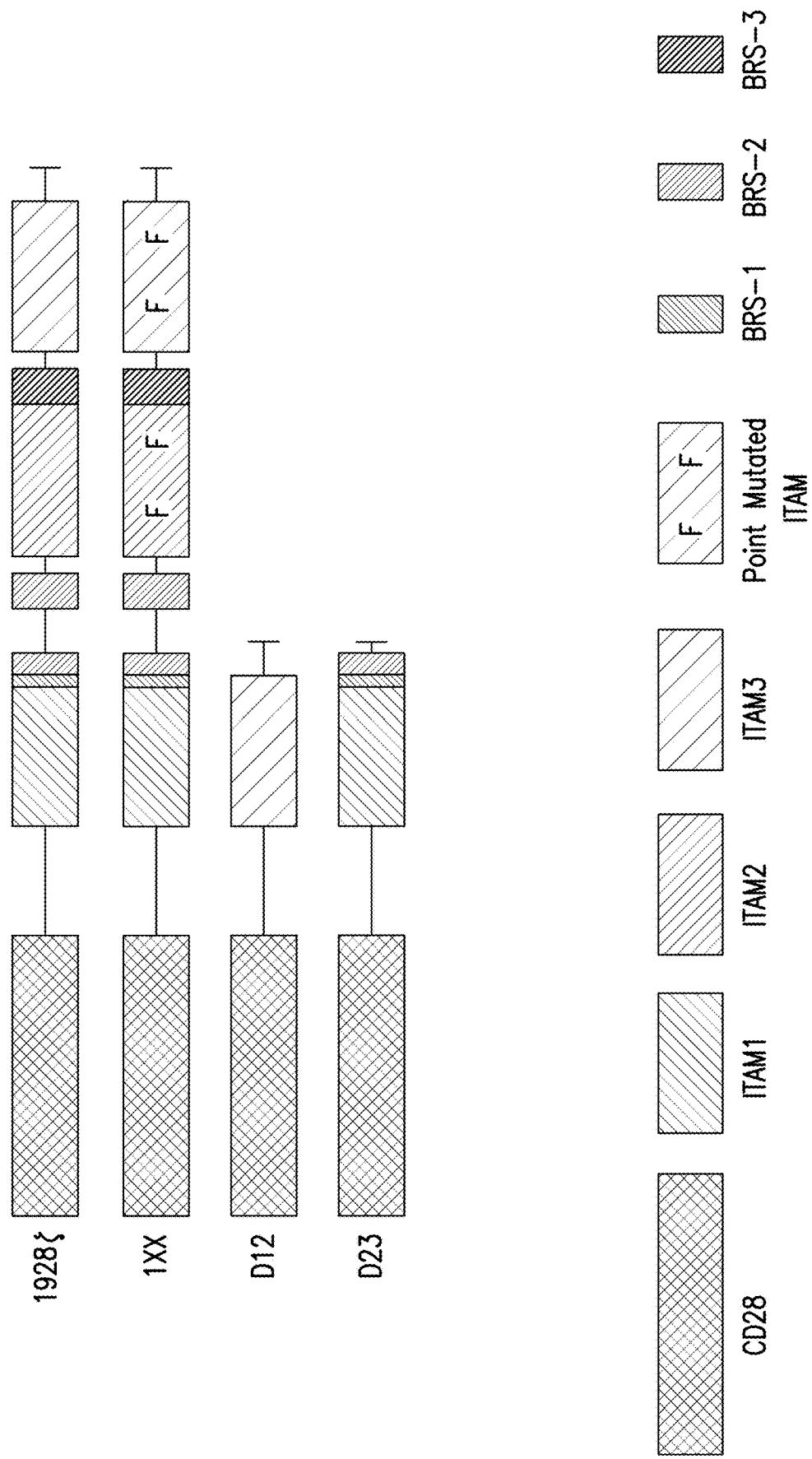
Figure 1C:
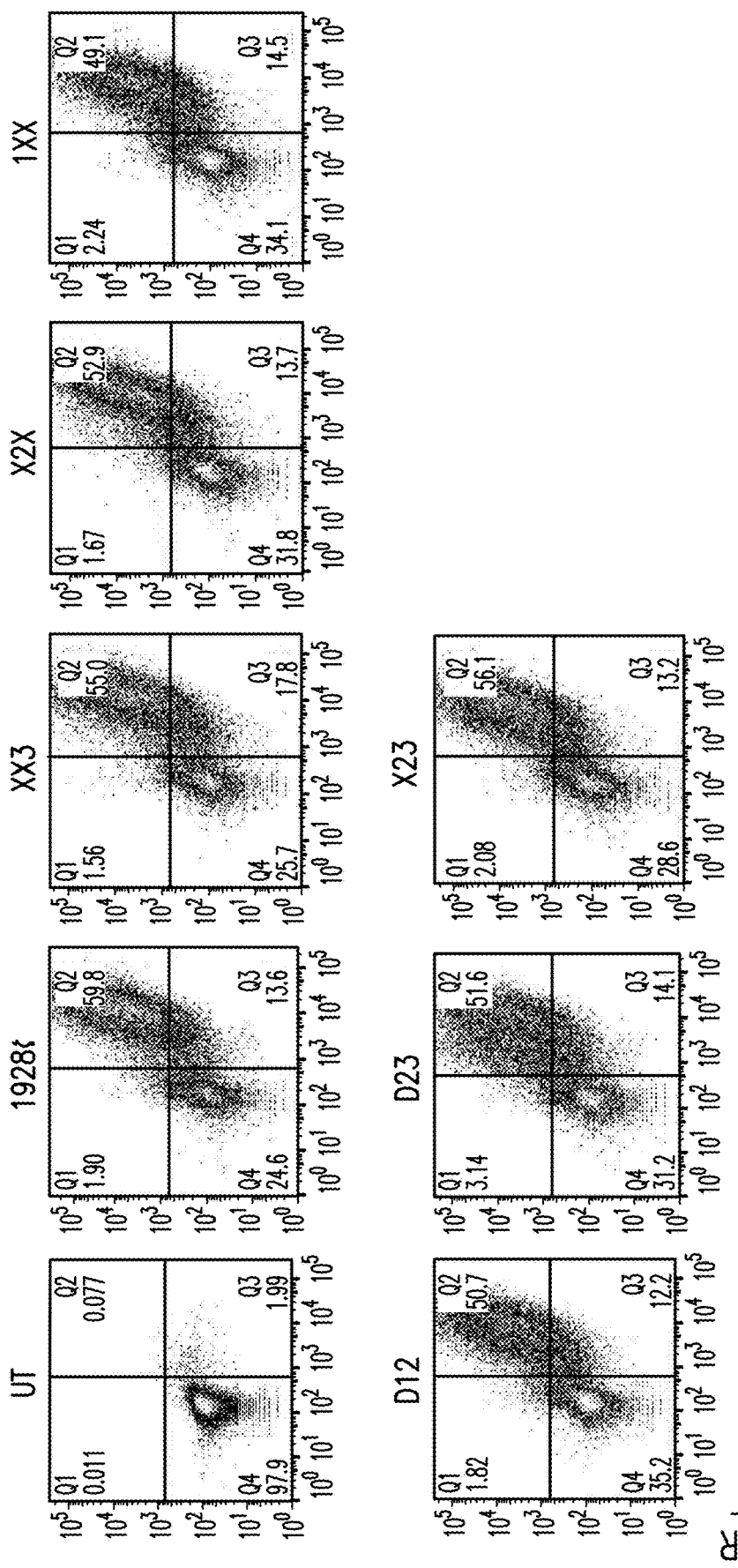

CD3ζ ITAM Domains in 1928ζ CARs Exert Qualitatively Differential CAR T-Cell Function The first step was to explore if each CD3ζ ITAM within the $2^{nd}$ generation 1928z-CAR construct contributes to qualitatively distinctive functions or if the individual ITAMs show overlapping and functional redundant properties. In order to evaluate the contribution of each individual ITAM to the function of the 1928z CAR, 1928z CARs with only one single functional ITAM domain were generated (1XX, X2X and XX3, see FIG. 1A). Signaling of the two remaining ITAMs was disrupted by insertion of point mutations converting the two tyrosines (Y) to phenylalanines (F) and thus disabling phosphorylation and consecutive recruitment of ZAP70 for full activation of downstream signaling pathways. T cells were effectively transduced using SFG retroviral vectors with comparable transduction rates between the different constructs (FIG. 1).

Figure 2A:
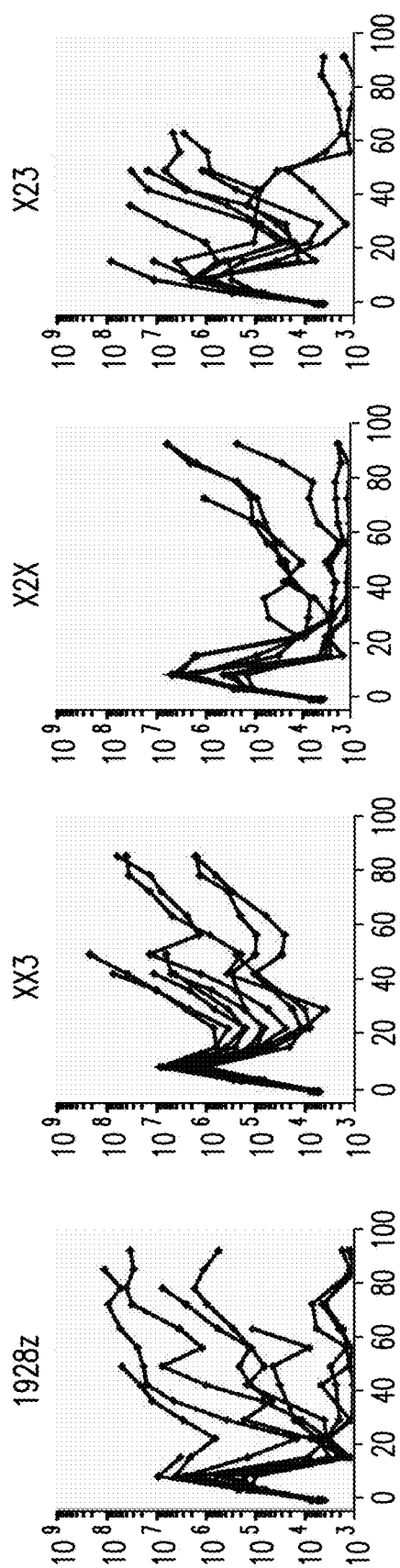
FIGS. 2A-2B depicts therapeutic potency of T cells comprising the novel CAR design or control 1928ζ(1928z) CAR. Therapeutic potency of 1928ζ(1928z) CAR T cells is improved by mutation of the CD3ζ chain in the CAR construct. Tumor burden (average radiance) of NALM-6-bearing mice treated with $0.05 \times 10^6$ CAR T cells (n=9-10, pooled data from 2 independent experiments).
Figure 2B:
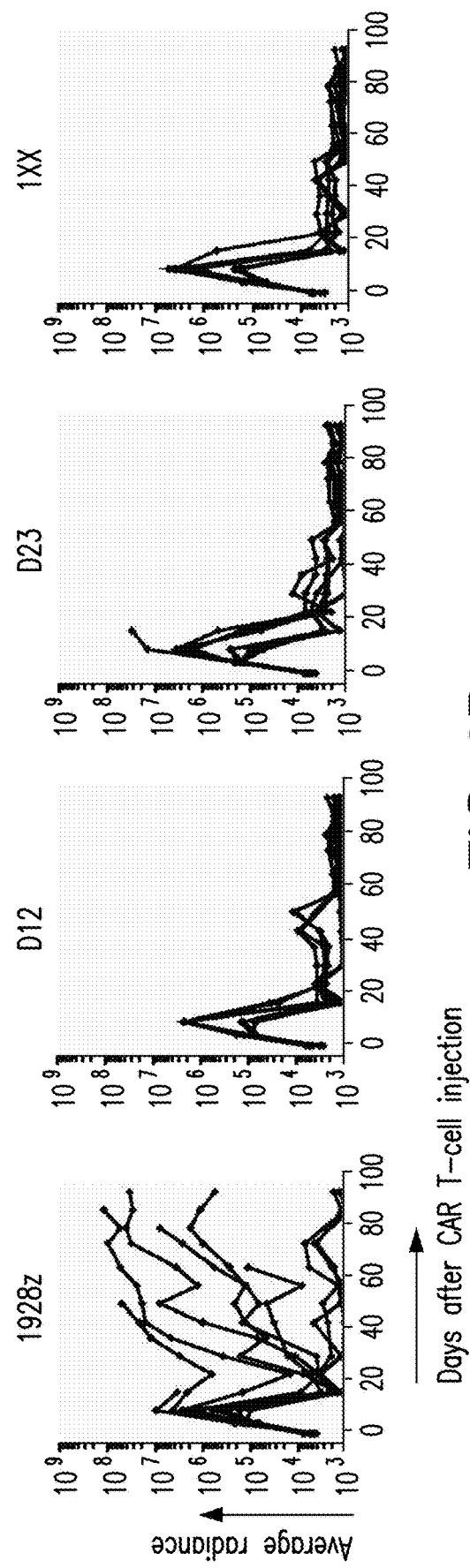

In order to compare the therapeutic potential of the generated 1928z mutants, a suboptimal CAR T-cell dose of $5 \times 10^4$ CAR⁺ T cells were administered in a previously described pre-B acute lymphoblastic leukaemia NALM-6 mouse model and compared efficacy to treatment with 1928z wild type (1928z WT) mice (FIG. 2).

Figure 3B:
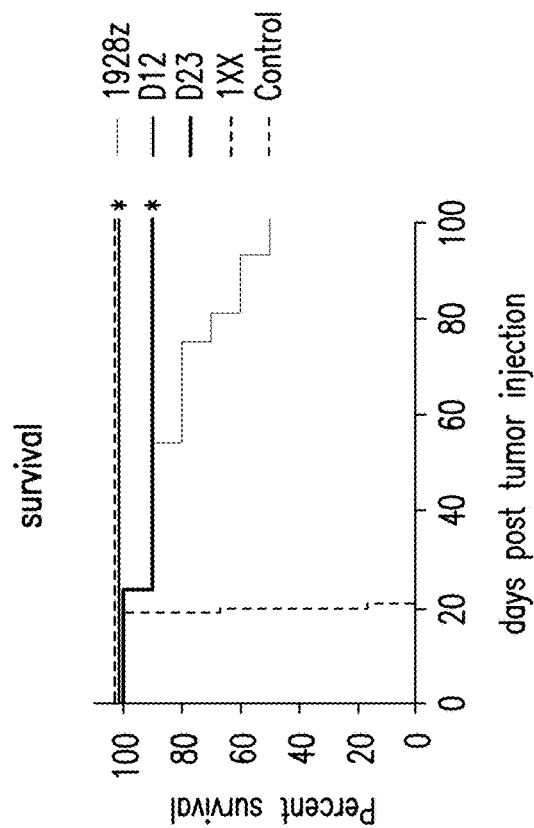
FIGS. 3A-3B depict survival following treatment with the same dose of CAR T cells expressing 1928ζ (1928z) control or novel CAR constructs. Nalm-6 bearing mice were treated with $5 \times 10^4$ CAR$^+$ T cells.

A gradual difference in tumor eradication and survival of mice in relation to the relevant functional ITAM was found: unmodified ITAM1 (1XX) or ITAM2 (X2X) in their original 1928z CAR position showed improved antitumor activity compared to 3 functional ITAMs as in the original 1928z wild type (WT). In contrast, ITAM3 as the only functional ITAM in combination with dysfunctional ITAMs 1 and 2 (XX3) performed poorly, with diminished tumor eradication and reduced survival of mice (FIG. 3).

Therefore, individual ITAMs in 1928z CARs exerted qualitatively differential functions when maintaining the original position in the $2^{nd}$ generation 1928z structure. Efficacy of tumor eradication gradually decreased with each further distal position of the functional ITAM: 1XX consistently showed rapid tumor eradication and achieved long term complete remissions whereas treatment with X2X delayed tumor progression and was superior to 1928z WT, but eventually relapses occurred. XX3 with its un-mutated (native) ITAM in the most distal position did not achieve tumor control, leading to rapid tumor progression and reduced survival rates (FIG. 3). In conclusion 1928z CARs with 1 or 2 ITAMs in the second or third ITAM position (XX3, X2X, X23) were less active or no more therapeutically active (in vivo) than 1928z wild type.

One Single Functional CD3 ITAM at the Right Position is Sufficient for Potent Antitumor Activity The next question addressed was if the combination of the two functional ITAMs in distal position—ITAM2 and ITAM3 (X23, FIG. 1A)—which are supposed to have lower affinity to ZAP70 than ITAM1—could together improve potency of their relevant single ITAM 1928ζ mutant (X2X/XX3). In vivo analysis revealed dismal tumor clearance and survival of mice treated with X23, comparable to outcome of mice treated with XX3 (FIGS. 2 and 3). In contrast, 1928z mutant CARs with only one single functional ITAM in either first (1XX) or second (X2X) position emerged to be superior to 1928z CARs with two (X23) or three (WT) functional ITAMs as reflected in the course of tumor burden and survival. 1XX consistently was proved to be the most potent 1928z mutant, achieving rapid and durable tumor eradication even at very low treatment dose. The results thus indicate that one single ITAM is sufficient for efficient killing, but also reveal significant differences in therapeutic potency of CAR T cells dependent on which ITAM within the CD3ζ is functional.

Next analyzed was whether the reduced CAR function in XX3 was attributed to the individual specificity of ITAM3 or related to the more distal position of ITAM3 in the context of a $2^{nd}$ generation CAR compared to its natural position. 1928z mutant CARs with ITAM1 or ITAM3 in exactly the same proximal CAR position (D12 and D23,) and deletion of the remaining CD3ζ chain, enabling direct comparison of the two ITAMs in the 1928-CAR context (FIG. 1) were therefore generated. The results demonstrated that ITAM3 in a more proximal position (D12) was sufficient for rapid and efficient long-term tumor clearance (FIGS. 2 and 3), displaying comparable results to D23. Despite sharing the same ITAM (ITAM3), D12 clearly outperformed XX3 and achieved effective antitumor potency. The significant difference in therapeutic potency between D12 and XX3 thus demonstrates the impact of the ITAM position within the $2^{nd}$ generation CAR. In conclusion, 1928z CARs with a single ITAM (either ITAM1 in 1XX and D23 or ITAM 3 in D12) in the first ITAM position were more therapeutically active (in vivo) than 1928z wild type.

Figure 4:
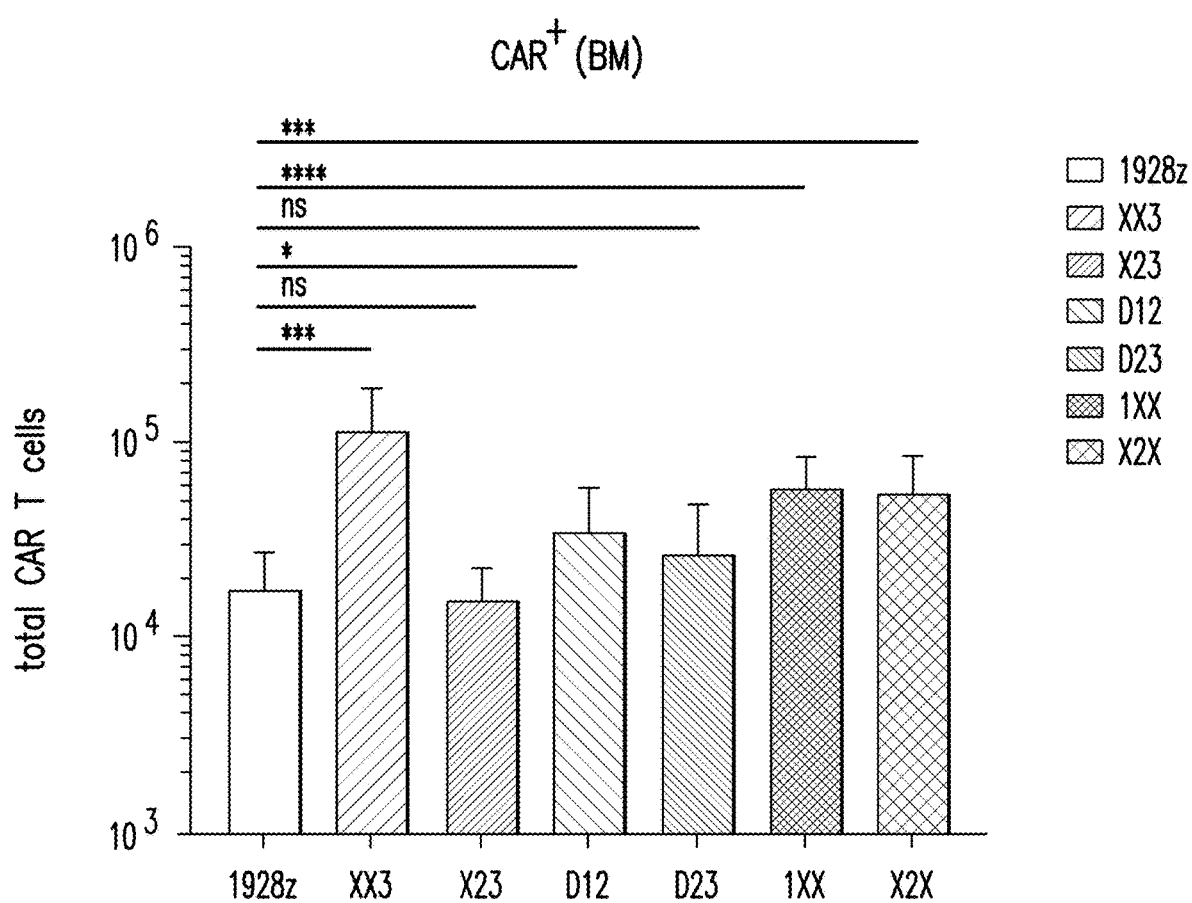
FIG. 4 depicts enumeration of CAR T cells in tumor bearing mice. NALM-6-bearing mice were treated with $5 \times 10^4$ CAR T cells (n=10 per group; pooled data from 2 independent experiments) and euthanized at day 17 after infusion; bone marrow CAR T cells and NALM-6 cells were analyzed and counted by FACS. All data are means SD. *P<0.05, *P<0.001, **P<0.0001 (unpaired student's t test).
Figure 5C:
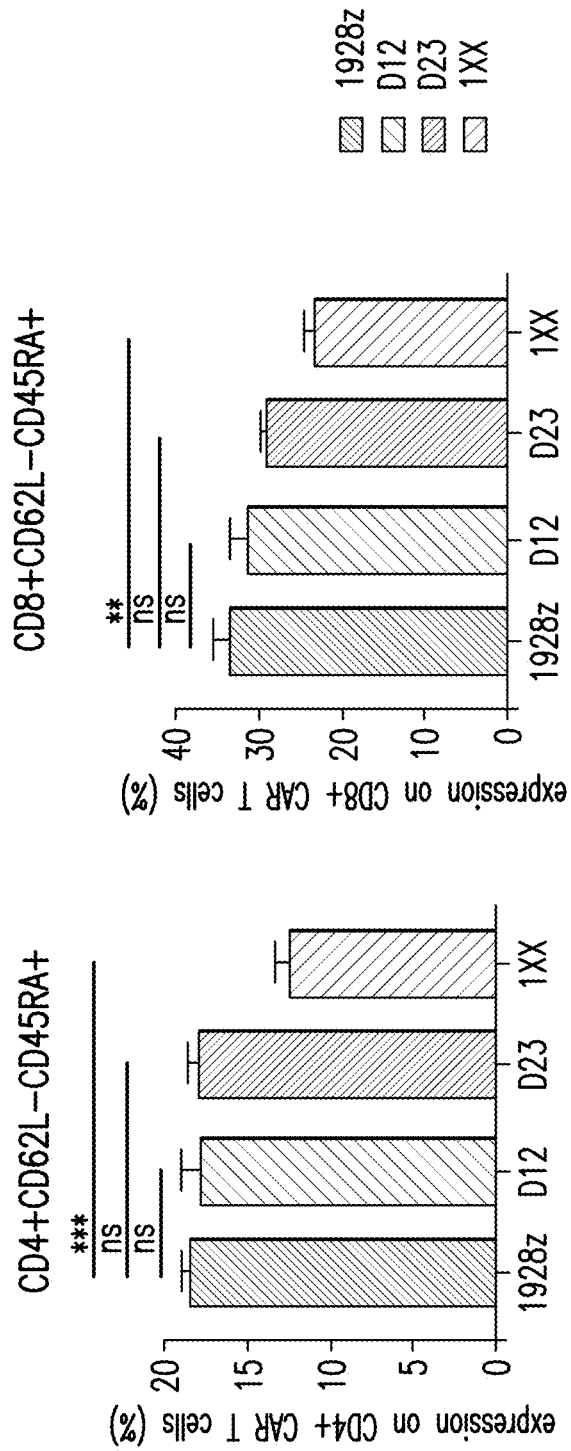

Although D23 and 1XX have ITAM1 as the only functional ITAM in common, 1XX showed improved functional properties compared to D23, resulting in higher T-cell proliferation and favorable T-cell phenotype (FIGS. 4 and 5). This supports that the basic rich stretch (BRS) within the CD3ζ chain—which has previously been shown to mediate membrane association and to modulate signaling—may attribute to functional properties of the 1928z CAR (FIG. 1B).

Additional mutations in the structure of 1XX CAR were therefore inserted, thereby disrupting signaling of BRS-2 and -3 (=1XX $BRS_{negative}$). It was demonstrated that the BRS regions were essential for the function of 1XX as 1XX $BRS_{negative}$ showed reduced proliferative and killing function in vitro and in vivo. Therefore, we demonstrate functional importance of the BRS regions in 1XX.

CD3ζ ITAM Mutations Permit Enhanced T-Cell Proliferation in 1928ζ CARs and Limit T-Cell Differentiation and Exhaustion In vivo studies revealed enhanced CAR T-cell accumulation for all CAR groups with one functional ITAM and two mutated ITAM regions: cell numbers of XX3, X2X and 1XX achieved significantly higher T-cell accumulation at the tumor sites compared to 1928z WT after 17 days (FIG. 4). T cells expressing mutant 1928z CARs containing a single ITAM (XX3, X2X, 1XX) accumulated in vivo to a higher level than T cells expressing the wild-type 28z CAR. CARs containing 2 or more ITAMs (1928z and X23) showed decreased accumulation relative to T cells expressing a single-ITAM CAR (XX3, X2X, 1XX, D23 and D12).

Figure 6:
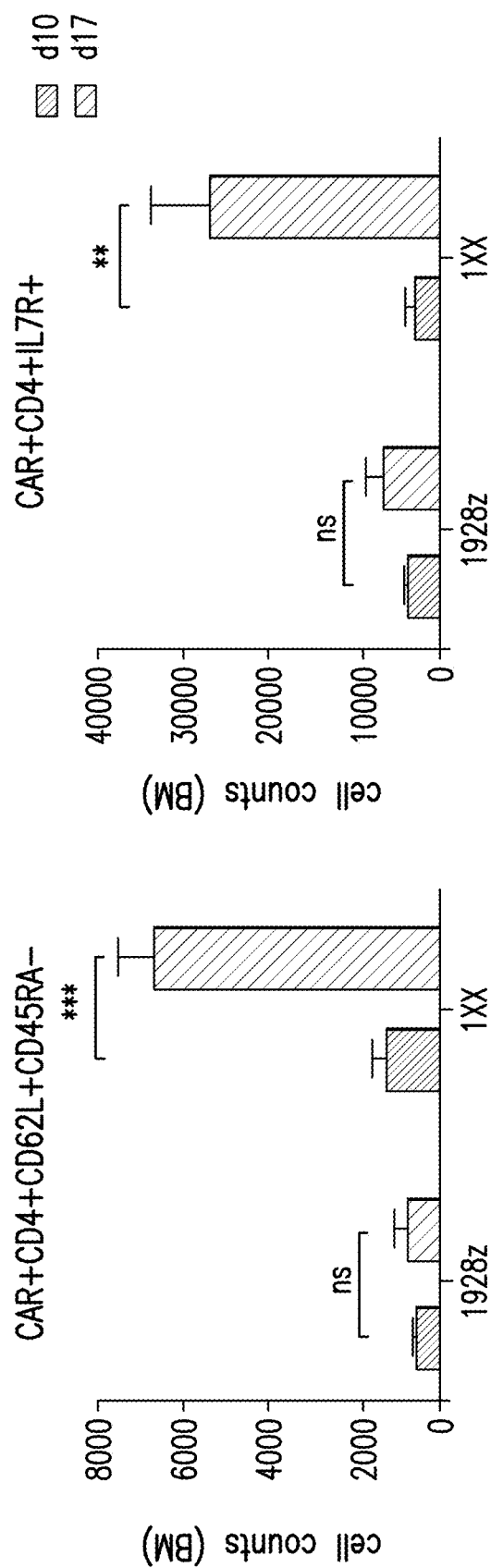
FIG. 6 depicts analysis of cell numbers of central memory CD4+ CAR Tells (CAR+CD4+CD62L+CD45RA−) and TL7R-expressing CD4+ CAR T cells (data are means±SEM, each bar represents n=5 mice) in the bone marrow of mice 10 and 17 days after T-cell administration. P<0.01, *P<0.001 (unpaired student's t test).

Higher T-cell accumulation was associated with less T-cell differentiation as reflected in the percentage of central memory (CD62L+CD45RA−) ($T_{CM}$) and effector (CD62L− CD45RA+) ($T_{EFF}$) cells in CD4$^+$ and CD8$^+$ CAR T cells: 1XX showed a significantly higher percentage of $T_{CM}$—a T-cell phenotype which is associated with improved in vivo proliferation potential—and significantly lower percentage of terminally differentiated $T_{EFF}$ compared to 1928z WT (FIG. 5). Besides, 1XX showed significantly higher numbers of $T_{CM}$ cells and of T cells expressing the memory-associated marker IL7R in the bone marrow of treated mice at day 17 post CAR infusion. Furthermore, both T-cell populations showed a significant increase from day 10 to day 17 post CAR administration (FIG. 6). Overall, 1XX elicited the largest fraction of memory T cells, and D23 was the second best in long-term in vitro assay. Delayed differentiation and an increase in IL7R-expressing CAR T cells was also observed in vitro upon repetitive exposure to antigen (data not shown).

Figure 7:
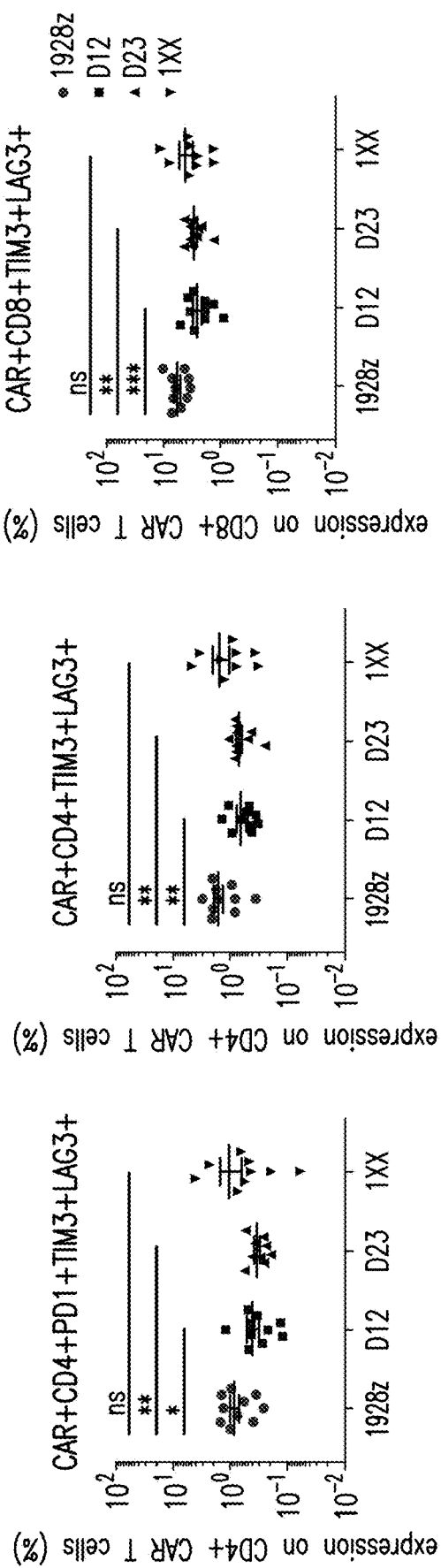
FIG. 7 depicts analysis of T cell exhaustion. NALM-6-bearing mice were treated with $5 \times 10^4$ CAR T cells (n=9-10 per group; pooled data from 2 independent experiments) and euthanized at day 10 after CAR infusion; bone marrow CAR T cells were analyzed by FACS. Percentage of CD4$^+$ and CD8$^+$ CAR T cells expressing exhaustion markers quantified by FACS 10 days after CAR infusion. Data are means±SEM, each dot represents one mouse. *P<0.05, P<0.01, *P<0.001, (unpaired student's t test).

Furthermore, the 1928z mutants differed in the degree of T-cell exhaustion as determined by the co-expression of inhibitory molecules PD1, TIM3 and LAG3 which are associated with diminished anti-tumor activity. 1928z mutant groups with one single functional ITAM and deletion of the two other ITAMs (D12 and D23) showed significantly lower expression of exhaustion markers (FIG. 7).

Figures 8A, 8B, 8C:
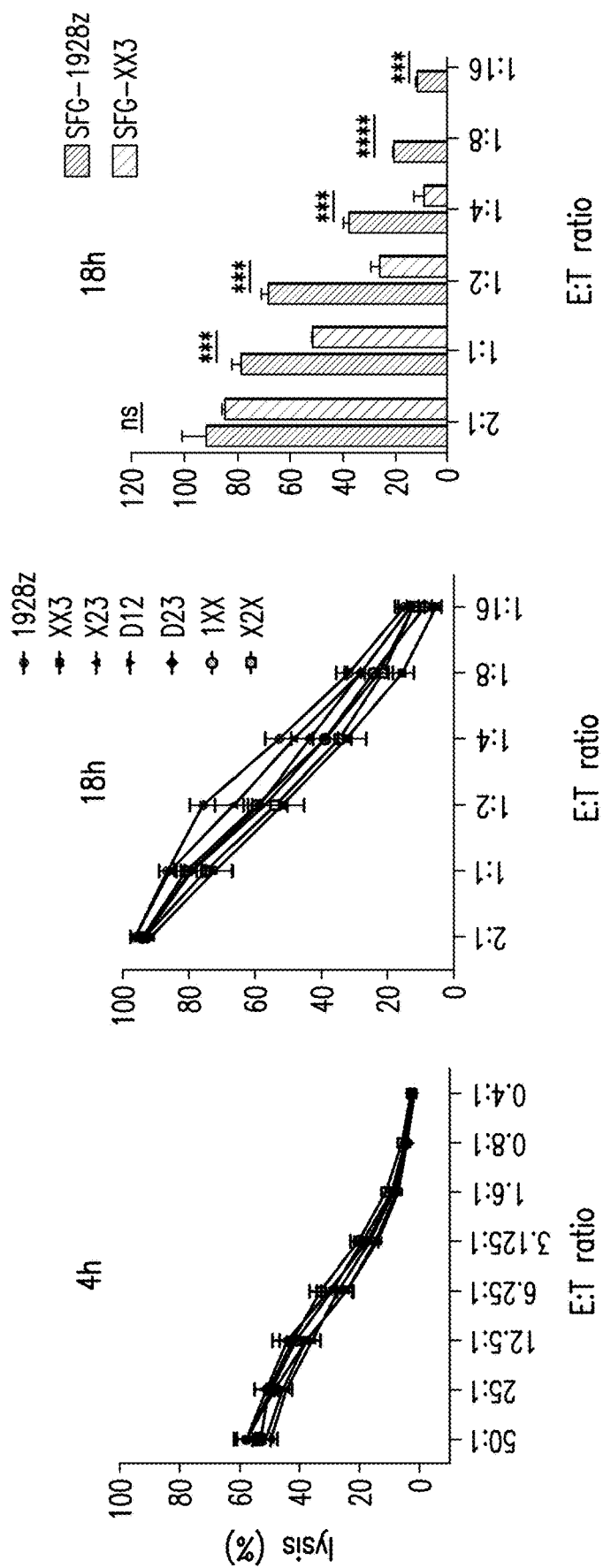
FIGS. 8A-8C depict in vitro functional tests of CAR T cell potency.
Figure 9A:
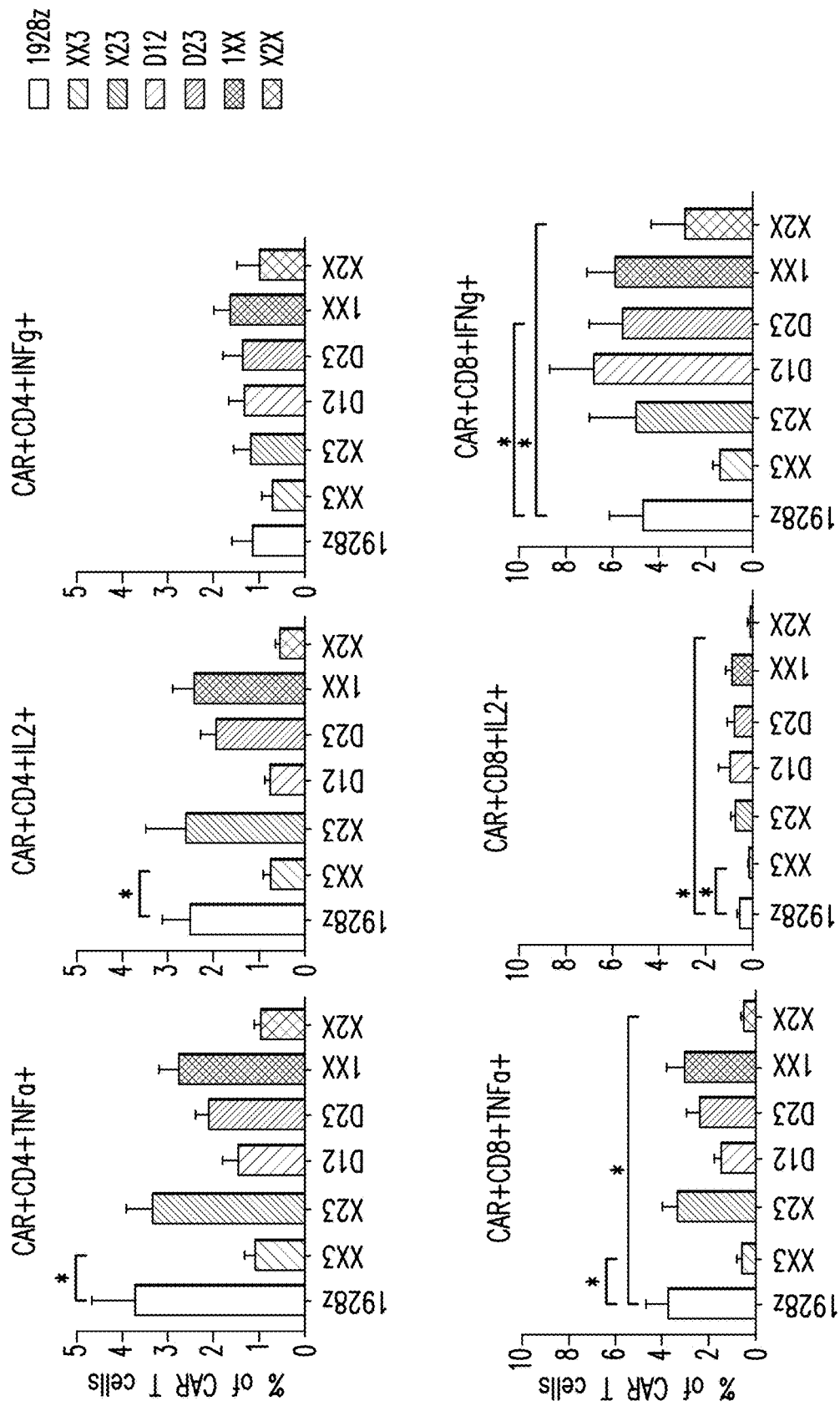
FIGS. 9A and 9B depict in vitro cytokine profiles of CAR T cells. Percentage of CD4$^+$ and CD8$^+$ CAR T cells with positive expression of single (A) and double positive Th1 cytokines as determined by intracellular cytokine staining 18 h after $2^{nd}$ stimulation with 3T3-CD19 (data are means±SEM and compared to 1928ζ WT, paired student's t test, n=3-5 independent experiments). *P<0.05, **P<0.01.
Figure 9B:
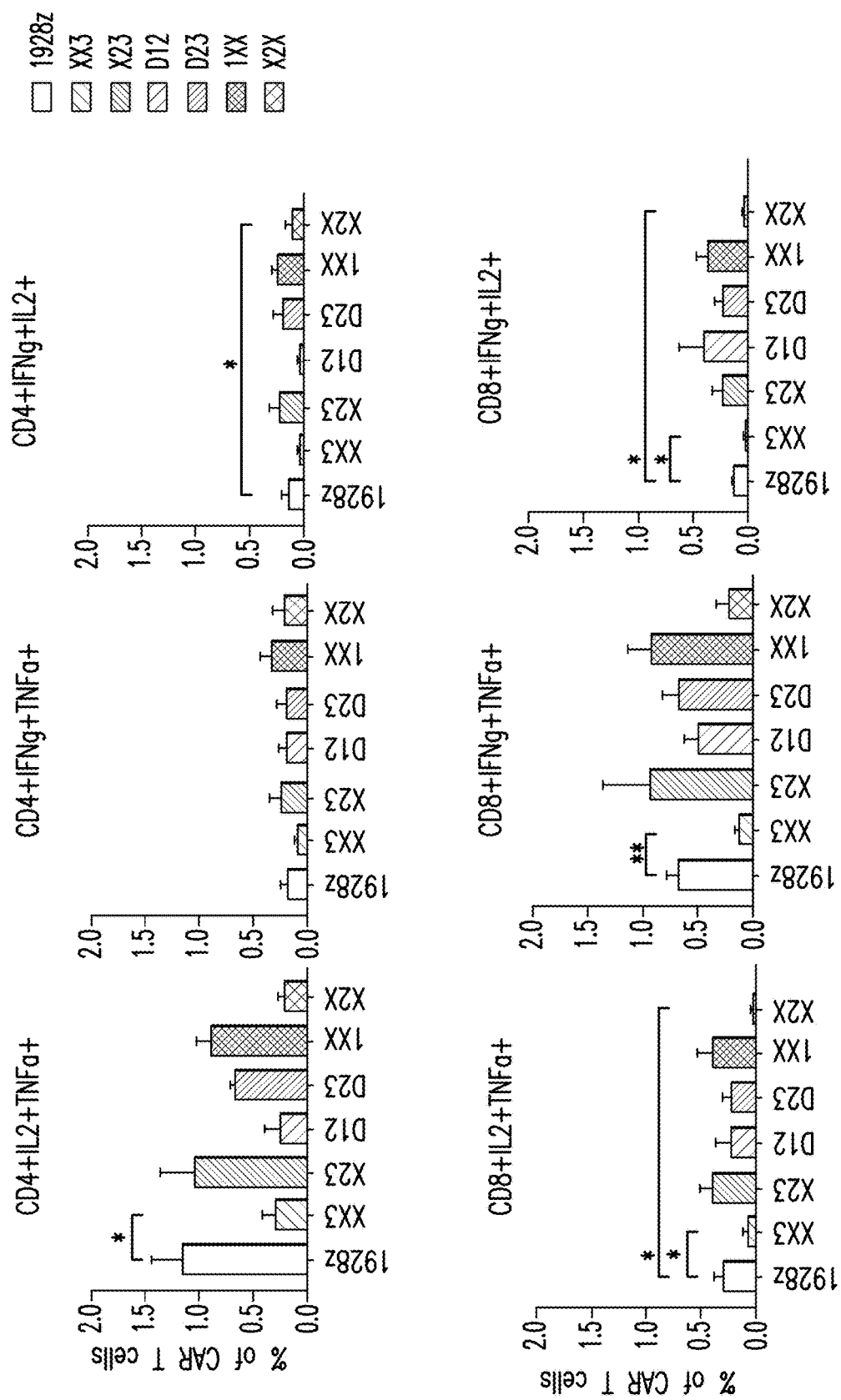

XX3 exceeded 1928z WT in CAR numbers at the tumor site (FIG. 4) and showed high percentage of $T_{CM}$, but these cells were not able to prevent tumor progression. XX3-treated mice demonstrated an initial treatment response, but relapsed after short time. Functional in vitro analysis demonstrated reduced killing activity as well as diminished Th1 cytokine and Granzyme B (GrB) secretion in XX3 (FIGS. 8 and 9). FIG. 8 shows that in standard in vitro cytotoxicity assays, all CARs lyse tumor cells similarly, with the exception of XX3 which displays diminished cytolytic activity. Although all constructs showed similar and potent cytotoxic activity after initial T-cell transduction, differences emerged after CAR expansion upon repetitive Ag exposure (FIGS. 8A-8C). FIGS. 9A and 9B shows that standard in vitro cytokine assays do not correlate with in vivo functional characteristics, but 1XX and D23 show favorable profiles (IL2 and anti-tumor cytokines such as IFNg and TNFα)

These findings indicate uncoupling of effector and proliferation function in XX3 and show that expansion and persistence of CAR T cells were not sufficient for effective tumor eradication. In contrast, 1928z WT exerted high cytotoxic activity, but acquired an early differentiation into effector cells and increased upregulation of inhibitory molecules, leading to exhaustion and reduced persistence of 1928z CARs.

Conclusion

Functional redundancy and increased signaling due to combined CD3ζ activation and CD28 costimulation in 2d generation 1928z CARs might lead to early T-cell differentiation and exhaustion, thus diminishing antitumor activity. The contribution of single ITAMs for CAR function was therefore analyzed. Position, affinity and number of ITAMs within the CD3ζ chain differentially affected functional properties of 1928z CAR T cells. Overall, 1928z CARs containing a single ITAM direct superior T cell accumulation, memory formation and decreased exhaustion (FIGS. 4-7) but the single ITAM must be placed in the first position to provide the highest therapeutic (anti-tumor) activity (FIGS. 2-3). 1XX comprised the most favorable properties of both, effector and memory cells, thereby balancing activation and differentiation. 1XX regulates the strong activation of combined CD3ζ signaling and CD28 costimulation and fine-tunes intensity into appropriate intracellular signals, thus modulating CAR-mediated signaling which then results in superior long-term tumor eradication.

Example 2—Alternative Hinge/Spacer Regions and Transmembrane Domains of CAR

Figure 10:
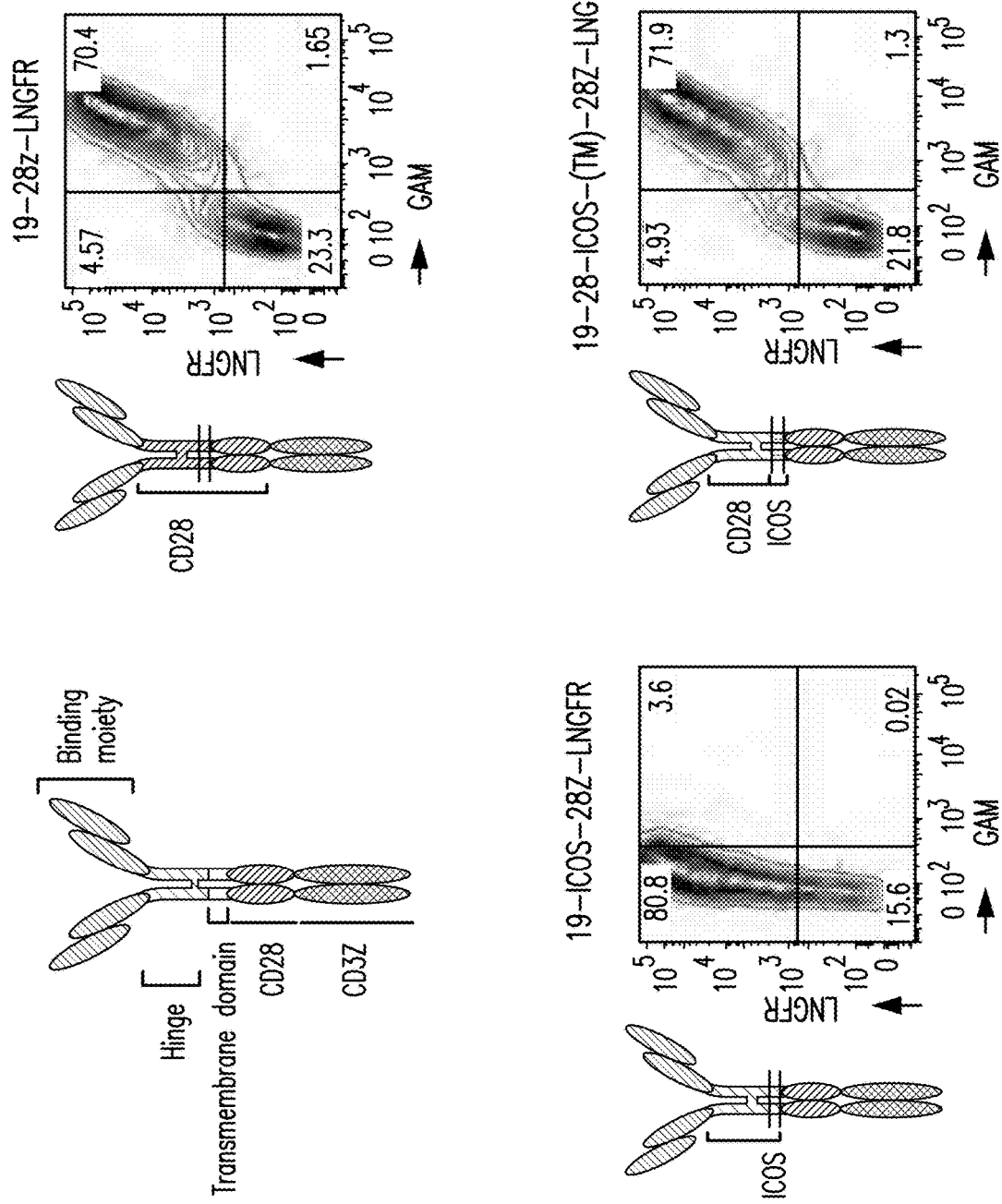
FIG. 10 depicts schematic representation of 1XX CARs bearing different hinges (H) and trans-membrane domains (TM). The flow cytometric profiles show CAR and LNGFR expression using Goat IgG anti-Mouse IgG (F (ab')2) fragment and anti-LNGFR respectively. The 1928z-LNGFR CAR containing CD28/CD28 H/TM regions is used as a control.
Figure 10:
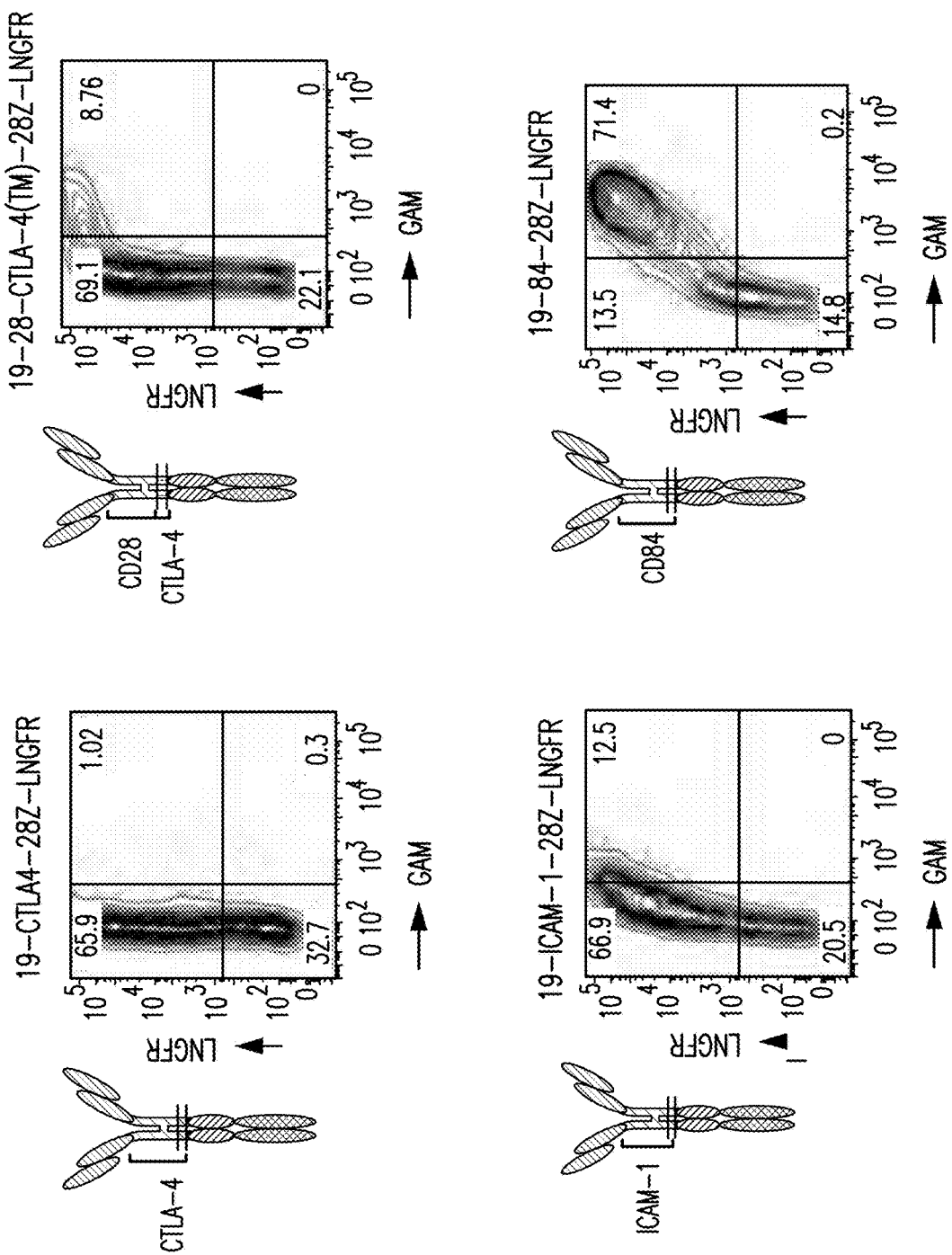
Figure 10:
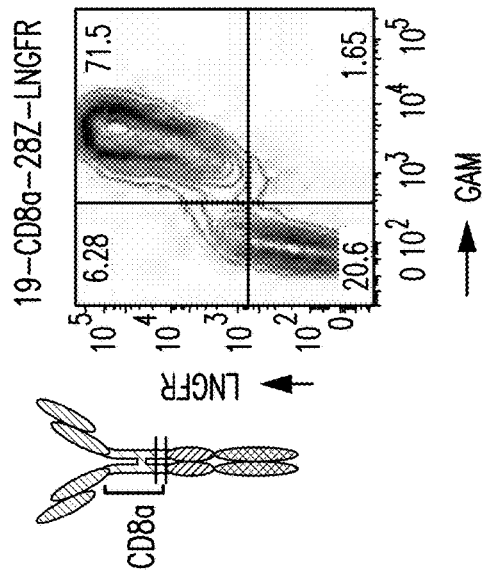
Figure 10:
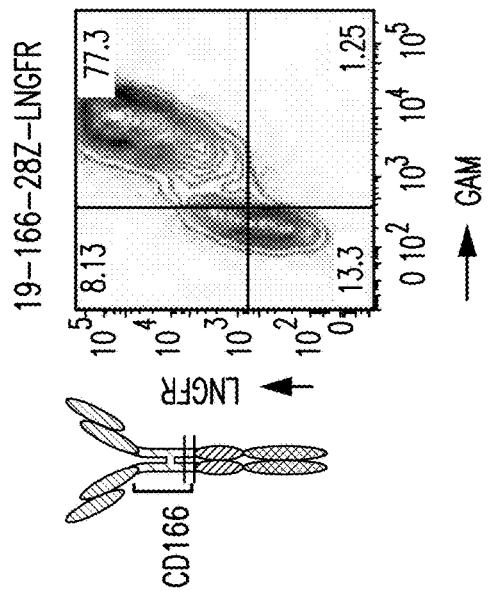
Figure 10:
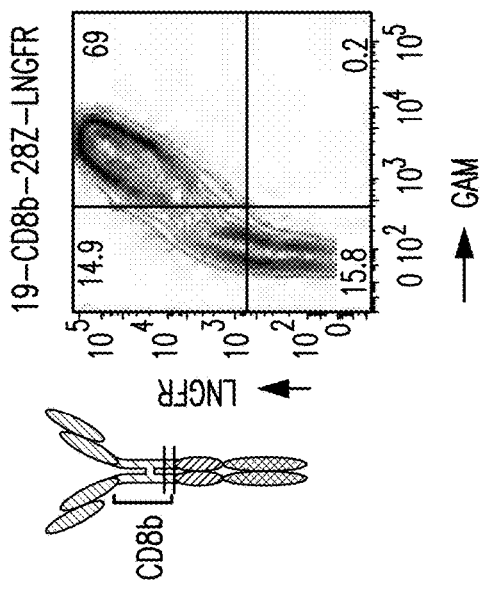

Alternative hinge/spacer regions and transmembrane domains were tested in CAR constructs. Schematic representation of 1XX CARs bearing different hinges (H) and trans-membrane domains (TM) are shown in FIG. 10. All tested hinges and trans-membrane domains belong to the immunoglobulin superfamily (IgSF) and are able to form cell-surface homodimers. All constructs were cloned into a P2A bicistronic oncoretroviral vector (SFG) encoding the CAR and LNGFR. The flow cytometric profiles show CAR and LNGFR expression using Goat IgG anti-Mouse IgG (F (ab')2) fragment and anti-LNGFR respectively. T cells were obtained from PBMC (peripheral blood mononuclear cells) of healthy donors, stably transduced 48 h after activation, and analyzed for CAR expression at multiple time points. The 1928z-LNGFR CAR containing CD28/CD28 H/TM regions was used as a control.

Replacing the CD28/CD28 (H/TM) with ICOS/ICOS (H/TM), CTLA-4/CTLA-4 (H/TM) or ICAM-1/ICAM-1 (H/TM) hinges abolished cell-surface expression of the CAR. CAR expression was however restored when the CD28 hinge was fused to the ICOS trans-membrane (CD28/ICOS; H/TM). However, CAR expression was not rescued in the CD28/CTLA-4 (H/TM) configuration. These findings indicated the non-obviousness of finding H/TM combinations that enable efficient CAR expression. In conclusion, 1XX CARs that possess either CD84/CD84, CD166/CD166, CD8a/CD8a, CD8b/CD8b or CD28/ICOS (H/TM) regions were similarly expressed at the T cell surface, of which 3 are unable to dimerize with CD28: CD166-28z, CD8a-28z, CD8b-28z.

Figure 11:
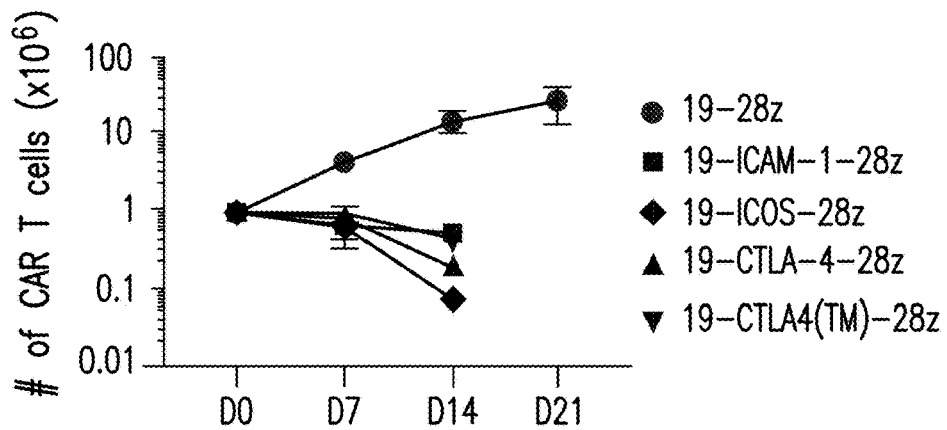
FIG. 11 depicts cumulative CAR T cell counts upon weekly stimulation starting from $10^6$ cells/ml CAR T cells. Arrows indicate stimulation time points. Data are means±SEM. n=3.
Figure 11:
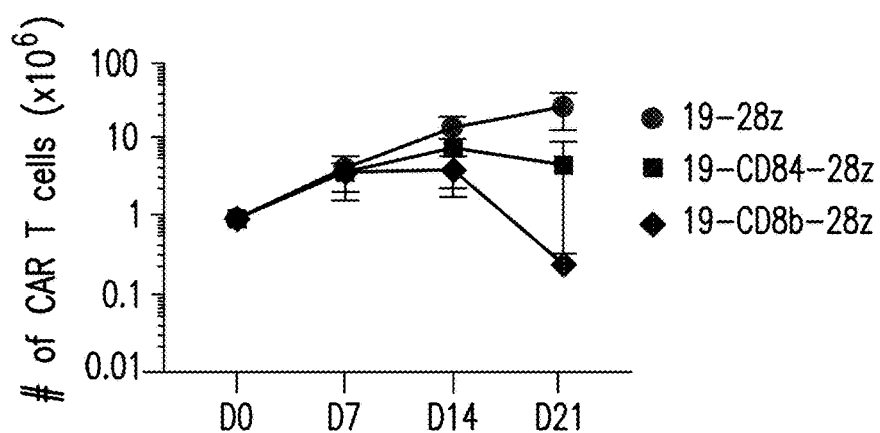
Figure 11:
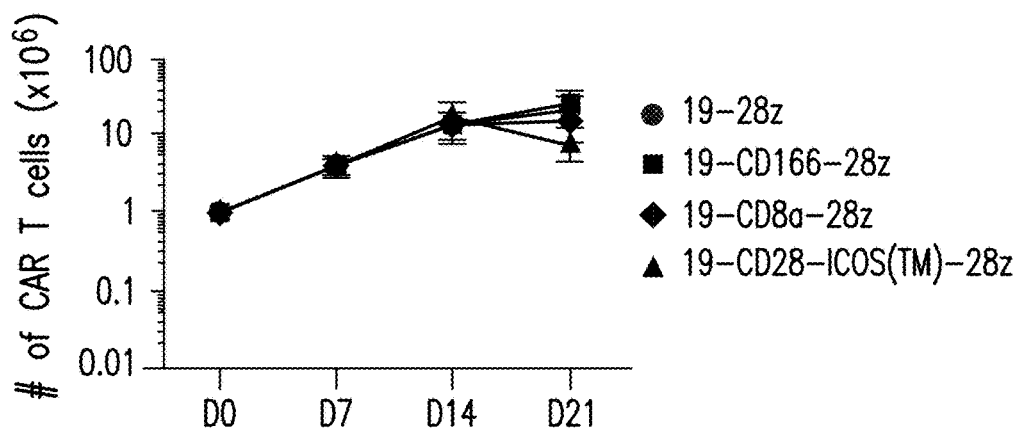

Cumulative CAR T cell counts upon weekly stimulation starting from $10^6$ cells/ml CAR T cells are shown in FIG. 11. CAR T cell proliferation induced by weekly exposure to CD19 was first assessed in vitro over 21 days. CAR T cells were co-cultured with irradiated CD19+ NIH 3T3s without any exogenous cytokine. Each week, $10^6$ cells/ml CAR+ T cells were added to irradiated and fresh CD19+ NIH 3T3s. The 1928z-1XX-LNGFR CAR with CD28/CD28 (H/TM) was used as reference. In vitro proliferation of 19-CD166-28z was similar to 1928z wild type.

Data were organized based on CAR T cell surface detection. T cells transduced with CAR harboring ICOS/ICOS (H/TM), CTLA-4/CTLA-4 (H/TM), ICAM-1/ICAM-1 (or CD28/CTLA-4 (H: TM) were unable to accumulate after co-culture with CD19+ NIH 3T3 cells. CAR T cells with CD84/CD84 and CD8b/CD8b (H/TM) were able to accumulate after 2 round of stimulation. However, these cells lost their accumulation capacity after third round of stimulation. CAR T cells with CD166 (H/TM), CD8a (H/TM) domain and CD28/ICOS (H/TM) accumulate as effectively as the control 1928Z-1XX CAR T cells.

Figure 12:
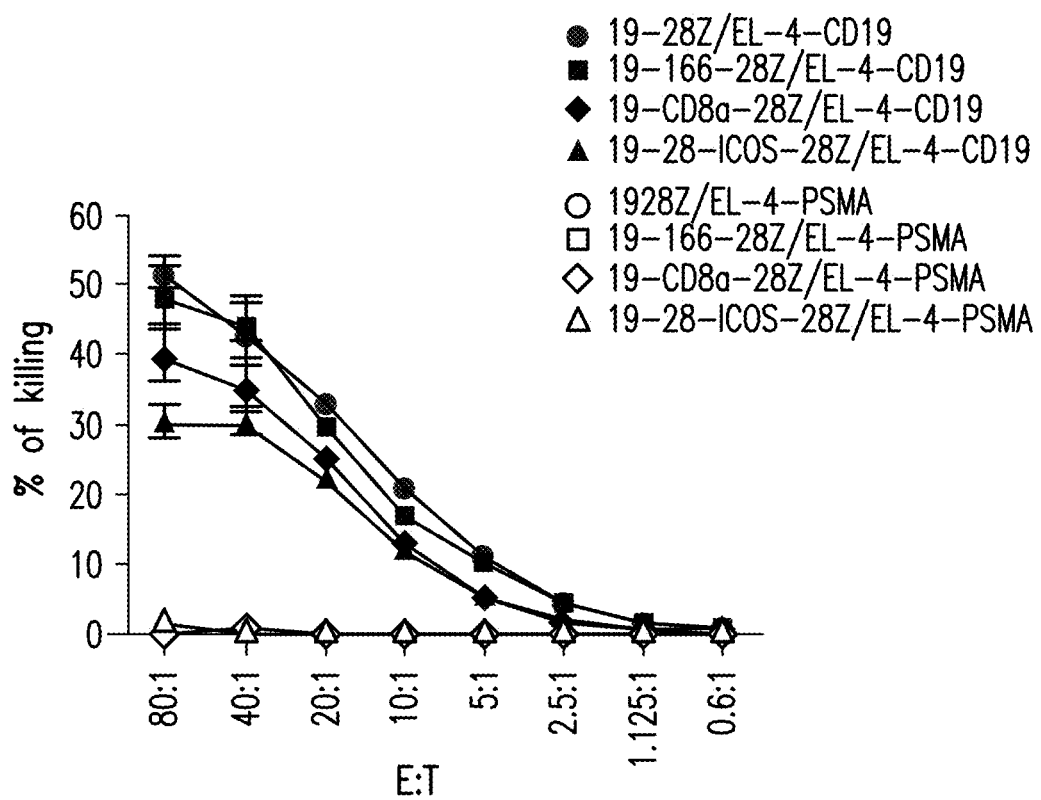
FIG. 12 depicts in vitro cytotoxicity of CAR T cells. Cytotoxic activity of CAR T cells is measured using a 4 hr $^{51}$Cr release assay at the end of the third stimulation (D21). T cells and EL-4-CD19$^+$ target cells were used at different Effector:Target ratio (E:T). Data are means±SEM. Data are representative of 4 independent experiments.

Cytotoxic activity of CAR T cells was measured using a 4 hr $^{51}$Cr release assay at the end of the third stimulation (D21), the results of which are show in FIG. 12. T cells and EL-4-CD19+ target cells were used at different Effector:Target ratio (E:T). EL-4-PSMA cells were used as a control. The in vitro cytotoxic potential of all well-expressed H/TM CD28/CD3z variants was similar, as expected. The cytotoxic capacity of CAR T cells with CD166 (H/TM), CD8a (H/TM) domain and CD28/ICOS (H/TM) was comparable to CAR T cells with CD28/CD28 (H/TM).

Figure 13:
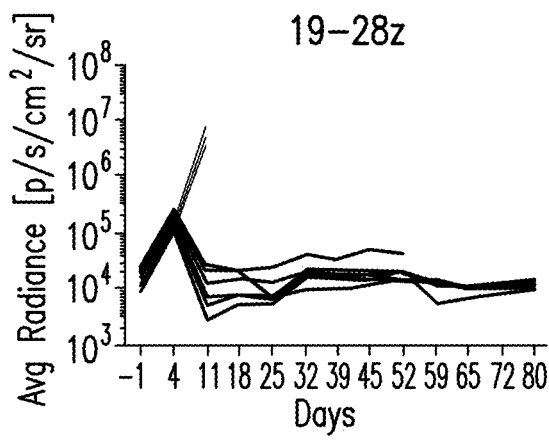
FIG. 13 depicts in vivo anti-tumor potency of different H/TM CAR T cells using NOD.Cg PrkdcscidIl2rgtm1Wjl/ SzJ (NSG) mice. Upper panel, tumor burden is followed by weekly quantification of the bioluminescent signal. CAR construct is indicated for each treatment. Lower panel, Kaplan-Meier analysis of tumor free survival of mice of the same experiment. Log-rank (Mantel-Cox) test is used for survival comparison. n=7 mice/group.
Figure 13:
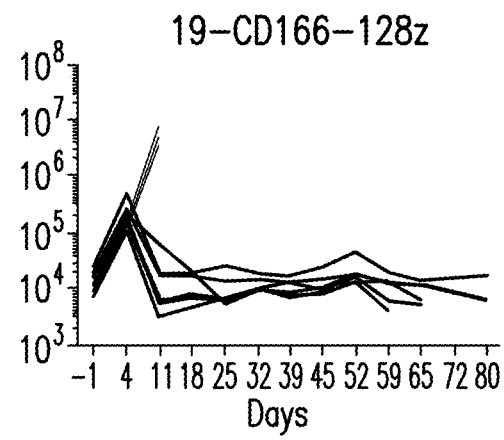
Figure 13:
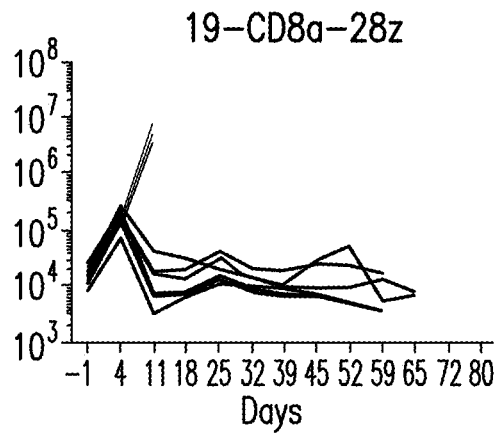
Figure 13:
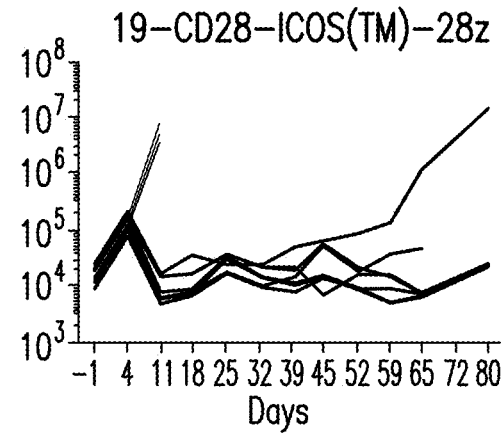
Figure 13:
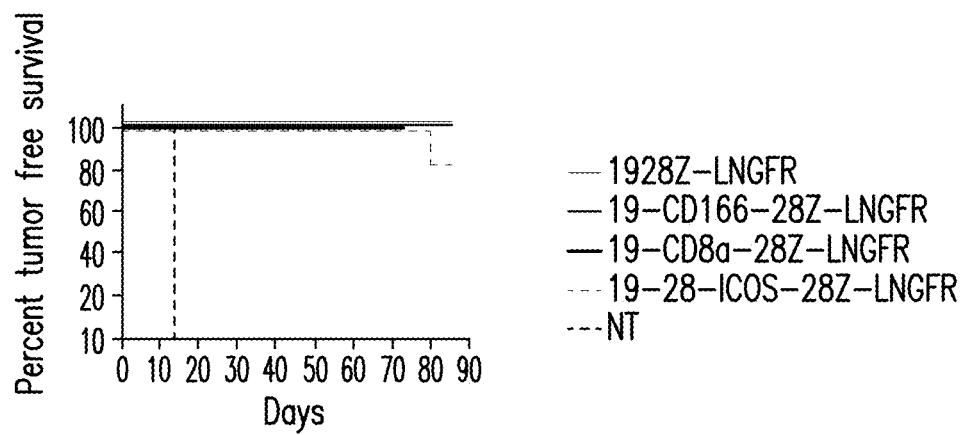

In vivo anti-tumor potency of different H/TM CAR T cells using NOD.Cg Prkdc$scid$Il2rgtm1Wjl/SzJ (Immuno-deficient NSG) mice is shown in FIG. 13. Mice were tail vein injected with 5×$10^5$ FFLuc-GFP NALM6 cells (pre-B ALL cell line) followed by 2×$10^5$ CAR T cells four days later. Tumor burden were followed by weekly quantification of the bioluminescent signal. All selected constructs for in vivo study, CD166/CD166 (H/TM), CD8a/CD8a (H/TM) and CD28/ICOS (H/TM) were able to completely eradicate tumor cells. No significant difference in term of tumor burden or survival was observed for any condition compared to the control group, 1928z CAR T cells.

Example 3—De-Immunization Strategy

Figure 14:
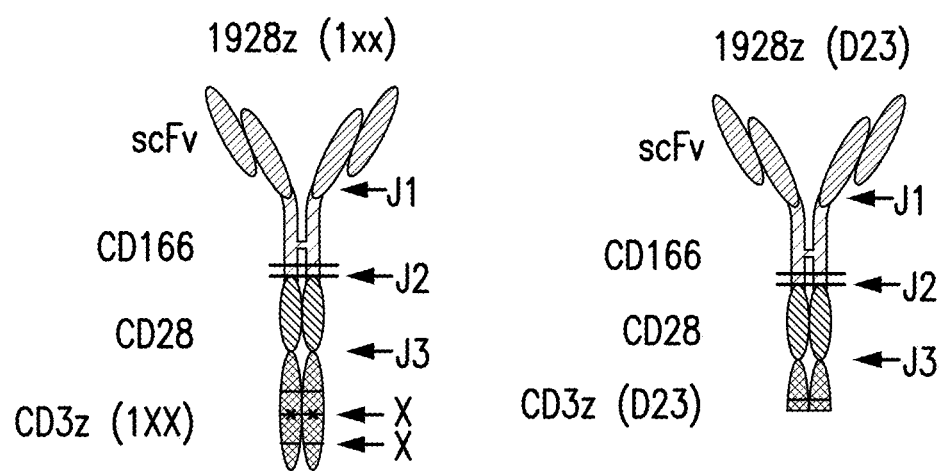
FIG. 14 depicts exemplary de-immunization strategies for novel CAR constructs. J1 and J2: no modification from the WT junction. J3: Substitution of the last amino acid of CD28 Ser (S) with Lys (K). J: Junction; X: point mutation.

The juxtaposition of human sequences or their mutation carries the risk of creating neoantigens. The novel CD166 junctions and the mutations in 1XX were thus de-immunized. Immunogenicity of junctions between different CAR moieties were predicted using NetMHC 4.0 Server. A total of 26 amino acids (13 amino acids from first moiety and 13 amino acids from the second moiety) were selected. For each generated peptide (14, 13, 12, 11, 10, 9 and 8 mers) containing at least 1 aa from next moiety, binding affinity to HLA A, B and C, for all alleles, were predicted. A score of immunogenicity of each peptide was assigned for each peptide. Immunogenicity score was calculated using the formula Immunogenicity score=[(50−binding affinity) *HLA frequency]n. 50 nm was used as a cutoff for strong binding affinity. HLA frequency in the Caucasian population was used. n=number of prediction for each peptide. HLA frequency below 1% in total population was excluded. For junctions de-immunization, shuffling of both amino acids forming the junction or deletion of amino acids from both sides of the junction were tested. Previously described strategy of immunogenicity prediction was used for each newly generated peptide. Junction with minimal immunogenicity score was used to construct a de-immunized CAR. Exemplary de-immunization strategies are shown in FIG. 14.

Example 4—Rescue of Relapses of CD19 Low ALL Following Treatment with 4-1BBz CAR T Cells Introduction Adoptive immunotherapy using chimeric antigen receptors (CARs) has shown remarkable clinical results in the treatment of leukemia and lymphoma and is a promising immunotherapy applicable in principle to a wide range of cancers. Two promising CAR designs have been successfully introduced in the clinic, one utilizing the cytoplasmic domain of CD28 as the costimulatory component and the other using the cytoplasmic domain of 4-1BB. In both instances, T cell activation is initiated through the fused cytoplasmic domain of the CD3 zeta chain. Whereas both designs have achieved remarkable results, the clinical outcomes are limited by shortcomings of these CAR structures. T cells expressing CD28-based CARs are potent but short-lived, while T cells expressing 4-1BB-based CARs are longer lived but allow antigen escape of tumor cells expressing low levels of the target antigen. Thus, there is a need of novel CAR designs that extend T cell persistence without compromising function.

Results

The presently disclosed CD28z CAR T cells can rescue relapses of CD19 low ALL following treatment with 4-1BBz CAR T cells. This can be a major rescue pathway for the many relapses occurring after treatment 4-1BBz CAR T cells, excluding those that are stably CD19-negative.

Figure 15:
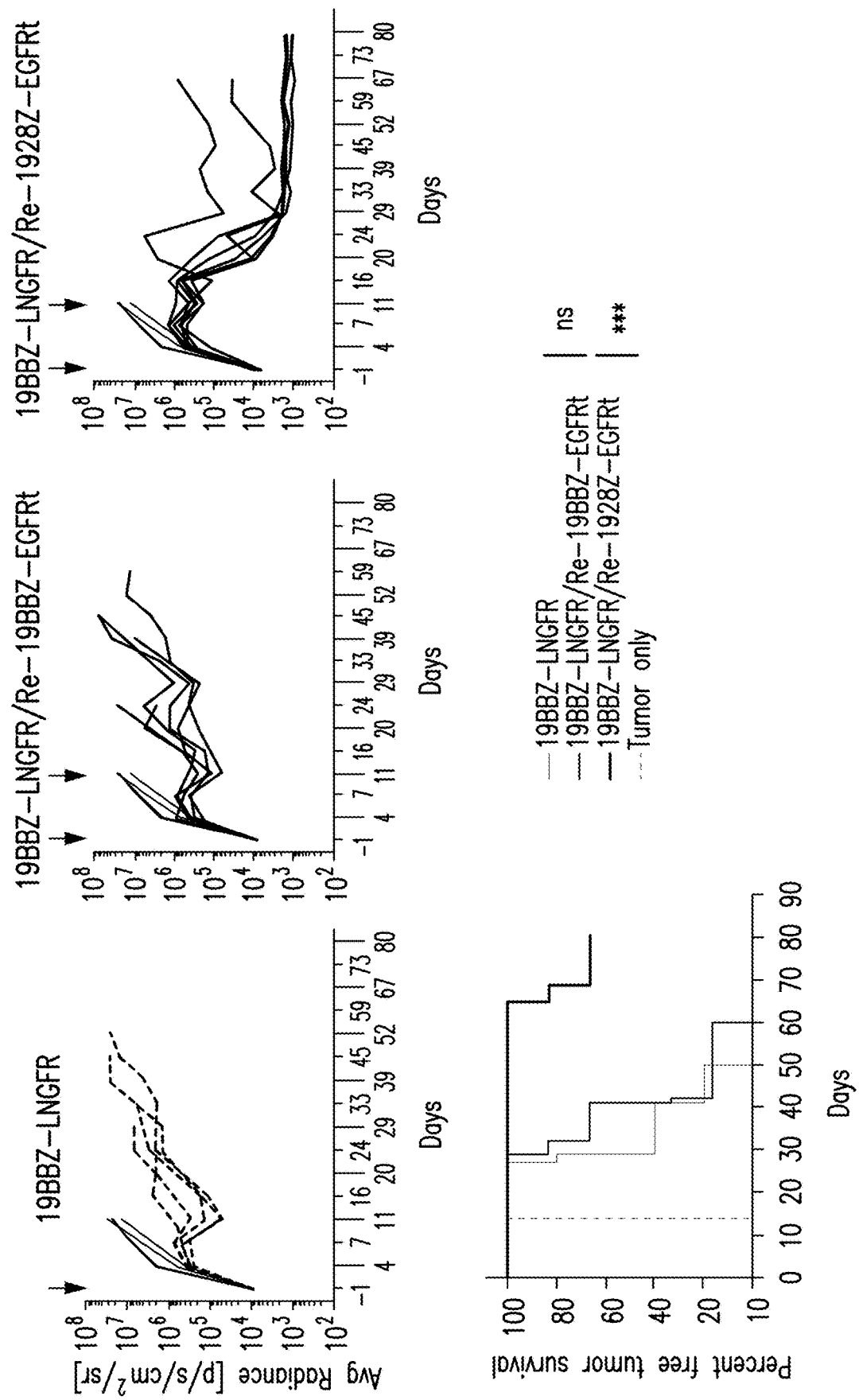
FIG. 15 depicts various survival curves of mice treated with CAR T cells. NSG mice were tail vein injected with $5 \times 10^5$ FFLuc-GFP NALM6 cells (pre-B ALL cell line) followed by $2 \times 10^5$ 19BBz CAR T cells four days later. Ten days after 1st T cell injection (an ineffective dose that only delayed tumor progression), mice were again injected with 19BBz CAR T cells or alternatively with either 1928z or ($5 \times 10^5$/mouse). Arrows indicate time of infusion of CAR T cells. Upper panel, tumor burden is followed by weekly quantification of the bioluminescent signal. Lower panel, Kaplan-Meier analysis of tumor free survival of mice of the same experiment. Log-rank (Mantel-Cox) test is used for survival comparison. n=7 mice/group.

NSG mice were tail vein injected with 5×$10^5$ FFLuc-GFP NALM6 cells (pre-B ALL cell line) followed by 2×$10^5$ 19BBz CAR T cells four days later. Ten days after 1st T cell injection (an ineffective dose that only delayed tumor progression), mice were again injected with 19BBz CAR T cells or alternatively with either 1928z or ($5 \times 10^5$/mouse). Various survival curves are shown in FIG. 15. Only fresh injection ($2^{nd}$ injection) of 1928z based CAR T cells were able to rescue mice treated with NALM-6 from relapse. No significant increase in survival rate was observed after injection of freshly 19BBz CAR T cells.

In conclusion, CD28z CAR T cells can rescue failures of 4-1BBz CAR T cells. In view of the examples above, modified CD28z CAR T cells disclosed herein, such as 1XX, D23 and D12 CAR T cells (having various hinge/TM domains such as CD166 hinge/TM domains), can be even more effective than 1928z CAR T cells in rescue failures of 4-1BBz CAR T cells.

Example 5

This example is an updated and further investigation of certain aspects of Example 1.

Chimeric antigen receptors (CARs) are synthetic receptors that target and reprogram T cells to acquire augmented antitumor properties[1]. CD19-specific CARs that comprise CD28 and CD3ζ signaling motifs[2] have induced remarkable responses in patients with refractory leukemia[3-5] and lymphoma[6] and were recently approved by the US Food and Drug Administration[7]. These CARs program highly performing effector functions that mediate potent tumor elimination[4,8] despite the limited persistence they confer on T cells[3-6,8]. Extending their functional persistence without compromising their potency should improve current CAR therapies. Strong T cell activation drives exhaustion[9,10], which may be accentuated by the redundancy of CD28 and CD3 signaling[11,12] as well as the spatiotemporal constraints imparted by the structure of second-generation CARs[2]. Thus, it was hypothesized that calibrating the activation potential of CD28-based CARs would differentially reprogram T cell function and differentiation. Here, CARs encoding a single immunoreceptor tyrosine-based activation motif direct T cells to different fates by balancing effector and memory programs, thereby yielding CAR designs with enhanced therapeutic profiles.

Figure 16A:
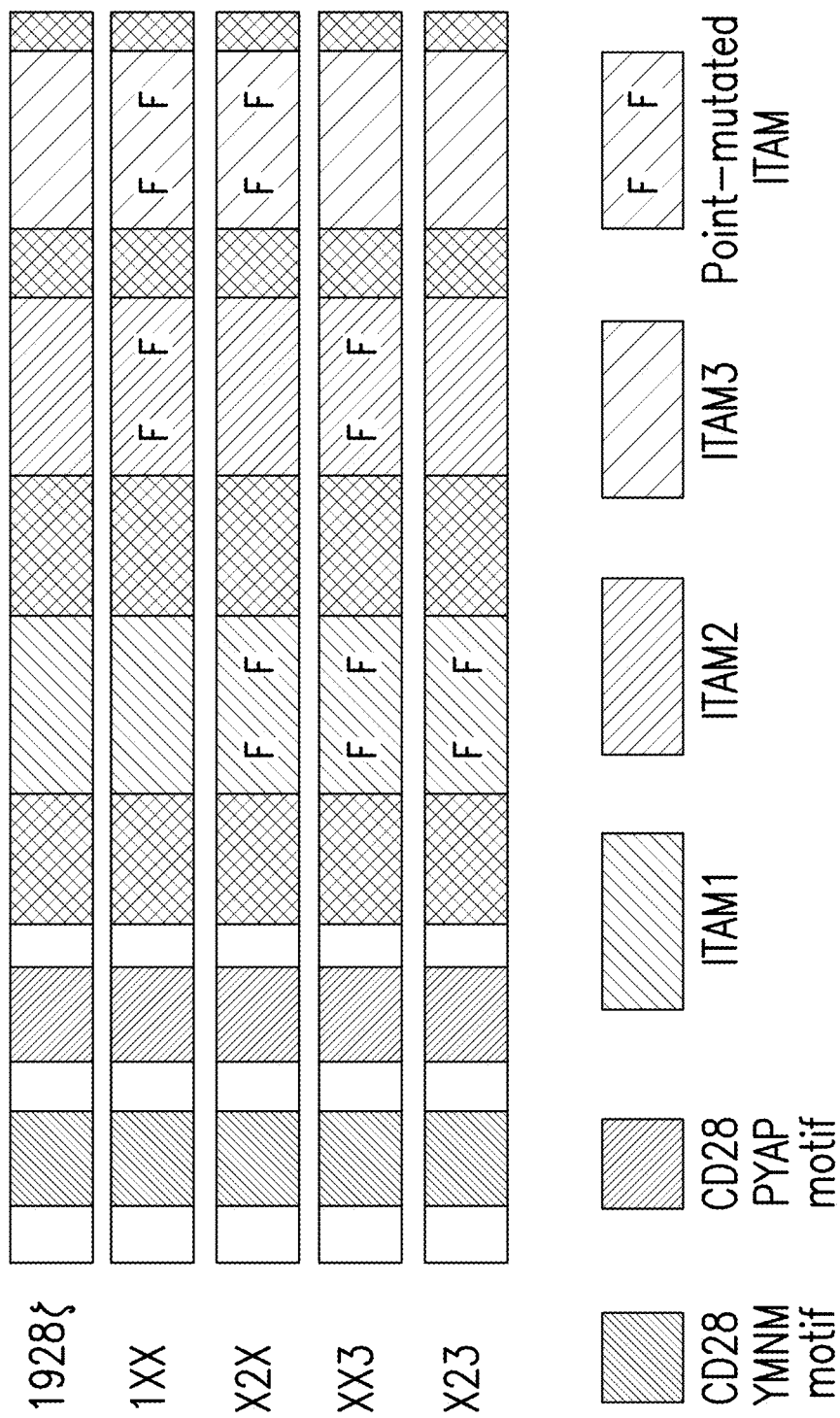
FIGS. 16A-16E depict that 1928ζ iTAMs differentially regulate CAR T cell potency.
Figure 16B:
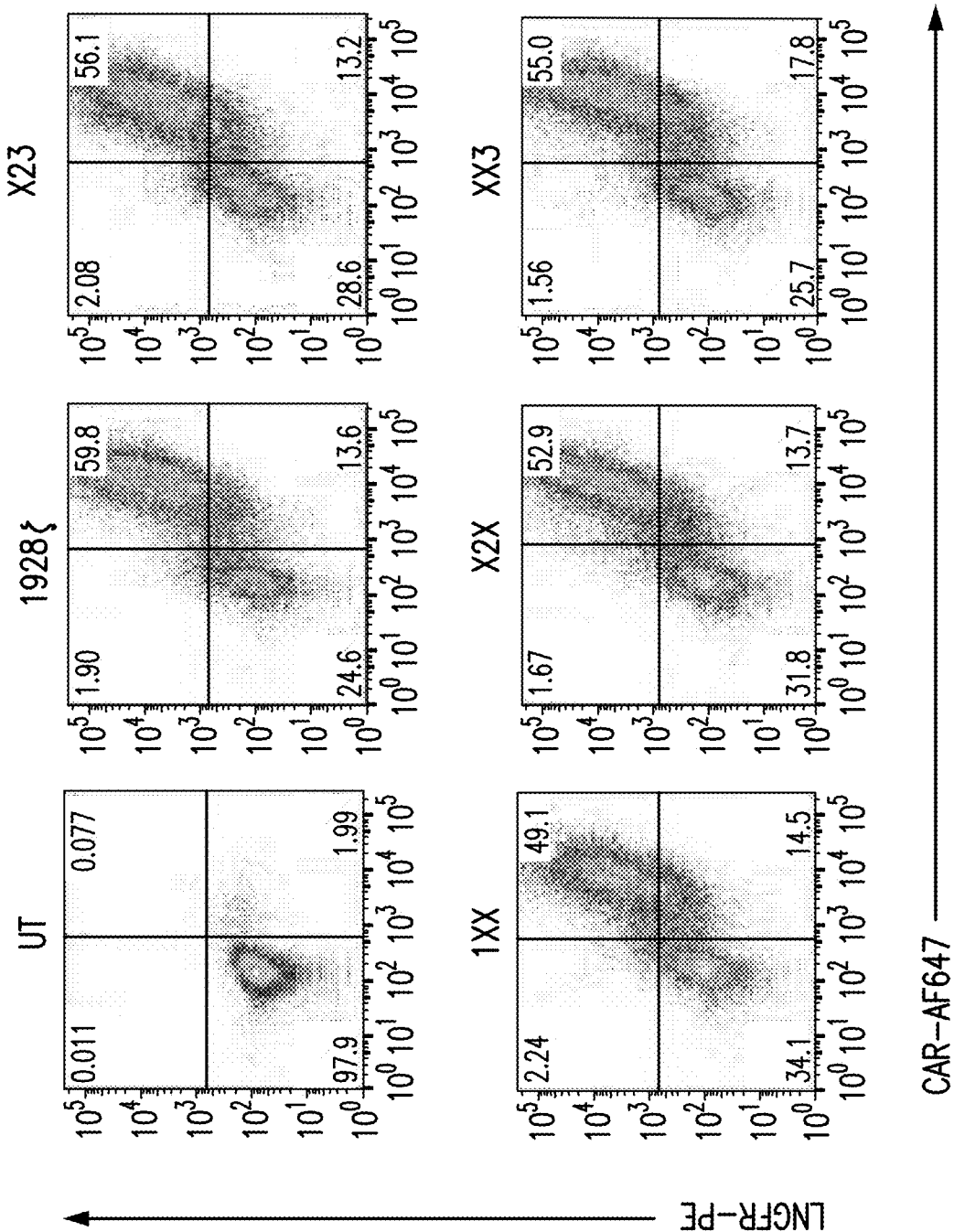
Figure 20B:
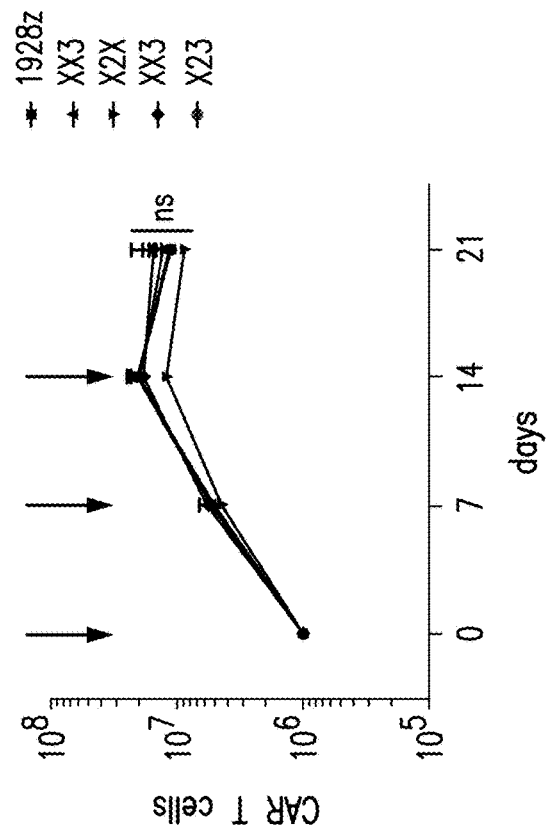
FIGS. 20A-20E depict impact of ITAM-mutated 1928ζ CARs on T cell function in vitro, T cell differentiation and antitumor activity in vivo.
Figure 20A:
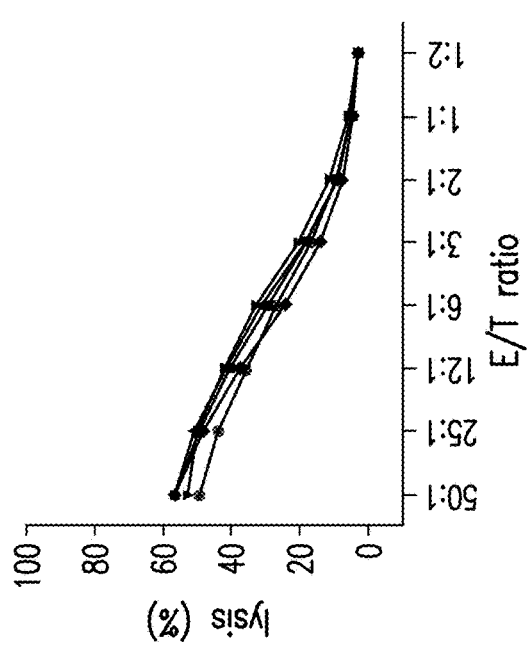

It was hypothesized that the redundancy of CD28 and CD3 signaling in a chimeric antigen receptor (CAR) design incorporating all three CD3 immunoreceptor tyrosine-based activation motifs (ITAMs)[11,13] may foster counterproductive T cell differentiation and exhaustion[9,10]. Therefore, ITAM activity was calibrated by mutating tyrosine residues to impede their phosphorylation and downstream signaling[14-17]. To investigate the contribution of each of the three CD3 ITAMs to the function, differentiation, and therapeutic potency of 1928z-engineered T cells, single ITAM-containing 1928z mutants termed 1XX, X2X, and XX3 were generated (FIG. 16A). In one additional mutant, termed X23, the two distal ITAMs (ITAM2 and ITAM3) were retained, both of which have been shown to display lower binding affinity for tyrosine-protein kinase ZAP-70 relative to ITAM1[13,18] All mutant CARs were similarly expressed in retrovirally transduced human peripheral blood T cells (FIG. 16B); they were found to direct indistinguishable cytotoxicity in a 4-h chromium-51 ($^{51}$Cr) release assay and proliferation in response to three weekly stimulations with CD19 antigen (FIGS. 20A-20B).

Figure 16C:
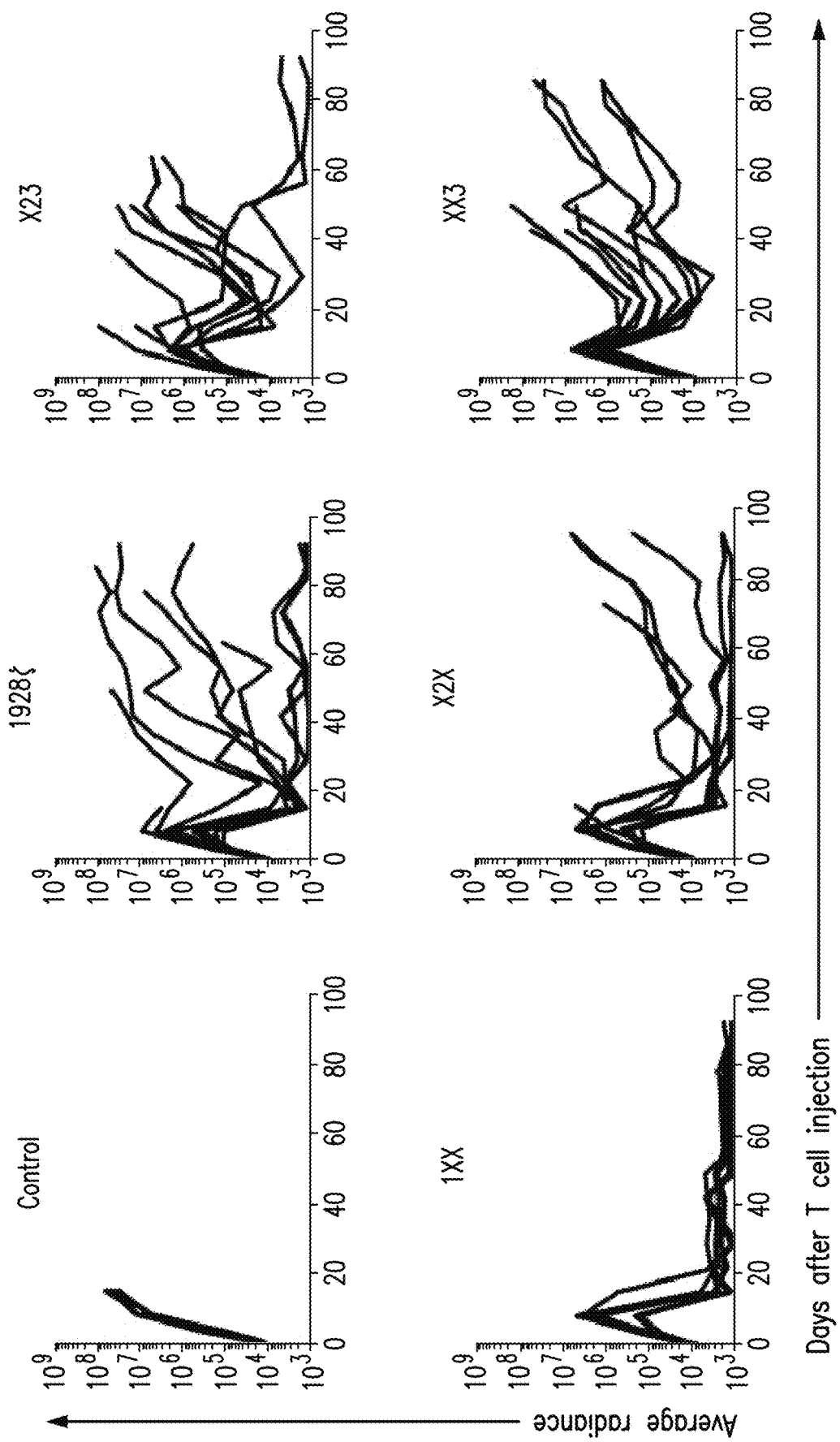
Figure 20C:
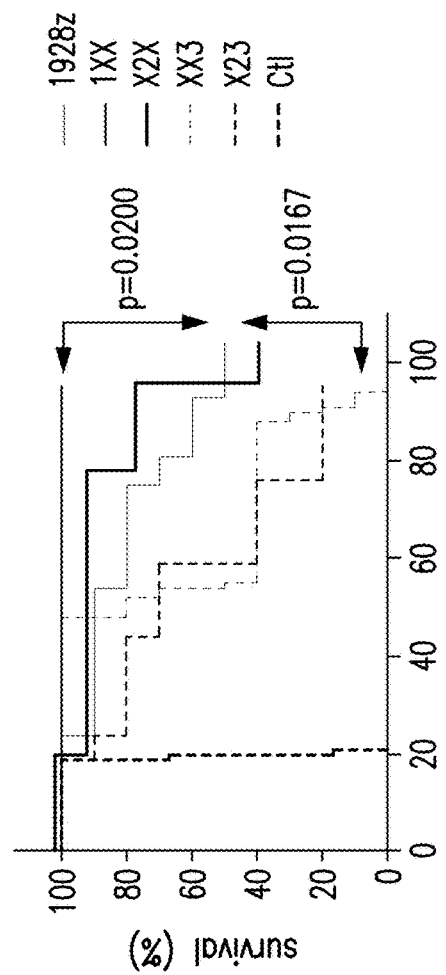

Remarkably, the therapeutic efficacy of CAR T cells expressing these mutant CARs differed singularly in the well-established pre-B acute lymphoblastic leukemia Nalm6 mouse models[8,19,20]. CAR T cell doses were deliberately lowered to better compare T cell potency, as previously described in the CAR stress test[8]. Relative to the parental 1928, XX3 showed markedly diminished antitumor efficacy, only achieving a transient reduction of tumor burden, whereas 1XX exceeded 1928z, inducing long-term remission in all mice (FIG. 16C and FIG. 20C). Treatment with X2X and X23 did not significantly alter survival rates compared to 1928 (1928 versus X2X: P=0.6942; 1928 versus X23: P=0.1085).

Thus, while the presence of one (1XX, X2X, XX3), two (X23), or three (1928z) functional ITAMs did not noticeably alter short-term in vitro function, a single ITAM-containing CAR outperformed the triple- and double-ITAM-containing CARs in vivo. Efficacy of tumor eradication gradually decreased with increasing distal positioning of the functional ITAM. The 1XX CAR consistently showed rapid tumor eradication and was the only CAR design to achieve durable and complete remissions at the lowest T cell dose. Treatment with X2X slightly delayed tumor progression compared to wild-type 1928z, but relapses eventually developed. The XX3 CAR did not achieve any tumor control, leading to rapid tumor progression and significantly reduced survival (FIG. 16C and FIG. 20C).

Figure 20D:
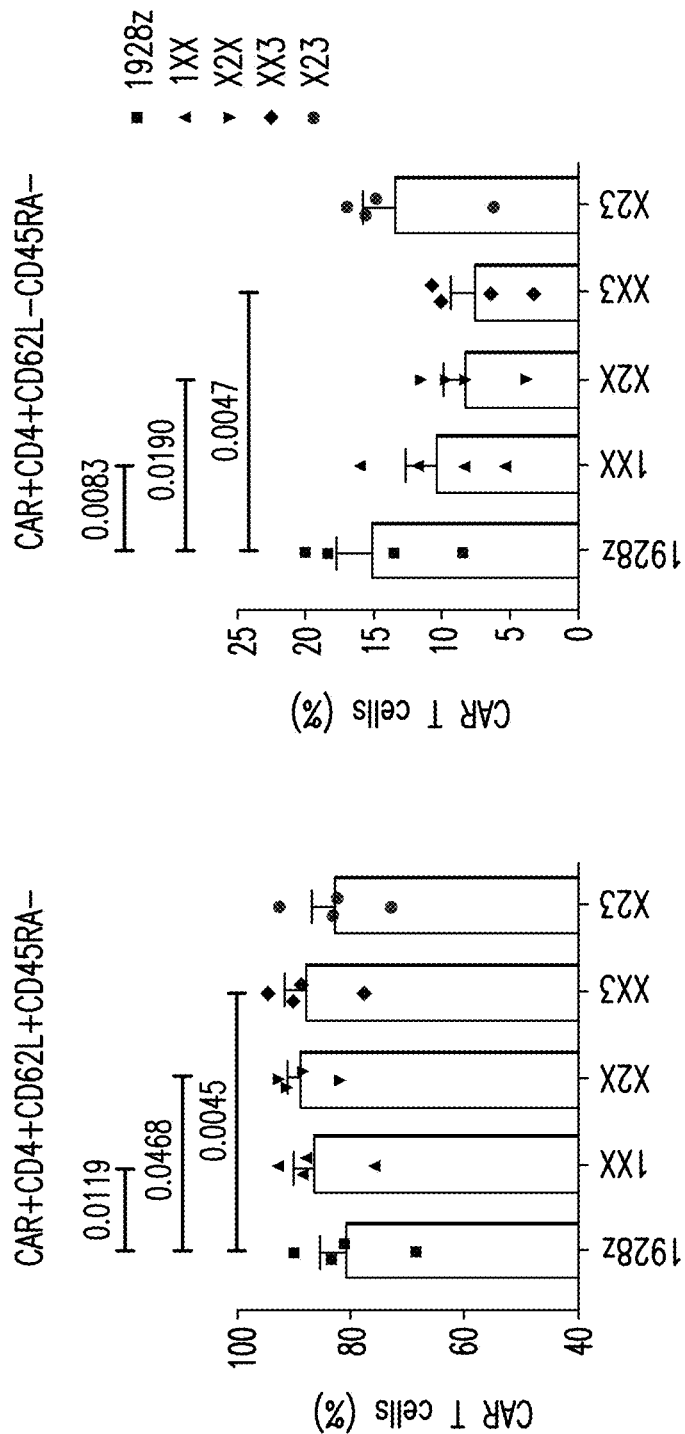
Figure 21B:
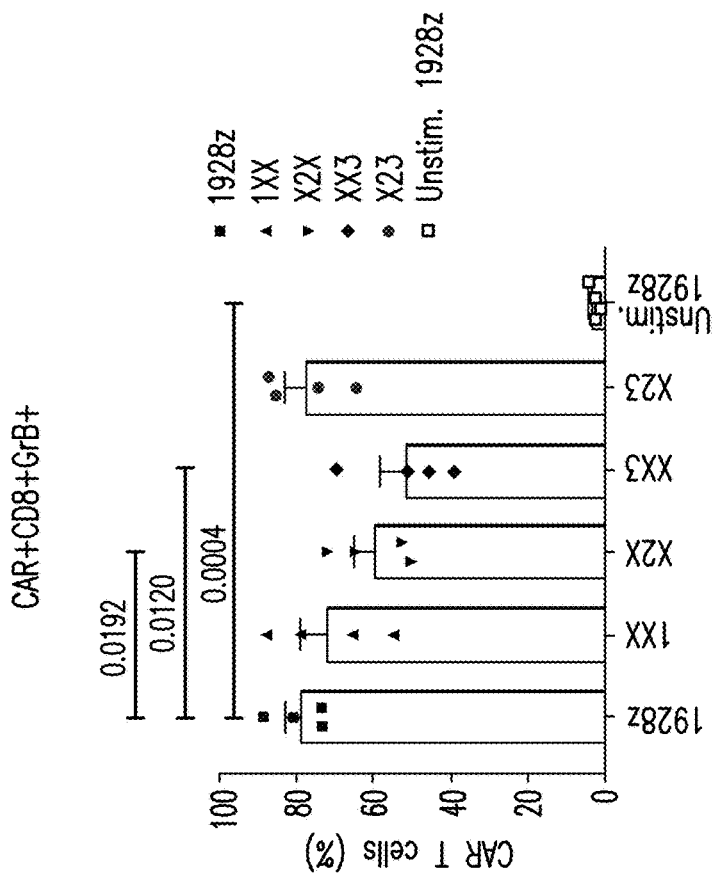
FIGS. 21A-21C depict analysis of effector function in 1928ζ mutants compared to wild-type 1928ζ.
Figure 21A:
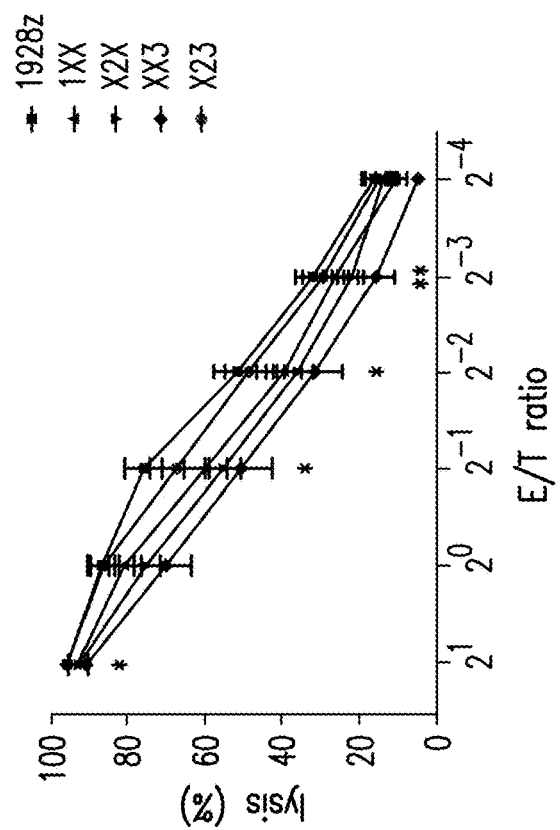
Figure 21C:
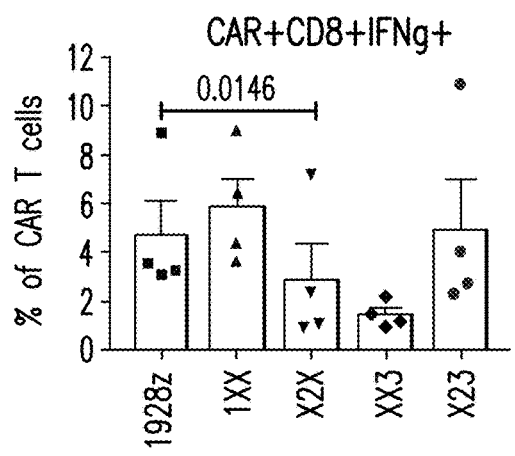
Figure 21C:
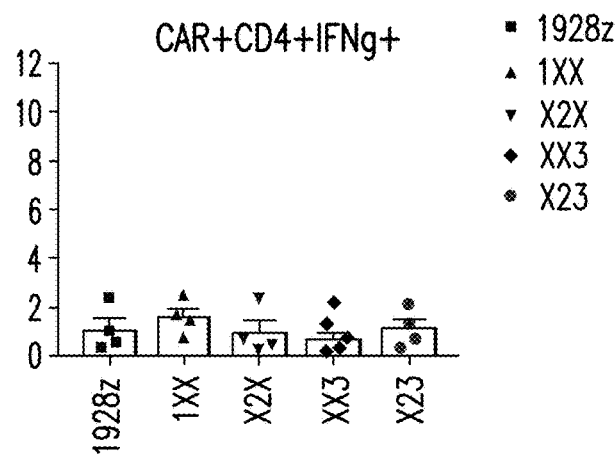
Figure 21C:
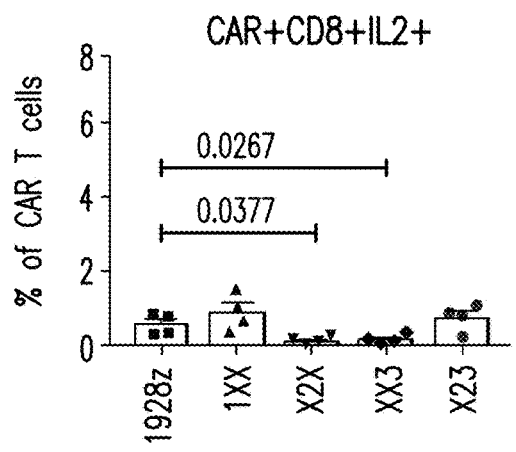
Figure 21C:
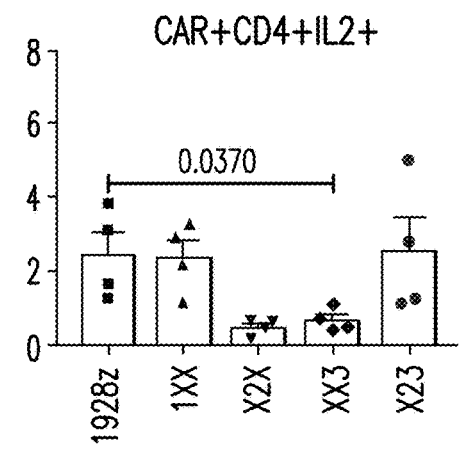
Figure 21C:
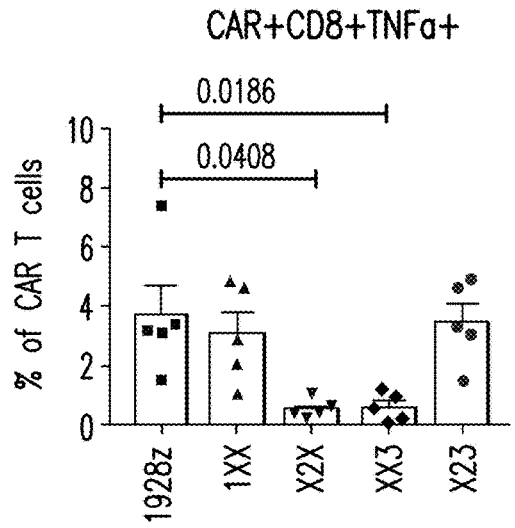
Figure 21C:
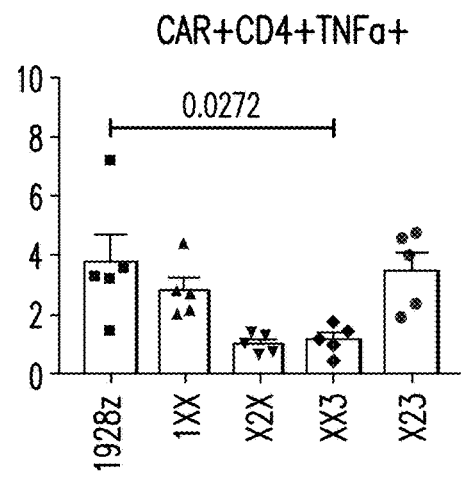
Figure 23A:
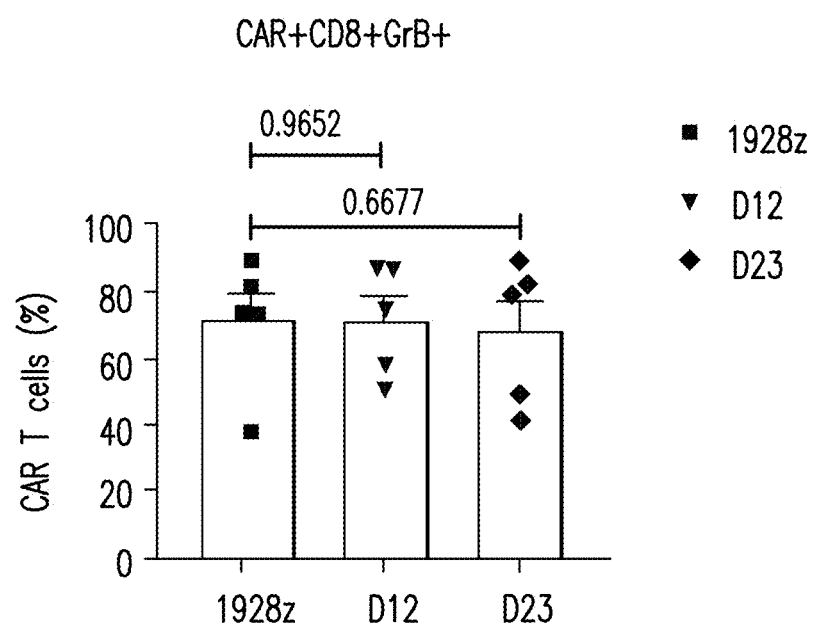
FIGS. 23A-23B depict influence of iTAM location within 1928ζ CARs on effector function in vitro.
Figure 23B:
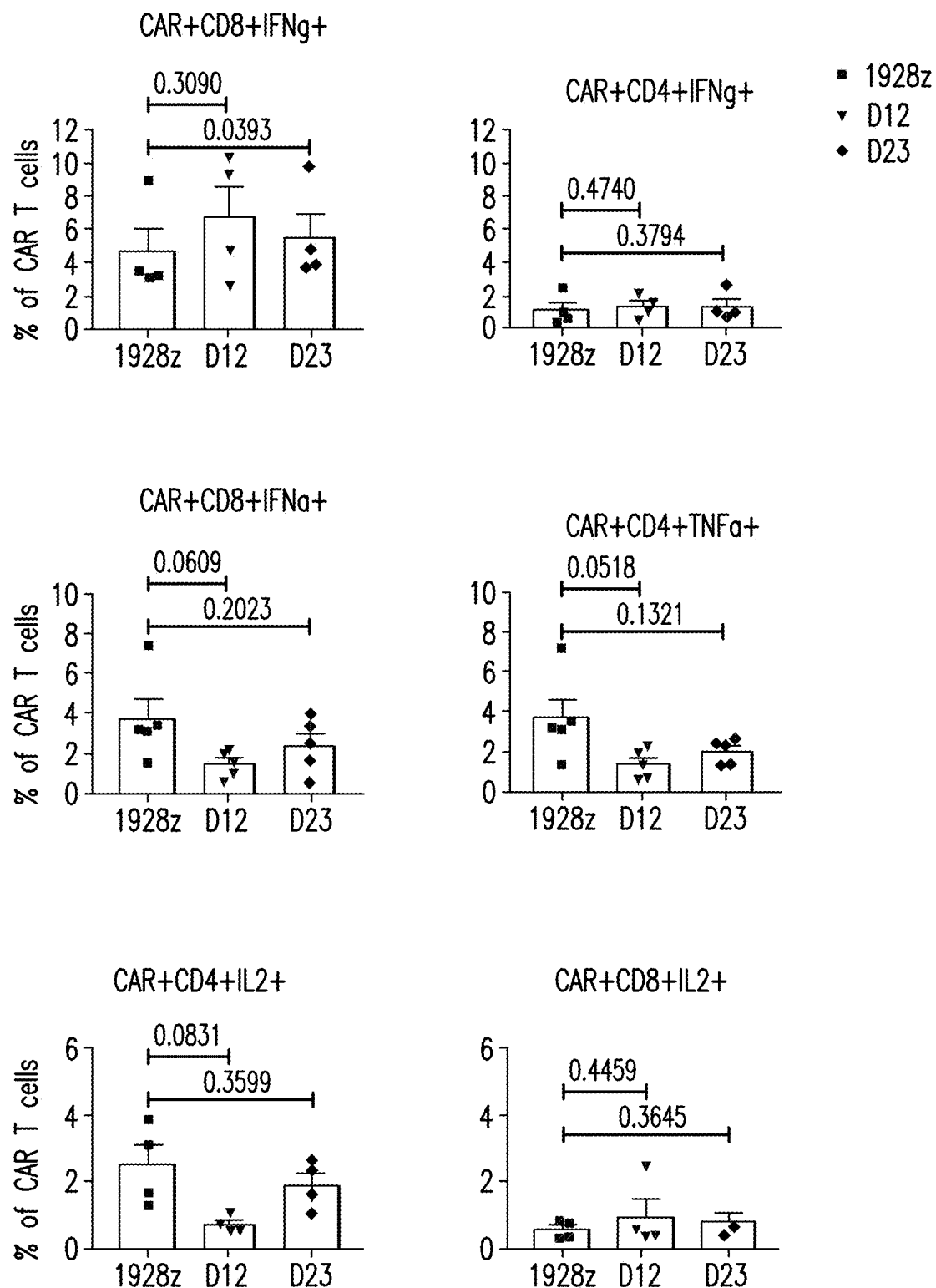

To investigate the functional basis for these major differences in antitumor efficacy, the responses imparted by these CARs were examined in greater depth. In prolonged (18-h) cytotoxicity assays at a low effector-to-target ratio, XX3 proved to be less active than 1928z and the other mutants (FIG. 21A). The diminished effector function of XX3 was further corroborated by reduced gran-zyme B (GrB) expression (FIG. 21B) and decreased single and polyfunctional type 1 T helper cell ($T_H1$) cytokine secretion (FIG. 21C) following stimulation with CD19$^+$ targets. Inclusion of a single ITAM (either ITAM1, 2, or 3) limited T cell differentiation as determined by CD62L/CD45RA expression, resulting in an increased fraction of central memory CAR T cells and a reduced proportion of effector cells in response to repeated in vitro stimulation with CD19$^+$ targets (FIG. 20D).

Figure 16D:
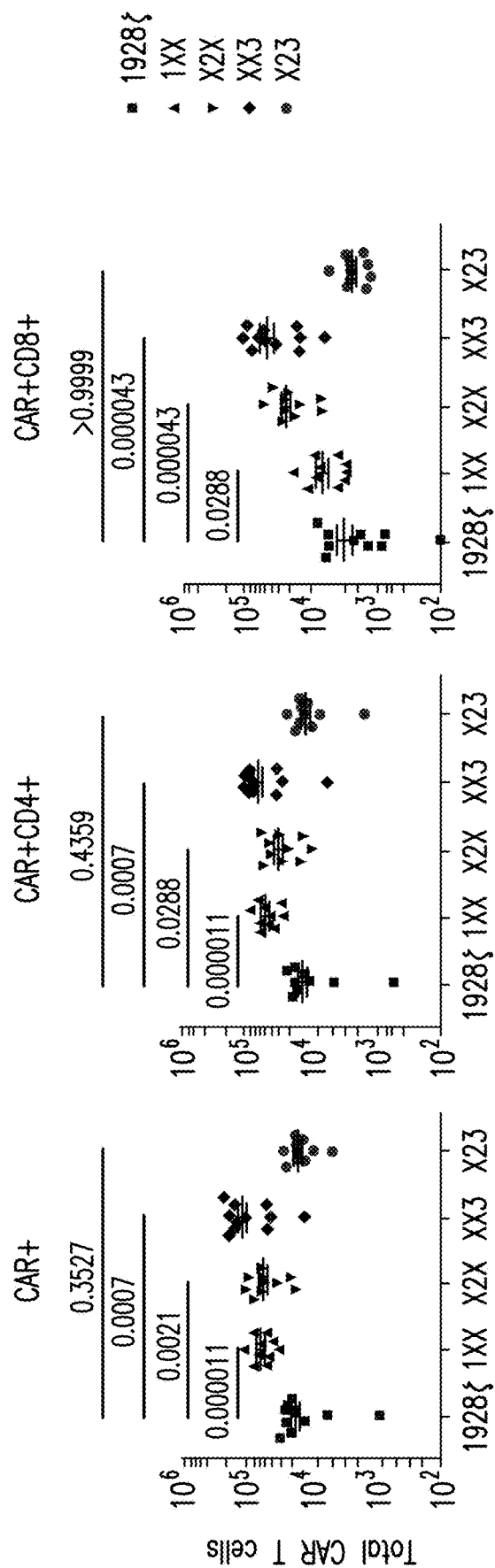
Figure 16E:
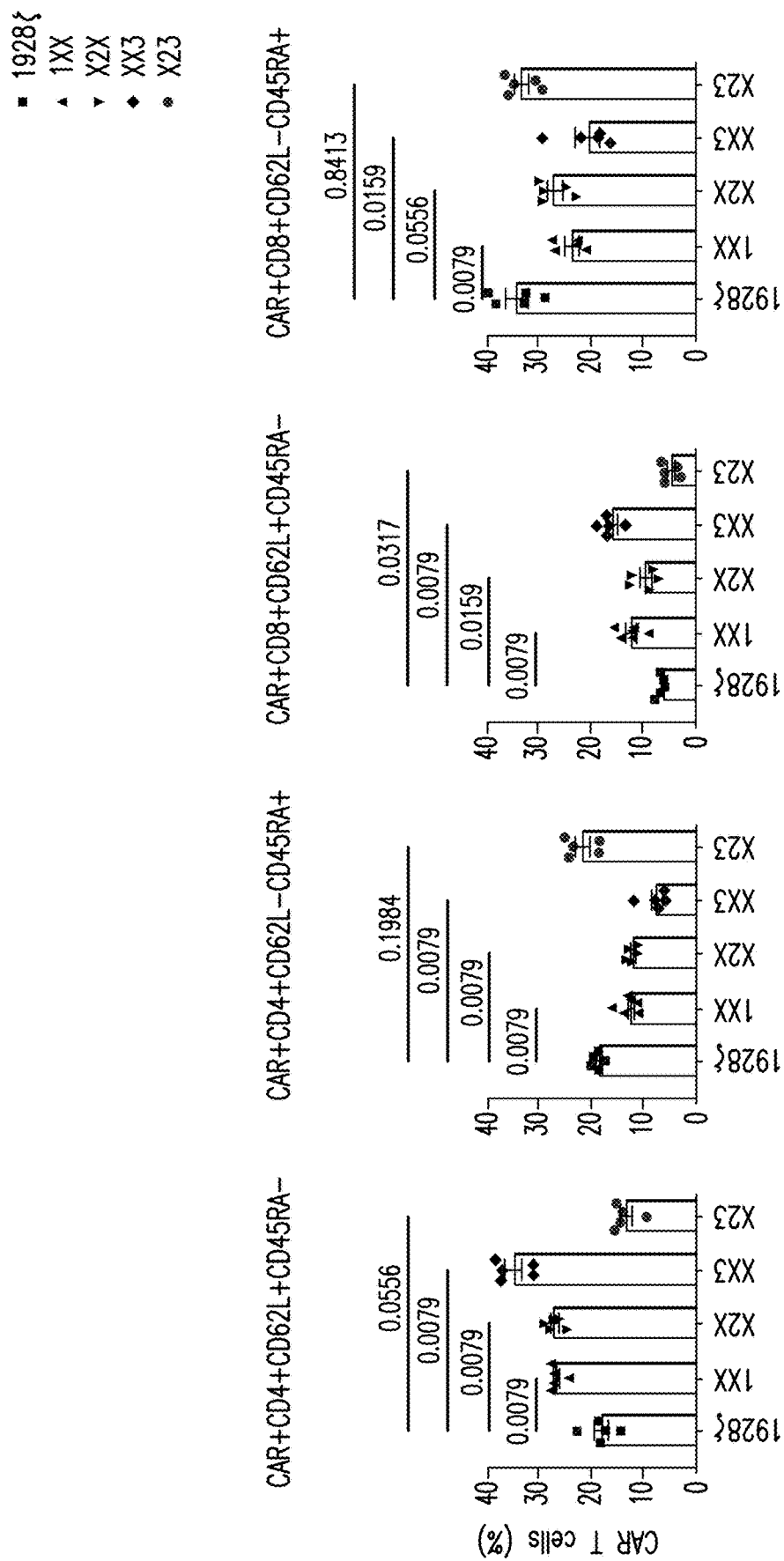
Figure 20E:
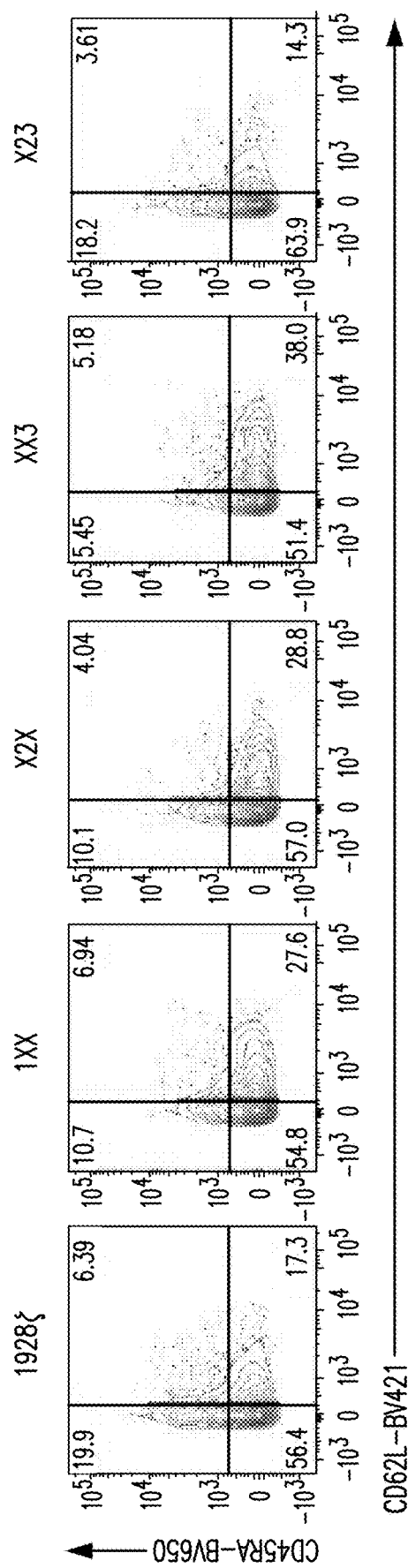

These findings were extended in vivo as CAR T cells with two inactive CD3 ITAM domains exhibited increased persistence (FIG. 16D) and delayed T cell differentiation (FIG. 16E). 1XX, X2X, and XX3 CAR T cells all demonstrated a higher percentage of CD62L$^+$CD45RA$^-$ central memory T cells $_{(TCM)}$ and a decrease in the fraction of terminally differentiated CD62L$^-$CD45RA$^+$ effector cells $_{(TEFF)}$ (FIG. 16E and FIG. 20E). The attenuation of effector differentiation in CD4$^+$ and CD8$^+$ CAR T cells was associated with increased accumulation of both T cell subsets at the tumor sites (FIG. 16D), establishing the benefit of reducing CD3 signaling within CD28-based, second-generation CARs.

Figure 17A:
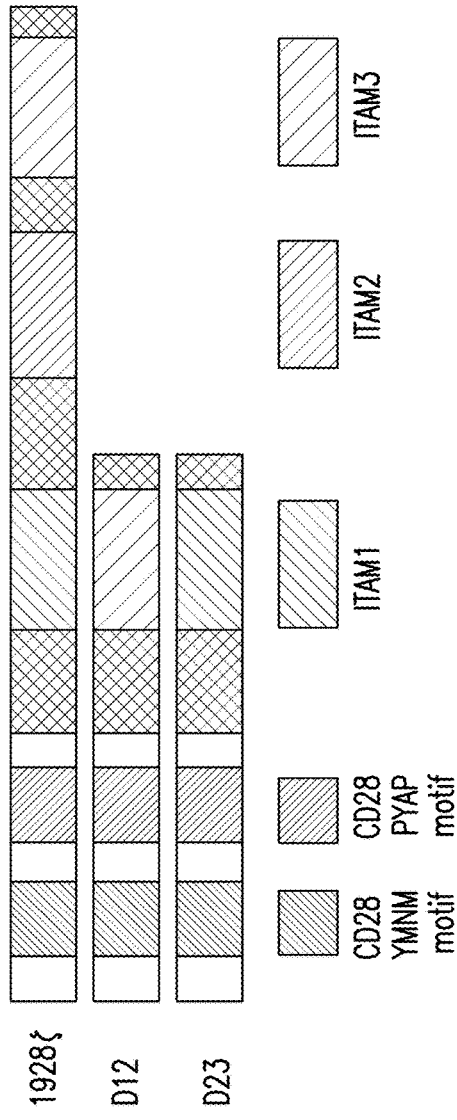
FIGS. 17A-17E depict that iTAM position within 1928ζ CARs determines antitumor efficacy.
Figure 17B:
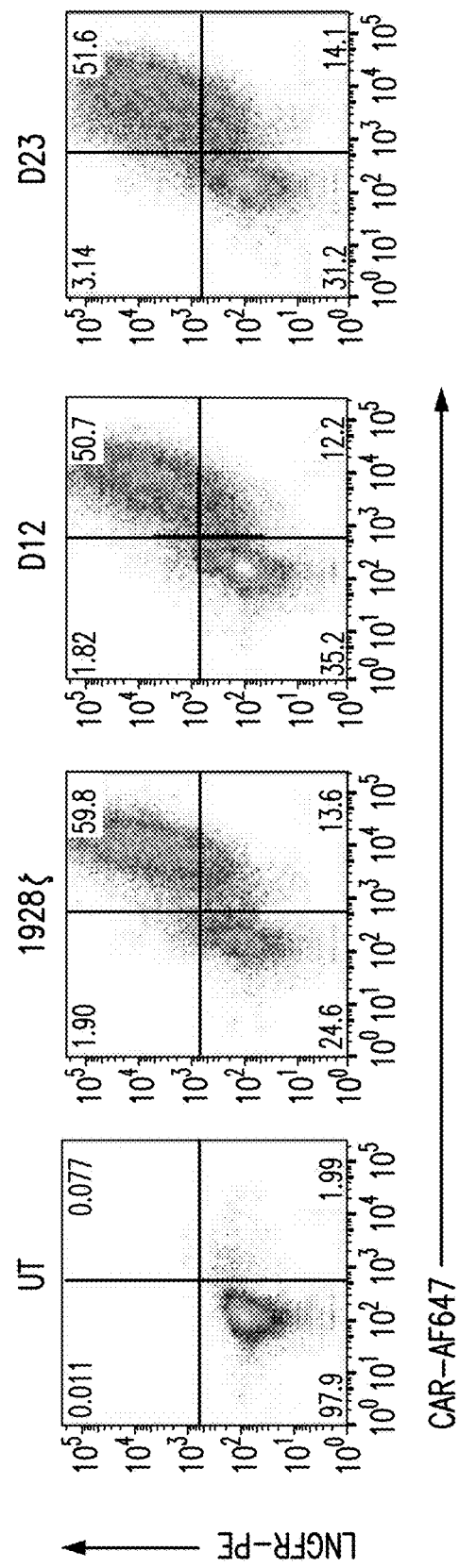
Figure 17C:
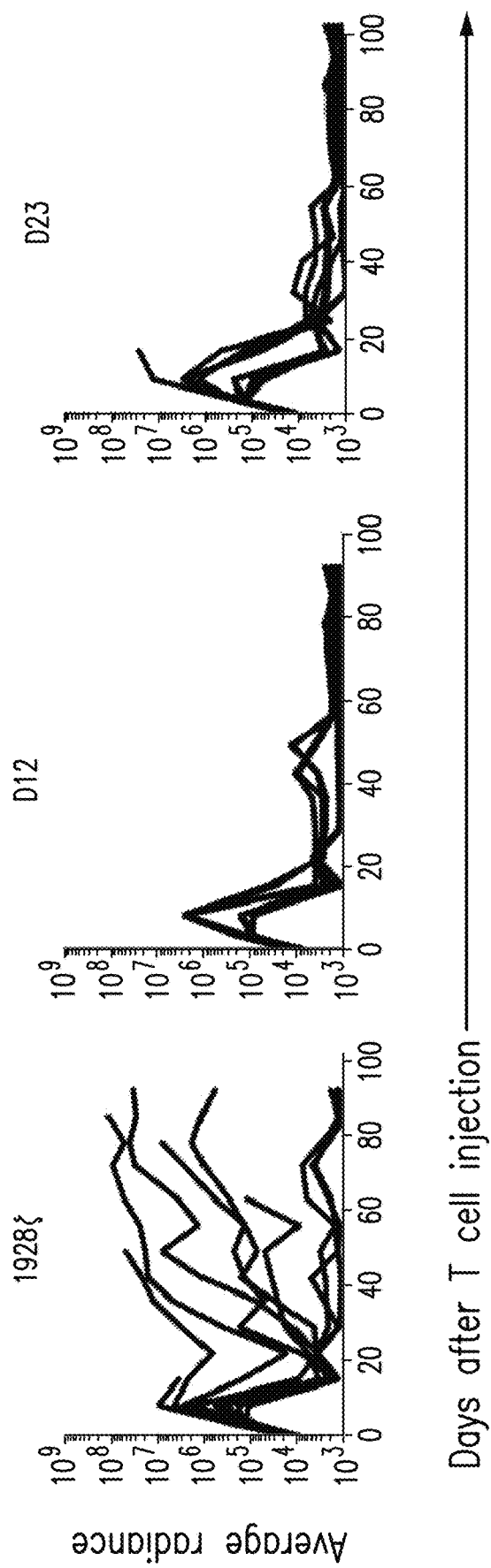
Figure 17D:
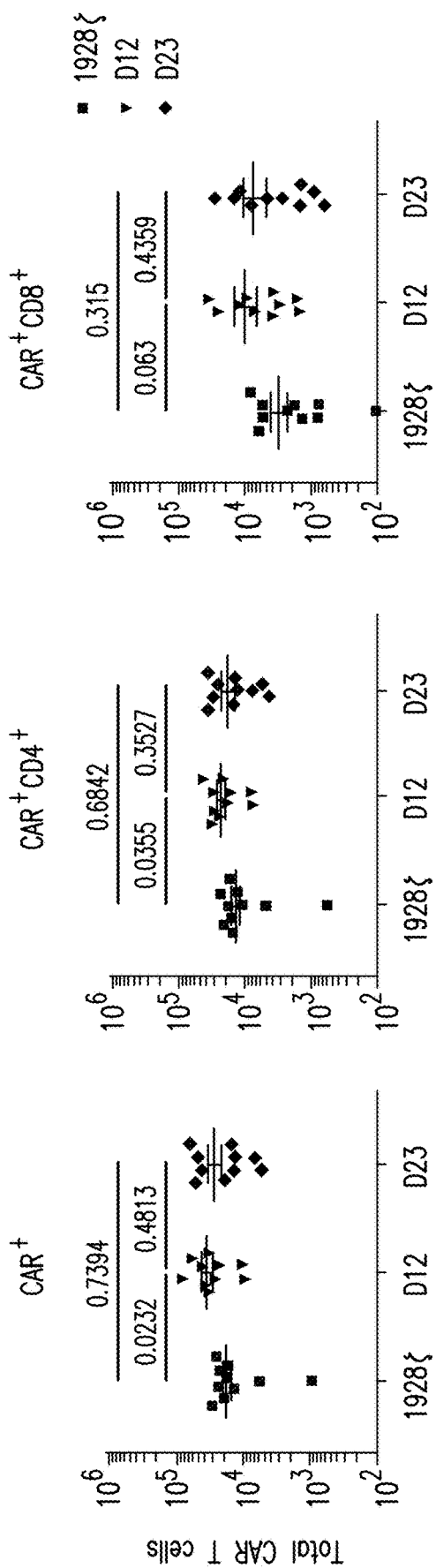
Figure 17E:
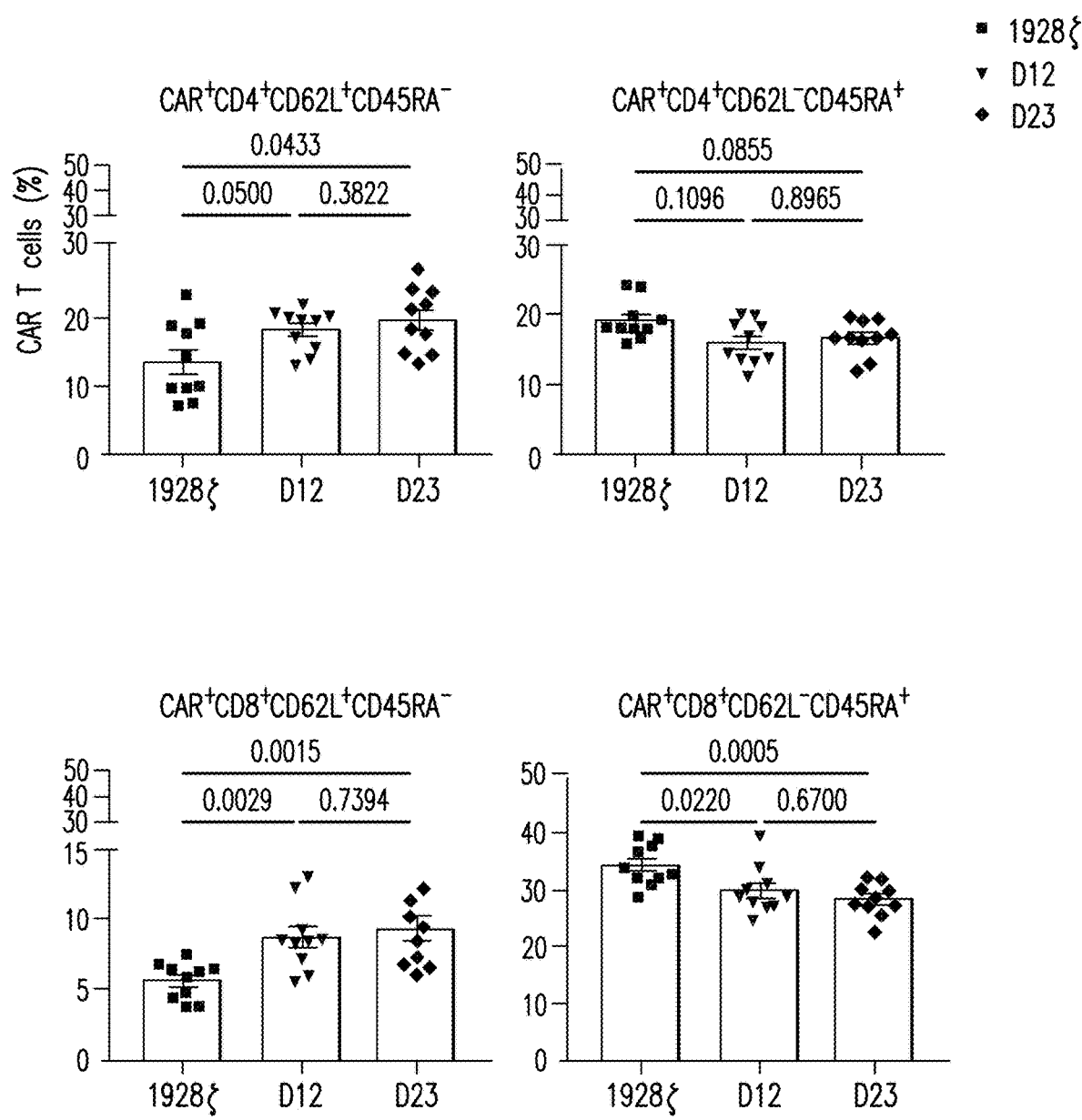

Whether the lesser potency of XX3 is intrinsic to ITAM3 or due to its distal position were next investigated. Therefore, 1928ζ mutant CARs with either ITAM1 or ITAM3 at the same proximal CAR position through deletion of the remaining CD3ζ chain were generated (D12 and D23, FIGS. 17A-17B). In vitro studies demonstrated equipotent cytolytic activity between all constructs in 4- and 18-h assays, undiminished cytokine and GrB secretion, and comparable proliferative potential between D12, D23, and 1928ζ (FIGS. 21 and 22). However, D12 and D23 both outperformed 1928ζ in vivo, achieving complete tumor eradication (FIG. 17C and FIG. 22D). Both CAR constructs moderately diminished T cell differentiation and promoted higher CAR T cell accumulation at the tumor site relative to 1928ζ (FIGS. 17D-17E). These findings show the importance of ITAM dosage and position within 1928ζ CARs. A single functional ITAM is sufficient for potent antitumor efficacy and superior to that afforded by the triple-ITAM-containing wild-type CD3ζ chain. Furthermore, the therapeutic potency imparted by ITAM3 is less than that of ITAM1 in their respective native positions (XX3 versus 1XX), but comparable at the same proximal position (D12 versus D23). Despite sharing the same ITAM sequence, D12 achieved superior tumor eradication relative to XX3, demonstrating the importance of ITAM location within second-generation CARs.

Figure 3A:
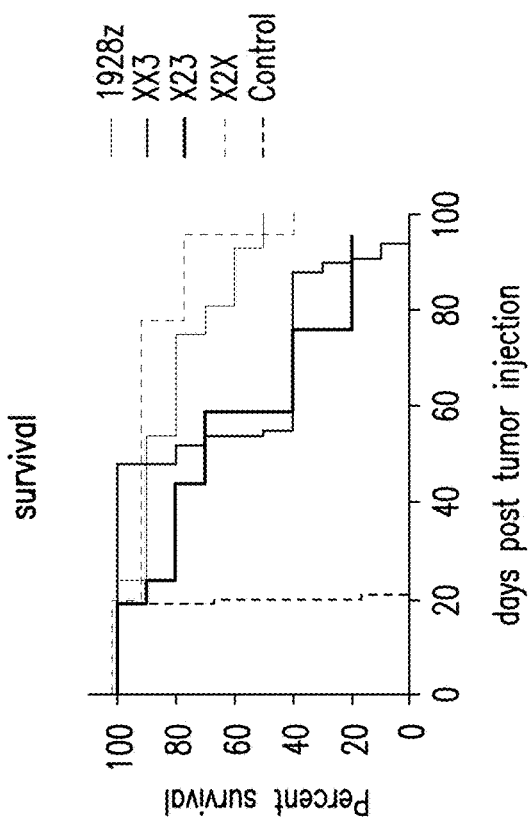
Figure 18A:
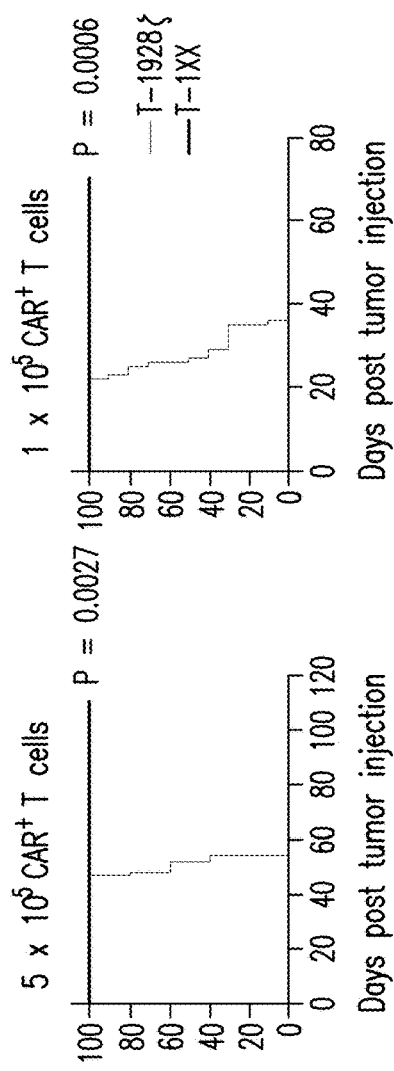
Figure 18B:
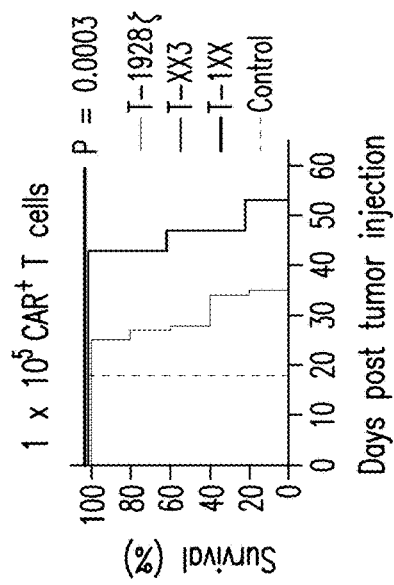
Figure 18D:
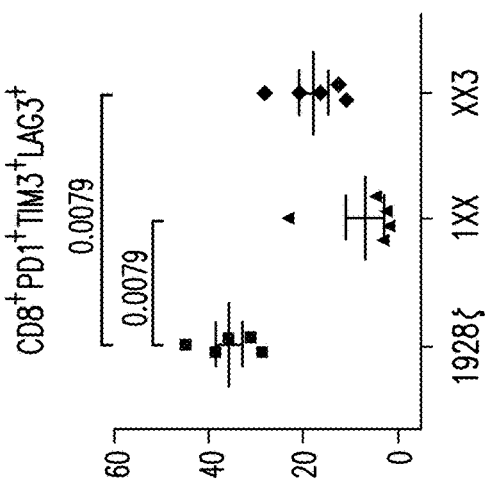
Figure 18D:
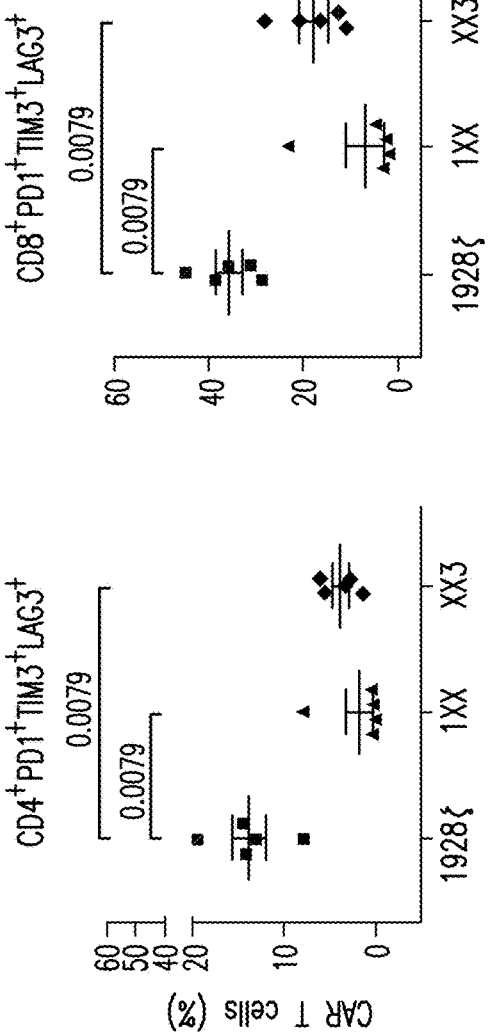
Figure 18C:
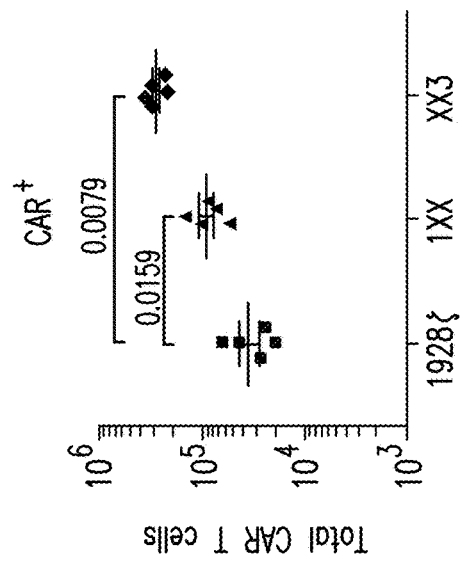
Figure 24A:
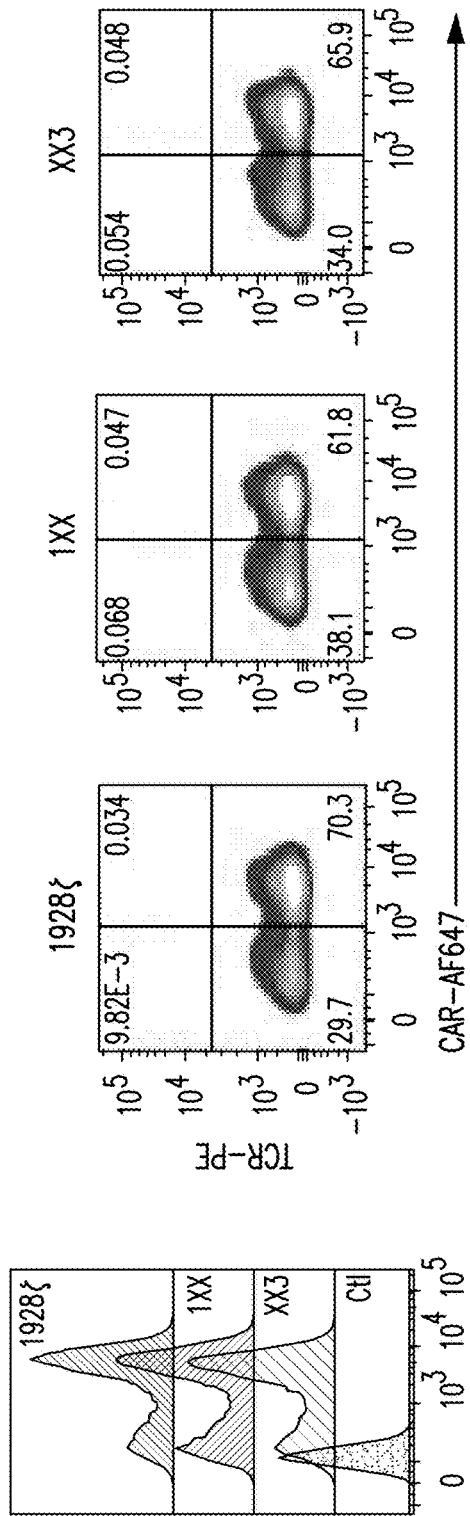
FIGS. 24A-24F depict T cell differentiation and effector function of TRAC-encoded 1928ζ mutants. NALM6-bearing mice were treated with 1×10⁵ CAR T cells and euthanized at day 17 after infusion. Bone marrow and spleen CAR T cells were analyzed and counted by FACS.
Figure 24B:
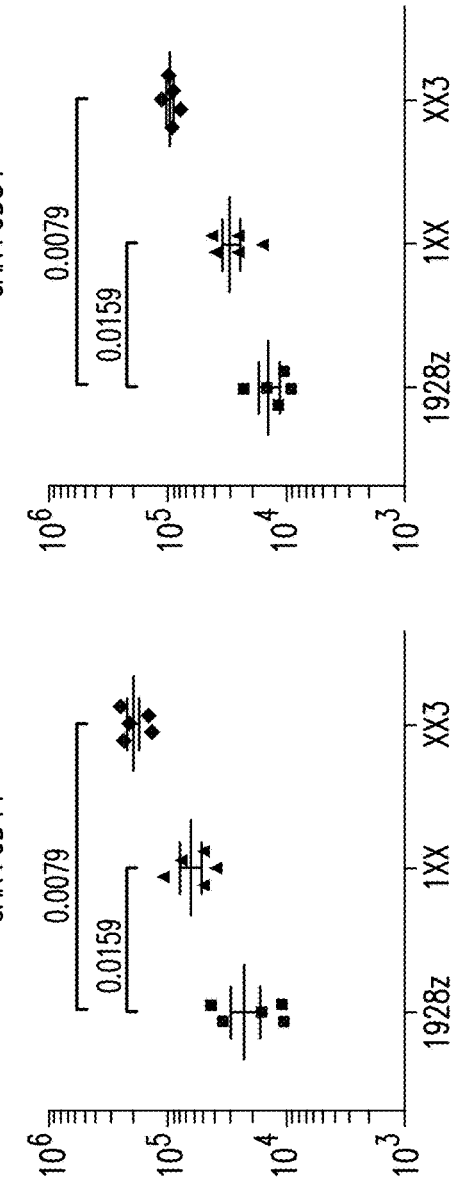
Figure 24C:
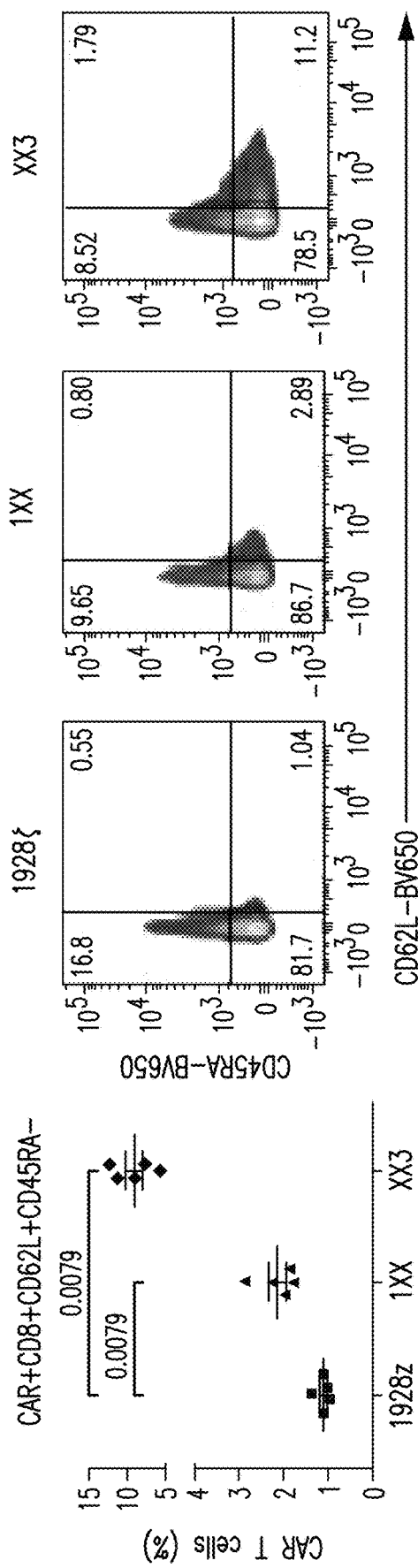
Figure 24D:
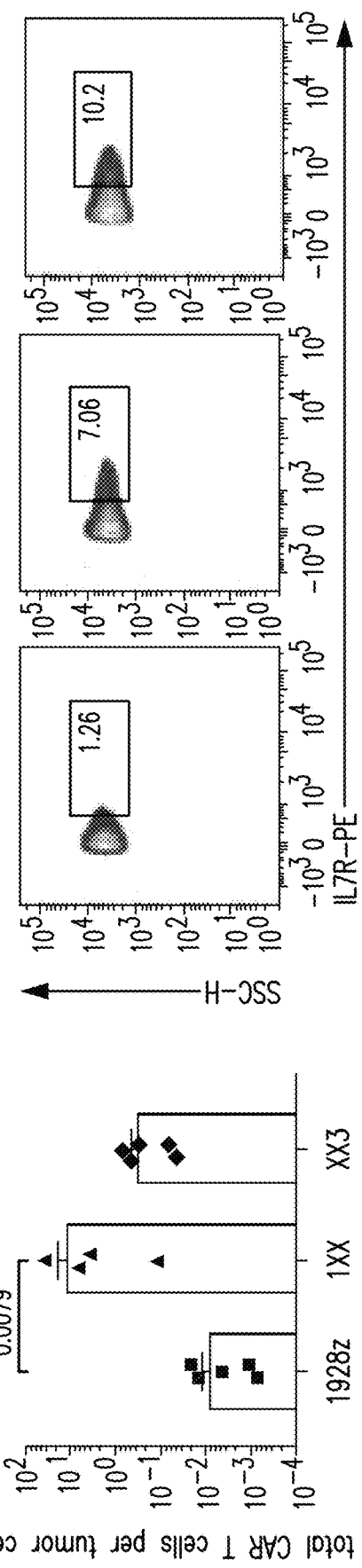
Figure 24E:
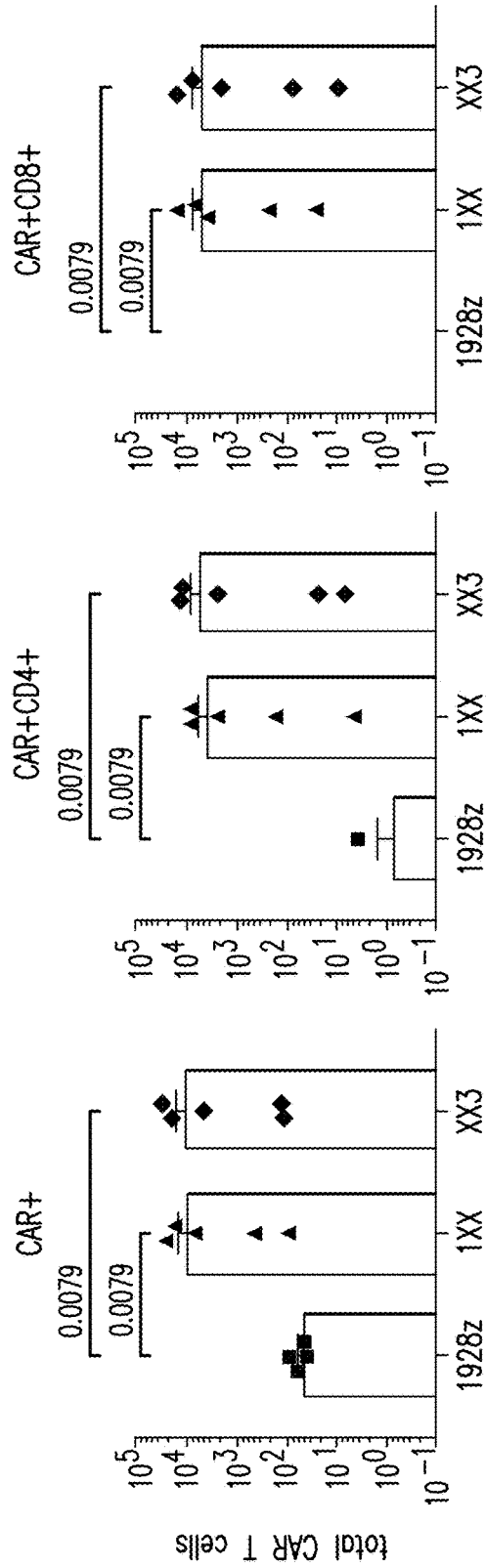
Figure 24F:
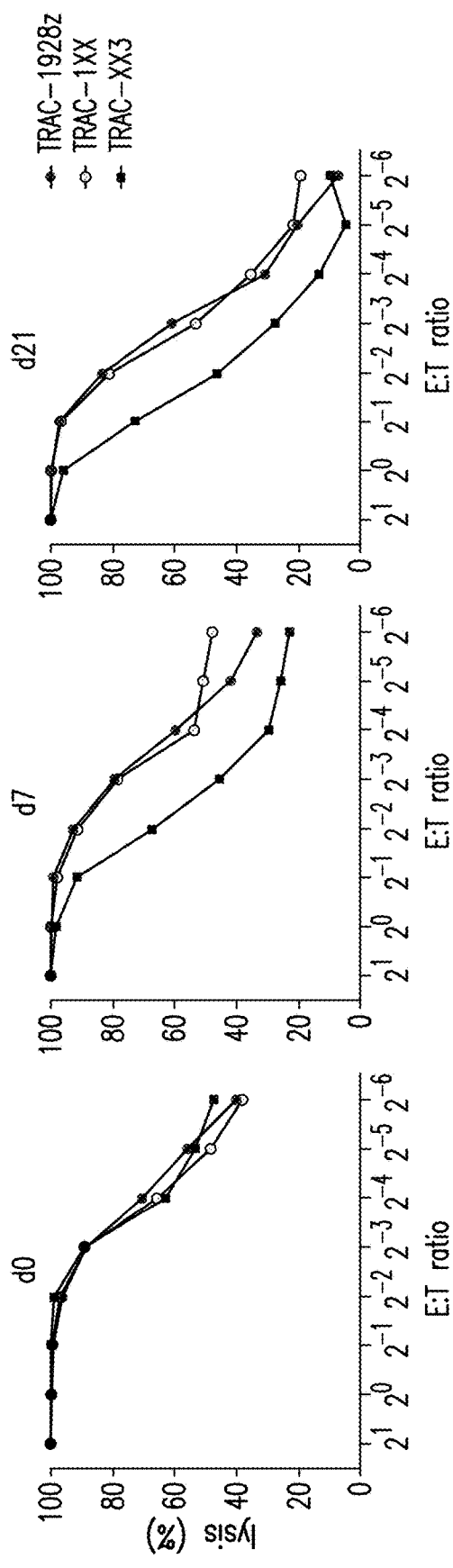
Figure 25A:
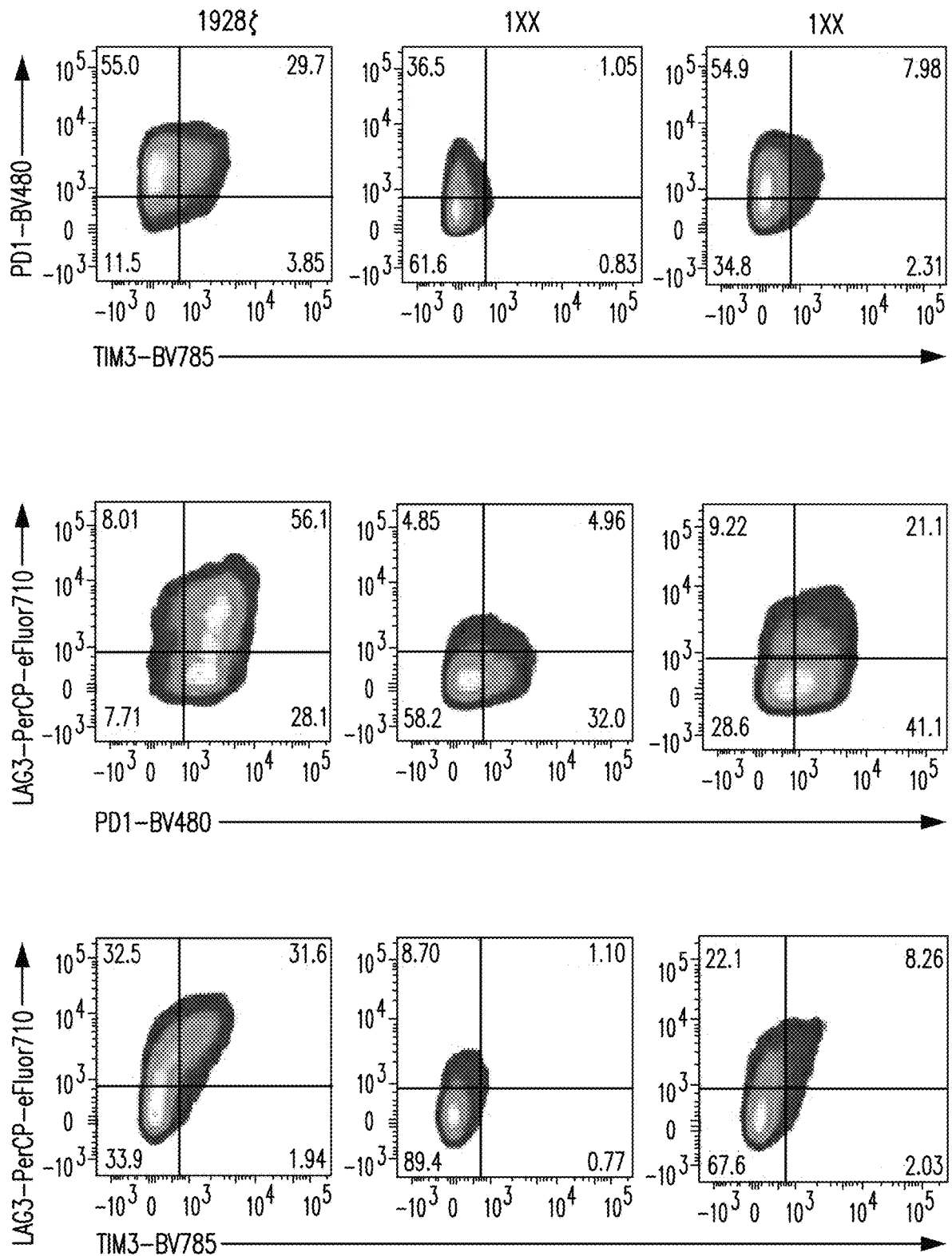
Figure 25B:
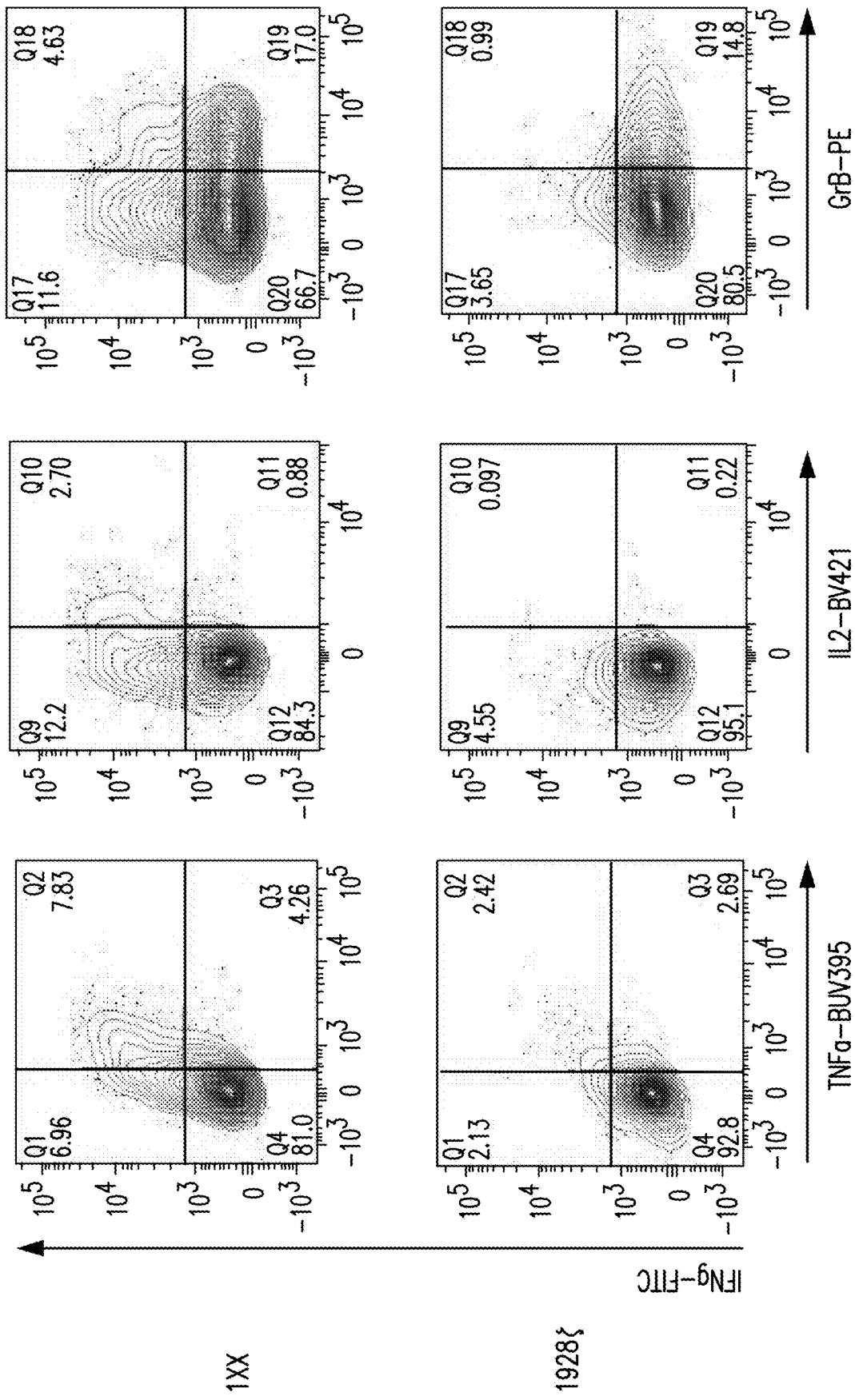
Figure 25C:
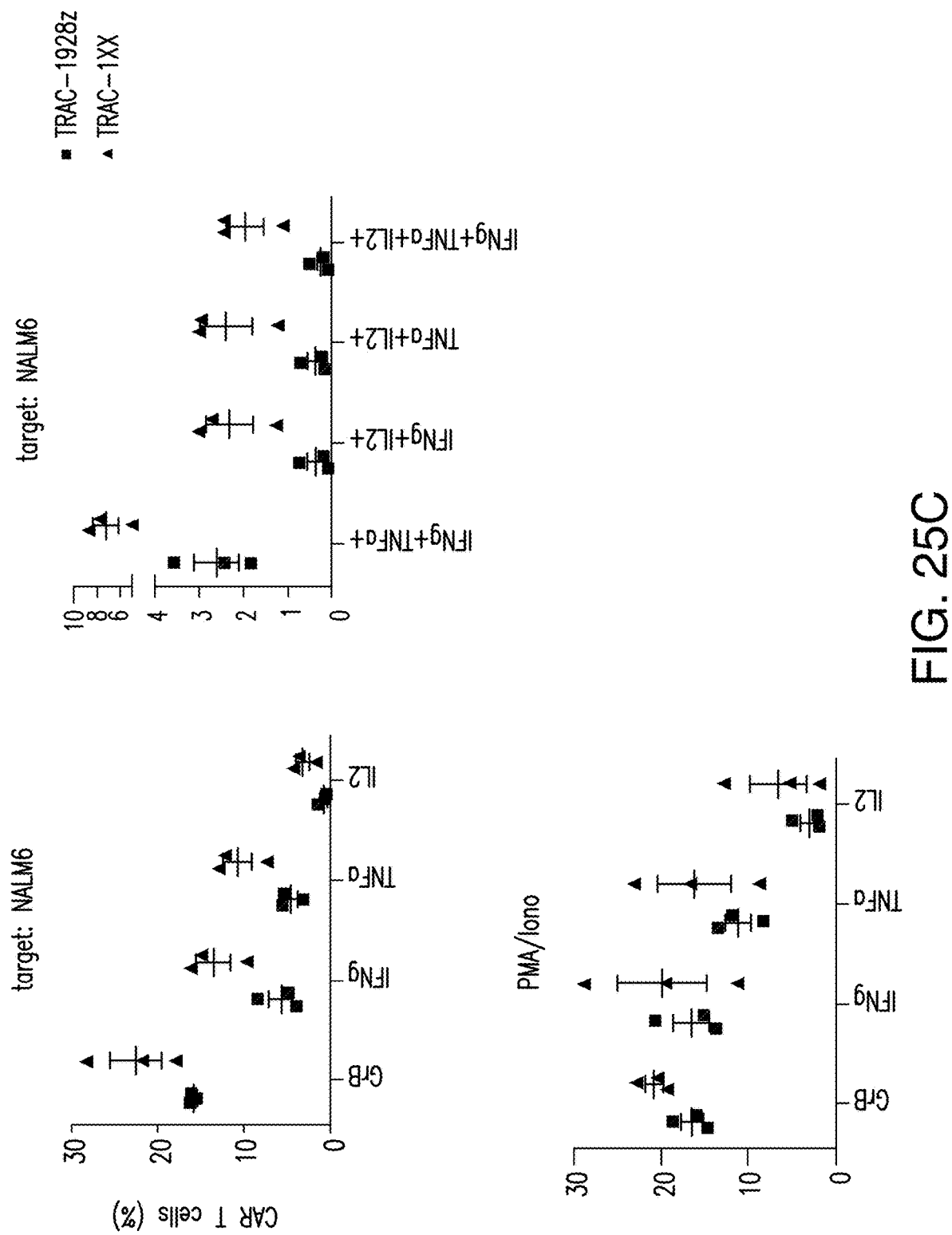
Figure 25F:
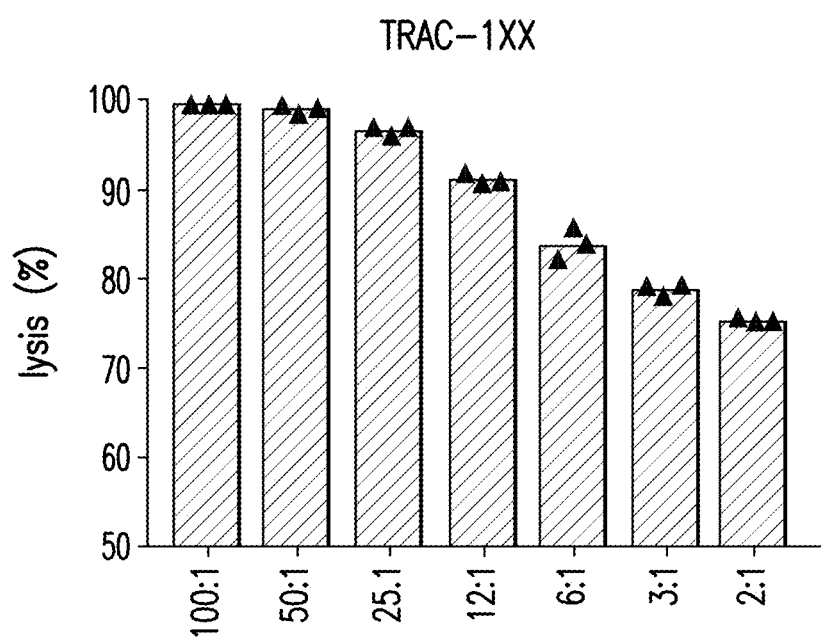
Figure 25G:
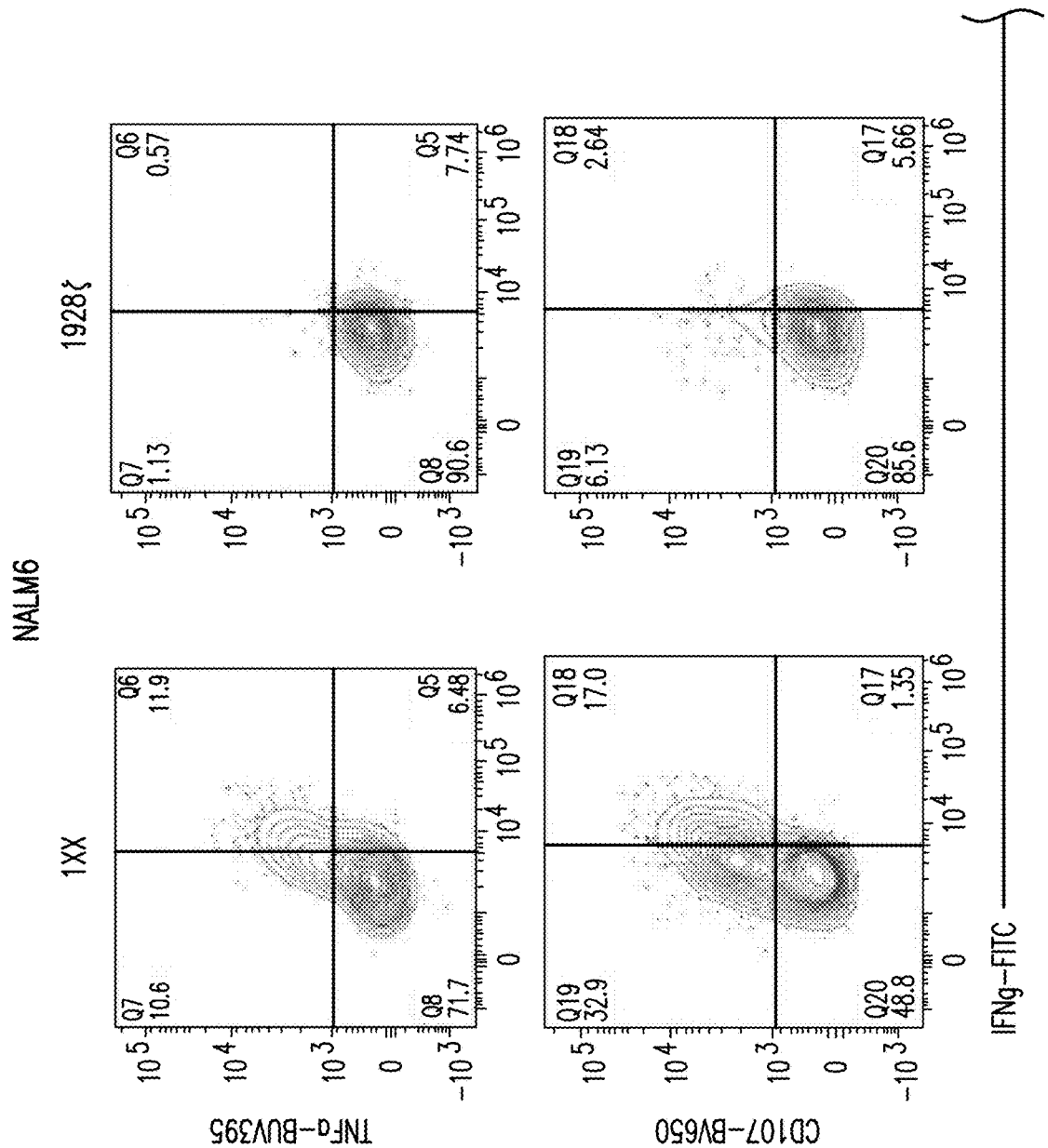
Figure 25G:
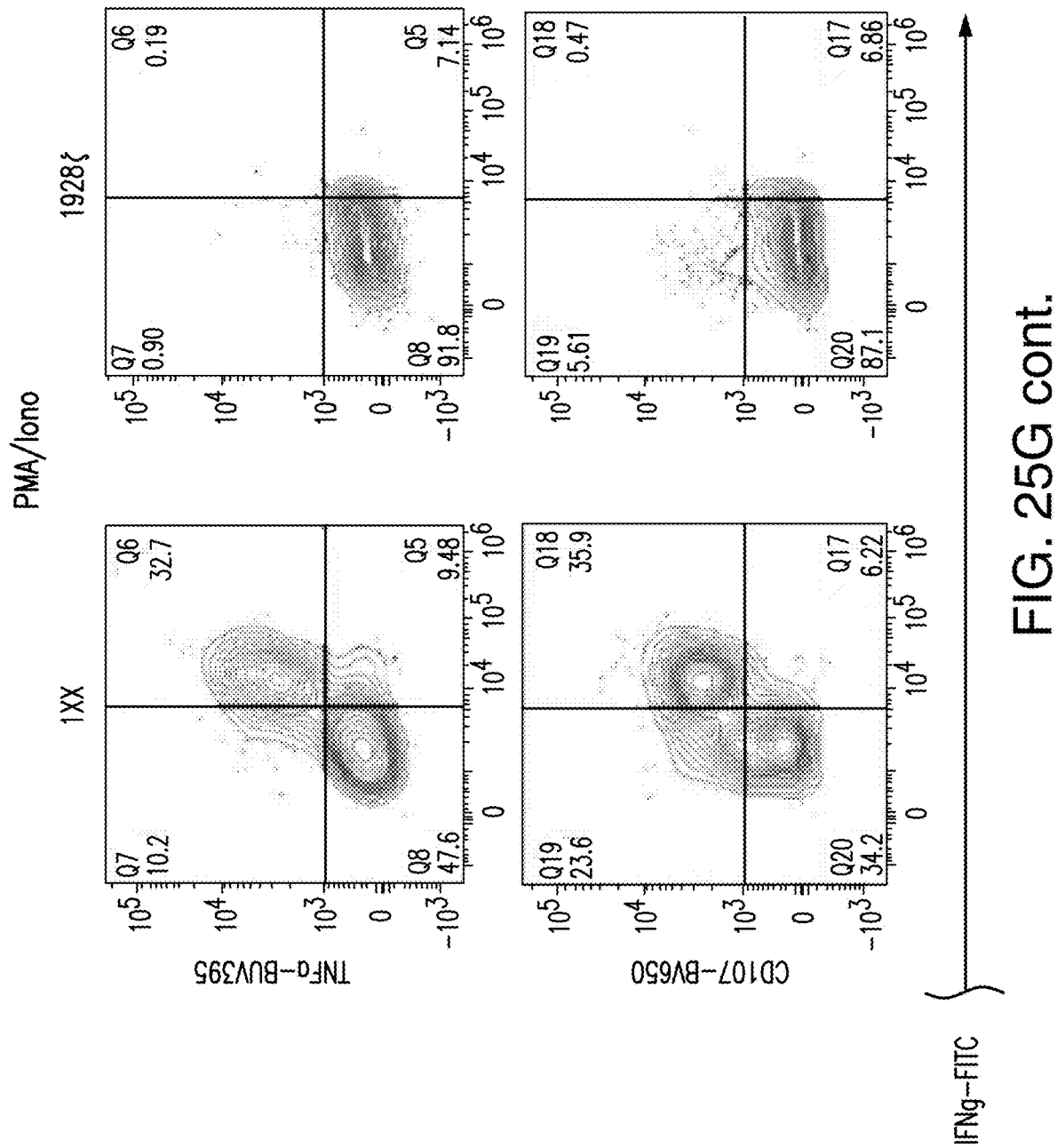

To rule out potentially confounding effects arising from subtly different CAR expression levels, the CAR complementary DNAs (cDNAs) were targeted to the TRAC locus[19], thereby normalizing transgene regulation and copy number while simultaneously removing the endogenous T cell receptor (TCR; FIG. 24A). Under these conditions, 1XX CAR T cells again surpassed those expressing 1928z or XX3 (FIG. 3a). TRAC-1XX T cells achieved complete remissions within 21 d, while TRAC-XX3 T cells only delayed tumor progression and could not achieve tumor control (FIG. 18A). Analyses of CAR T cells and tumor cells retrieved 17 d post-CAR infusion showed higher accumulation of TRAC-1XX and TRAC-XX3 CAR T cells compared to TRAC-1928z in both CD4$^+$ and CD8$^+$ subsets (FIG. 18C and FIGS. 24B and 24E). Increased CAR T cell persistence was associated with a higher percentage of $T_{CM}$ and interleukin-7 receptor (IL7R)$^+$ CAR T cell counts (FIGS. 24C and 24D), reinforcing the findings of delayed T cell differentiation in 19280 mutants. Similar to retrovirally engineered T cells, TRAC-XX3 T cells lost their cytolytic potential over time in contrast to TRAC-1928z and TRAC-1XX cells (FIG. 24F). The expression of exhaustion markers was reduced in 1928z mutants compared to TRAC-1928z, and functional exhaustion of TRAC-1928z was confirmed by reduced $T_H1$ cytokine secretion and GrB/CD107a expression after CAR isolation from treated mice and ex vivo re-exposure to Nalm6 cells (FIG. 18D and FIG. 25). Whereas TRAC-1XX retained high cytolytic function and the capacity of coproducing multiple cytokines, TRAC-1928z displayed progressive inability to secrete $T_H1$ cytokines associated with increased expression of exhaustion markers.

Figure 29A:
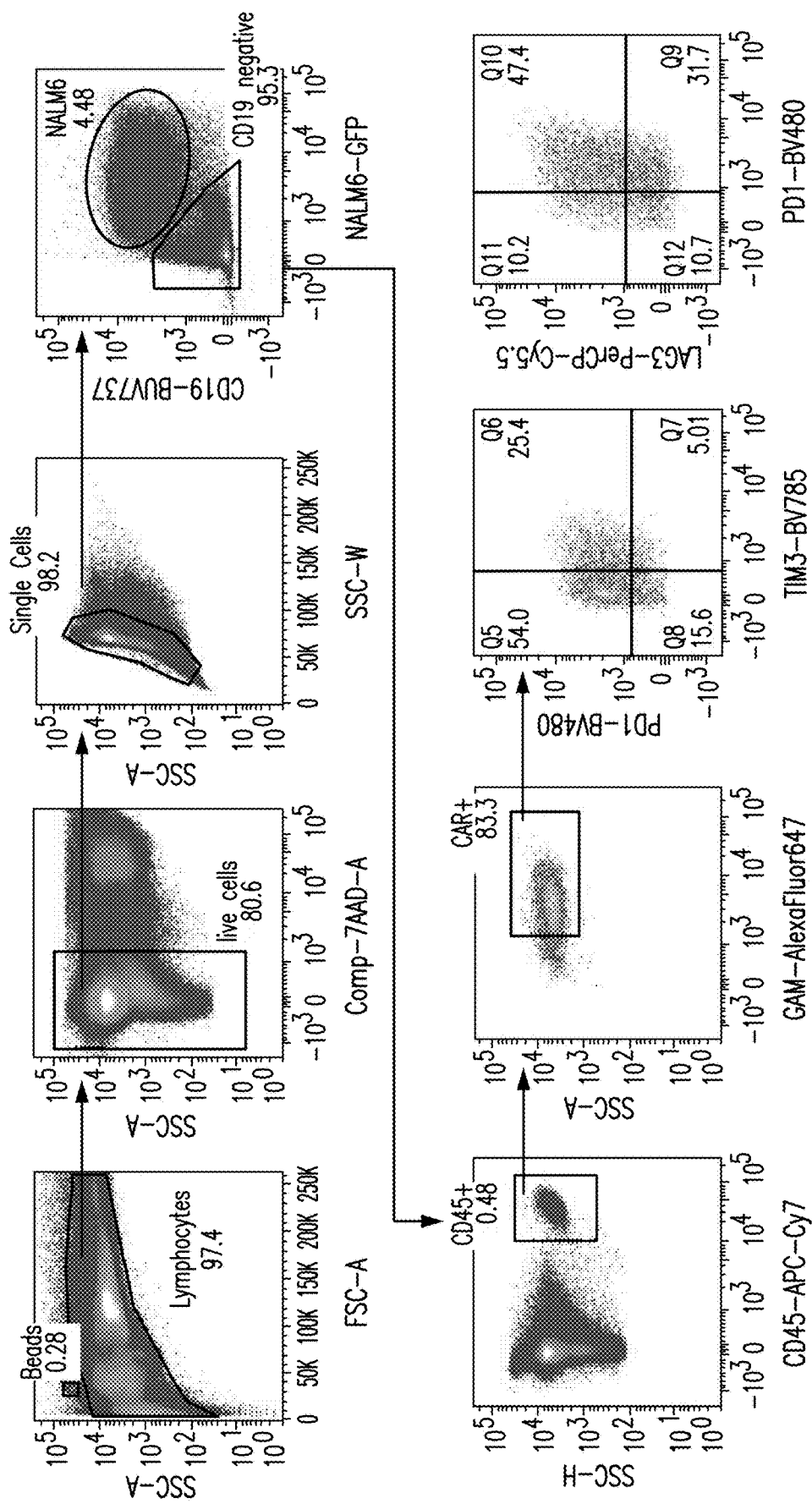
FIGS. 29A-29B depict gating strategy to analyze CAR T cells obtained from bone marrow of treated mice.
Figure 29B:
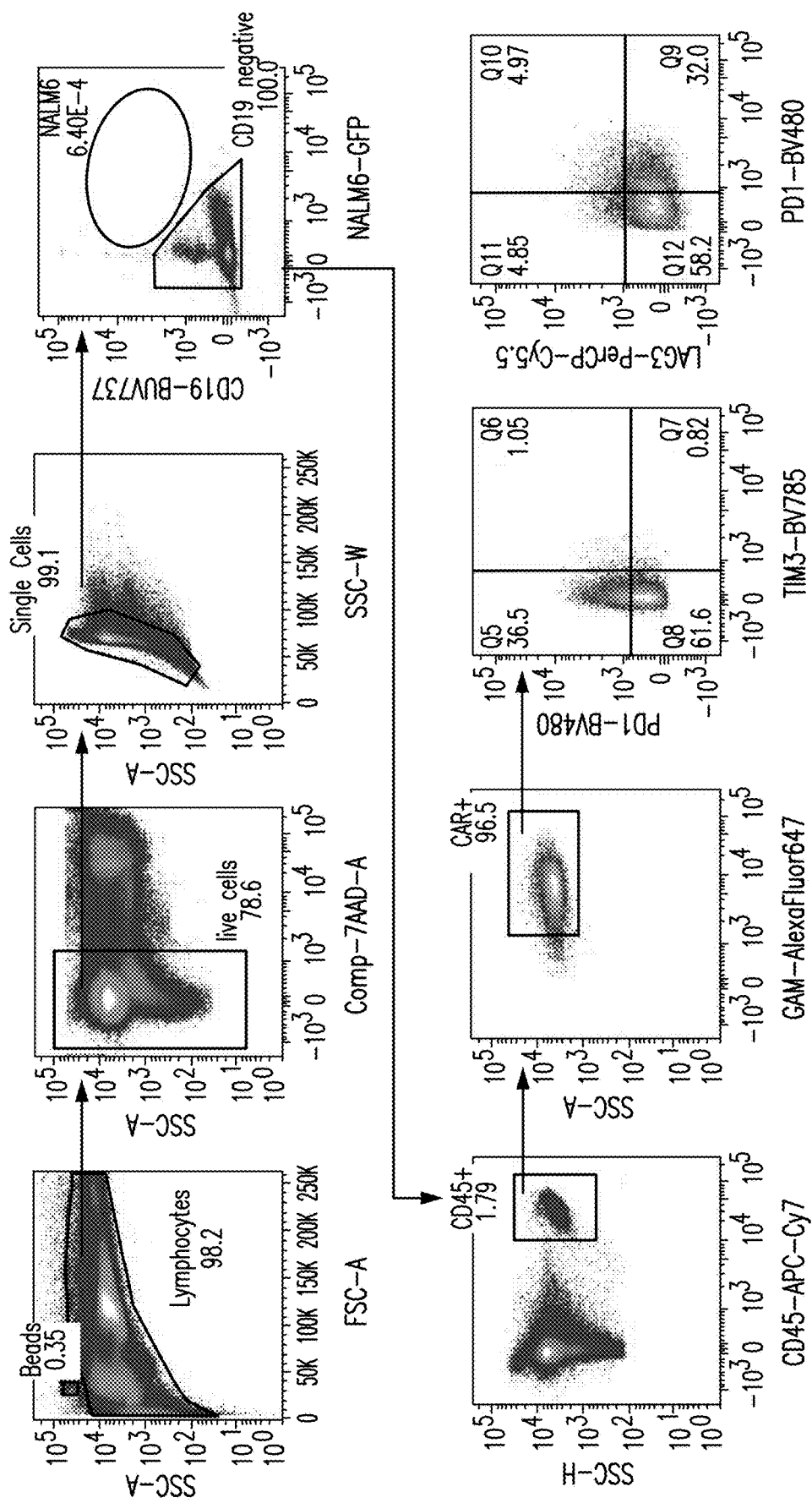

Long-term follow-up studies after administration of two different T cell doses (5×10$^5$ and 1×10$^5$ CAR$^+$ T cells) unequivocally demonstrated the therapeutic superiority of TRAC-1XX. While tumor-related deaths occurred in less than 60 d (treatment with 5×10$^5$ CAR$^+$ T cells) or less than 40 d (treatment with 1×10$^5$ CAR$^+$ T cells), all mice treated with TRAC-1XX showed complete tumor eradication and enhanced survival throughout the observation period (FIG. 18B and FIG. 29).

Figure 18E:
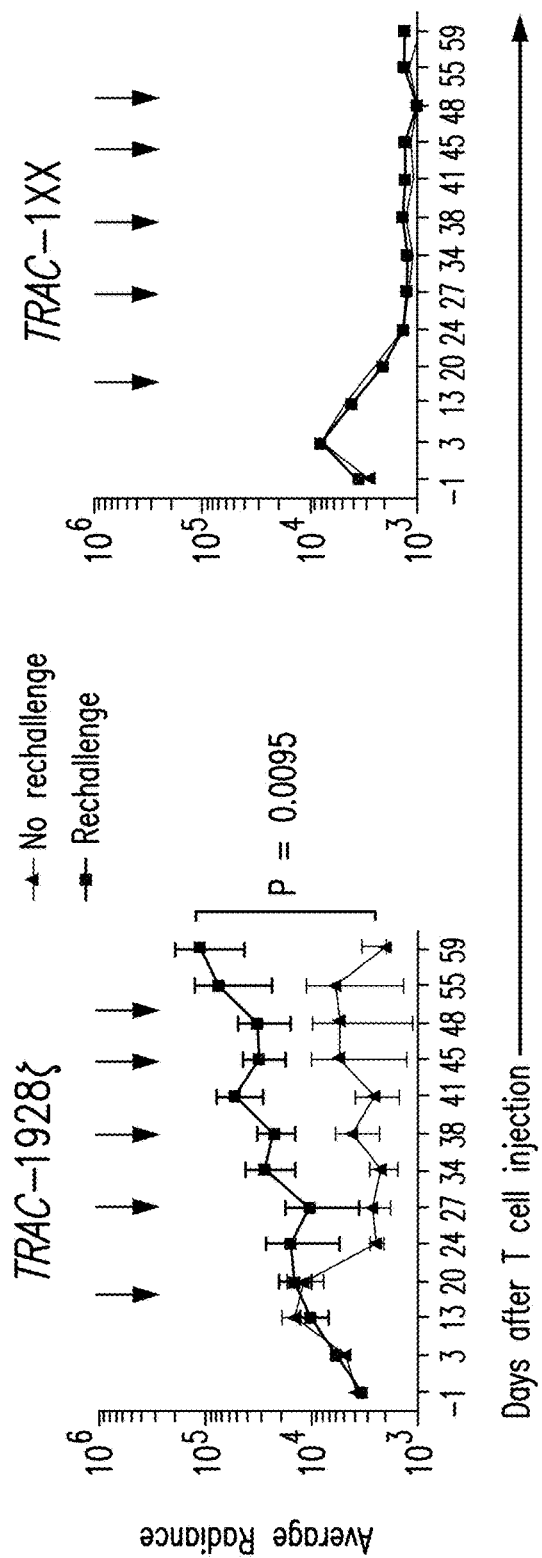
Figure 18F:
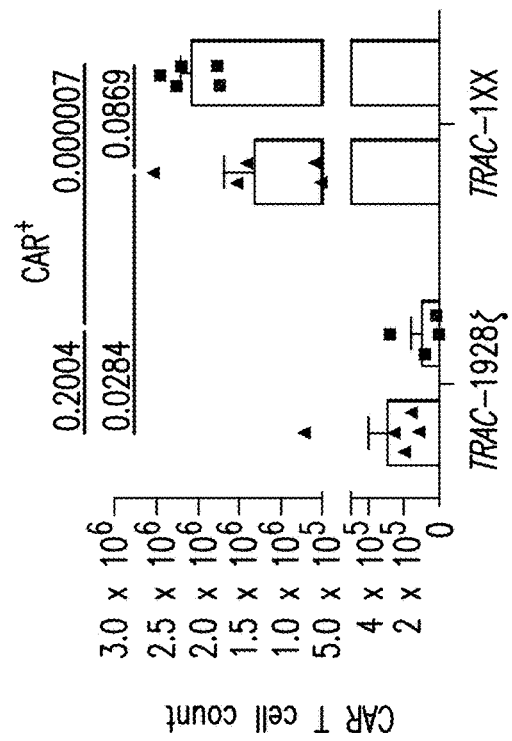
Figure 26A:
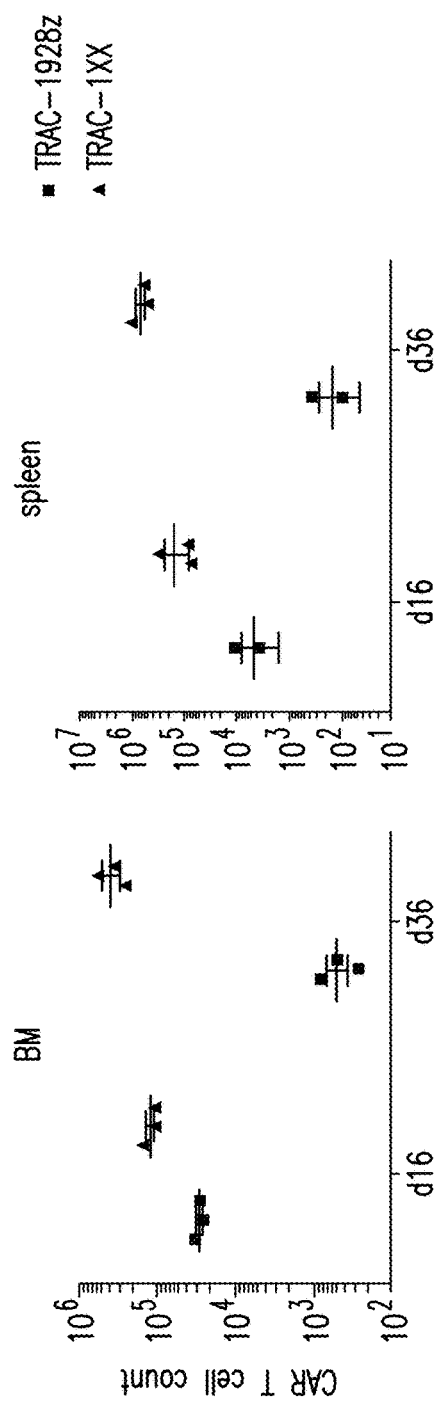
FIGS. 26A-26G depict T cell memory formation in TRAC-1XX compared to wild-type TRAC-1928ζ. NALM6-bearing mice were treated with 1×10⁵ or 5×10⁵ TRAC-edited naive T cells.
Figure 26B:
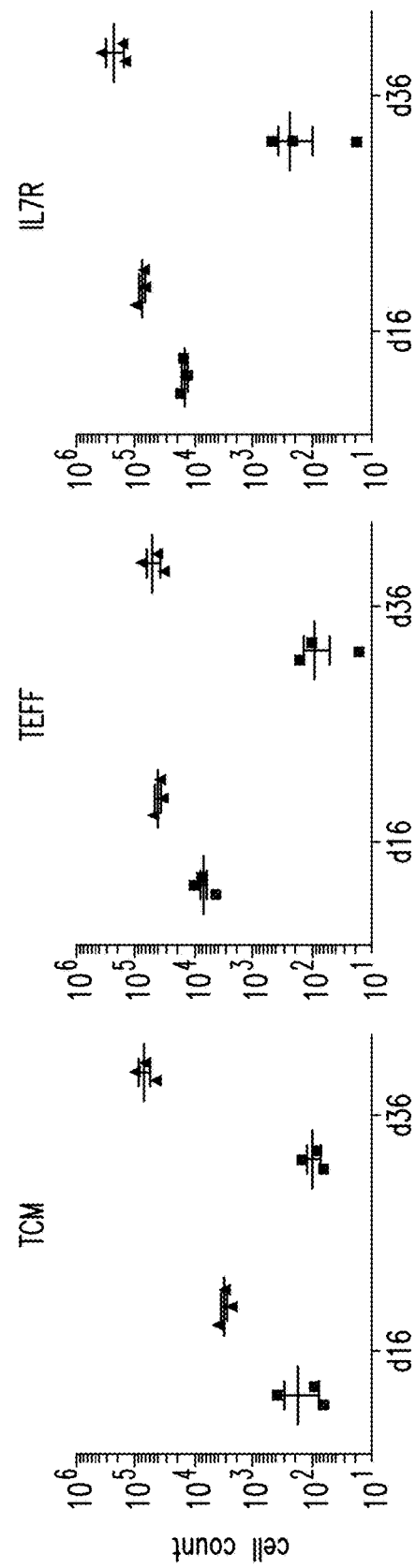
Figure 26C:
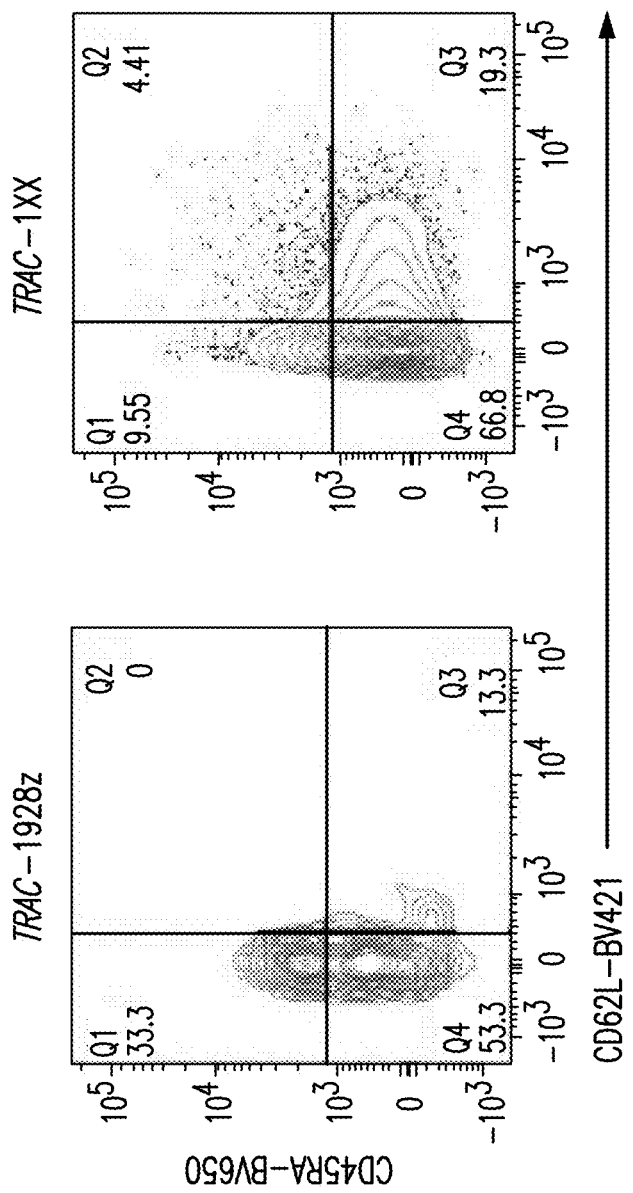
Figure 26D:
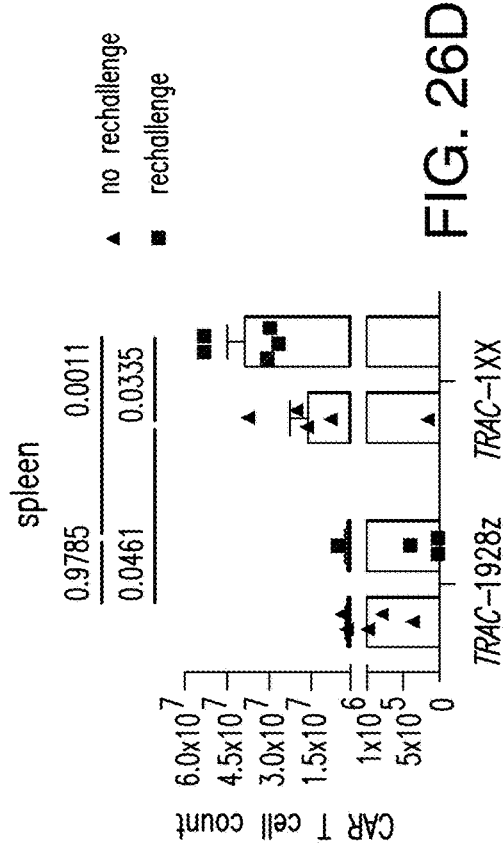
Figure 26E:
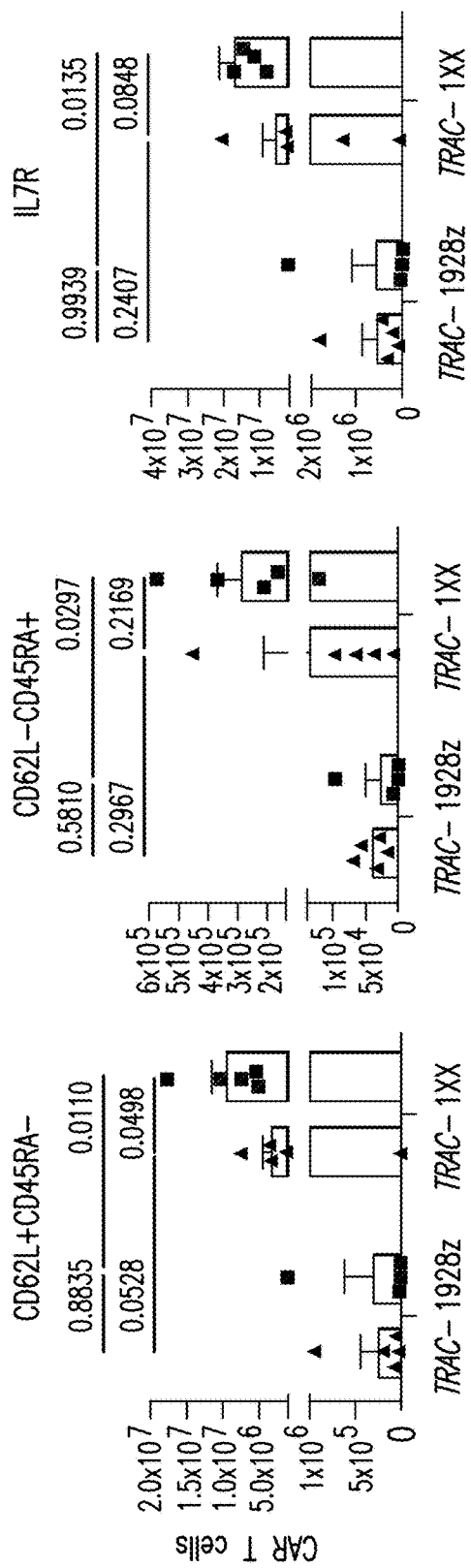
Figure 26F:
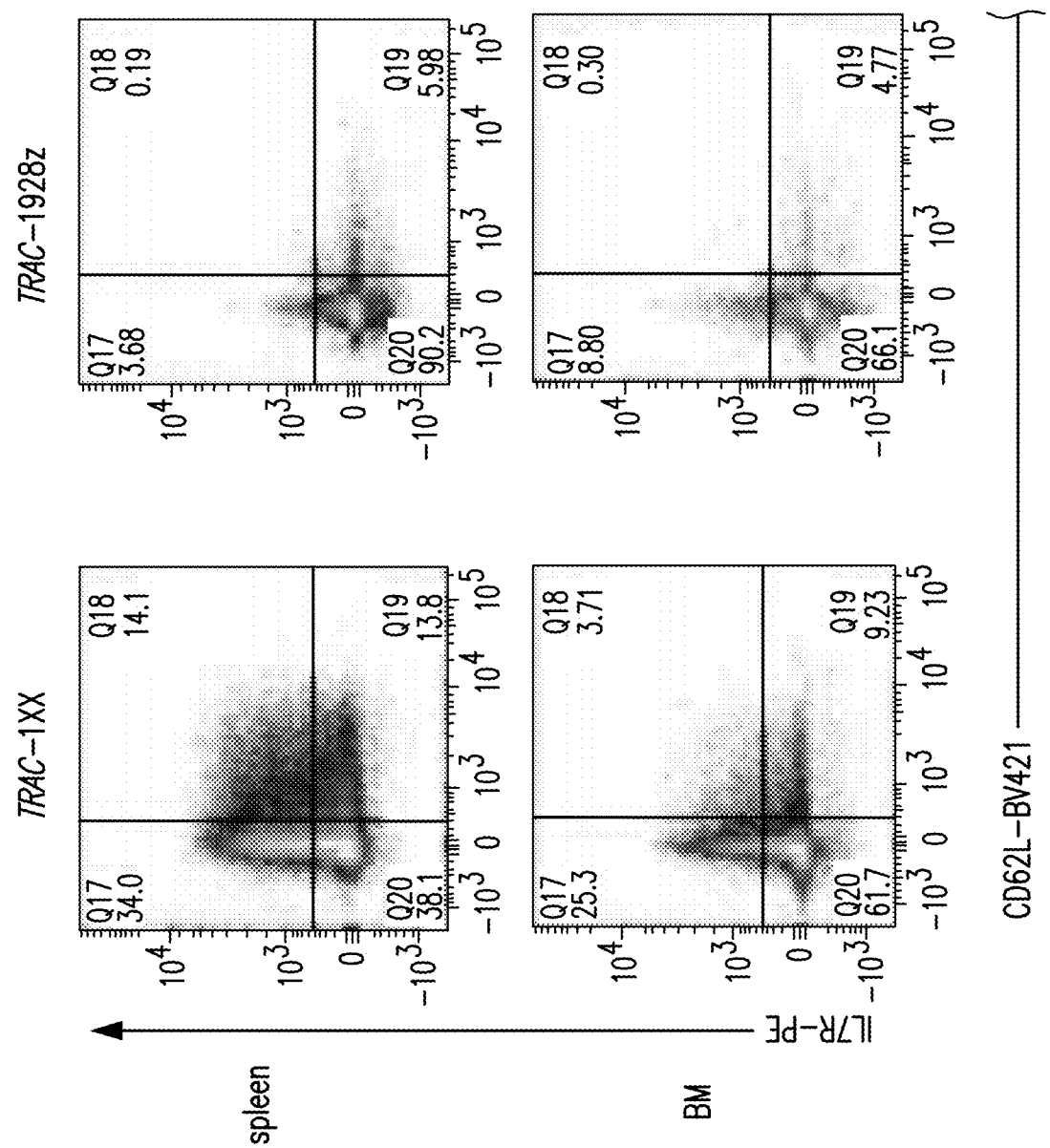
Figures 26F, 26G:
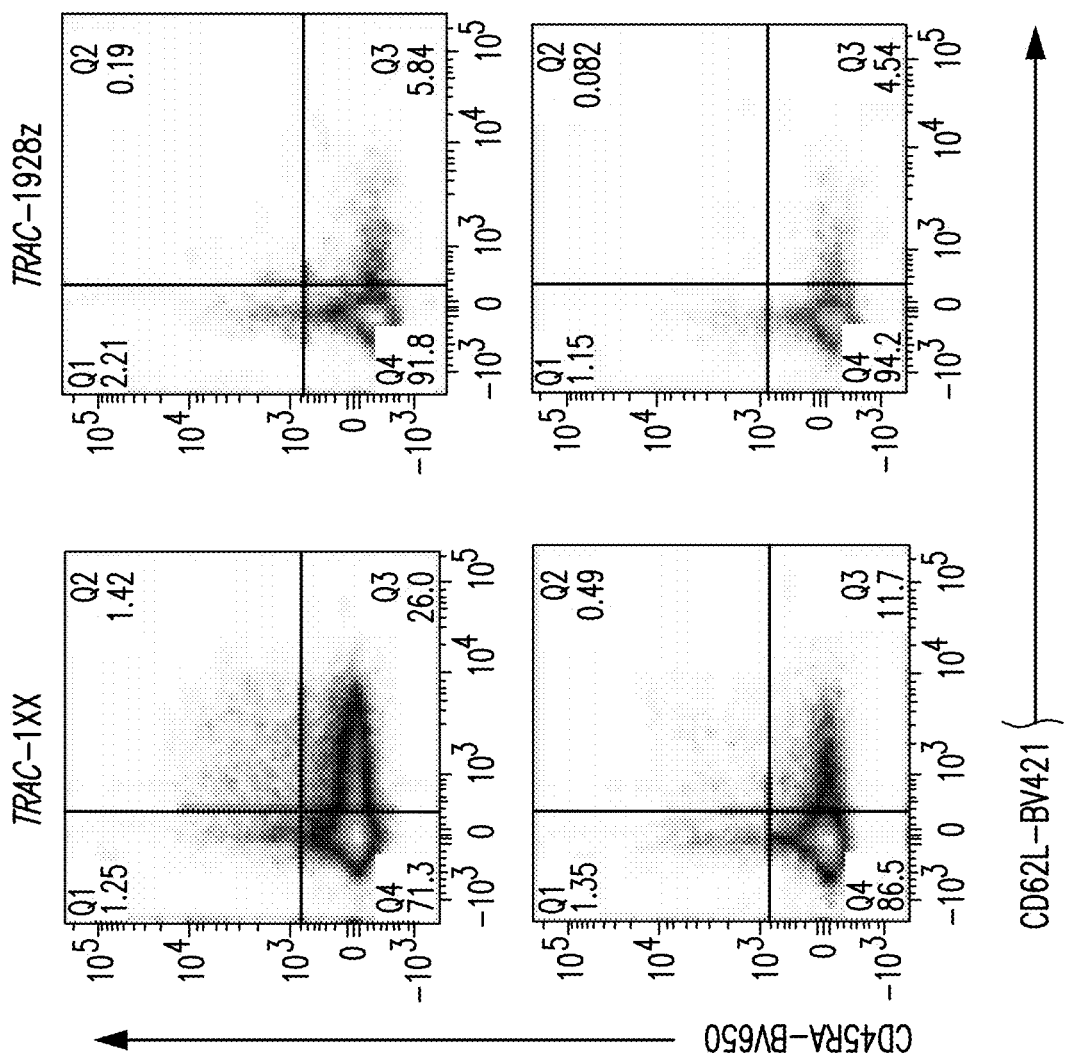

The enhanced ability of 1XX to develop into highly functional, long-lived memory cells was further demonstrated when sorted naive T cells were used for in vivo therapy. TRAC-1XX showed an increase in the population of $T_{CM}$ and IL7R-expressing cells over time (FIGS. 26A-26C), associated with enhanced persistence of highly potent CAR T cells. Importantly, TRAC-1XX CARs were capable of eliciting effective recall responses, achieving complete tumor control following tumor rechallenge (FIG. 18E). Persisting 1XX CAR T cells comprised increased numbers of TCM, TEFF, and IL7R$^+$ CARs (FIGS. 18F and 18G and FIGS. 26D-26F). In contrast, TRAC-1928z more readily acquired an exhausted phenotype (FIG. 3h and Extended Data FIG. 7g) accompanied by reduced CAR T cell persistence without memory formation and the inability to control tumor rechallenge.

Figure 19A:
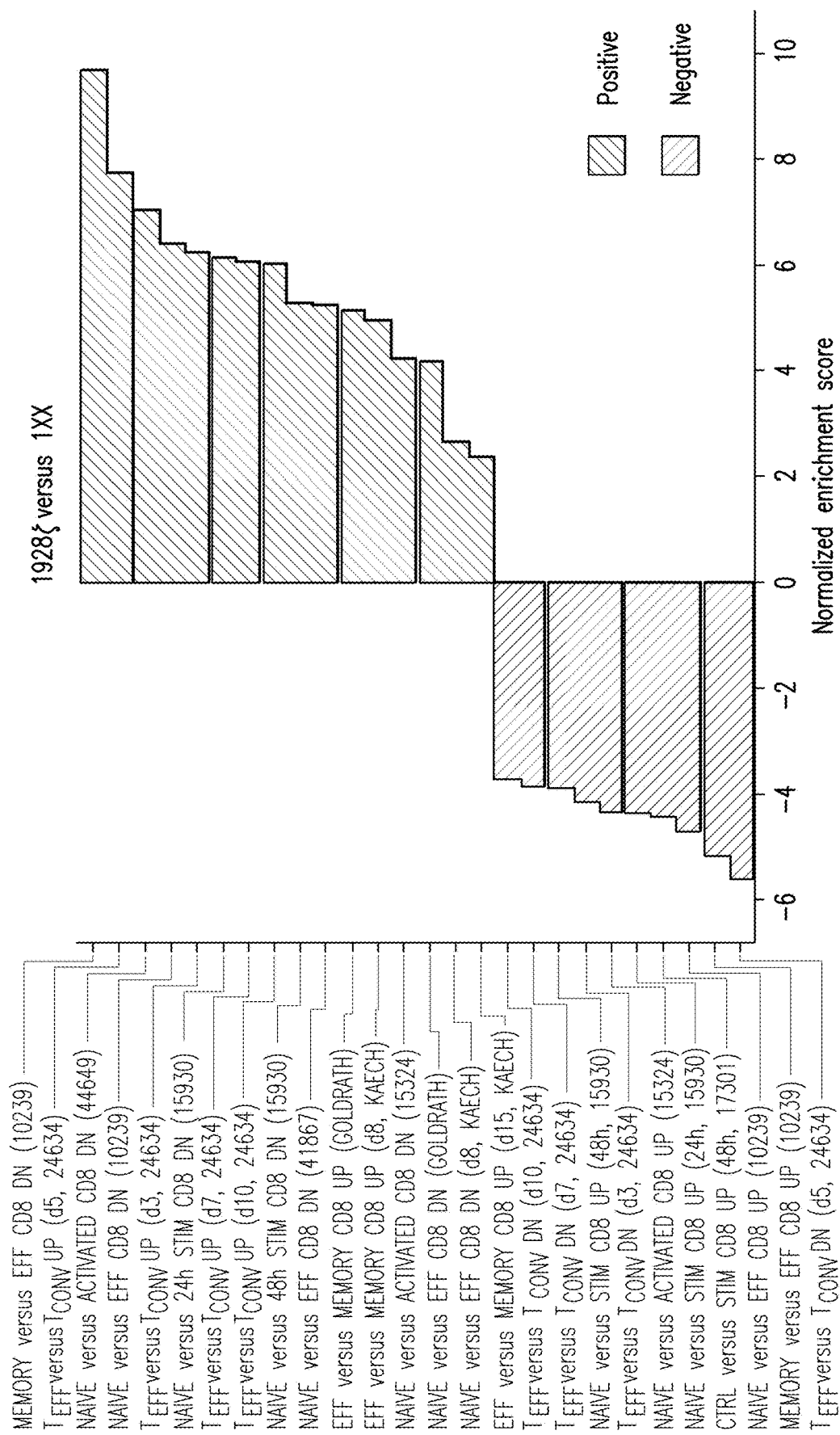
FIGS. 19A-19D depict that CD3ζ ITAM mutations in 1928ζ CARs establish distinct transcriptional signatures. Gene expression profiles of CD8+ TRAC-1928 ζ, TRAC-1XX, and TRAC-XX3 CAR T cells (initially sorted naive T cells) 24 h post stimulation with CD19+ target cells.
Figure 19A:
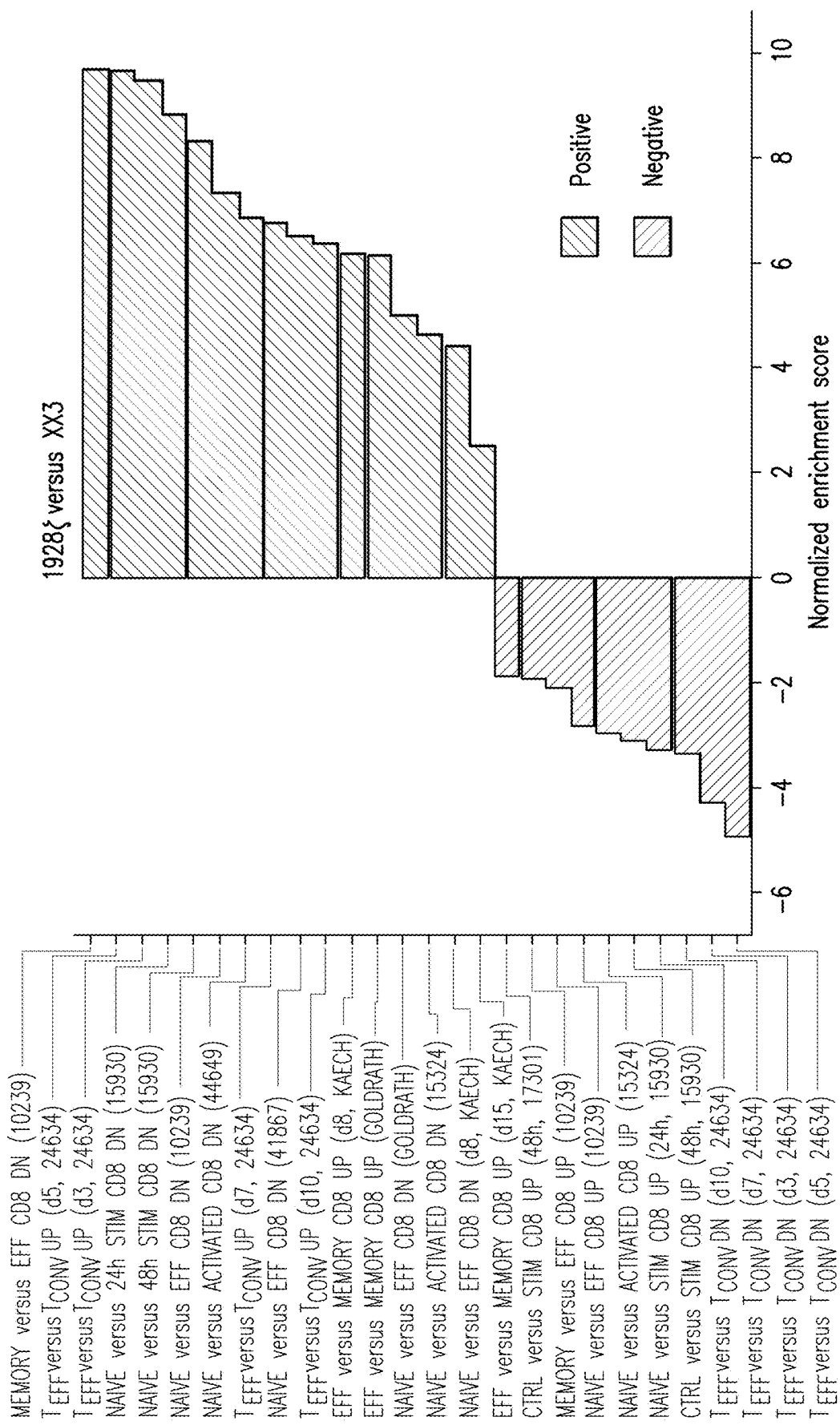
Figure 19B:
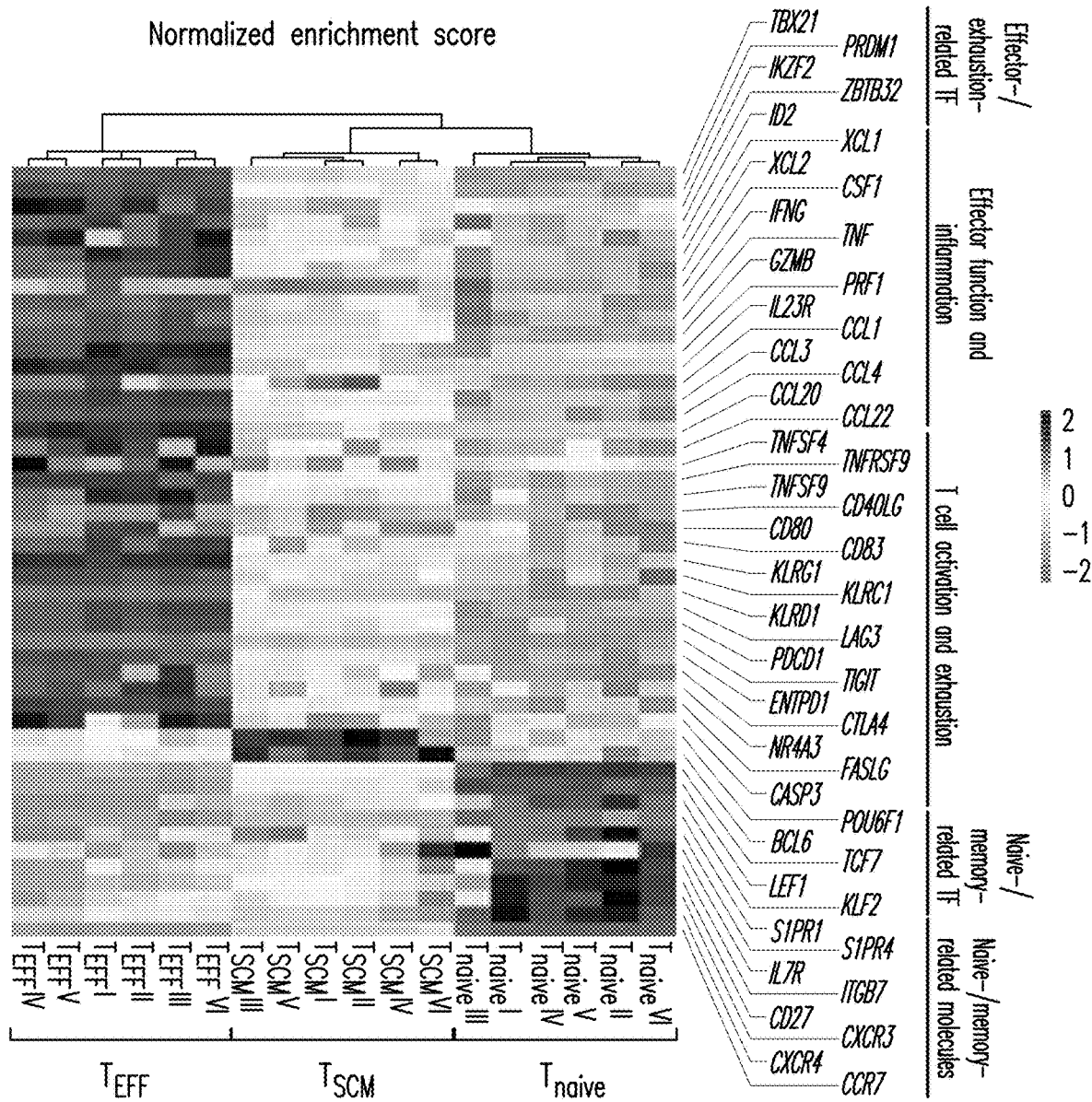
Figure 19B:
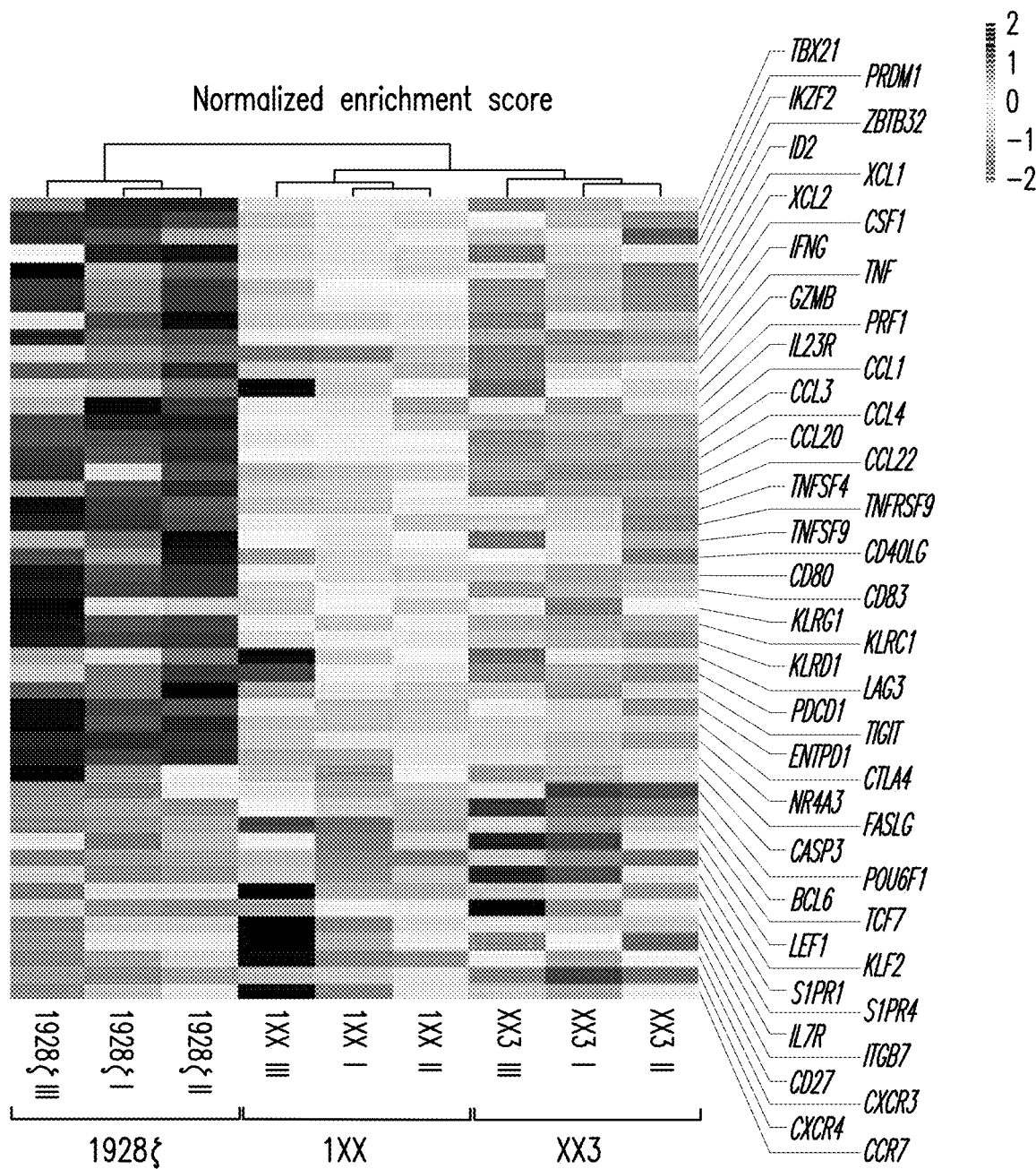
Figure 19C:
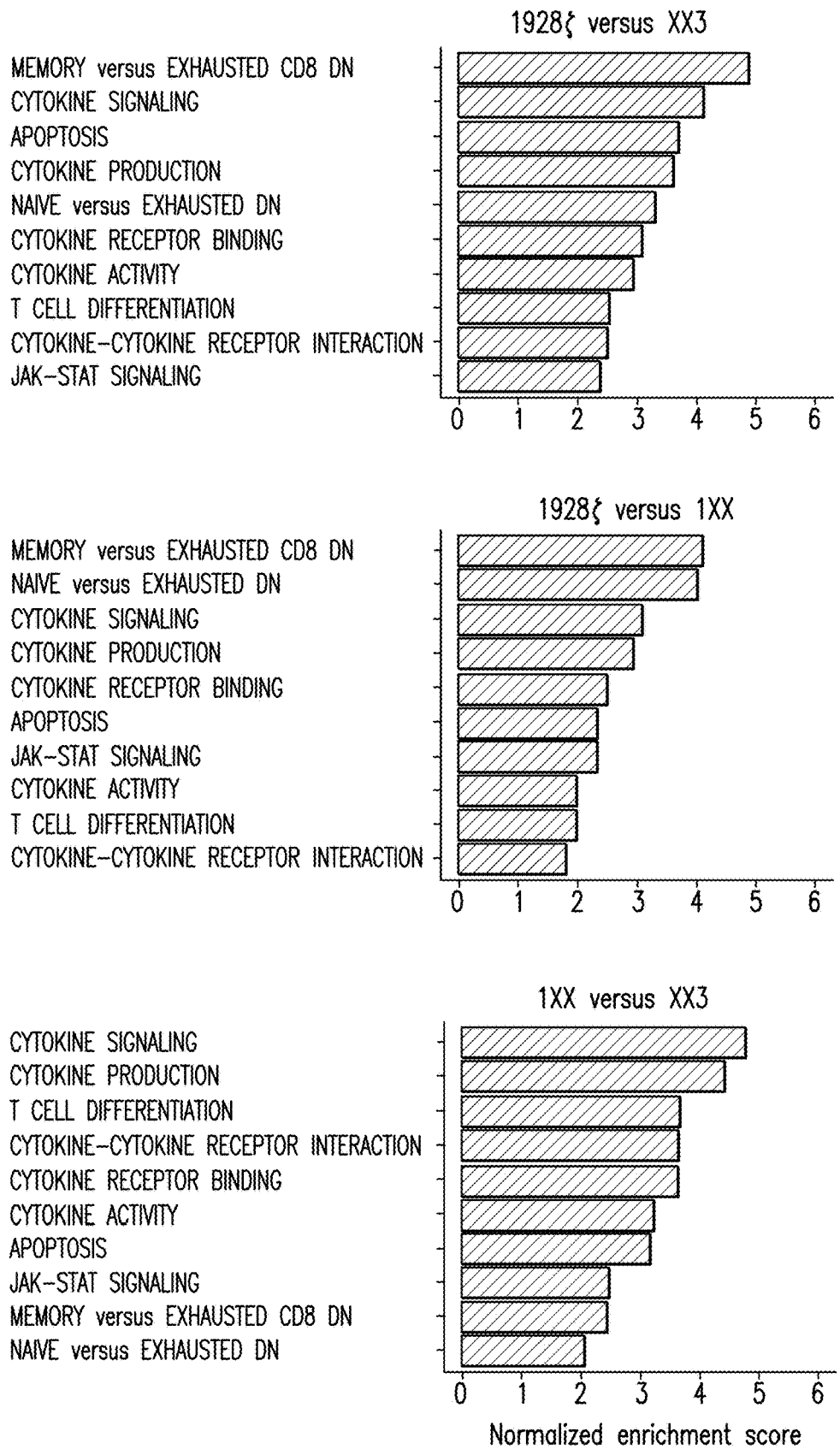
Figure 27A:
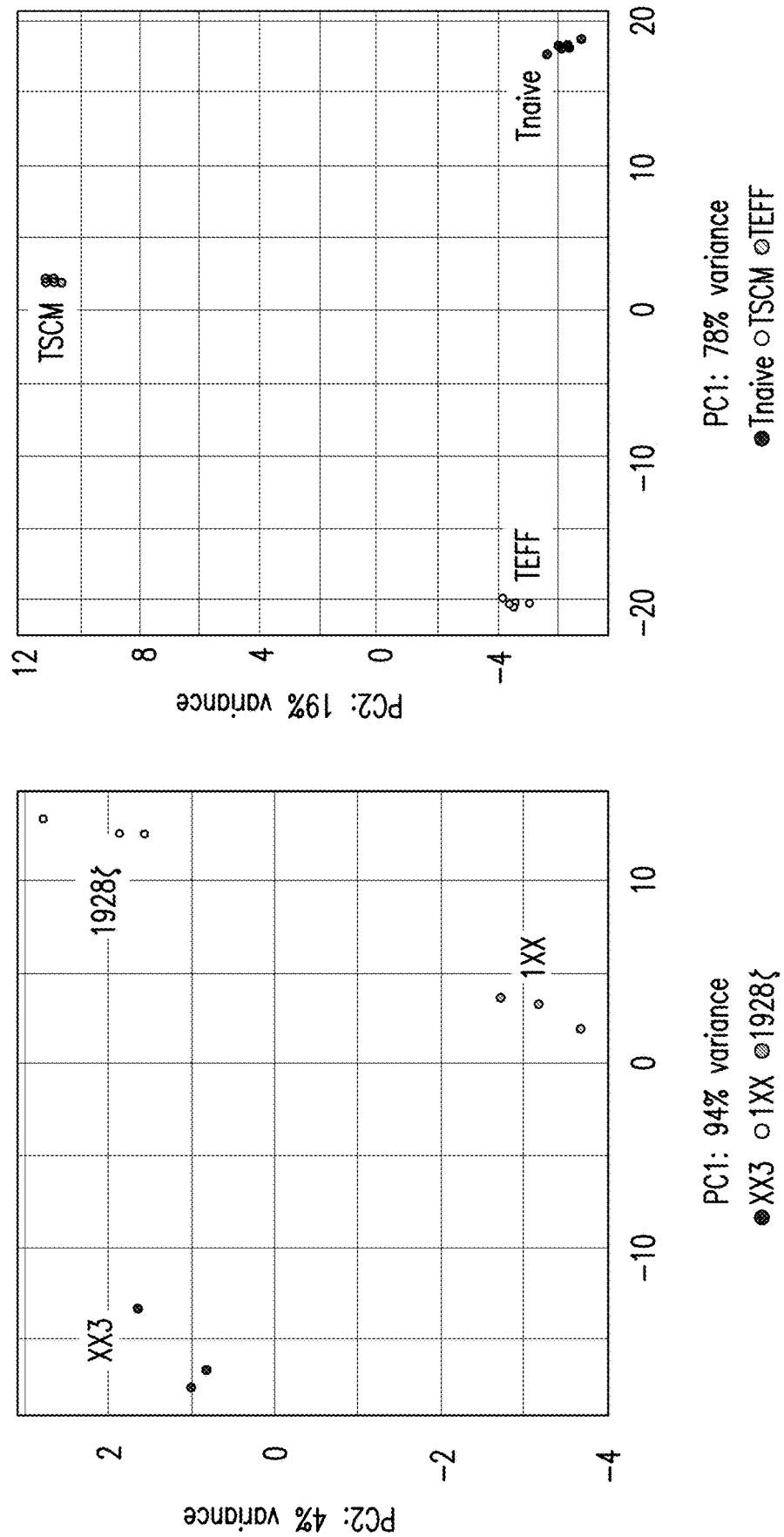
FIGS. 27A-27C depict transcriptional profiles of TRAC-encoded 1928ζ mutants and sorted control T cells.
Figure 27B:
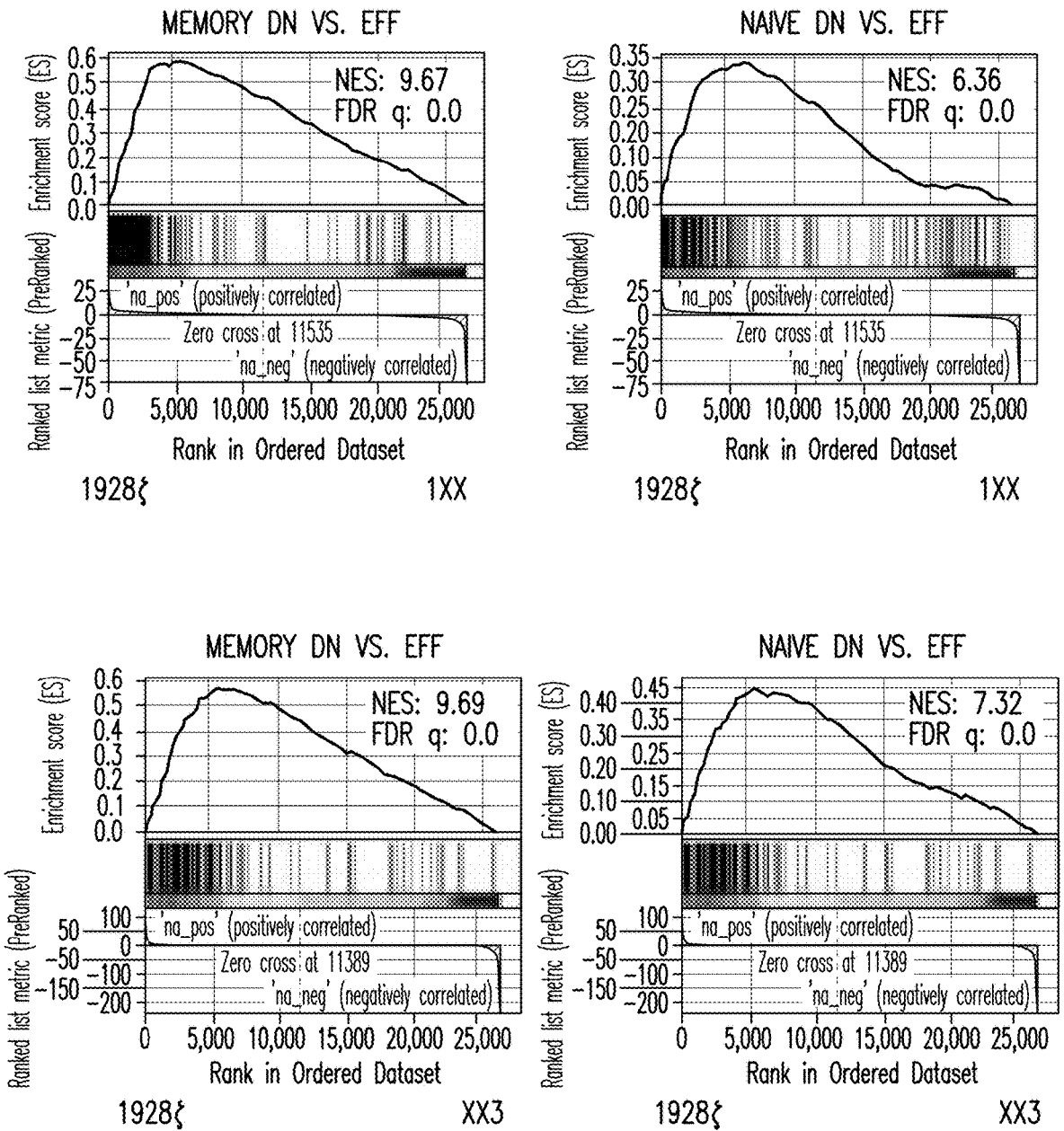
Figure 27C:
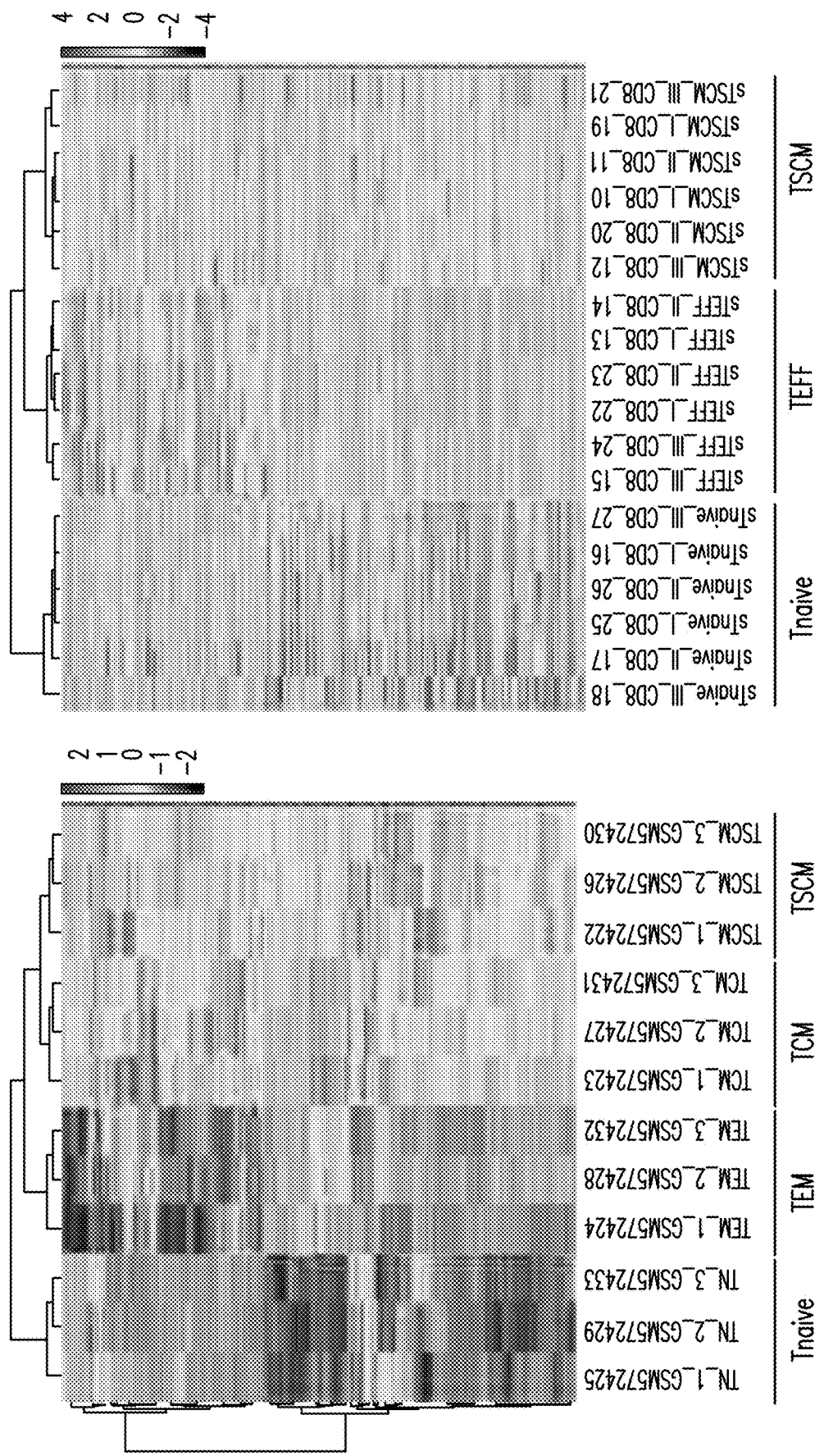
Figure 28A:
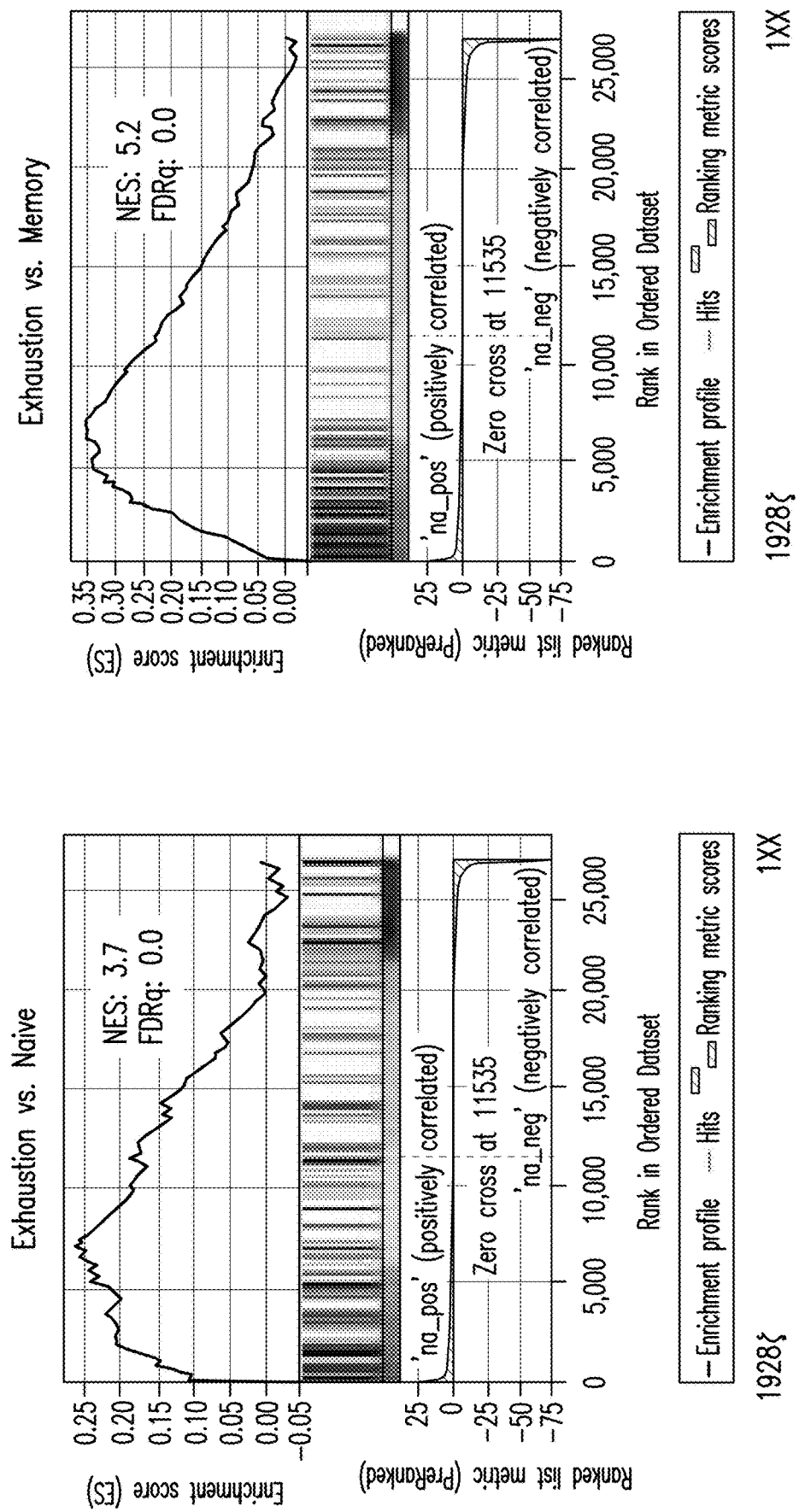
FIGS. 28A-28D depict impact of CD3ζ ITAM mutations in TRAC-1928ζ on T cell differentiation state and effector profile.
Figure 28A:
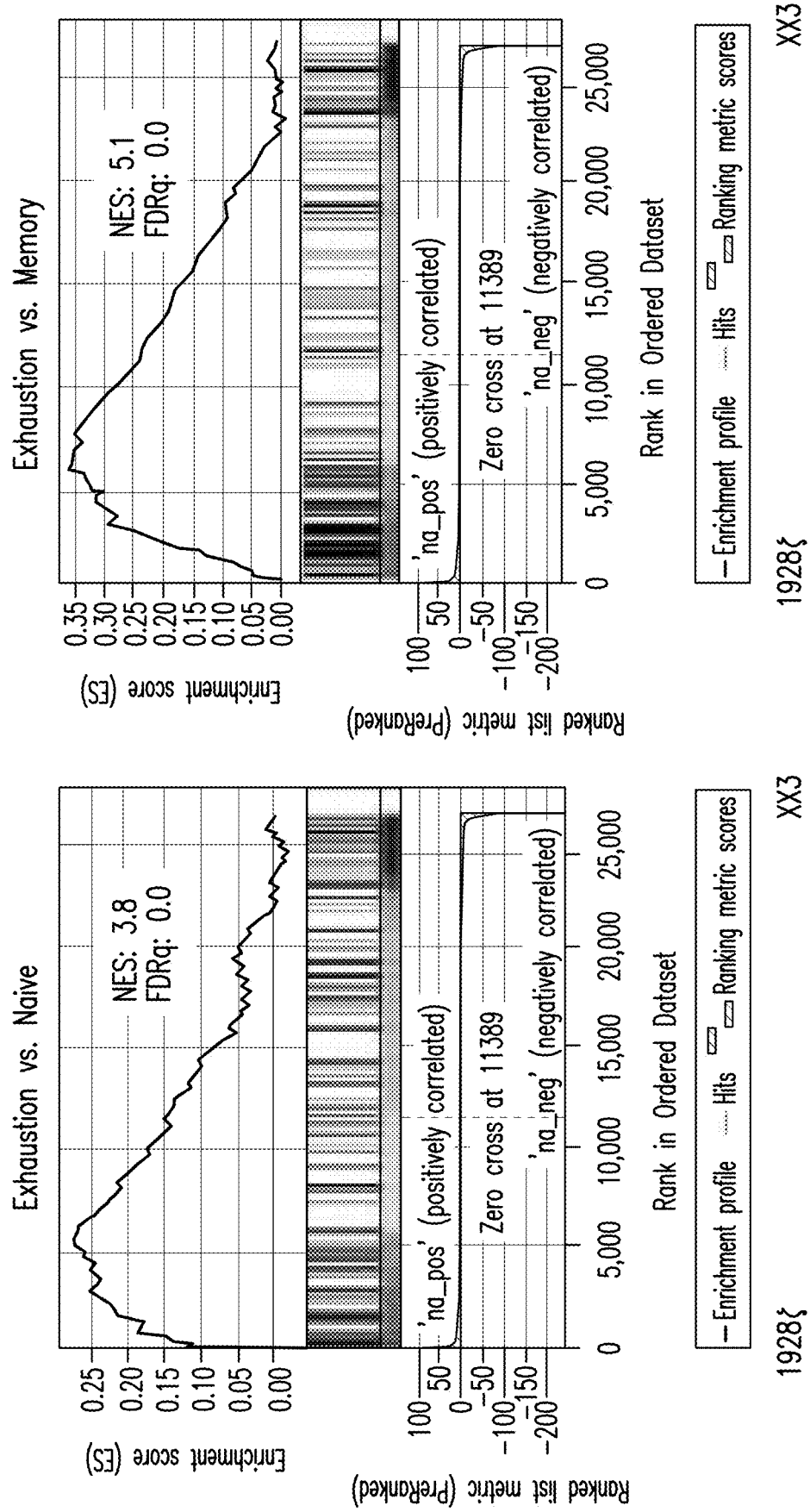
Figure 28A:
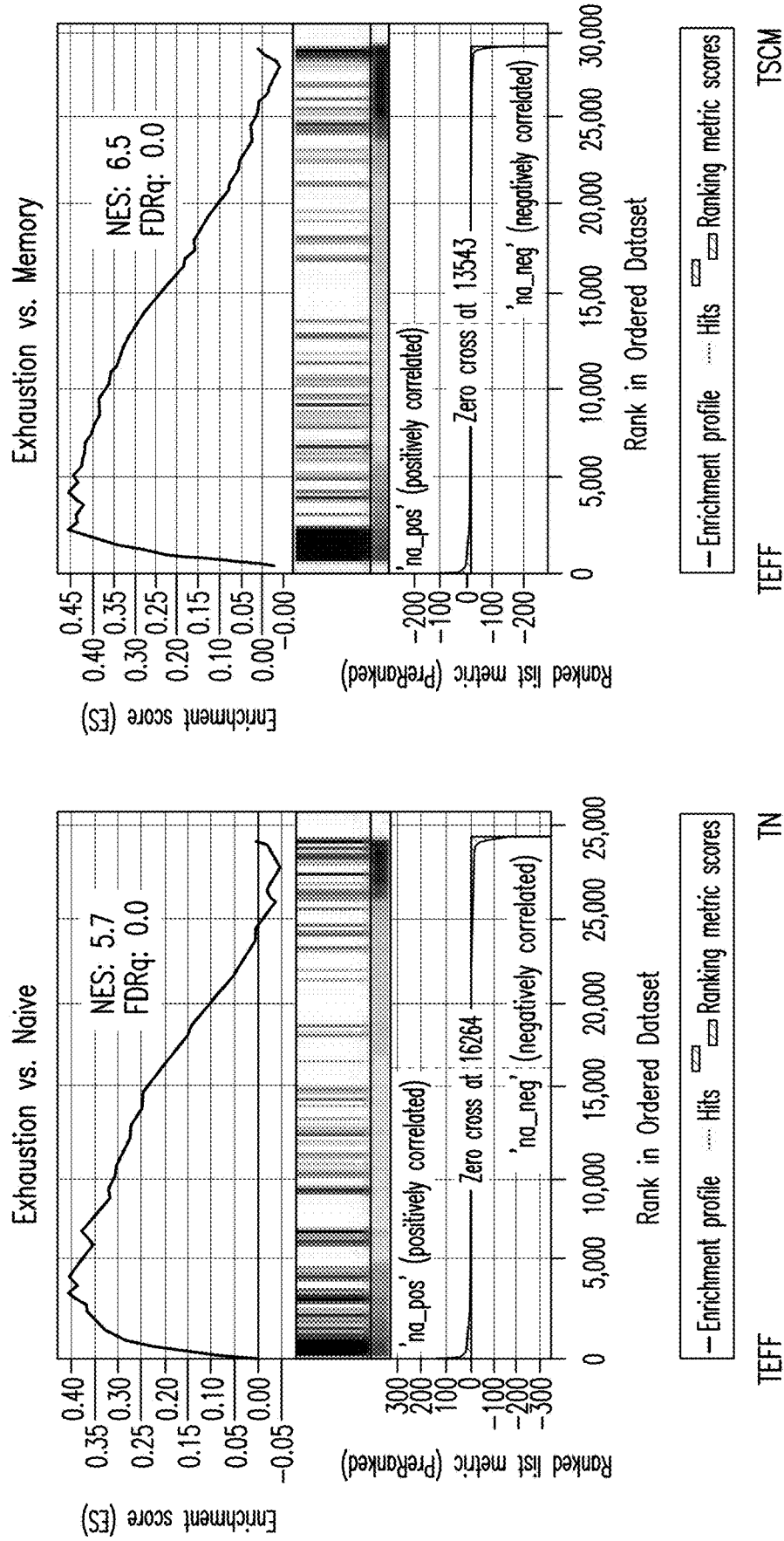
Figure 28B:
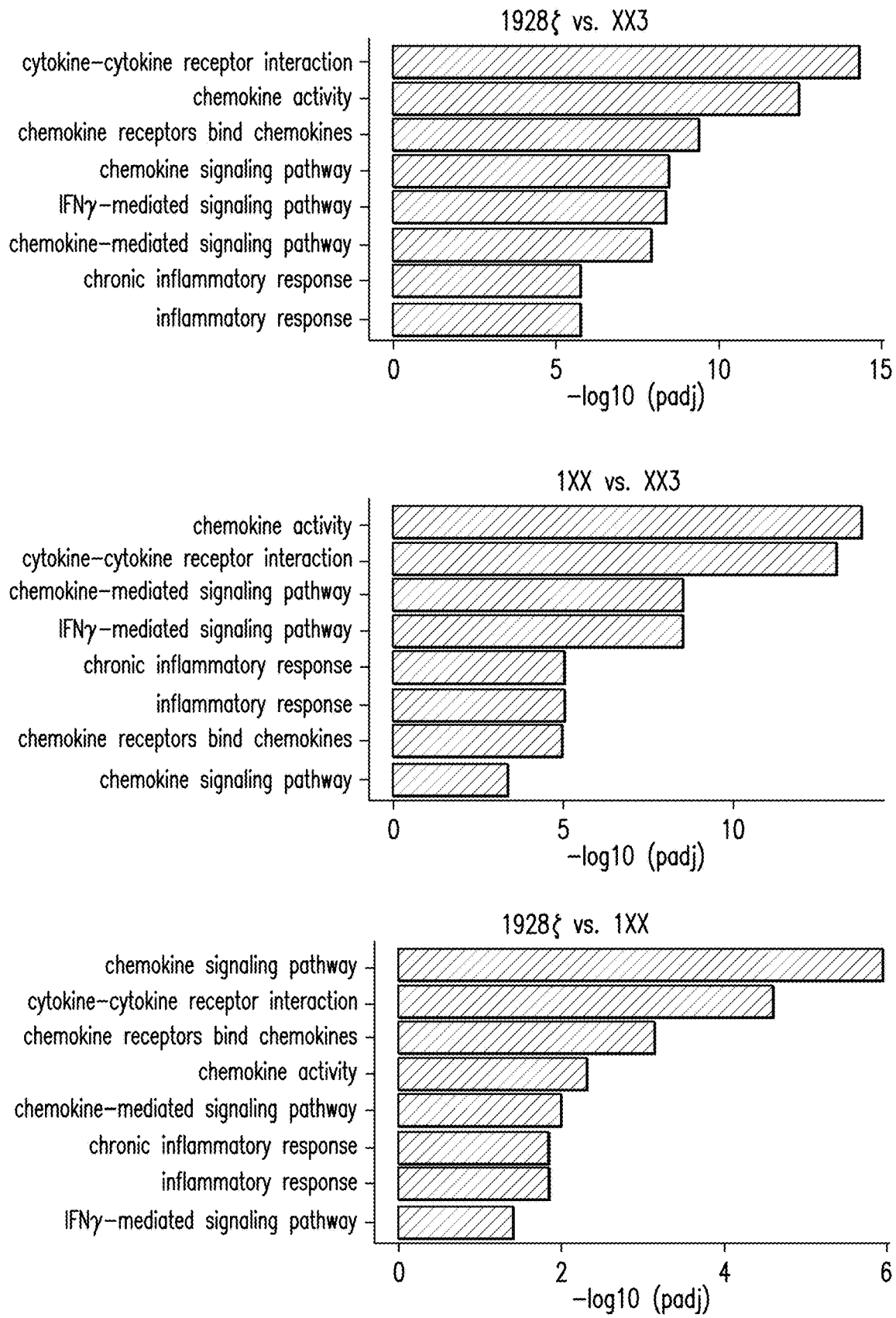
Figure 28C:
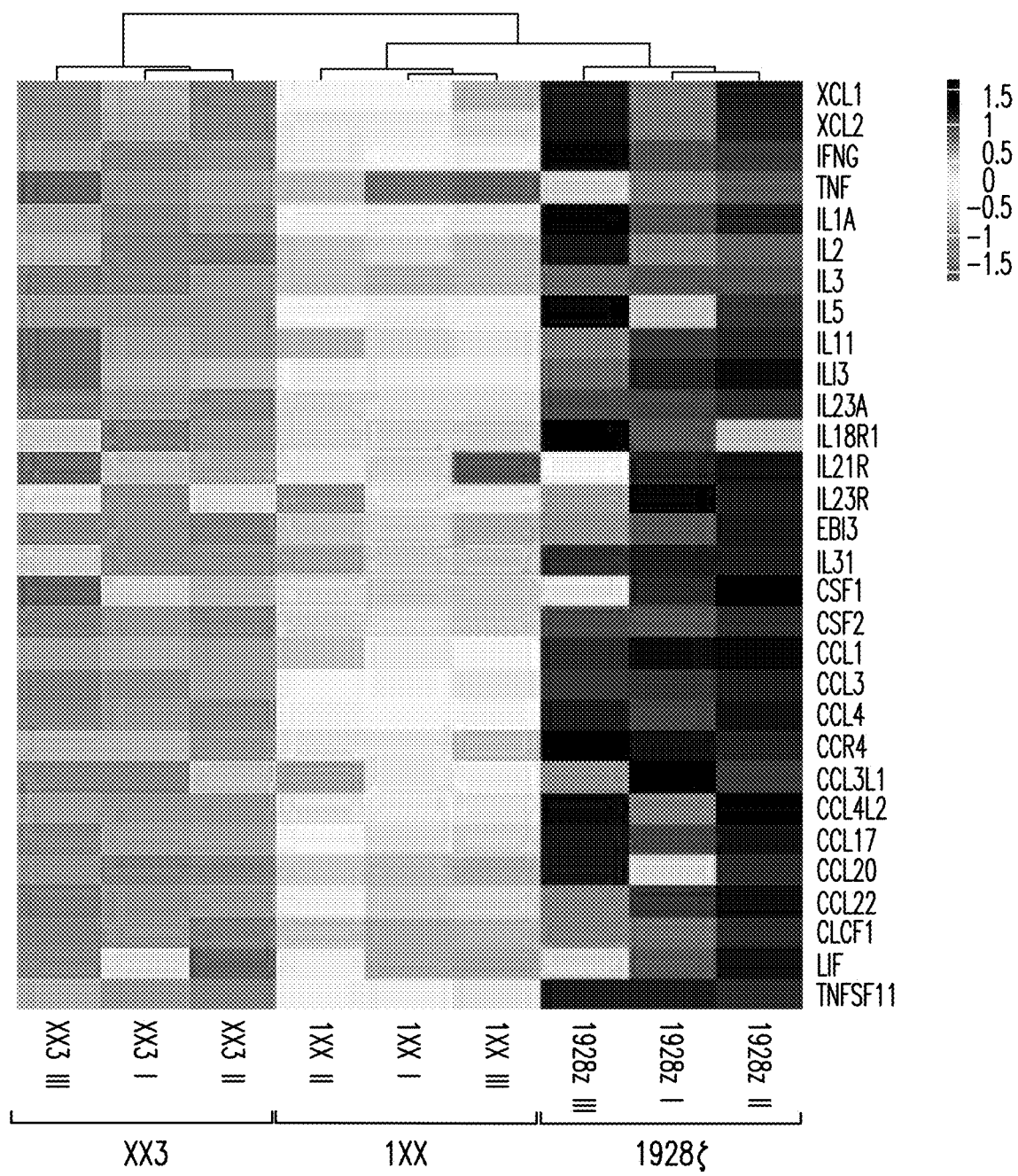

To further characterize these different phenotypic and functional patterns, the genome-wide transcriptional profiles of 1928z, 1XX, and XX3 were compared after CD19 antigen stimulation of TRAC-edited naive T cells. Principal component analysis demonstrated distinct clustering of CAR T cells dependent on their CD3z mutation (FIG. 27A). Consistent with functional studies, major differences emerged in transcriptomic profiles related to T cell function, differentiation, and exhaustion. Gene set enrichment analysis (GSEA) revealed downregulation of naive/memory-associated genes and enrichment of T cell activation- and effector-related genes in 1928z relative to both XX3 and 1XX (FIG. 19A and FIG. 27B). As expected, 1928z CAR T cells showed the greatest upregulation of T cell differentiation, exhaustion, and apoptosis gene expression profiles (FIGS. 19B and 19C and FIG. 28A). Gene ontology and GSEA analyses identified significant upregulation of the gene sets associated with inflammation, cytokine, and chemokine activity in 1928z compared to XX3 and in 1XX compared to XX3 (FIG. 19C and FIGS. 28B and 28C). These gene sets were also enriched in 1928z relative to 1XX, albeit to a lesser extent, consistent with the intermediate status of 1XX relative to 1928z and XX3 (FIGS. 19B and 19C and FIGS. 28B and 28C). To compare TRAC-edited CAR T cells to the effector and memory features of nongenetically modified CD8$^+$ T cell subsets, naive ($T_N$), stem cell memory ($T_{SCM}$ two or more), and $T_{EFF}$ were sorted from resting peripheral blood mononuclear cells as their characteristic transcriptional profiles were previously determined[21] (FIG. 27C). Differentially expressed genes (adjusted P<0.05) associated with effector versus naive/memory T cell fate distinguished these CAR constructs (FIG. 19B). Interestingly, TRAC-1XX cells exhibited more similarity to TSCM than TRAC-1928z and TRAC-XX3 T cells, which in turn were more similar to $T_{EFF}$ and $T_N$ cells, respectively (FIG. 19B).

Figure 19D:
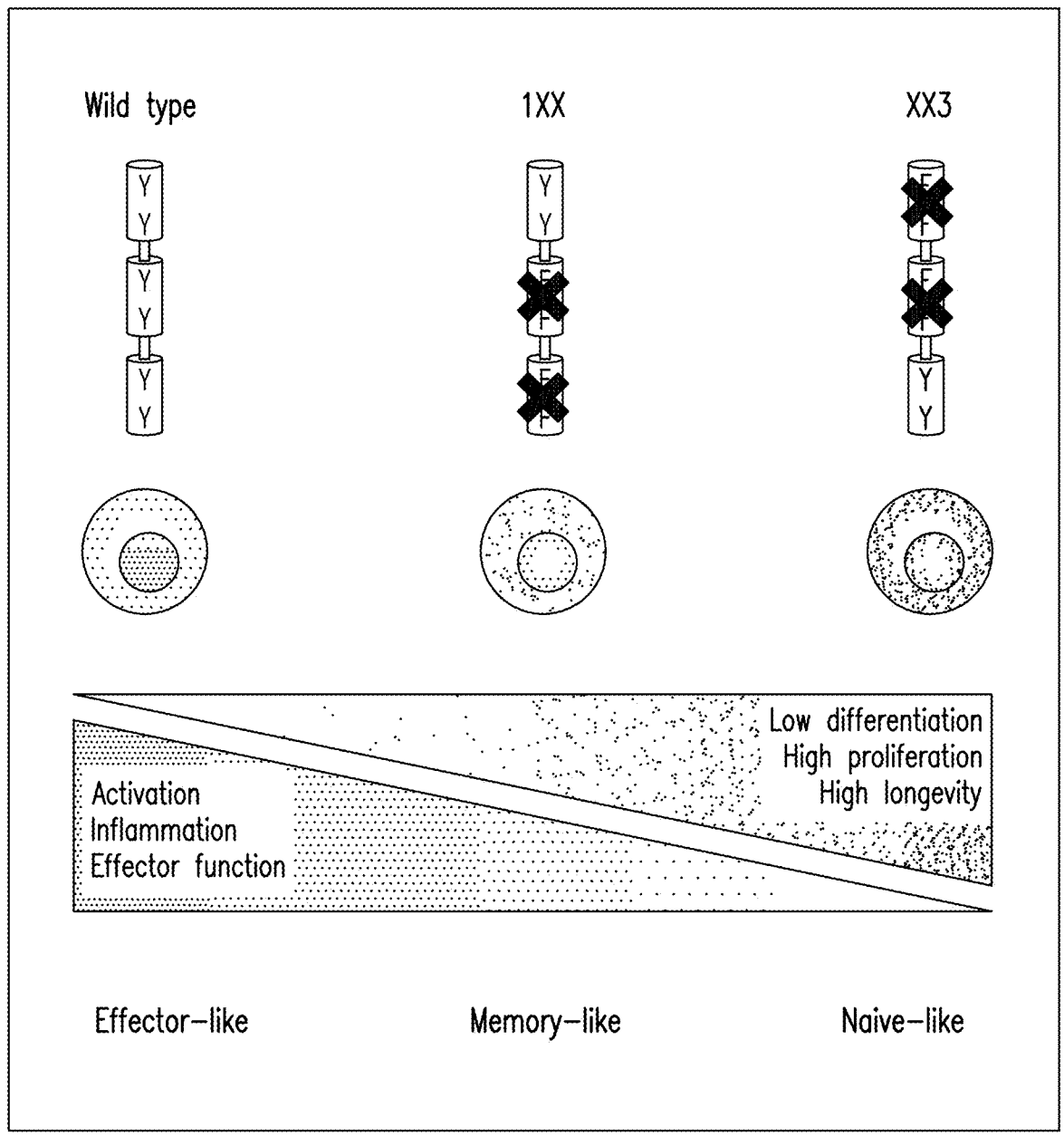
Figure 28D:
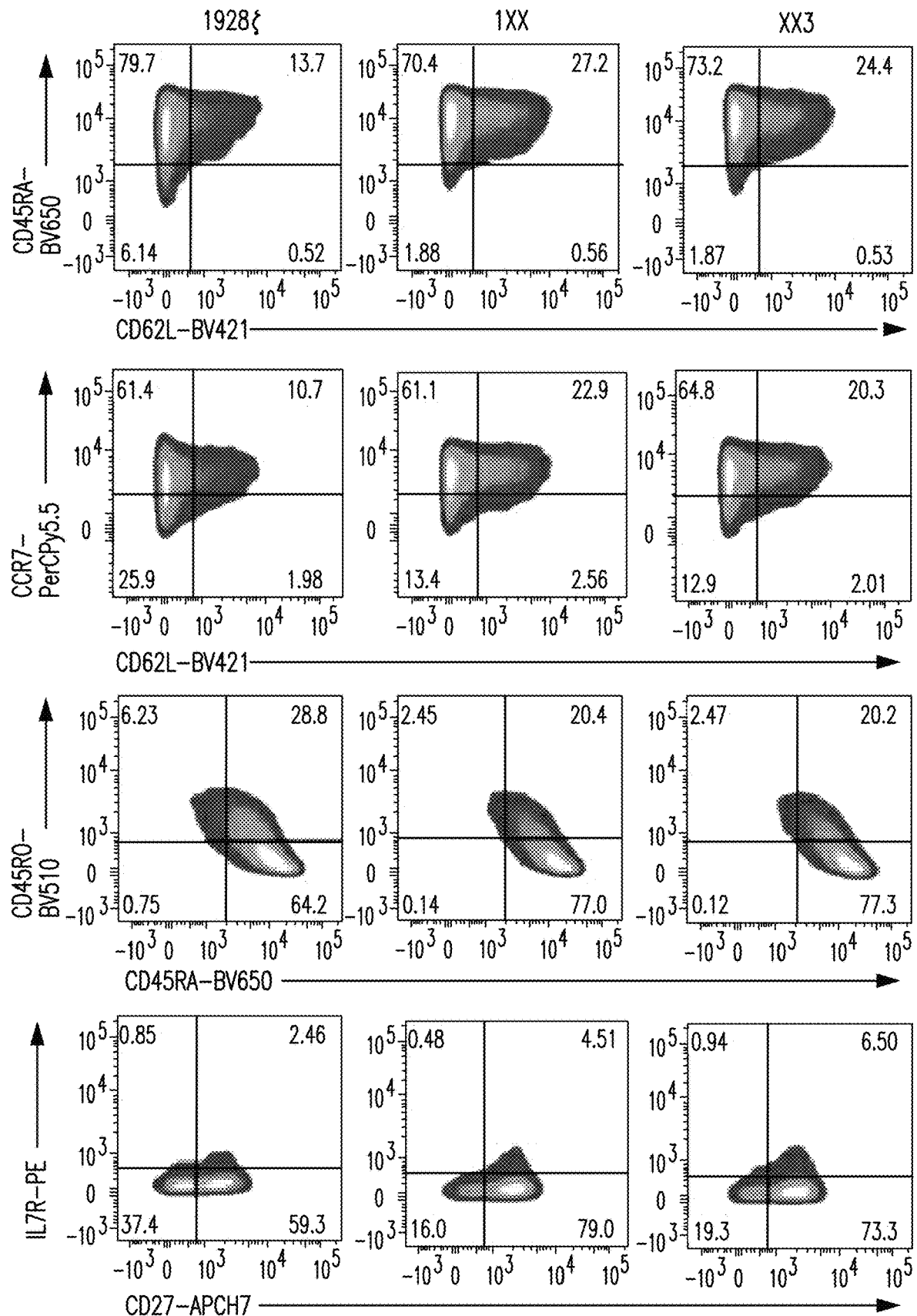

Upregulation of key regulators of effector differentiation such as T-bet (and T-bet:Eomes ratio), PR domain zinc finger protein 1 (PRDM1), and DNA-binding protein inhibitor ID-2 (refs. 22-24) with concurrent loss of naive/memory-associated markers (for example, CCR7, CD27, and IL7R[21]) corroborated the rapid acquisition of an effector state seen with 1928z (FIG. 19B and FIGS. 28C and 28D). In contrast, the tuned signaling strength in 1XX resulted in decelerated T cell differentiation and preserved expression of important memory-associated transcription factors, such as transcription factor 7 (TCF7), B-cell lymphoma 6 protein (BCL6), lymphoid enhancer-binding factor 1 (LEF1), and Krüppel-like factor 2 (KLF2)[23-26] (FIG. 19B), further reflected in the upregulation of KLF2-regulated genes such as CCR7, CD62L, ITGB7, and S1PR1 (refs.[27,28]) (FIG. 19B and FIG. 28D). While 1XX T cells only demonstrated a partial shift toward a less-differentiated T cell state, XX3 revealed high levels of naive/memory-associated genes together with a systematic suppression of genes encoding master transcription factors for T cell differentiation and effector function (FIGS. 19B-19D). These findings underscore the critical role of ITAM dosage and position to impart different T cell fates. They further support models of memory formation that place cell fate under the control of strength of signaling[24,29].

Recent reports support the notion that less-differentiated T cell subsets and memory features are associated with increased antitumor potency and persistence of adoptively transferred T cells[30,31].

The results extend these findings in demonstrating that T cell differentiation states can be intrinsically controlled by mutations in the CD3z chain of CAR T cells. The CD28 and CD3z signaling domains are constrained into a 1:1 stoichiometry within CARs[2], differing from their natural spatiotemporal relationship[11]. Prior studies on CD3ζ mutations were limited to in vitro comparisons[32-34] that did not uncover major effects, in contrast to the crucial consequences uncovered in vivo (FIG. 16). The in vivo studies demonstrate that balancing T cell differentiation and acquisition of effector functions is essential to optimize therapeutic potency of CAR T cells based on a comparison of different signaling motifs expressed from a constant genomic locus (FIGS. 18 and 19). This experimental setting was believed to be optimal for quantitative CAR and TCR comparisons[19].

In summary, 1XX induced strong effector functions without shutting off memory programs and outperformed 1928ζ in stress test conditions. Further reducing T cell activation potential through XX3 resulted in highly persisting T cells but mediocre antitumor activity owing to insufficient elicitation of effector functions. Remarkably, the modified ITAM configuration in 1XX favors persistence of highly functional CARs, balancing the replicative capacity of long-lived memory cells and the acquisition of effective antitumor function. Preparations for clinical studies that utilize the 1XX CAR design are underway.

Methods

Cells Lines and Culture Conditions.

Nalm6 cells were transduced to express firefly luciferase (FFLuc)-green fluorescent protein (GFP), and murine thymoma EL4 cells and NIH/3T3 cells were transduced to express human CD19 as described previously[8,20]. Cells were regularly tested for *Mycoplasma* using the MycoAlert *Mycoplasma* Detection Kit (Lonza) and found to be negative.

Isolation and Expansion of Human T Cells.

Buffy coats from anonymous healthy donors were purchased from the New York Blood Center (institutional review board-exempted) and peripheral blood was obtained from healthy volunteers. All blood samples were handled following the required ethical and safety procedures. Peripheral blood mononuclear cells were isolated by density gradient centrifugation and activated with phytohemagglutinin (2 μg ml$^{-1}$) for experiments performed with retroviral vectors or T cells were purified using the Pan T Cell Isolation Kit (Miltenyi Biotec) and stimulated with CD3/CD28 T cell Activator Dynabeads (Invitrogen) as described previously[19] and cultured in X-VIVO 15 Serum-free Hematopoietic Cell Medium (Lonza), supplemented with 5% human serum (Gemini Bio-Products), 5 ng ml$^{-1}$ interleukin-7 (IL7) and 5 ng ml$^{-1}$ IL15 (BioLegend) for the gene targeting experiments. The medium was changed every 2 d, and cells were plated at 10$^6$ cells per ml.

For some experiments, naive (TCR$^+$CD62L$^+$CCR7$^+$CD45RA$^+$CD95$^-$), TSCM (TCR$^+$CD62L$^+$CCR7$^+$CD45RA$^+$CD95$^+$), and T$_{EFF}$ cells (TCR$^+$CD62L$^-$CCR7$^-$CD45RA$^+$CD95$^+$) were sorted by flow cytometry. The CAR cDNA was then targeted to the TRAC locus of sorted naive T cells, followed by in vitro culture and TCR-negative purification as described later on. Seven days after gene targeting was performed, T cells were stimulated with 3T3-CD19 for 24 h for further analysis or injected into tumor-bearing mice.

Genetic Modification of T Cells.

Plasmids encoding the SFGγ retroviral vector[35] were prepared using standard molecular biology techniques as described previously[20]. Vesicular stomatitis virus glycoprotein G (VSV-G) pseudotyped retroviral supernatants derived from transduced gpg29 fibroblasts (H29) were used to construct stable retroviral-producing cell lines[36].

Synthesis of SFG-1928ζ has been previously described[2,20,37]; it comprises a single-chain variable fragment specific for the human CD19, preceded by a CD8a leader peptide and followed by CD28 hinge-transmembrane-intracellular regions, and CD3ζ or ITAM-mutated/deleted CD3ζ intracellular domains linked to a P2A sequence to induce coexpression of truncated low-affinity nerve growth factor receptor (LNGFR). Standard molecular biology techniques were used to construct the 1928ζ mutants. Tyrosine-to-phenylalanine point mutations within the ITAMs of the CD3ζ chain were introduced to generate 1928ζ CARs with one or two functional ITAMs. For deletion mutations, the membrane-proximal ITAM sequence (ITAM1) was retained or substituted with the membrane-distal ITAM (ITAM3) sequence, and the remaining CD3ζ domain was deleted. 48-h after initiating T cell activation, T cells were transduced with retroviral supernatants by centrifugation on RetroNectin-coated plates (Takara), as described previously. Transduction efficiencies were determined 4 d later by flow cytometry, and CARs were either injected into tumor-bearing mice or used for in vitro experiments.

Gene targeting experiments were performed as described previously[19]. In short, modified guide RNAs (gRNAs) targeting the first exon of the constant chain of the TRA gene[19] and Cas9 messenger RNA (mRNA) were synthesized by TriLink BioTechnologies. The pAAV-TRAC-1928ζ was cloned based on a pAAV-GFP backbone (Cell Biolabs). The pAAV-TRAC-1928ζ contains 1.9 kb of genomic TRAC flanking the gRNA targeting sequences, a self-cleaving P2A peptide in-frame with the first exon of TRAC followed by the 1928ζ or 1928ζ mutant CAR as described earlier. The CAR cDNA is followed by the bovine growth hormone polyA signal.

CD3/CD28 beads were magnetically removed 48 h after initiating T cell activation. T cells were transfected by electrotransfer of Cas9 mRNA and gRNA using an AgilePulse MAX system (BTX) and recombinant AAV6 donor vector (manufactured by SignaGen Laboratories) was added to the culture following electroporation as described previously[19]. To obtain TCR-negative T cells, TCR-positive T cells were removed from the culture using magnetic biotin-anti-TCRαβ, anti-biotin microbeads, and LS columns (Miltenyi Biotec).

Cytotoxicity Assays.

The cytotoxicity of T cells transduced with a CAR was determined by standard $^{51}$Cr release assays and luciferase-based assays. For $^{51}$Cr release assays, EL4 expressing CD19 were used as target cells as described previously[38]. For luciferase-based assays, Nalm6-expressing FFLuc-GFP served as target cells. The effector and tumor target cells were cocultured in triplicates at the indicated effector/target ratio using black-walled 96-well plates with 5×10$^4$ target cells in a total volume of 100 μl per well in Nalm6 medium. Target cells alone were plated at the same cell density to determine the maximal luciferase expression (relative light units (RLU)); 18 h later, 100 luciferase substrate (Bright-Glo; Promega) was directly added to each well. Emitted light was detected in a luminescence plate reader. Lysis was determined as (1−(RLUsample)/(RLUmax))×100.

Antigen Stimulation and Proliferation Assays.

Four days after transduction, CAR T cells were cocultured with irradiated confluent CD19$^+$ NIH/3T3, at 10$^6$ CAR$^+$ cells per ml in 24-well tissue culture plates. Identical stimulations in fresh medium were performed weekly. Total cells were counted and CAR expression was determined weekly by flow cytometry. Subsequently, CAR T cells were restimulated under the same conditions.

Mouse Systemic Tumor Model.

6- to 12-week-old NOD/SCID/IL-2Rγ null male mice (The Jackson Laboratory) were used under a protocol approved by the Memorial Sloan Kettering Cancer Center (MSKCC) Institutional Animal Care and Use Committee.

All relevant animal use guidelines and ethical regulations were followed. Mice were inoculated with $0.5 \times 10^6$ FFLuc-GFP NALM6 cells by tail vein injection, followed by $5 \times 10^4$, $1 \times 10^5$, or $5 \times 10^5$ CAR T cells injected 4 d later. Tumor rechallenge experiments were performed by intravenous administration of $0.5 \times 10^6$, $1 \times 10^6$ or $2 \times 10^6$ FFLuc-GFP Nalm6 cells at intervals of 7-10 d at the indicated time points. Nalm6 produce very even tumor burdens, and no mice were excluded before treatment. No randomization or blinding methods were used. Bioluminescence imaging was performed using the IVIS Imaging System (PerkinElmer) with the Living Image software (PerkinElmer) for the acquisition of imaging datasets. Tumor burden was assessed as described previously[9].

RNA Extraction, Transcriptome Sequencing and RNA-Seq Analysis.

Seven days after gene targeting of sorted naive T cells was performed, TRAC-1928ζ, TRAC-XX3, and TRAC-1XX were stimulated with irradiated 3T3-CD19 for 24 h, followed by magnetic selection of CD8+ cells (Miltenyi Biotec). Washed T cells were resuspended in 250 µl PBS and placed in 750 µl TRIzol LS Reagent (Thermo Fisher Scientific). RNA was extracted using the RNeasy Mini Kit (QIAGEN) according to the instructions provided by the manufacturer. After RiboGreen RNA quantification and quality control using an Agilent Bioanalyzer, 500 ng of total RNA underwent polyA selection and TruSeq RNA library preparation according to the instructions provided by the manufacturer (TruSeq Stranded mRNA LT Kit; Illumina), with eight cycles of PCR. Samples were barcoded and run on a HiSeq 4000 (Illumina) in a 50 basepair (bp)/50 bp paired-end run, using the HiSeq 3000/4000 SBS Kit (Illumina). An average of 30.6 million paired reads was generated per sample. At the most, the ribosomal reads represented 4.69% of the total reads generated; the percentage of mRNA bases averaged 69.3%.

The output FASTQ data were mapped to the target genome using the STAR RNA-seq aligner (version 2.5.0a; two-pass method)[40], resolving reads across splice junctions. The first mapping pass uses a list of known annotated junctions from Ensemble (https://www.ensembl.org/index.html). Junctions found during the first pass are then added to the known junctions and a second mapping pass is done using the RemoveNoncanonical flag. After mapping, the output SAM files (SAMtools, version 0.1.19) were processed using PICARD tools (version 1.124; https://broadinstitute.github.io/picard/) to add read groups and AddOrReplaceReadGroups, which in addition sorts the file and converts it to the compressed BAM format. The expression count matrix was then computed from the mapped reads using HTSeq (version 0.5.3; https://htseq.readthedocs.io/en/release_0.10.0/) and one of several possible gene model databases. The R (version 3.2.0) package DESeq (https://www.huber.embl.de/users/anders/DESeq/) was used to both normalize the full dataset and analyze differential expression between sample groups.

Differentially expressed genes between T cell subsets ($T_N$, $T_{CM}$, $T_{SCM}$, $T_{EFF}$ cells) were retrieved from Gattinoni et al.[21]. GSEA was performed using a pre-ranked file generated using $\log_2$(fold change) on curated pathway gene sets from the Broad Institute Molecular Signature Database (http://www.broadinstitute.org/gsea/msigdb/). The gene signatures demonstrated are derived from immunological signatures C7, Reactome, KEGG and gene ontology (Biological Process) gene sets. GSE41867 was used for the GSEA of exhausted versus naive/memory CD8 T cells and to curate the signature of 200 genes upregulated in exhausted CD8 T cells (day 30 post-lymphocytic choriomeningitis virus infection) relative to memory and naive cells. Genes identified as differentially expressed between experimental conditions, with an adjusted P value <0.05 and absolute $\log_2$(fold change)>1, were used for gene ontology analysis using the R package enrichR (http://amp.pharm.mssm.edu/Enrichr/).

Antibodies and Intracellular Staining.

The following fluorophore-conjugated antibodies were used. From BD Biosciences: APC-Cy7 mouse anti-human CD8; APC-Cy7 mouse anti-human CD45; BUV395 mouse anti-human CD4; PE mouse anti-human CD4; BB515 mouse anti-human CD4; BV421 mouse anti-human CD62L; BV650 mouse anti-human CD45RA; BV421 mouse anti-human CD45RA; BV480 mouse anti-human CD279 (PD-1); BV650 mouse anti-human CD279 (PD-1); BUV737 mouse anti-human CD19; BV421 mouse anti-human TIM3 (CD366); BB515 mouse anti-human CD95; APC-H7 mouse anti-human CD27; PE mouse anti-human CD271 (LNGFR). From BioLegend: APC anti-human CD8a; APC/Cy7 anti-human CD62L; FITC anti-human CD45RA; Brillian Violet 785 anti-human CD366 (Tim-3); PE anti-human CD127 (IL-7Rα); Alexa Fluor 488 anti-human CD127 (IL-7Rα); PerCP/Cyanine5.5 anti-human CD197 (CCR7); Brilliant Violet 650 anti-human CD28. From Invitrogen: CD8a Monoclonal Antibody (RPA-T8), PE-Cyanine7; CD223 (LAG-3) monoclonal antibody (3DS223H) PerCP-eFluor 710; CD223 (LAG-3) Monoclonal Antibody (3DS223H), APC; InvitrogenTCR alpha/beta monoclonal antibody (IP26), PE-Cyanine7. From Miltenyi Biotec: human monoclonal Anti-TCRα/β-PE. 7-AAD (BD Biosciences) and LIVE/DEAD Fixable Violet Dead Cell Stain Kit (Invitrogen) were used as viability dyes.

For CAR staining, an Alexa Fluor 647 AffiniPure $F(ab')_2$ Fragment Goat Anti-Mouse IgG, $F(ab')_2$ fragment specific antibody was used (Jackson ImmunoResearch). For cell counting, CountBright Absolute Counting Beads were added (Invitrogen) according to the manufacturer's instructions. For in vivo experiments, Fc receptors were blocked using FcR Blocking Reagent, mouse (Miltenyi Biotec).

For intracellular cytokine secretion assay, T cells were cocultured with 3T3-CD19 or Nalm6 in the presence of the Golgi Plug protein transport inhibitor (BD Biosciences) for the last 4 h. For CD107a staining, Brilliant Violet 650 anti-human CD107a (LAMP-1) antibody (BioLegend) was added to the coculture. For ex vivo cytokine analyses, CAR T cells were obtained from the bone marrow and spleen of treated mice and purified using a mouse cell depletion kit (Miltenyi Biotec). Samples were processed in biological triplicates (d16) or pooled (due to low cell numbers in 1928ζ-treated mice), and technical triplicates (d36) were performed. Stimulation with phorbol myristate acetate (PMA)/ionomycin (Invitrogen) were performed as the positive control. T cells were subsequently washed, stained for cell surface markers, fixed, and permeabilized according to the manufacturer's instructions using a Cytofix/Cytoperm Fixation/Permeabilization Solution Kit (BD Biosciences). Intracellular cytokine staining was performed with BV421 rat anti-human IL2, BV650 mouse anti-human TNF, BUV395 mouse anti-human TNF, BUV395 mouse anti-human IFN-γ, or FITC mouse anti-human IFN-γ (all BD Biosciences), and APC or PE granzyme B monoclonal antibody (GB12, both Invitrogen).

Flow cytometry was performed on a LSR II or LSR-Fortessa instrument (BD Biosciences) and a FACSAria sorter (BD Biosciences) was used for cell sorting. Data were analyzed with the FlowJo software v.10.1 (FlowJo LLC).

Statistical analysis. All statistical analyses were performed using the Prism 7 (GraphPad) software. No statistical methods were used to predetermine sample size. Statistical comparisons between two groups were determined by two-tailed parametric or nonparametric (Mann-Whitney U-test) t-tests for unpaired data or by two-tailed paired Student's t-tests for matched samples. For in vivo experiments, the overall survival was depicted by a Kaplan-Meier curve and the log-rank test was used to compare survival differences between the groups. P values <0.05 were considered to be statistically significant. The statistical test used for each figure is described in the corresponding figure legend.

Reporting Summary. Further information on research design is available in the Nature Research Reporting Summary linked to this article.

Data Availability

The RNA-seq data have been deposited in the Gene Expression Omnibus and are available under accession number GSE121226. Raw data for the figures in the manuscript will be made available upon request to the corresponding author.

REFERENCES

1. Sadelain, M., Riviere, I. & Riddell, S. Therapeutic T cell engineering. *Nature* 545, 423-431 (2017).
2. Maher, J., Brentjens, R. J., Gunset, G., Rivière, I. & Sadelain, M. Human T-lymphocyte cytotoxicity and proliferation directed by a single chimeric TCRzeta/CD28 receptor. *Nat. Biotechnol.* 20, 70-75 (2002).
3. Brentjens, R. J. et al. CD19-targeted T cells rapidly induce molecular remissions in adults with chemotherapy-refractory acute lymphoblastic leukemia. *Sci. Transl. Med.* 5, 177ra38 (2013).
4. Lee, D. W. et al. T cells expressing CD19 chimeric antigen receptors for acute lymphoblastic leukaemia in children and young adults: a phase 1 dose-escalation trial. *Lancet* 385, 517-528 (2015).
5. Park, J. H. et al. Long-term follow-up of CD19 CAR therapy in acute lymphoblastic leukemia. *N. Engl. J. Med.* 378, 449-459 (2018).
6. Neelapu, S. S. et al. Axicabtagene Ciloleucel CAR T-cell therapy in refractory large B-cell lymphoma. *N. Engl. J. Med.* 377, 2531-2544 (2017).
7. Sadelain, M. CD19 CAR T cells. *Cell* 171, 1471 (2017).
8. Zhao, Z. et al. Structural design of engineered costimulation determines tumor rejection kinetics and persistence of CAR T cells. *Cancer Cell* 28, 415-428 (2015).
9. Youngblood, B., Davis, C. W. & Ahmed, R. Making memories that last a lifetime: heritable functions of self-renewing memory CD8 T cells. *Int. Immunol.* 22, 797-803 (2010).
10. Wherry, E. J. & Kurachi, M. Molecular and cellular insights into T cell exhaustion. *Nat. Rev. Immunol.* 15, 486-499 (2015).
11. Acuto, O. & Michel, F. CD28-mediated co-stimulation: a quantitative support for TCR signalling. *Nat. Rev. Immunol.* 3, 939-951 (2003).
12. Smith-Garvin, J. E., Koretzky, G. A. & Jordan, M. S. T cell activation. *Annu. Rev. Immunol.* 27, 591-619 (2009).
13. Love, P. E. & Hayes, S. M. ITAM-mediated signaling by the T-cell antigen receptor. *Cold Spring Harb. Perspect. Biol.* 2, a002485 (2010).
14. Kersh, E. N., Shaw, A. S. & Allen, P. M. Fidelity of T cell activation through multistep T cell receptor zeta phosphorylation. *Science* 281, 572-575 (1998).
15. Isakov, N. et al. ZAP-70 binding specificity to T cell receptor tyrosine-based activation motifs: the tandem SH2 domains of ZAP-70 bind distinct tyrosine-based activation motifs with varying affinity. *J. Exp. Med.* 181, 375-380 (1995).
16. van Oers, N. S. et al. The 21- and 23-kD forms of TCR zeta are generated by specific ITAM phosphorylations. *Nat. Immunol.* 1, 322-328 (2000).
17. Chae, W. J. et al. Qualitatively differential regulation of T cell activation and apoptosis by T cell receptor zeta chain ITAMs and their tyrosine residues. *Int. Immunol.* 16, 1225-1236 (2004).
18. Mukhopadhyay, H., Cordoba, S. P., Maini, P. K., van der Merwe, P. A. & Dushek, O. Systems model of T cell receptor proximal signaling reveals emergent ultrasensitivity. *PLoS Comput. Biol.* 9, e1003004 (2013).
19. Eyquem, J. et al. Targeting a CAR to the TRAC locus with CRISPR/Cas9 enhances tumour rejection. *Nature* 543, 113-117 (2017).
20. Brentjens, R. J. et al. Eradication of systemic B-cell tumors by genetically targeted human T lymphocytes co-stimulated by CD80 and interleukin-15. *Nat. Med.* 9, 279-286 (2003).
21. Gattinoni, L. et al. A human memory T cell subset with stem cell-like properties. *Nat. Med.* 17, 1290-1297 (2011).
22. Chang, J. T., Wherry, E. J. & Goldrath, A. W. Molecular regulation of effector and memory T cell differentiation. *Nat. Immunol.* 15, 1104-1115 (2014).
23. Yu, B. et al. Epigenetic landscapes reveal transcription factors that regulate $CD8^+$ T cell differentiation. *Nat. Immunol.* 18, 573-582 (2017).
24. Kaech, S. M. & Cui, W. Transcriptional control of effector and memory $CD8^+$ T cell differentiation. *Nat. Rev. Immunol.* 12, 749-761 (2012).
25. Ichii, H. et al. Role for Bcl-6 in the generation and maintenance of memory $CD8^+$ T cells. *Nat. Immunol.* 3, 558-563 (2002).
26. Zhou, X. & Xue, H. H. Cutting edge: generation of memory precursors and functional memory $CD8^+$ T cells depends on T cell factor-1 and lymphoid enhancer-binding factor-1. *J. Immunol.* 189, 2722-2726 (2012).
27. Carlson, C. M. et al. Kruppel-like factor 2 regulates thymocyte and T-cell migration. *Nature* 442, 299-302 (2006).
28. Bai, A., Hu, H., Yeung, M. & Chen, J. Kruppel-like factor 2 controls T cell trafficking by activating L-selectin (CD62L) and sphingosine-1-phosphate receptor 1 transcription. *J. Immunol.* 178, 7632-7639 (2007).
29. Daniels, M. A. & Teixeiro, E. TCR signaling in T cell memory. *Front. Immunol.* 6, 617 (2015).
30. Fraietta, J. A. et al. Determinants of response and resistance to CD19 chimeric antigen receptor (CAR) T cell therapy of chronic lymphocytic leukemia. *Nat. Med.* 24, 563-571 (2018).
31. Sommermeyer, D. et al. Chimeric antigen receptor-modified T cells derived from defined $CD8^+$ and $CD4^+$ subsets confer superior antitumor reactivity in vivo. *Leukemia* 30, 492-500 (2016).
32. Zhao, Y. et al. A herceptin-based chimeric antigen receptor with modified signaling domains leads to enhanced survival of transduced T lymphocytes and antitumor activity. *J. Immunol.* 183, 5563-5574 (2009).
33. James, J. R. Tuning ITAM multiplicity on T cell receptors can control potency and selectivity to ligand density. *Sci. Signal.* 11, eaan1088 (2018).
34. Kochenderfer, J. N., Yu, Z., Frasheri, D., Restifo, N. P. & Rosenberg, S. A. Adoptive transfer of syngeneic T cells transduced with a chimeric antigen receptor that recognizes murine CD19 can eradicate lymphoma and normal B cells. *Blood* 116, 3875-3886 (2010).
35. Riviere, I., Brose, K. & Mulligan, R. C. Effects of retroviral vector design on expression of human adenosine deaminase in murine bone marrow transplant recipients engrafted with genetically modified cells. *Proc. Natl Acad. Sci. USA* 92, 6733-6737 (1995).
36. Gong, M. C. et al. Cancer patient T cells genetically targeted to prostate-specific membrane antigen specifically lyse prostate cancer cells and release cytokines in response to prostate-specific membrane antigen. *Neoplasia* 1, 123-127 (1999).
37. Brentjens, R. J. et al. Genetically targeted T cells eradicate systemic acute lymphoblastic leukemia xenografts. *Clin. Cancer Res.* 13, 5426-5435 (2007).
38. Ghosh, A. et al. Adoptively transferred TRAIL+ T cells suppress GVHD and augment antitumor activity. *J. Clin. Invest.* 123, 2654-2662 (2013).
39. Gade, T. P. et al. Targeted elimination of prostate cancer by genetically directed human T lymphocytes. *Cancer Res.* 65, 9080-9088 (2005).
40. Dobin, A. et al. STAR: ultrafast universal RNA-seq aligner. *Bioinformatics* 29, 15-21 (2013).

EMBODIMENTS OF THE PRESENTLY DISCLOSED SUBJECT MATTER

From the foregoing description, it will be apparent that variations and modifications may be made to the presently disclosed subject matter to adopt it to various usages and conditions. Such embodiments are also within the scope of the following claims.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of reducing tumor burden in a subject and/or treating a neoplasm in a subject, the method comprising administering to the subject an effective amount of immunoresponsive cells or a pharmaceutical composition comprising thereof, wherein the immunoresponsive cells comprises:
a chimeric antigen receptor (CAR) comprising an extracellular antigen-binding domain, a transmembrane domain, and an intracellular signaling domain comprising a modified CD3ζ polypeptide, wherein the modified CD3ζ polypeptide comprises amino acids 374 to 485 of SEQ ID NO: 43.

2. A method of treating a subject having a relapse of a neoplasm, wherein i) the subject has a relapse of a disease, ii) the subject received treatment which leads to residual tumor cells, or iii) the subject received an immunoresponsive cell comprising an antigen recognizing receptor comprising a 4-1BB costimulatory signal, the method comprising administering to the subject an effective amount of immunoresponsive cells or a pharmaceutical composition comprising thereof, wherein the immunoresponsive cells comprises:
a chimeric antigen receptor (CAR) comprising an extracellular antigen-binding domain, a transmembrane domain, and an intracellular signaling domain comprising a modified CD3ζ polypeptide, wherein the modified CD3ζ polypeptide comprises amino acids 374 to 485 of SEQ ID NO: 43.

3. The method of claim 1, wherein the transmembrane domain comprises a CD8 polypeptide, a CD28 polypeptide, a CD3ζ polypeptide, a CD4 polypeptide, a 4-1BB polypeptide, an OX40 polypeptide, a CD166 polypeptide, a CD166 polypeptide, a CD8a polypeptide, a CD8b polypeptide, an ICOS polypeptide, an ICAM-1 polypeptide, a CTLA-4 polypeptide, a CD27 polypeptide, a CD40/My88 peptide, a NKGD2 peptide, or a combination thereof.

4. The method of claim 3, wherein the transmembrane domain comprises a CD166 polypeptide.

5. The method of claim 4, wherein the CD166 polypeptide comprises amino acid 528 to 553 of SEQ ID NO: 3.

6. The method of claim 1, wherein the CAR further comprises a hinge/spacer region comprising a CD8 polypeptide, a CD28 polypeptide, a CD3ζ polypeptide, a CD4 polypeptide, a 4-1BB polypeptide, an OX40 polypeptide, a CD166 polypeptide, a CD166 polypeptide, a CD8a polypeptide, a CD8b polypeptide, an ICOS polypeptide, an ICAM-1 polypeptide, a CTLA-4 polypeptide, a CD27 polypeptide, a CD40/My88 peptide, a NKGD2 peptide, or a combination thereof.

7. The method of claim 6, wherein the transmembrane domain and the hinge/spacer region are derived from the same molecule or from different molecules.

8. The method of claim 7, wherein
(a) the hinge/spacer region comprises a CD28 polypeptide and the transmembrane domain comprises a CD28 polypeptide;
(b) the hinge/spacer region comprises a CD84 polypeptide and the transmembrane domain comprises a CD84 polypeptide;
(c) the hinge/spacer region comprises a CD166 polypeptide and the transmembrane domain comprises a CD166 polypeptide;
(d) the hinge/spacer region comprises a CD8a polypeptide and the transmembrane domain comprises a CD8a polypeptide;
(e) the hinge/spacer region comprises a CD8b polypeptide and the transmembrane domain comprises a CD8b polypeptide; or
(f) the hinge/spacer region comprises a CD28 polypeptide and the transmembrane domain comprises an ICOS polypeptide.

9. The method of claim 8, wherein the CAR comprises amino acids 489 to 553 of SEQ ID NO: 3.

10. The method of claim 1, wherein the intracellular signaling domain further comprises a co-stimulatory signaling domain.

11. The method of claim 10, wherein the co-stimulatory signaling domain comprises a CD28 polypeptide.

12. The method of claim 1, wherein the CAR is placed at an endogenous gene locus of the immunoresponsive cell.

13. The method of claim 12, wherein the endogenous gene locus is a TRAC locus, a TRBC locus or a TRGC locus.

14. The method of claim 13, wherein the endogenous gene locus is a TRAC locus.

15. The method of claim 12, wherein the placement of the CAR disrupts or abolishes the endogenous expression of a TCR.

16. The method of claim 1, wherein the immunoresponsive cell is selected from the group consisting of a T cell, a Natural Killer (NK) cell, a cytotoxic T lymphocyte (CTL), a regulatory T cell, a Natural Killer T (NKT) cell, a myeloid cell, a human embryonic stem cell, and a pluripotent stem cell from which lymphoid cells may be differentiated.

17. The method of claim 1, wherein the extracellular antigen-binding domain binds to a tumor antigen.

18. The method of claim 17, wherein the tumor antigen is selected from the group consisting of CD19, MUC16, MUC1, CA1X, CEA, CD8, CD7, CD10, CD20, CD22, CD30, CLL1, CD33, CD34, CD38, CD41, CD44, CD49f, CD56, CD74, CD133, CD138, EGP-2, EGP-40, EpCAM, erb-B2,3,4, FBP, Fetal acetylcholine receptor, folate receptor-a, GD2, GD3, HER-2, hTERT, IL-13R-a2, K-light chain, KDR, LeY, L1 cell adhesion molecule, MAGE-A1, Mesothelin, ERBB2, MAGEA3, p53, MART1, GP100, Proteinase3 (PR1), Tyrosinase, Survivin, hTERT, EphA2, NKG2D ligands, NY-ESO-1, oncofetal antigen (h5T4), PSCA, PSMA, ROR1, TAG-72, VEGF-R2, WT-1, BCMA, CD123, CD44V6, NKCS1, EGF1R, EGFR-VIII, and CD99, CD70, ADGRE2, CCR1, LILRB2, PRAME, CCR4, CD5, CD3, TRBC1, TRBC2, TIM-3, Integrin B7, ICAM-1, CD70, Tim3, CLEC12A and ERBB.

19. The method of claim 18, the antigen is CD19.

20. The method of claim 19, the CAR comprises the amino acid sequence set forth in SEQ ID NO: 43.

21. The method of claim 2, wherein the transmembrane domain comprises a CD8 polypeptide, a CD28 polypeptide, a CD3ζ polypeptide, a CD4 polypeptide, a 4-1BB polypeptide, an OX40 polypeptide, a CD166 polypeptide, a CD166 polypeptide, a CD8a polypeptide, a CD8b polypeptide, an ICOS polypeptide, an ICAM-1 polypeptide, a CTLA-4 polypeptide, a CD27 polypeptide, a CD40/My88 peptide, a NKGD2 peptide, or a combination thereof.

22. The method of claim 21, wherein the transmembrane domain comprises a CD166 polypeptide.

23. The method of claim 22, wherein the CD166 polypeptide comprises amino acid 528 to 553 of SEQ ID NO: 3.

24. The method of claim 2, wherein the CAR further comprises a hinge/spacer region comprising a CD8 polypeptide, a CD28 polypeptide, a CD3ζ polypeptide, a CD4 polypeptide, a 4-1BB polypeptide, an OX40 polypeptide, a CD166 polypeptide, a CD166 polypeptide, a CD8a polypeptide, a CD8b polypeptide, an ICOS polypeptide, an ICAM-1 polypeptide, a CTLA-4 polypeptide, a CD27 polypeptide, a CD40/My88 peptide, a NKGD2 peptide, or a combination thereof.

25. The method of claim 24, wherein the transmembrane domain and the hinge/spacer region are derived from the same molecule or from different molecules.

26. The method of claim 25, wherein
(a) the hinge/spacer region comprises a CD28 polypeptide and the transmembrane domain comprises a CD28 polypeptide;
(b) the hinge/spacer region comprises a CD84 polypeptide and the transmembrane domain comprises a CD84 polypeptide;
(c) the hinge/spacer region comprises a CD166 polypeptide and the transmembrane domain comprises a CD166 polypeptide;
(d) the hinge/spacer region comprises a CD8a polypeptide and the transmembrane domain comprises a CD8a polypeptide;
(e) the hinge/spacer region comprises a CD8b polypeptide and the transmembrane domain comprises a CD8b polypeptide; or
(f) the hinge/spacer region comprises a CD28 polypeptide and the transmembrane domain comprises an ICOS polypeptide.

27. The method of claim 26, wherein the CAR comprises amino acids 489 to 553 of SEQ ID NO: 3.

28. The method of claim 2, wherein the intracellular signaling domain further comprises a co-stimulatory signaling domain.

29. The method of claim 28, wherein the co-stimulatory signaling domain comprises a CD28 polypeptide.

30. The method of claim 2, wherein the CAR is placed at an endogenous gene locus of the immunoresponsive cell.

31. The method of claim 30, wherein the endogenous gene locus is a TRAC locus, a TRBC locus or a TRGC locus.

32. The method of claim 31, wherein the endogenous gene locus is a TRAC locus.

33. The method of claim 30, wherein the placement of the CAR disrupts or abolishes the endogenous expression of a TCR.

34. The method of claim 2, wherein the immunoresponsive cell is selected from the group consisting of a T cell, a Natural Killer (NK) cell, a cytotoxic T lymphocyte (CTL), a regulatory T cell, a Natural Killer T (NKT) cell, a myeloid cell, a human embryonic stem cell, and a pluripotent stem cell from which lymphoid cells may be differentiated.

35. The method of claim 2, wherein the extracellular antigen-binding domain binds to a tumor antigen.

36. The method of claim 35, wherein the tumor antigen is selected from the group consisting of CD19, MUC16, MUC1, CA1X, CEA, CD8, CD7, CD10, CD20, CD22, CD30, CLL1, CD33, CD34, CD38, CD41, CD44, CD49f, CD56, CD74, CD133, CD138, EGP-2, EGP-40, EpCAM, erb-B2,3,4, FBP, Fetal acetylcholine receptor, folate receptor-a, GD2, GD3, HER-2, hTERT, IL-13R-a2, K-light chain, KDR, LeY, L1 cell adhesion molecule, MAGE-A1, Mesothelin, ERBB2, MAGEA3, p53, MART1, GP100, Proteinase3 (PR1), Tyrosinase, Survivin, hTERT, EphA2, NKG2D ligands, NY-ESO-1, oncofetal antigen (h5T4), PSCA, PSMA, ROR1, TAG-72, VEGF-R2, WT-1, BCMA, CD123, CD44V6, NKCS1, EGF1R, EGFR-VIII, and CD99, CD70, ADGRE2, CCR1, LILRB2, PRAME, CCR4, CD5, CD3, TRBC1, TRBC2, TIM-3, Integrin B7, ICAM-1, CD70, Tim3, CLEC12A and ERBB.

37. The method of claim 36, the antigen is CD19.

38. The method of claim 37, the CAR comprises the amino acid sequence set forth in SEQ ID NO: 43.

39. The method of claim 7, wherein
(a) the hinge/spacer region comprises a CD28 polypeptide and the transmembrane domain comprises a CD28 polypeptide;
(b) the hinge/spacer region comprises a CD166 polypeptide and the transmembrane domain comprises a CD166 polypeptide;

(c) the hinge/spacer region comprises a CD8a polypeptide and the transmembrane domain comprises a CD8a polypeptide; or
(d) the hinge/spacer region comprises a CD28 polypeptide and the transmembrane domain comprises an ICOS polypeptide.

40. The method of claim 25, wherein
(a) the hinge/spacer region comprises a CD28 polypeptide and the transmembrane domain comprises a CD28 polypeptide;
(b) the hinge/spacer region comprises a CD166 polypeptide and the transmembrane domain comprises a CD166 polypeptide;
(c) the hinge/spacer region comprises a CD8a polypeptide and the transmembrane domain comprises a CD8a polypeptide;
(d) the hinge/spacer region comprises a CD28 polypeptide and the transmembrane domain comprises an ICOS polypeptide.

* * * * *